US008865704B2

(12) United States Patent
Varrone et al.

(10) Patent No.: US 8,865,704 B2
(45) Date of Patent: Oct. 21, 2014

(54) WNT PATHWAY ANTAGONISTS

(75) Inventors: Maurizio Varrone, Siena (IT); Arianna Nencini, Siena (IT); Joanna Margaret Quinn, Siena (IT); Andrea Caricasole, Siena (IT); Annette Cornelia Bakker, Sienna (IT); Giovanni Gaviraghi, Siena (IT); Massimilano Salerno, Siena (IT)

(73) Assignee: Siena Biotech S.p.A., Siena (IT)

( * ) Notice: Subject to any disclaimer, the term of this patent is extended or adjusted under 35 U.S.C. 154(b) by 0 days.

(21) Appl. No.: 13/500,582

(22) PCT Filed: Oct. 6, 2010

(86) PCT No.: PCT/EP2010/006055
§ 371 (c)(1),
(2), (4) Date: Apr. 5, 2012

(87) PCT Pub. No.: WO2011/042145
PCT Pub. Date: Apr. 14, 2011

(65) Prior Publication Data
US 2012/0196851 A1  Aug. 2, 2012

(30) Foreign Application Priority Data

Oct. 7, 2009 (EP) ..................................... 09172403

(51) Int. Cl.
| | | |
|---|---|---|
| C07D 217/14 | (2006.01) | |
| C07D 235/26 | (2006.01) | |
| C07D 239/22 | (2006.01) | |
| C07D 239/80 | (2006.01) | |
| C07D 239/96 | (2006.01) | |
| A61K 31/4166 | (2006.01) | |
| A61K 31/4184 | (2006.01) | |
| A61K 31/437 | (2006.01) | |
| A61K 31/472 | (2006.01) | |
| A61K 31/517 | (2006.01) | |
| A61K 31/5377 | (2006.01) | |
| A61K 31/5513 | (2006.01) | |
| C07D 471/04 | (2006.01) | |
| C07D 417/12 | (2006.01) | |
| C07D 243/10 | (2006.01) | |
| C07D 403/12 | (2006.01) | |
| C07D 407/12 | (2006.01) | |
| C07D 409/12 | (2006.01) | |
| C07D 413/08 | (2006.01) | |
| C07D 401/12 | (2006.01) | |
| C07D 405/12 | (2006.01) | |

(52) U.S. Cl.
CPC ............ *C07D 217/14* (2013.01); *C07D 239/22* (2013.01); *C07D 471/04* (2013.01); *C07D 417/12* (2013.01); *C07D 243/10* (2013.01); *C07D 403/12* (2013.01); *C07D 407/12* (2013.01); *C07D 235/26* (2013.01); *C07D 239/80* (2013.01); *C07D 409/12* (2013.01); *C07D 239/96* (2013.01); *C07D 413/08* (2013.01); *C07D 401/12* (2013.01); *C07D 405/12* (2013.01)
USPC ...................... 514/221; 514/231.5; 514/234.5; 514/266.2; 514/266.21; 514/266.23; 514/269; 514/363; 540/506; 544/139; 544/284; 544/285; 544/295; 544/363; 544/370

(58) Field of Classification Search
USPC ........... 514/221, 231.5, 234.5, 266.2, 266.21, 514/266.23, 269, 363; 540/506; 544/139, 544/284, 285, 295, 363, 370
See application file for complete search history.

(56) References Cited

U.S. PATENT DOCUMENTS

| | | | |
|---|---|---|---|
| 2006/0205941 A1 | 9/2006 | Bressi et al. | |
| 2006/0258694 A1 | 11/2006 | Bressi et al. | |
| 2009/0163545 A1* | 6/2009 | Goldfarb ....................... 514/312 |

OTHER PUBLICATIONS

Vaisburg et al., "N-(2-Amino-phenyl)-4-(heteroarylmethyl)-benzamides as new histone deacetylase inhibitors", Bioorganic & Medicinal Chemistry Letters, Pergamon, Elsevier Science, GB, vol. 17, No. 24, Oct. 18, 2007, pp. 6729-6733, XP022339563.
Chen et al., "2,4-Diamino-quinazolines as inhibitors of beta-catenin/Tcf-4 pathway: Potential treatment for colorectal cancer", Bioorganic & Medicinal Chemistry Letters, vol. 19, Jul. 17, 2009, pp. 4980-4983, XP002616492.
Akiri, G. et al. "Wnt pathway aberrations including autocrine Wnt activation occur at high frequency in human non-small-cell-lung carcinoma". Oncogene. 2009, vol. 28, pp. 2163-2172.
Colnot, S. et al. "Liver-targeted disruption of Apc in mice activates β-catenin signaling and leads to hepatocellular carcinomas". PNAS. Dec. 7, 2004, vol. 101, No. 49, pp. 17216-17221.
Derkesen, P.W. et al. "Illegitimate WNT signaling promotes proliferation of multiple myeloma cells", PNAS. Apr. 20, 2014, vol. 101, No. 16, pp. 6122-6127.
Kinzler, K.W. et al. "Identification of FAP Locus Genes from Chromosome 5q21". Science. Aug. 9, 1991, vol. 253, pp. 661-665.
Major, M.B. et al. "Wilms Tumor Suppressor WTX Negatively Regulates WNT/β-Catenin Signaling". May 18, 2007, Science. vol. 316, pp. 1043-1046.
Matsuda, Y. et al. "WNT signaling enhances breast cancer cell motility and blockade of the WNT pathway by sFRP1 suppresses MDA-MB-231 zenograft growth". Breast Cancer Research. 2009, vol. 11, pp. 1-16.

(Continued)

*Primary Examiner* — Bruck Kifle
(74) *Attorney, Agent, or Firm* — Arent Fox LLP

(57) ABSTRACT

The present invention relates to known and novel compounds of formula (I) as herein described and pharmaceutical compositions thereof. The compounds of formula (I) have inhibitory effect on the Wnt pathway and are therefore useful in the preparation of a medicament, in particular for the treatment of cancer.

9 Claims, No Drawings

(56) References Cited

OTHER PUBLICATIONS

Molenaar, M. et al. "XTcf3 Transcription Factor Mediates β-Catenin-Induced Axis Formation in Xenopus Embryos". DOI:http//dx.doi.org/10.1016/S0092-8674(00)80112-9.
Nawroth, R. et al. "Extracellular Sulfatases, Elements of the Wnt Signaling Pathway, Positively Regulate Growth and Tumorigenicity of Human Pancreatic Cancer Cells", PLoS ONE, Apr. 2007, Issue 4, pp. 1-11.
Nguyen, D.X. et al. "WNT/TCF signalling through LEF1 and HOXB9 mediates lung adenocarcinoma metastasis". Cell. Jul. 10, 2009, vol. 138, No. 1, pp. 1-20.
Nishisho, I. et al. "Mutations of Chromosome 5q21 Genes in FAP and Colorectal Cancer Patients", Science. Aug. 9, 1991, vol. 253, pp. 665-669.
O'Connell, M.P. "Heparan Sulfate Proteoglycan Modulation of Wnt5A Signal Transduction in Metastatic Melanoma Cells". The Journal of Biological Chemistry. Oct. 16, 2009, vol. 284, No. 42. pp. 28704-28712.
Pu, P. et al. "Downregulation of Wnt2 and β-catenin by siRNA suppresses malignant glioma cell growth". Cancer Gene Therapy. 2009, vol. 16, pp. 351-361.
Rivera, M.N. et al. "An X Chromosome Gene, WTX, Is Commonly Inactivated in Wilms Tumor". Science. Feb. 2, 2007, vol. 315, pp. 642-645.
Sakariassen, P.Ø. et al. "Angiogenesis-independent tumor growth mediated by stem-like cancer cells". PNAS. Oct. 31, 2006, vol. 103, No. 44, pp. 16466-16471.
Schlange, T. et al. "Autocrine WNT signaling contributes to breast cancer cell proliferation via the canonical WNT pathway and EGFR transactivation". Breast Cancer Research. 2007, vol. 9, pp. 1-48.
Staal, F.J. "Uncontrolled Wnt signalling causes leukemia", Blood. 2007, vol. 109, pp. 5073-5074.
Taniguchi, H. "Frequent epigenetic inactivation of Wnt inhibitory factor-1 in human gastrointestinal cancers". Oncogene. 2005, pp. 1-7.
Tickenbrock, L. et al. "Activation of Wnt signalling in acute myeloid leukemia by induction of Frizzled-4". International Journal of Oncology. 2008, vol. 33, pp. 1215-1221.
Vibhakar, R. et al, "Dickkopf-1 is an epigenetically silenced candidate tumor suppressor gene in medulloblastoma". Neuro-Oncology. Apr. 2007, pp. 135-144.
Yang, S.H. et al. "Pathological responses to oncogenic Hedgehog signaling in skin are dependent on Canonical Wnt/β-catenin signaling". Nat Genet. Sep. 2008, vol. 40, No. 9, pp. 1130-1135.
Zhao, C. et al. "Loss of β-catenin Impairs the Renewal of Normal and CML Stem Cells in Vivo". Cancer Cell. Dec. 2007, vol. 12, No. 6, pp. 528-541.
Scifinder. CAS Registry No. 919722-35-3. p. 1. American Chemical Society (ACS). 2014.
Scifinder. CAS Registry No. 902016-90-4. p. 2. American Chemical Society (ACS). 2014.
Scifinder. CAS Registry No. 919721-51-0. p. 3. American Chemical Society (ACS). 2014.
Scifinder. CAS Registry No. 900881-81-4. p. 4. American Chemical Society (ACS). 2014.
Scifinder. CAS Registry No. 919726-81-1. p. 6. American Chemical Society (ACS). 2014.
Scifinder. CAS Registry No. 919724-95-1. p. 8. American Chemical Society (ACS). 2014.
Scifinder. CAS Registry No. 901270-24-4. p. 10. American Chemical Society (ACS). 2014.
Scifinder. CAS Registry No. 900898-69-3. p. 11. American Chemical Society (ACS). 2014.
Scifinder. CAS Registry Number: 951926-44-6. p. 12. American Chemical Society (ACS). 2014.
Scifinder. CAS Registry No. 919728-55-5. p. 13. American Chemical Society (ACS). 2014.
Scifinder, CAS Registry No. 900901-05-5. p. 14. American Chemical Society (ACS). 2014.
Scifinder. CAS Registry No. 951969-57-6. p. 15. American Chemical Society (ACS). 2014.
Scifinder. CAS Registry No. 879475-56-6. p. 1. American Chemical Society (ACS). 2014.
Scifinder. CAS Registry No. 879468-92-5. p. 2. American Chemical Society (ACS). 2014.
Scifinder. CAS Registry No. 1023811-39-3. p. 3. American Chemical Society (ACS). 2014.
Scifinder. CAS Registry No. 879580-23-1. p. 4. American Chemical Society (ACS). 2014.
Scifinder. CAS Registry No. 896377-43-8. p. 5. American Chemical Society (ACS). 2014.
Scifinder. CAS Registry No. 896375-78-3. p. 6. American Chemical Society (ACS). 2014.
Scifinder. CAS Registry No. 896377-15-4. p. 7. American Chemical Society (ACS). 2014.
Scifinder. CAS Registry No. 1212143-80-0. p. 8. American Chemical Society (ACS). 2014.
Scifinder. CAS Registry No. 688774-50-7. p. 10. American Chemical Society (ACS). 2014.
Scifinder. CAS Registry No. 896367-75-2. p. 11. American Chemical Society (ACS). 2014.
Scifinder. CAS Registry No. 896368-20-0. p. 12. American Chemical Society (ACS). 2014.
Scifinder. CAS Registry No. 896368-58-4. p. 13. American Chemical Society (ACS). 2014.
Scifinder. CAS Registry No. 896367-52-5. p. 14. American Chemical Society (ACS). 2014.
Scifinder. CAS Registry No. 896368-12-0. p. 15. American Chemical Society (ACS). 2014.
Scifinder. CAS Registry No. 879577-53-4. p. 3. American Chemical Society (ACS). 2014.
Scifinder. CAS Registry No. 879583-31-0. p. 5. American Chemical Society (ACS). 2014.
Scifinder. CAS Registry No. 879479-62-6. p. 6. American Chemical Society (ACS). 2014.
Scifinder. CAS Registry No. 879577-41-0. p. 1. American Chemical Society (ACS). 2014.
Scifinder. CAS Registry No. 896375-82-9. p. 1. American Chemical Society (ACS). 2014.
Scifinder. CAS Registry No. 896364-68-4. p. 7. American Chemical Society (ACS). 2014.
Scifinder. CAS Registry No. 919726-77-5. p. 1. American Chemical Society (ACS). 2014.
Scifinder. CAS Registry No. 892636-17-8. p. 1. American Chemical Society (ACS). 2014.
Scifinder. CAS Registry No. 902007-44-7. p. 1. American Chemical Society (ACS). 2014.
Scifinder. CAS Registry No. 900897-34-9. p. 1. American Chemical Society (ACS). 2014.
Scifinder. CAS Registry No. 900874-00-2. p. 1. American Chemical Society (ACS). 2014.
Scifinder. CAS Registry No. 1023476-15-4. p. 1. American Chemical Society (ACS). 2014.
Scifinder. CAS Registry No. 896364-68-4. p. 2. American Chemical Society (ACS). 2014.
Scifinder. CAS Registry No. 879577-53-4. p. 1. American Chemical Society (ACS). 2014.

* cited by examiner

WNT PATHWAY ANTAGONISTS

CROSS-REFERENCED TO RELATED APPLICATION

This application is a National Stage entry of International Application PCT/EP2010/006055, filed Oct. 6, 2010, which claims priority to European Patent Application No. 09172403.9, filed Oct. 7, 2009, each of the disclosures of the prior applications being hereby incorporated in their entirety by reference.

The present invention relates to compounds, some of which are novel, having inhibitory effect on the Wnt pathway, and to their pharmaceutical uses.

BACKGROUND TO THE INVENTION

The Wnt gene family encodes a large class of secreted proteins related to the Int1/Wnt11 proto-oncogene and *Drosophila* wingless ("Wg"), a *Drosophila* Wnt1 homologue (Cadigan et al. (1997) Genes & Development 11:3286-3305). Wnts are expressed in a variety of tissues and organs and are required for developmental processes, including segmentation in *Drosophila*; endoderm development in *C. elegans*; and establishment of limb polarity, neural crest differentiation, kidney morphogenesis, sex determination, and brain development in mammals (Parr, et al. (1994) Curr. Opinion Genetics & Devel. 4:523-528). The Wnt pathway is a master regulator in animal development, both during embryogenesis and in the mature organism (Eastman, et al. (1999) Curr Opin Cell Biol 11: 233-240; Peifer, et al. (2000) Science 287: 1606-1609). The variety of biological processes to which they take part during embryonic development and adult homeostasis is paralleled by the diversification within genomes into Wnt orthologues (19 identified Wnts in humans) and by the capacity to activate at least three intracellular signalling pathways (Moon et al., 2002; Nelson and Nusse, 2004; Seto and Bellen, 2004), the calcium-mediated and planar polarity pathways (Strutt, 2003; Veeman et al., 2003; Kuhl, 2004) and the canonical Wnt-β-catenin pathway. In the canonical Wnt pathway, Wnt ligands bind to their Frizzled receptor of a family of 10 reported Frizzled ("Fz") seven transmembrane domain receptors (Bhanot et al. (1996) Nature 382:225-230). So doing, they activate the cytoplasmic protein Dishevelled (Dvl-1, 2 and 3 in humans and mice) (Boutros, et al. (1999) Mech Dev 83: 27-37) and phosphorylate LRP5/6. A signal is thereby generated which prevents the phosphorylation and degradation of Armadillo/β-catenin, in turn leading to an increase in cytoplasmic β-catenin (Perrimon (1994) Cell 76:781-784). This β-catenin translocates to the nucleus where it binds TCF (T cell factor) transcription factors (also known as lymphoid enhancer-binding factor-1 (LEF1)), serving as a coactivator of TCF/LEF-induced transcription (Bienz, et al. (2000) Cell 103: 311-320; Polakis, et al. (2000) and finally leading to the increased gene expression of Wnt target genes. In the absence of Wnt, cytoplasmic β-catenin protein is constantly degraded by the action of the Axin complex, which is composed of the scaffolding protein Axin, the tumor suppressor adenomatous polyposis coli gene product (APC), casein kinase 1 (CK1), and glycogen synthase kinase 3 (GSK3). CK1 and GSK3 sequentially phosphorylate the amino terminal region of β-catenin, resulting in β-catenin recognition by β-Trcp, an E3 ubiquitin ligase subunit, and subsequent β-catenin ubiquitination and proteasomal degradation (He et al., 2004). This continual elimination of β-catenin prevents β-catenin from reaching the nucleus, and Wnt target genes are thereby repressed by the DNA-bound T cell factor/lymphoid enhancer factor (TCF/LEF) family of proteins.

An increasing number of studies suggest how Wnt signalling related disorders can be initiated not only by mutations involving APC or Axin proteins (e.g., colorectal cancer), responsible for β-catenin degradation but also by alternative mechanisms. Hyperactivating mutations at the LRP5 co-receptor level are associated with high bone-density familial autosomal dominant syndrome (Boyden et al., N Engl J. Med. 2002; 346(20):1513-21). Autocrine Wnt signaling mediated by specific Wnt ligands was in fact linked to lung (Akiri et al. Oncogene 2009 28(21):2163-72), breast (Schlange et al., Breast Cancer Res. 2007; 9(5):R63 and Matsuda et al., Breast Cancer Res. 2009; 11(3):R32) and pancreatic (Nawroth et al., PLoS One. 2007 Apr. 25; 2(4):e392) tumors, but also malignant melanoma cells spreading (O'Connell et al., J Biol. Chem. 2009 Aug. 20, Epub ahead of print). Wnt signals form a class of paracrine growth factors act to influence multiple myeloma cell growth (Derksen et al., PNAS. 2004; 101(16): 6122-7). The metastatic process, an ominous feature of most malignant tumors represents an additional area of intervention for Wnt inhibitors (Nguyen et al., Cell. 2009; 138(1):51-62) or tumor recurrence in glioblastoma patients (Sakarlassen et al., PNAS 2006, 103 (44) 16466) where different pathways seem to rule primary versus recurrent tumors. Moreover, there is strong evidence of the Wnt pathway involvement in cancers such as gastric cancer (Taniguchi et al, Oncogene. 2005 Nov. 24; 24(53):7946-52), medulloblastoma (Vibhakar et al., Neuro Oncol. 2007 April; 9(2):135-44), glioblastoma (Pu et al., Cancer Gene Ther. 2009 (4):351-61), hepatocellular carcinomas (Colnot et al., Proc Natl Acad Sci USA. 2004 Dec. 7; 101(49):17216-2), basal cell carcinoma (Yang et al., Nat. Genet. 2008 September; 40(9):1130-5), leukaemia (Staal, Blood, 109, 12, 5073-5074, 2007; Tickenbrock et al., Int. J. Oncol., 33, 1215-1221, 2008; Zhao, Cancer Cell, 12, 528-541, 2007), Wilm's tumours (Rivera et al., Science, 315, 642-645, 2007 and Major et al., Science, 316, 1043-1046, 2007) and Familial Adenomatous Polyposis (Kinzler et al., Science 253,661-665, 1991 and Nishisho et al., Science 253, 665-669, 1991).

PRIOR ART

The 41 compounds listed below that fall under the scope of the present invention are known.

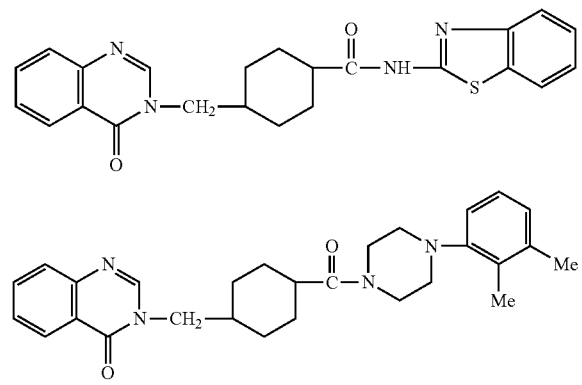

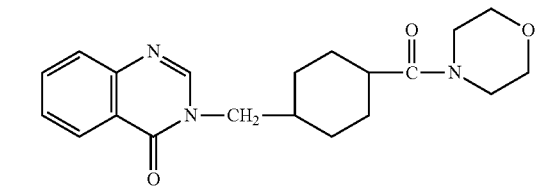
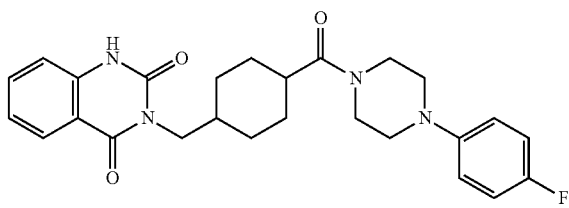
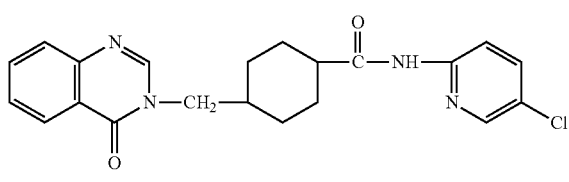
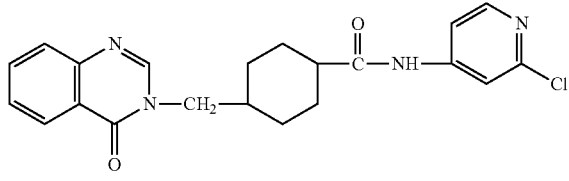
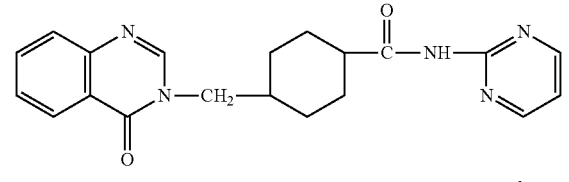
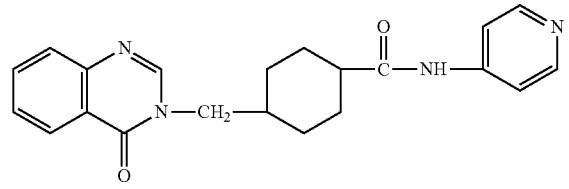
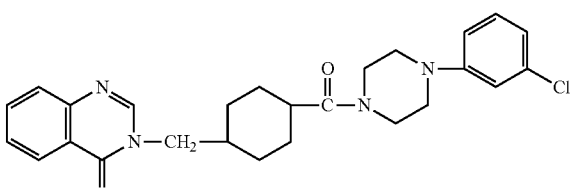
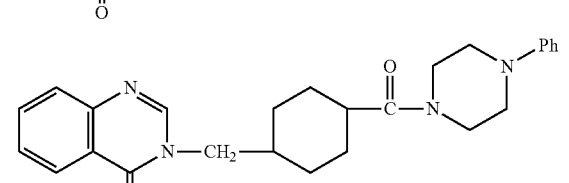
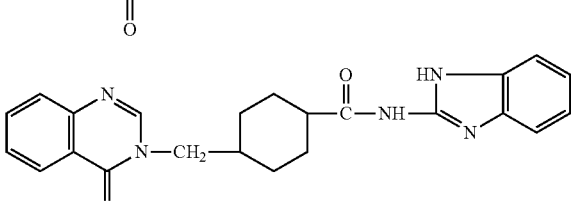
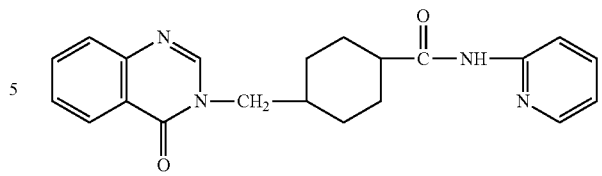
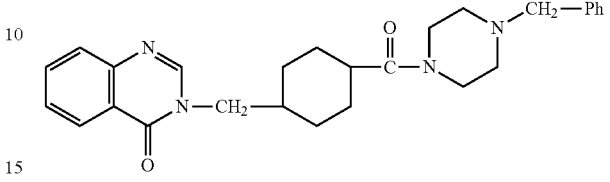
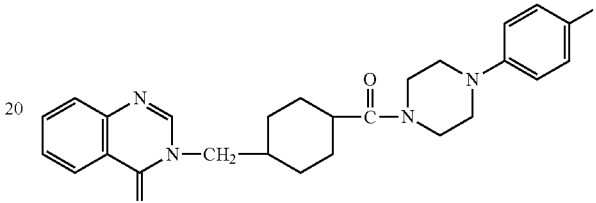
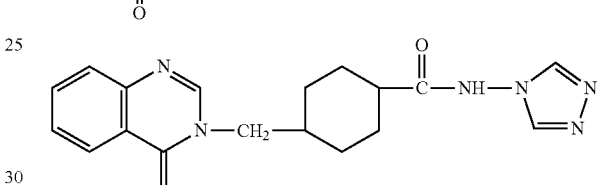
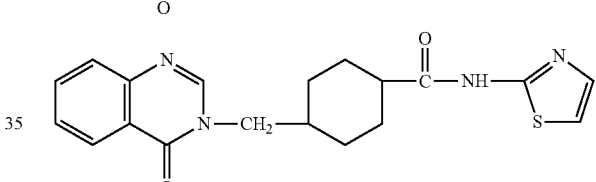
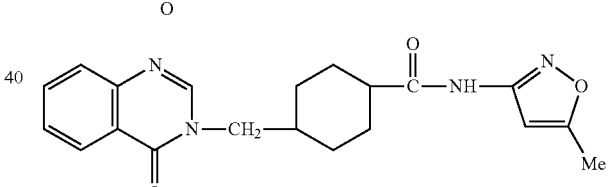
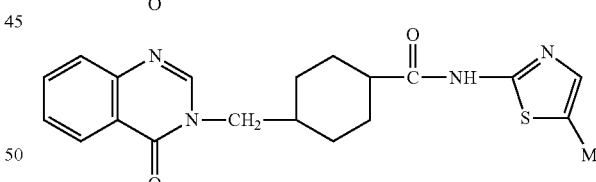
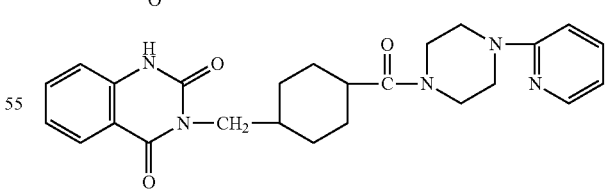
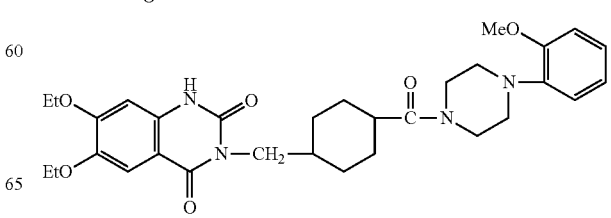

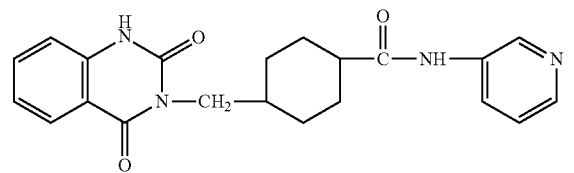
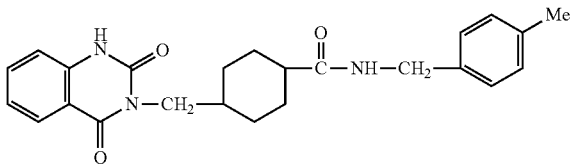
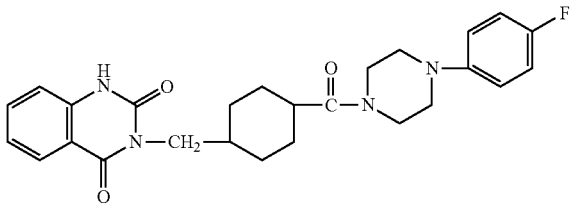
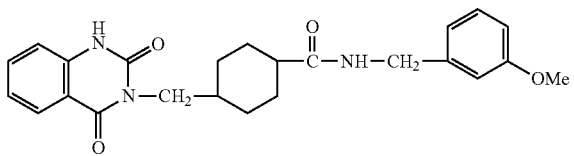
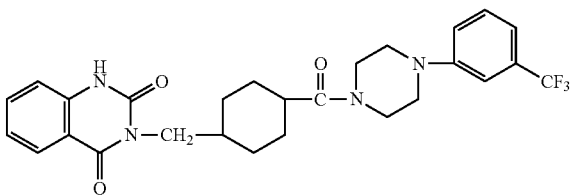
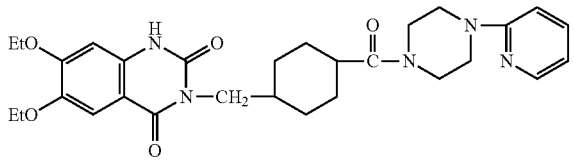
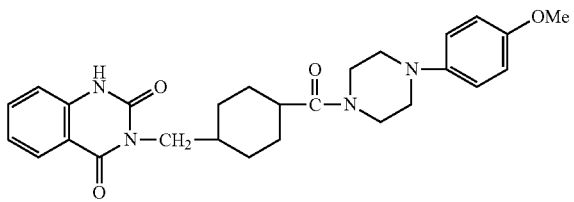
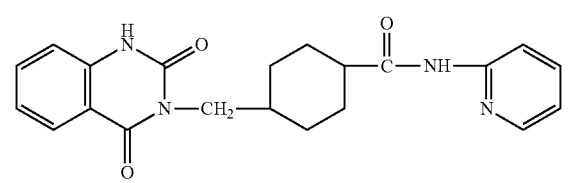
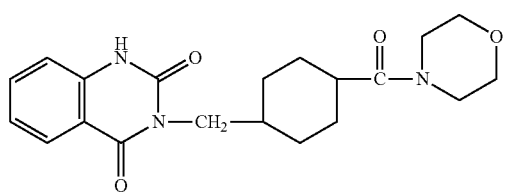
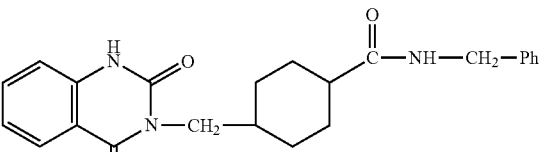
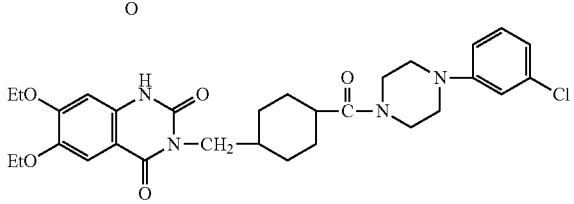
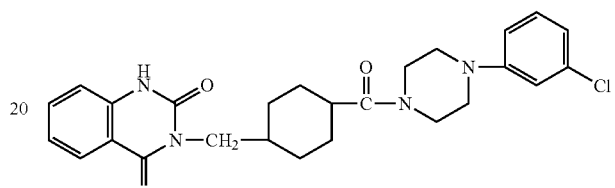
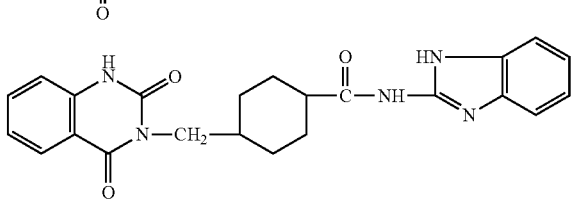
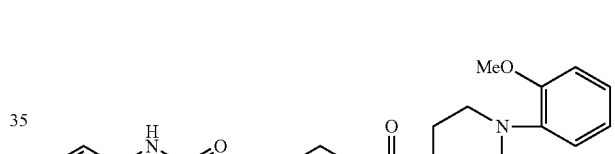
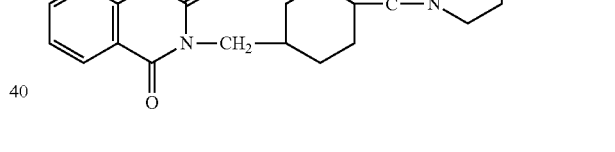
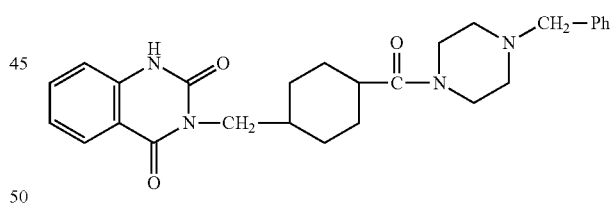
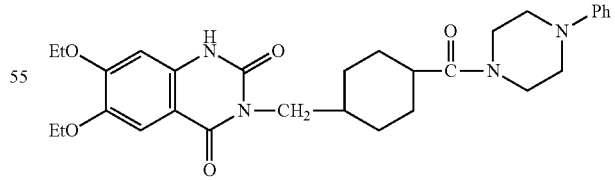
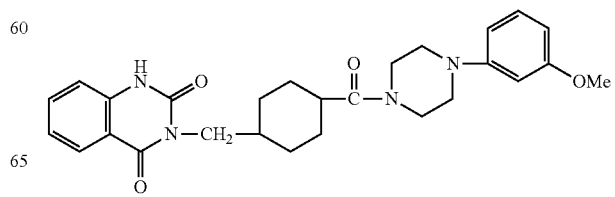

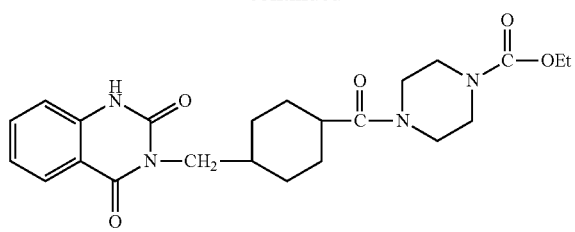

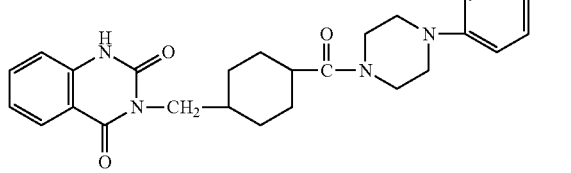

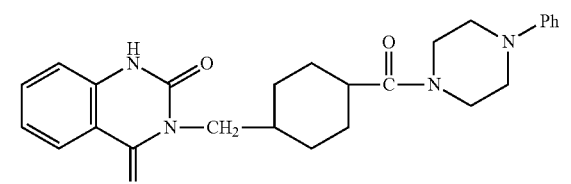

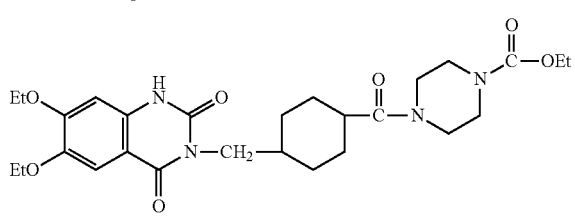

However, none of these 41 compounds listed above are known to possess biological activity that would render them suitable for pharmacological applications.

DETAILED DESCRIPTION OF THE INVENTION

In the following description the symbol • indicates the rest of the molecule to which the relevant substituent is attached.

According to a first aspect of the present invention, there is provided a compound of formula (I),

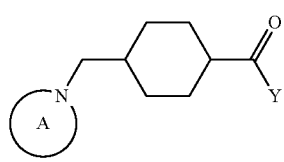
(I)

wherein

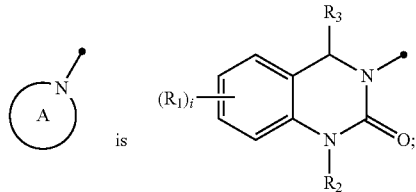

is $R_1$ is Cl, F, OH, $C_1$-$C_3$ alkyl, oxalkyl, alkyloxy, oxalkyloxy;

i equals 0, 1 or 2;

$R_2$ is hydrogen or $C_1$-$C_4$ linear, branched or cyclic alkyl group;

$R_3$ may be H; a $C_1$-$C_3$ linear, branched or cyclic alkyl group; or $R_3$, taken together with the carbon atom to which it is attached, may form an oxo group;

Z is a linear, cyclic or branched $C_1$-$C_6$ alkyl group; a linear, cyclic or branched $C_1$-$C_8$ alkylcarbonyl, oxaalkylcarbonyl, alkyloxycarbonyl, alkylaminocarbonyl or oxaalkylaminocarbonyl; $Ar_2$; C(O)—$Ar_2$; a benzyl or $C_1$-$C_3$alkylphenyl optionally substituted with one or more methyl, ethyl, methoxy or chloro groups;

$Ar_1$ is a 5 to 10 membered heteroaromatic ring optionally substituted with one or more methyl, ethyl, methoxy or chloro groups;

$Ar_2$ is 5 to 6 membered aromatic or heteroaromatic ring optionally substituted with one or more methyl, ethyl, methoxy or chloro groups;

T may be H; a $C_1$-$C_3$ linear, branched or cyclic alkyl; or T, taken together with the —CH— group to which it is attached, may form an oxo group;
wherein any carbon-bound hydrogen atom may optionally be substituted with a fluorine atom; salts, stereoisomers and stereoisomeric mixture thereof, with the exception of
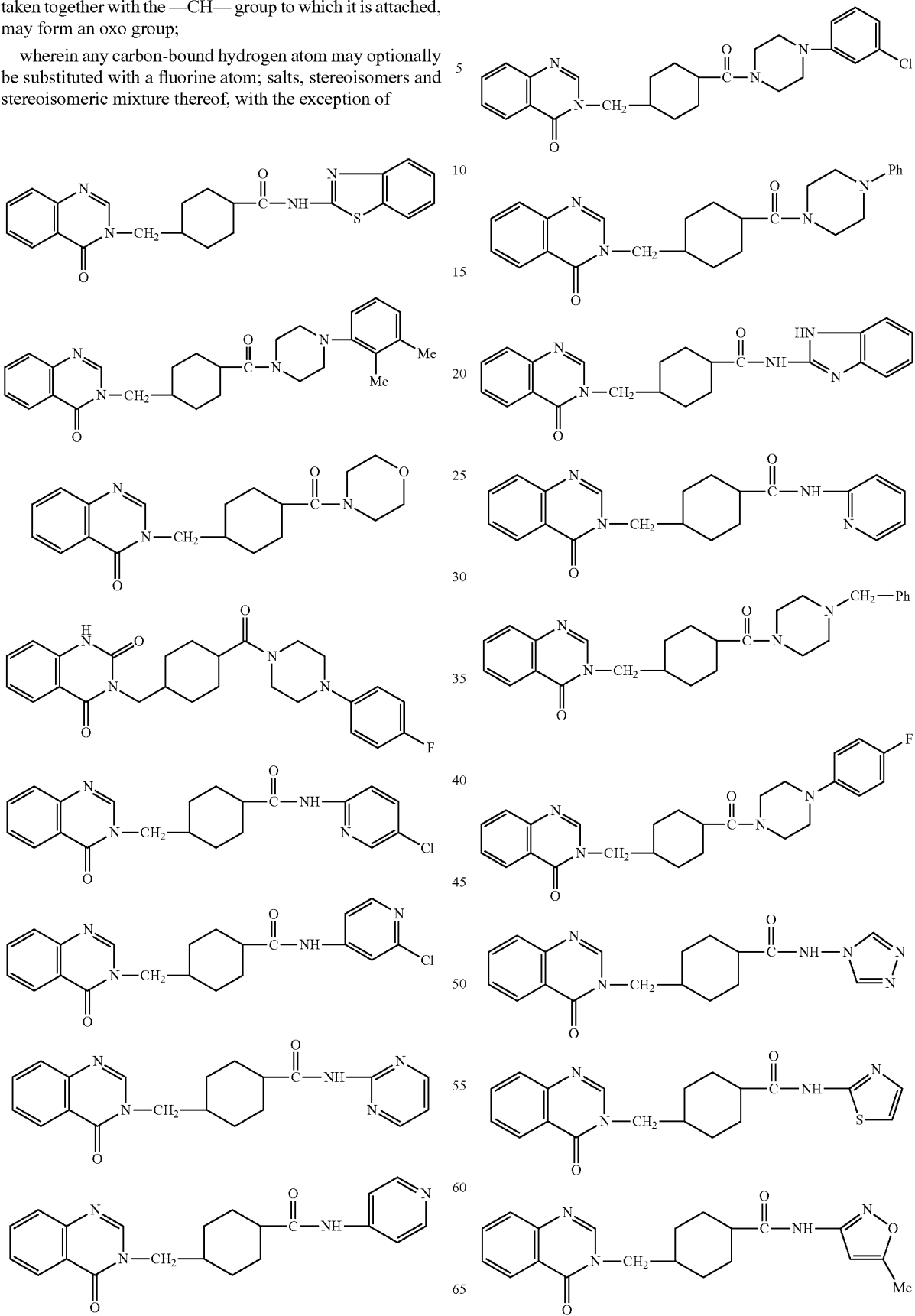

11
-continued
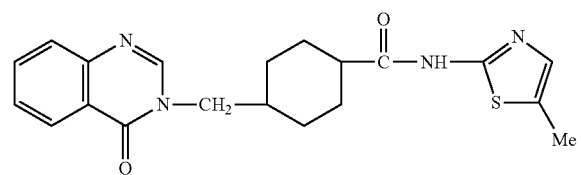
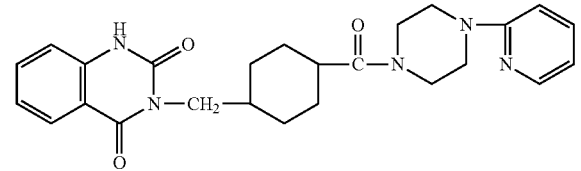
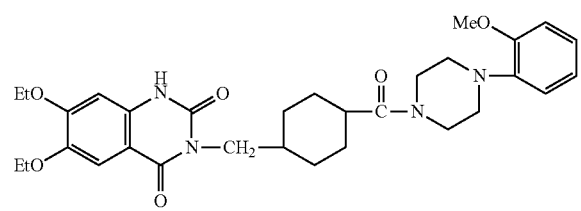
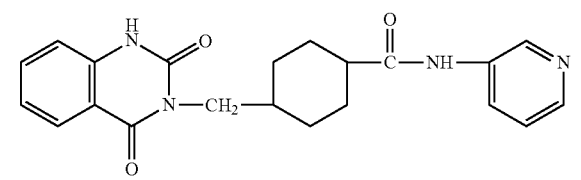
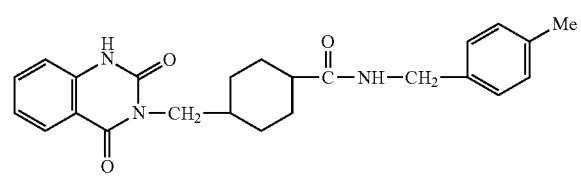
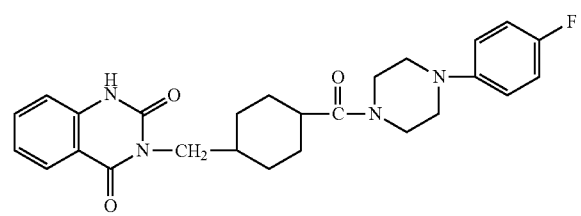
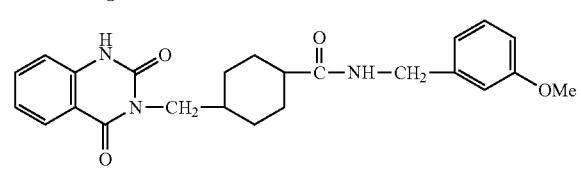
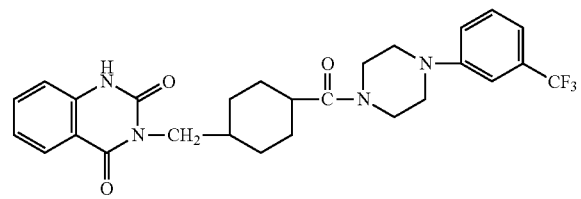
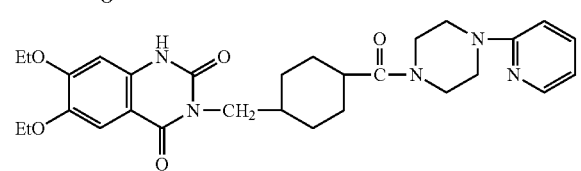
12
-continued
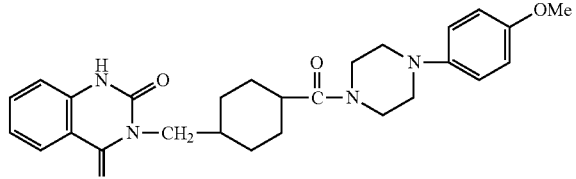
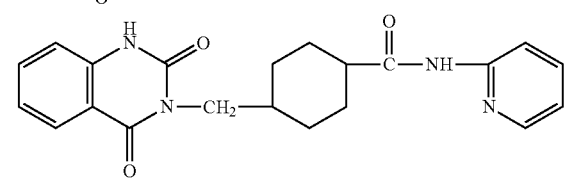
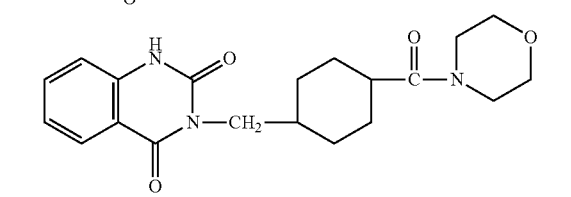
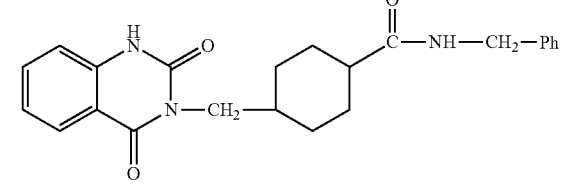
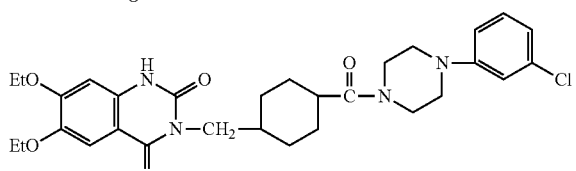
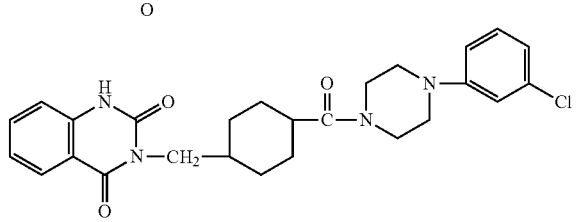
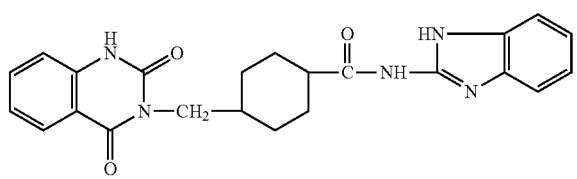
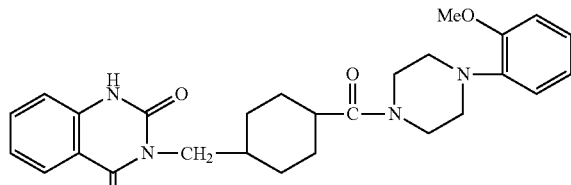
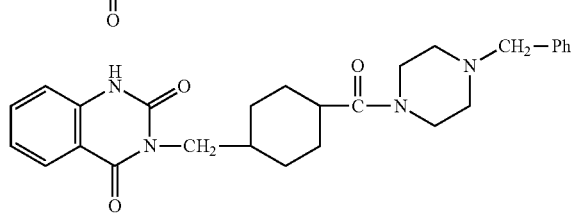

-continued

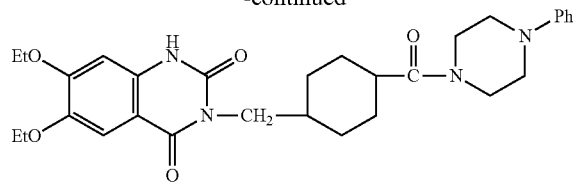
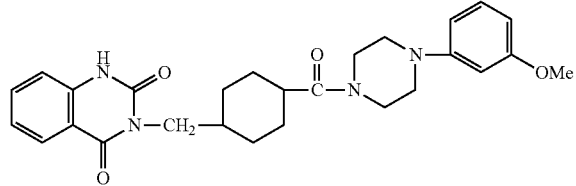
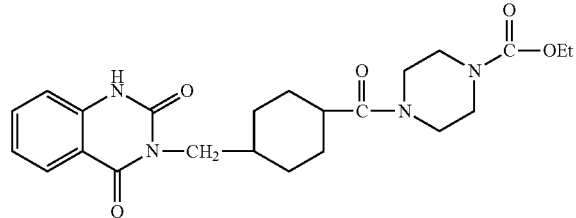
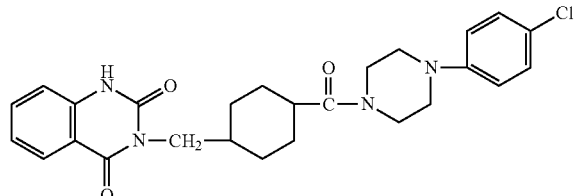
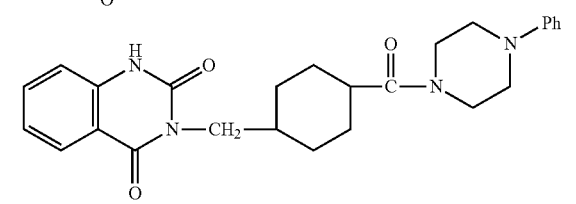
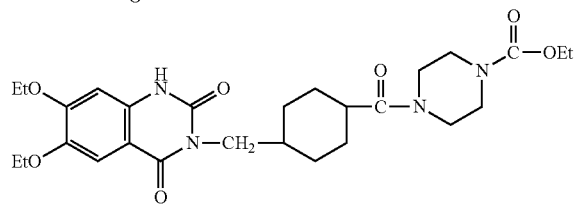

According to another aspect of the present invention, there is provided a compound of formula (I)

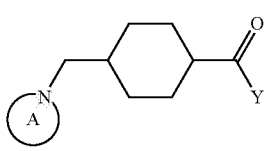
(I)

Wherein

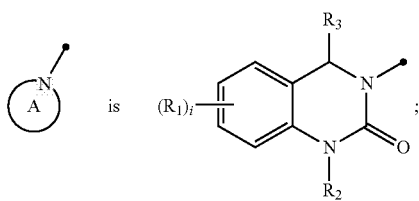

-continued

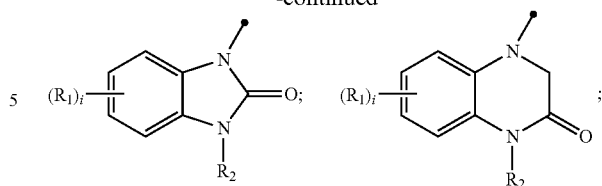
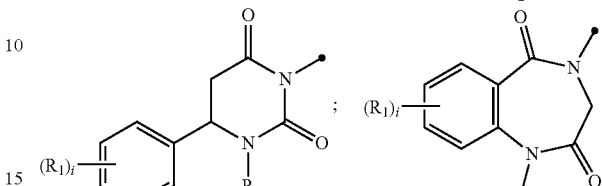
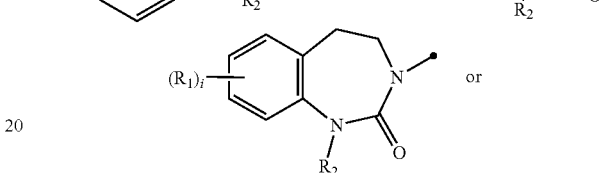
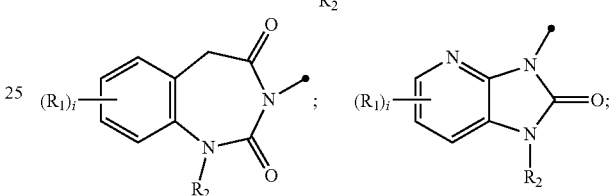
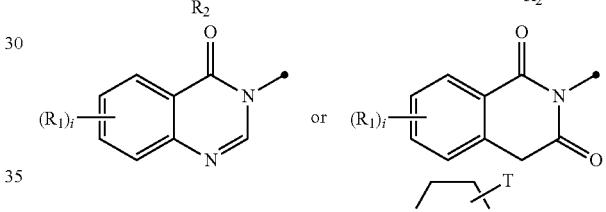
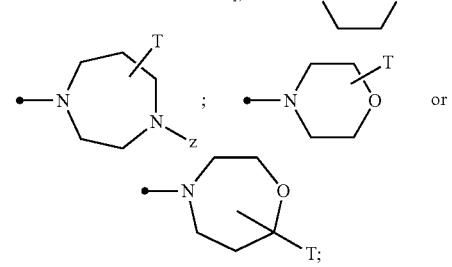

$R_1$ is Cl, F, OH, $C_1$-$C_3$ alkyl, oxalkyl, alkyloxy, oxalkyloxy; i equals 0, 1 or 2;

$R_2$ is hydrogen or $C_1$-$C_4$ linear, branched or cyclic alkyl group;

$R_3$ may be H; a $C_1$-$C_3$ linear branched or cyclic alkyl group; or $R_3$, taken together with the carbon atom to which it is attached, may form an oxo group;

Z is a linear, cyclic or branched $C_1$-$C_6$ alkyl group; a linear, cyclic or branched $C_1$-$C_8$ alkylcarbonyl, oxaalkylcarbonyl, alkyloxycarbonyl, alkylaminocarbonyl or oxaalkylaminocarbonyl; $Ar_2$; C(O)—$Ar_2$; a benzyl or $C_1$-$C_3$alkylphenyl optionally substituted with one or more methyl, ethyl, methoxy or chloro groups;

$Ar_1$ is a 5 to 10 membered heteroaromatic ring optionally substituted with one or more methyl, ethyl, methoxy or chloro groups;

$Ar_2$ is 5 to 6 membered aromatic or heteroaromatic ring optionally substituted with one or more methyl, ethyl, methoxy or chloro groups;

T may be H; a $C_1$-$C_3$ linear, branched or cyclic alkyl; or T, taken together with the —CH— group to which it is attached, may form an oxo group;

wherein any carbon-bound hydrogen atom may optionally be substituted with a fluorine atom; salts, stereoisomers and stereoisomeric mixture thereof, for use in the preparation of a medicament, in particular for the treatment of cancer.

Compounds falling under formula I above can exist in stereoisomeric forms and mixtures that are characterised by the relative substitution at the cyclohexyl moiety. Amongst these, preferred compound are the trans isomers falling under formulae (Ia) and (Ib)

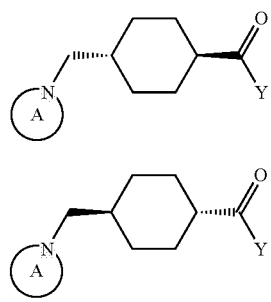

Wherein the

group and Y are as defined above and wherein any carbon-bound hydrogen atom may optionally be substituted with a fluorine atom In a particular embodiment i is 0.

In a preferred embodiment,

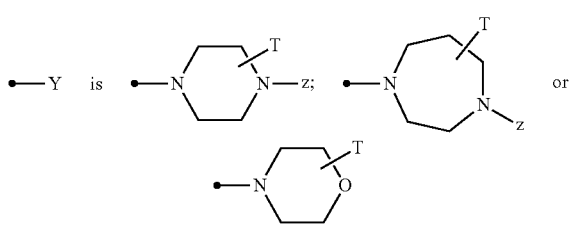

and Z is a $C_3$-$C_6$ iso- or cycloalkyl group; a linear, cyclic or branched $C_1$-$C_6$ alkylcarbonyl, oxaalkylcarbonyl, alkyloxycarbonyl, alkylaminocarbonyl or oxaalkylaminocarbonyl.

In yet another embodiment,

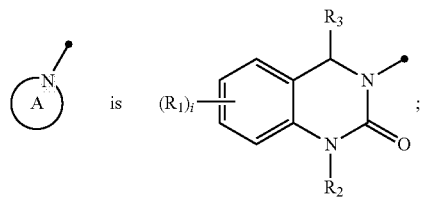

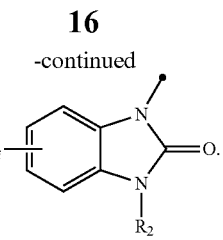

And in a further, particular embodiment

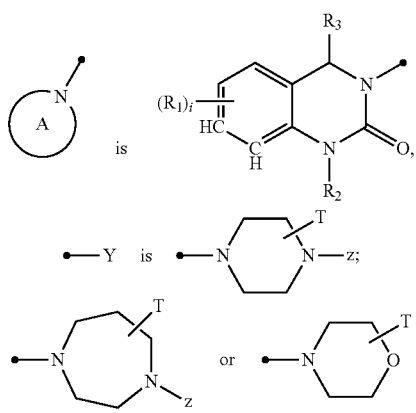

and Z is a $C_3$-$C_6$ iso- or cycloalkyl group; a linear, cyclic or branched $C_1$-$C_6$ alkylcarbonyl, oxaalkylcarbonyl, alkyloxycarbonyl, alkylaminocarbonyl or oxaalkylaminocarbonyl.

Preferred compounds under this particular embodiment are those in which i is 1; $R_1$ is a linear or branched $C_1$-$C_3$ alkyloxy group; $R_2$ is either H or a linear, branched or cyclic $C_1$-$C_4$ alkyl group; $R_3$ taken together with the carbon atom to which it is attached, forms an oxo group;

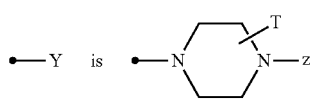

T is either H or a linear, cyclic or branched $C_1$-$C_3$ alkyl group; Z is a linear, branched or cyclic $C_1$-$C_6$ alkylcarbonyl, oxalkylcarbonyl alkyloxycarbonyl group; and wherein any carbon-bound hydrogen atom may optionally be substituted with a fluorine atom.

The 54 compounds listed below are most preferred:

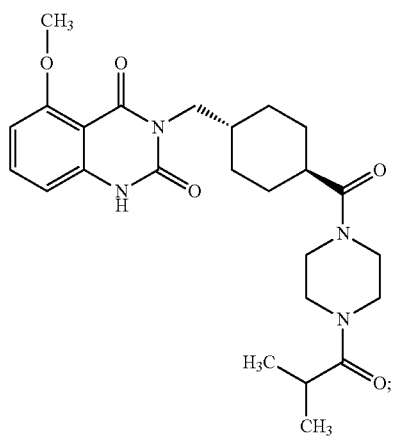

-continued
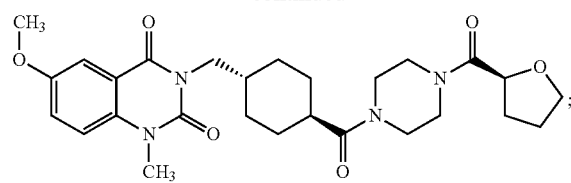
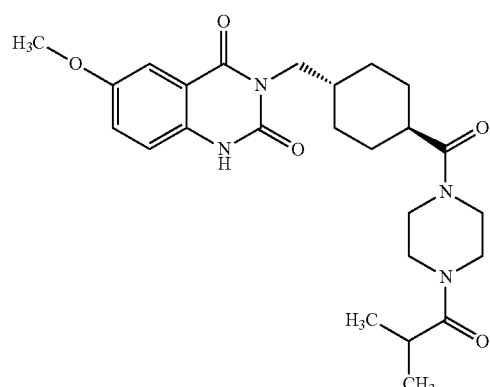
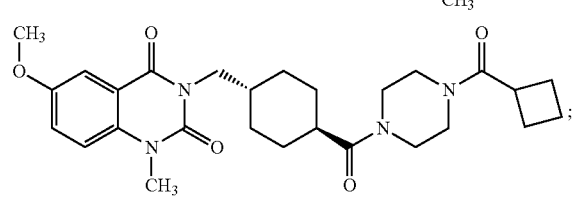
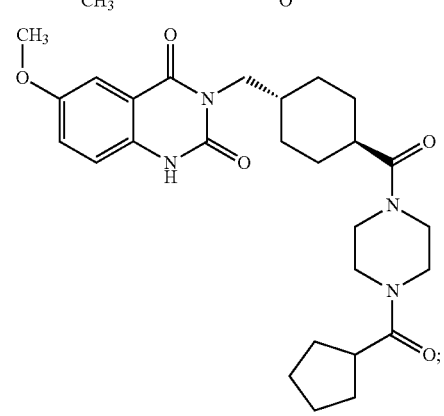
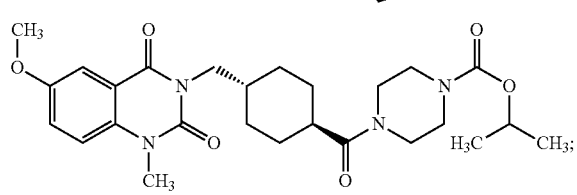
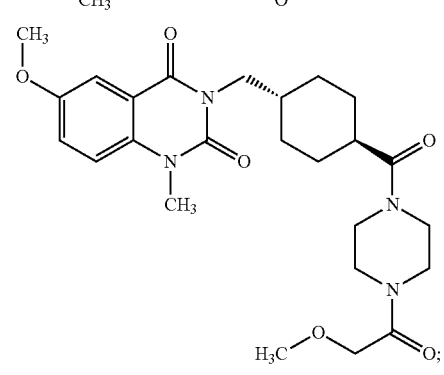
-continued
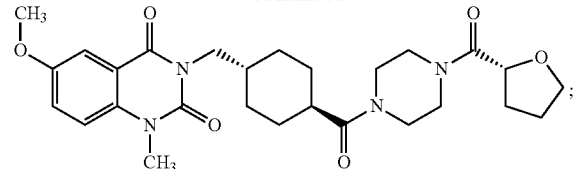
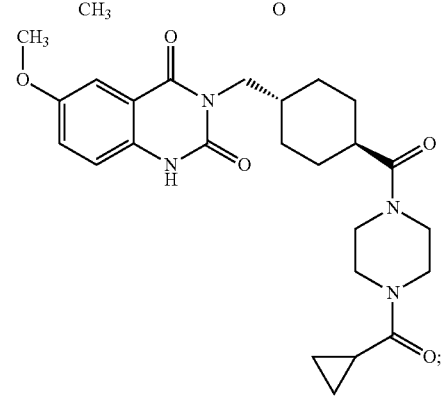
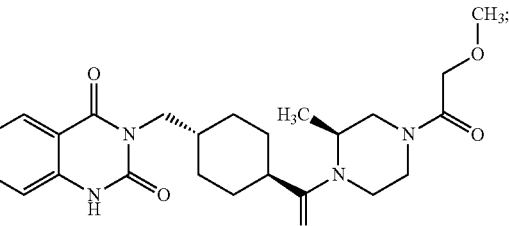

-continued
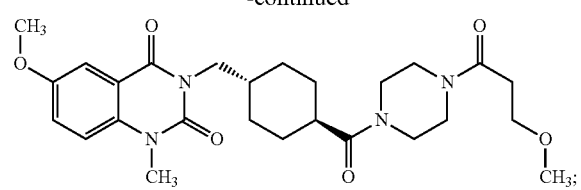
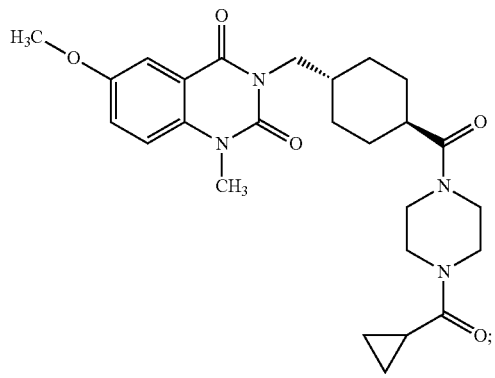
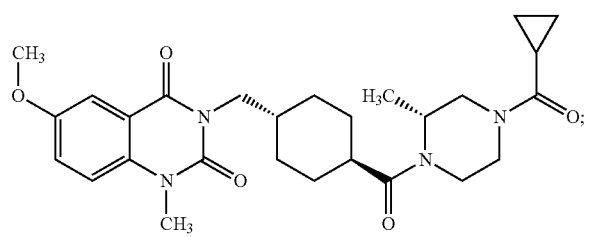
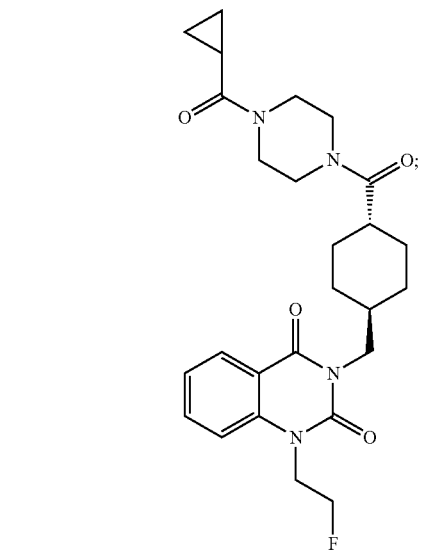
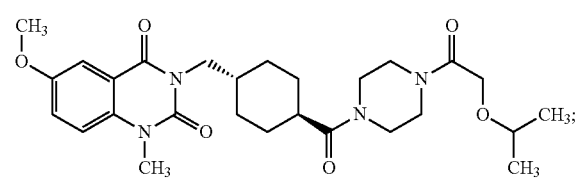
-continued
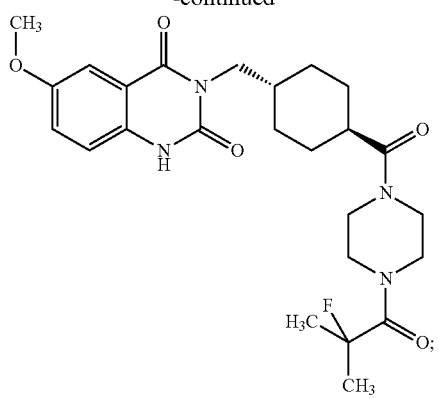
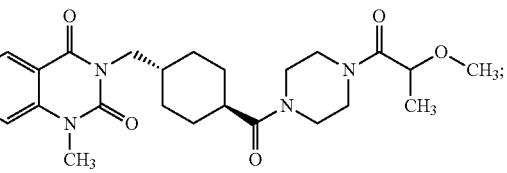
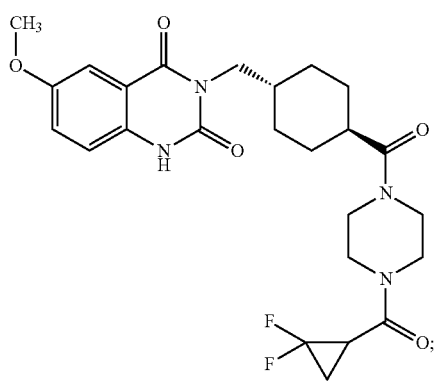
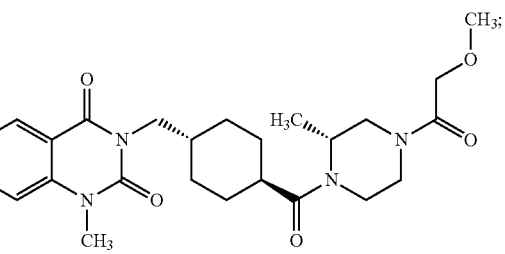
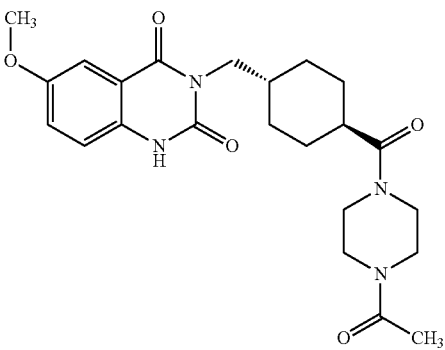

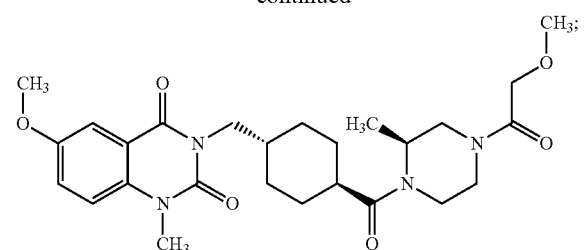
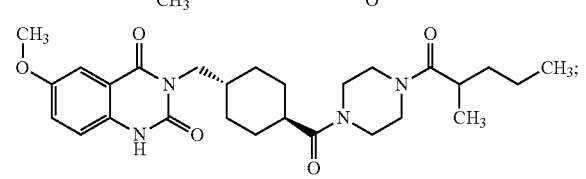
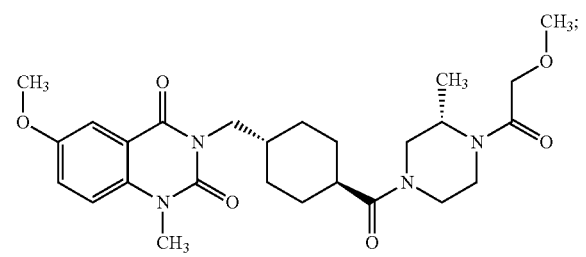
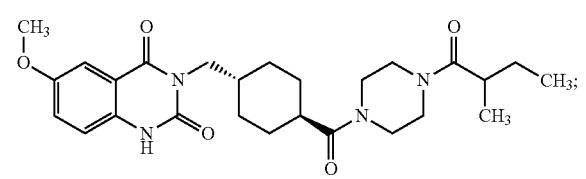
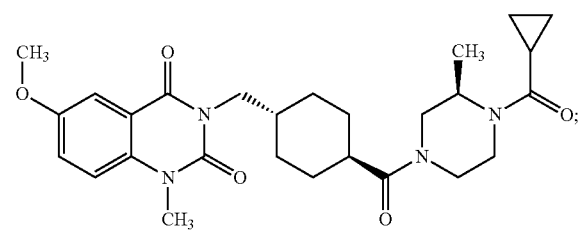
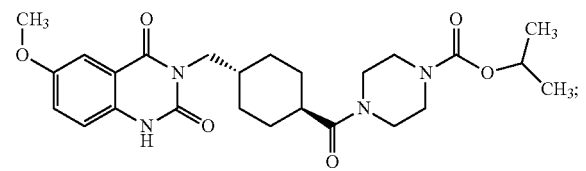
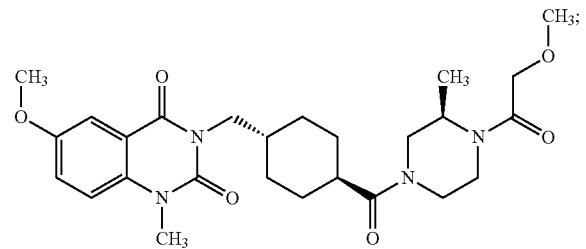
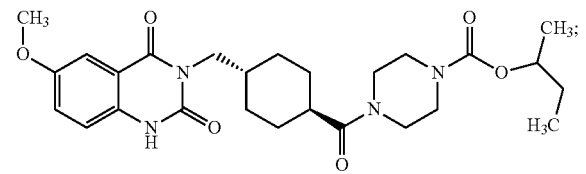
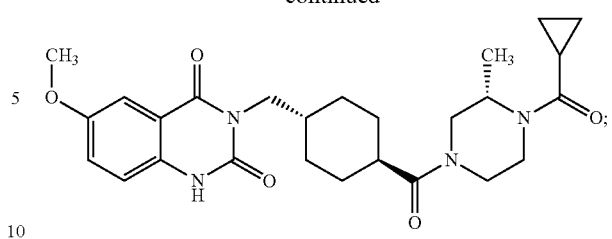
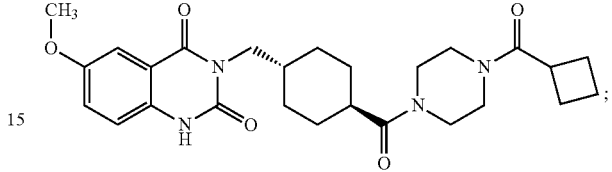
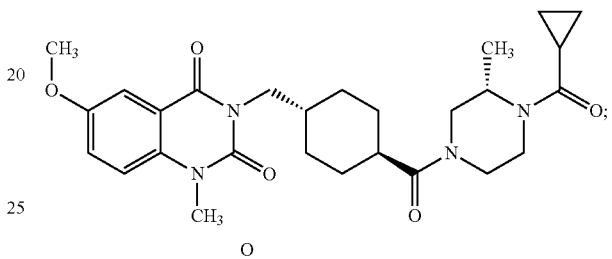
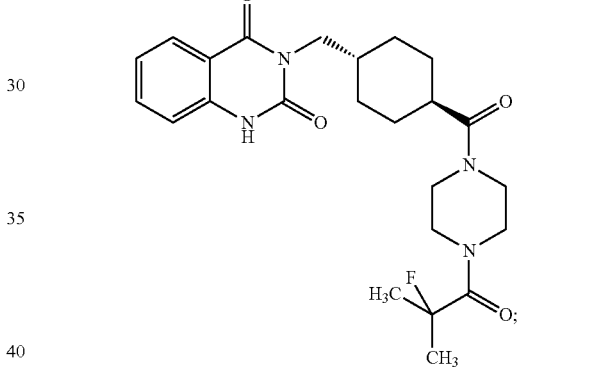
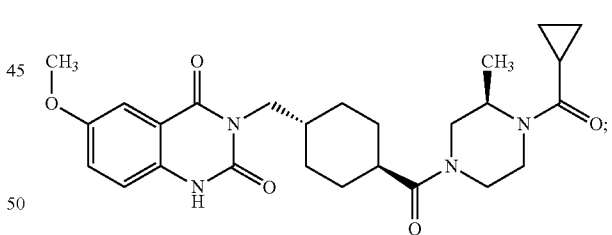
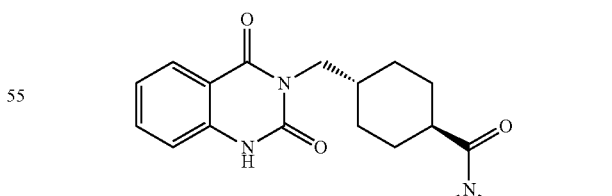
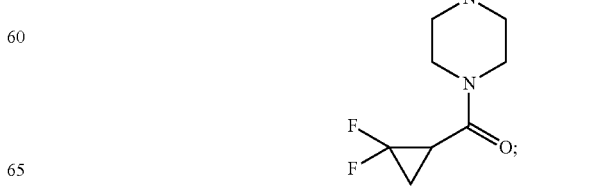

-continued
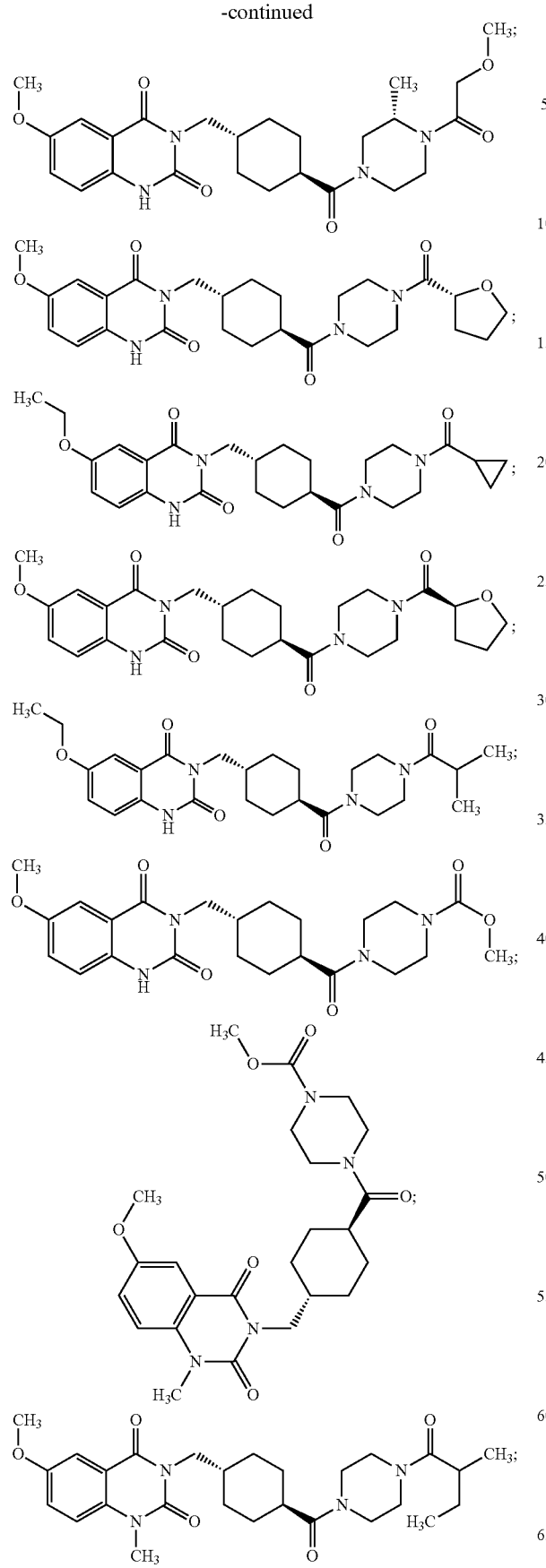
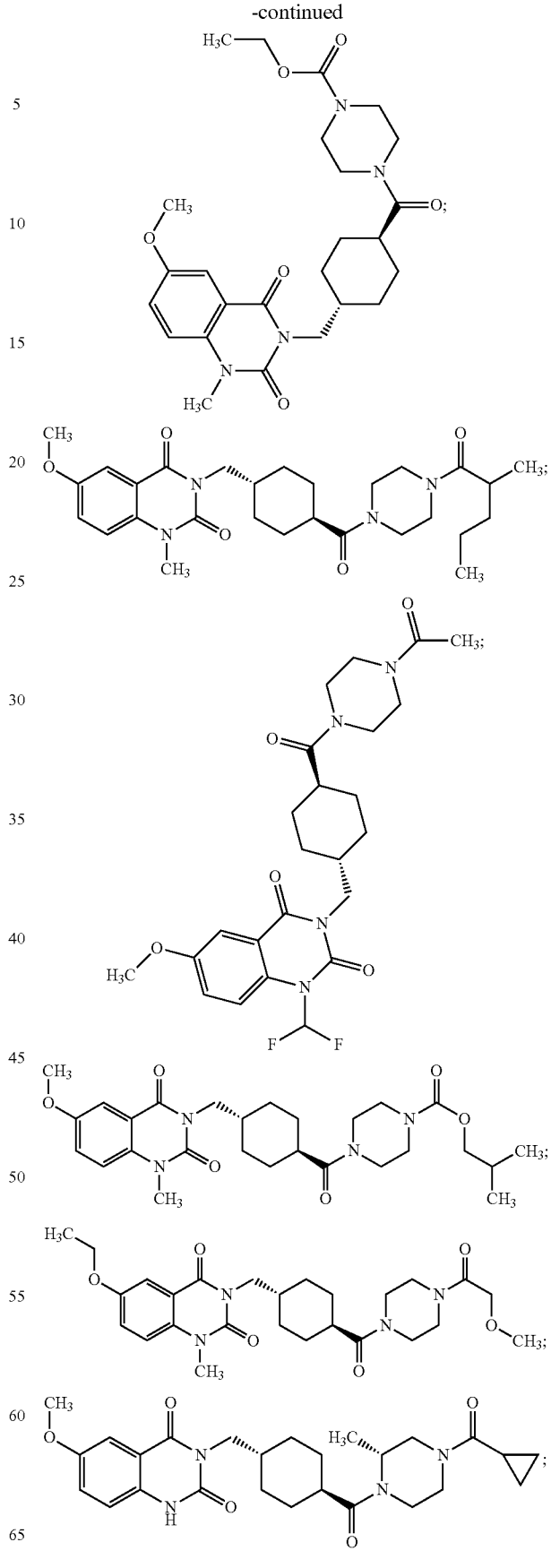

-continued
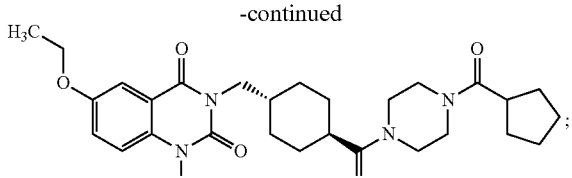
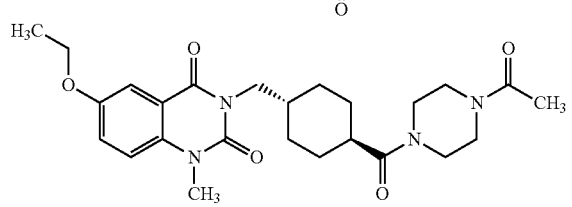
Compounds Synthesis
When not commercially available, and depending on the exact nature of the compound, compounds of the invention may be obtained under general schemes 1-13, wherein $R_1$, $R_2$, $R_3$, Y, T, Z, n and i are as defined in formula (I).
Compounds of formula Ia, can be prepared according to Scheme 1 Method A.
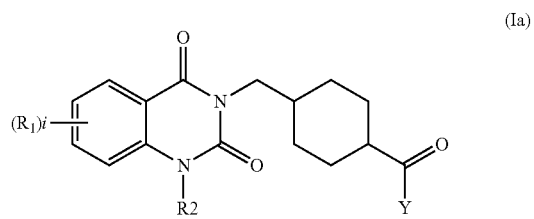
Scheme 1 Method A
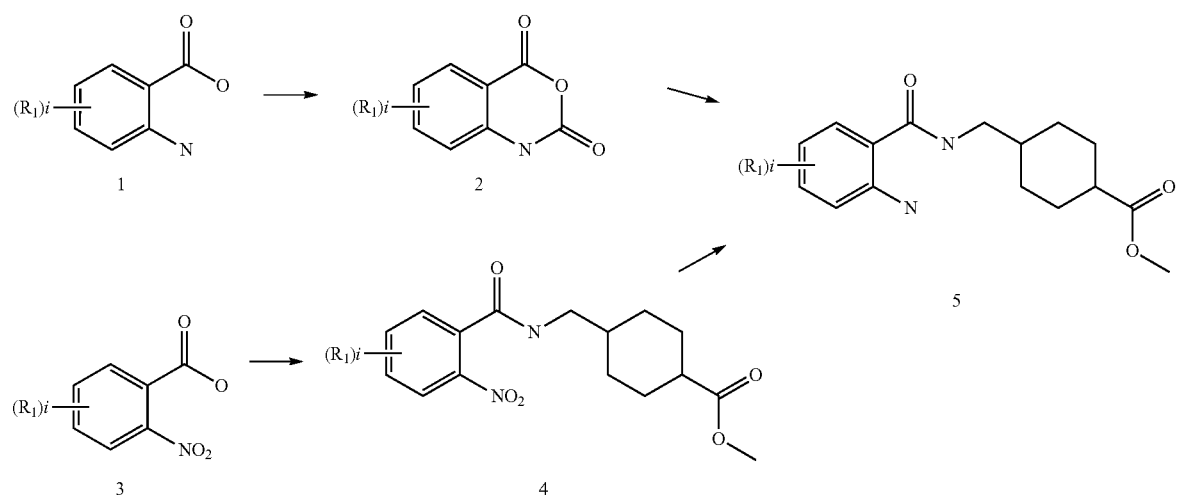
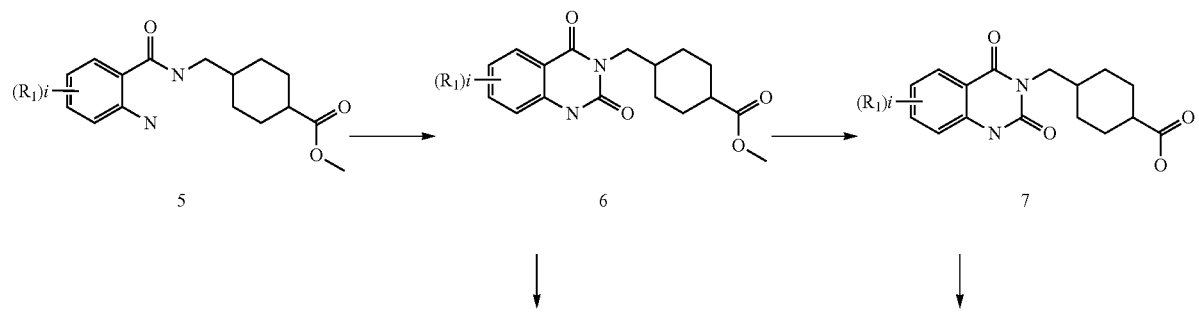

-continued

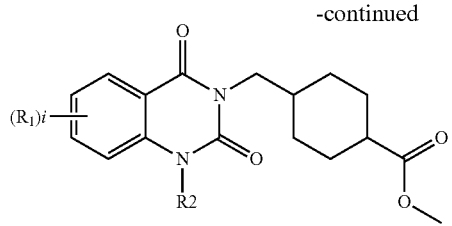

9

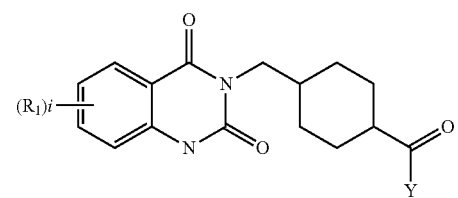

8

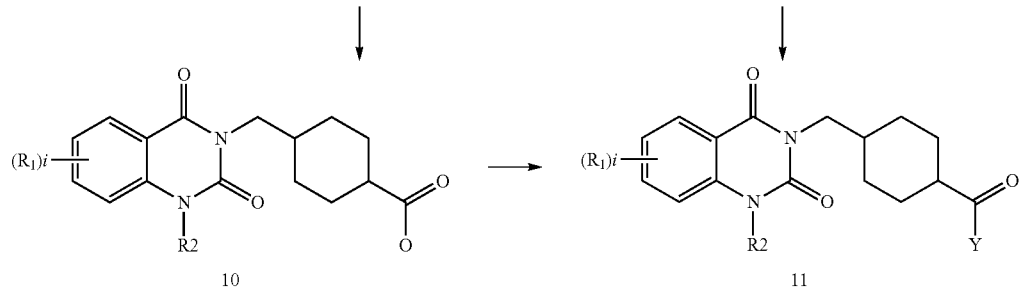

10      11

Anhydrides of the general structure 2 are either commercially available or can be synthesized from the appropriately substituted anilines 1 by reaction with either CDI (1,1-carbonyldiimidazole), triphosgene (Bis(trichloromethyl) carbonate) or ethyl chloroformate similarly to previously reported method (see for example N. A. Abood et al. Bioorg. Med. Chem. Lett., 7, 16, 2105-2108, 1997). Anhydrides 2 can be reacted with 4-aminomethyl-cyclohexanecarboxylic methyl ester in presence of a base to give compounds 5. 4-aminomethylcyclohexane carboxylic methyl ester can be synthesized from the corresponding acid in analogy to the reported methods (see for example WO07064273). Compounds of the general formula 5 may also be synthesized starting from the corresponding nitro benzoic acid 3 which are either commercially available or can be obtained by fuctionalization of commercially available nitrobenzoic acids. Compounds of the general formula 5 can be reacted with CDI or triphosgene to give compounds of the formula 6 which can be hydrolyzed to the corresponding acids 7 using standard procedures. These acids can then be reacted with an amine in presence of an appropriate coupling agent such as CDI, HATU to give compounds 8. Compounds 8 can eventually be alkylated in presence of a strong base to give compounds 11.

Compounds 11 can also be obtained alkylating the intermediates 6 to give intermediates 9 which can then be hydrolyzed to the corresponding acids 10 and then coupled with an amine to give the compounds 11.

Compounds of formula Ia can also be prepared according to method B reported in Scheme 2. In this method the N-protection of the 4-aminomethyl-cyclohexanecarboxylic acid 12 is followed by an amide coupling to obtain compounds 14 and deprotection to give amines of the general formula 15. Amines 15 can be reacted with isatoic anhydrides 2 to give the intermediate amides 16 which as described above can then be converted to compounds of the formula 17 by cyclisation with CDI and then eventually alkylated to give compounds of the formula 18.

Scheme 8: Method H

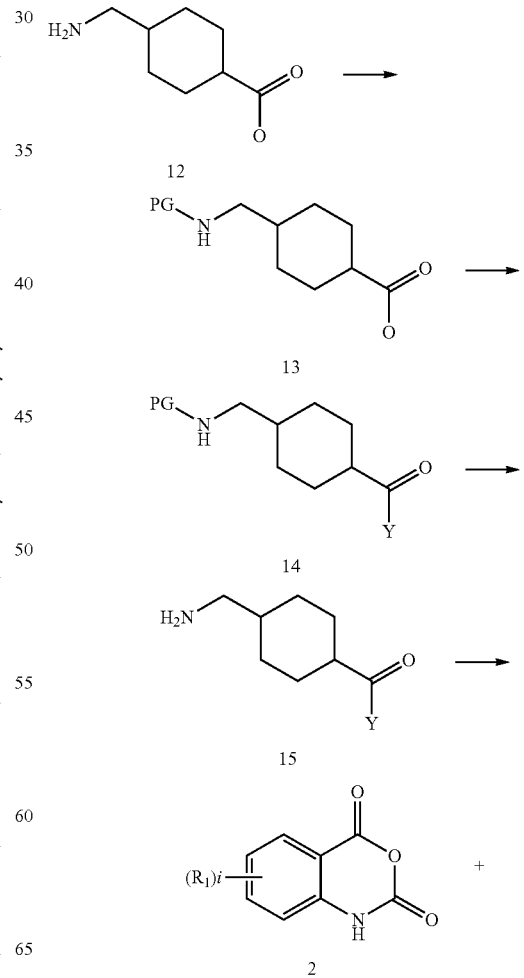

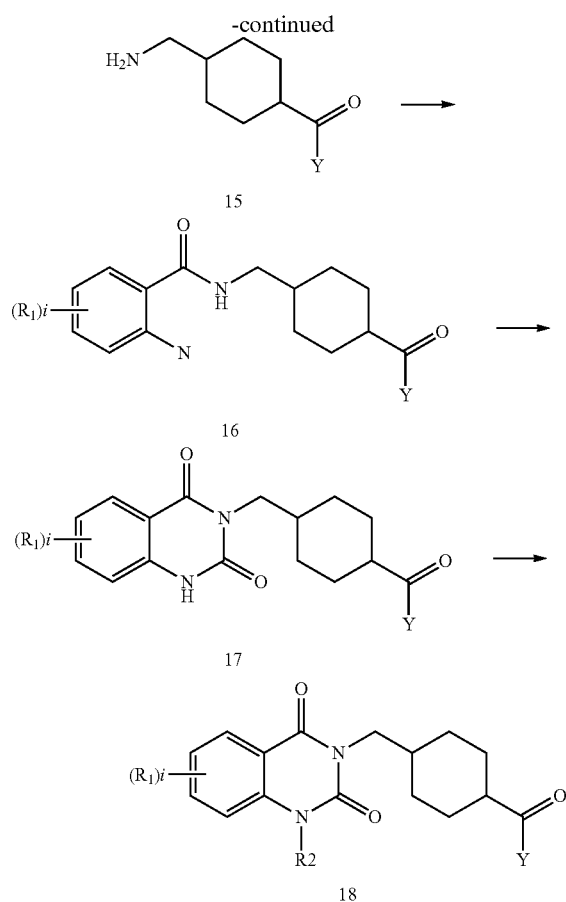

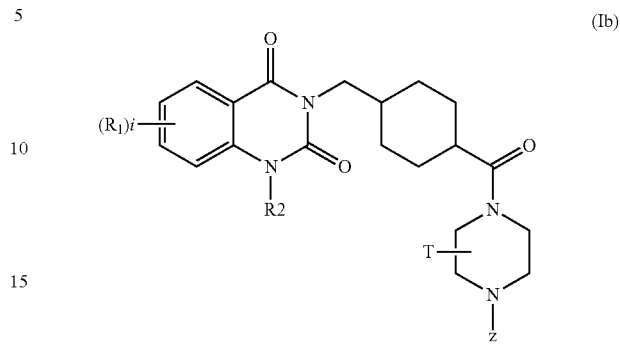

Compounds of formula Ib, can be prepared according to method C reported in Scheme 3.

Acids of the general formulae 7 or 10 synthesised according to scheme 1 method A can be reacted with a mono protected diamine. Subsequent removal of the protecting group can then give compounds 19 or 21. Compounds of the general formula Ib can then be obtained by direct reaction of intermediates 19 or 21 with acyl chlorides or anhydrides in presence of a base or by reaction with acids in presence of standard coupling agents known to those skilled in the art. Alternatively the amine intermediates 19 or 21 may be functionalized by other methods know to those skilled in the art such as reductive amination, alkylation, Buchwald coupling, aromatic nucleophilic substitution or direct reaction with isocyanate. Compounds of the formula Ib where R2=H can eventually be alkylated using a suitable alkylating agent and strong base such as NaH to give compounds where R2=alkyl.

Scheme 3: Method C

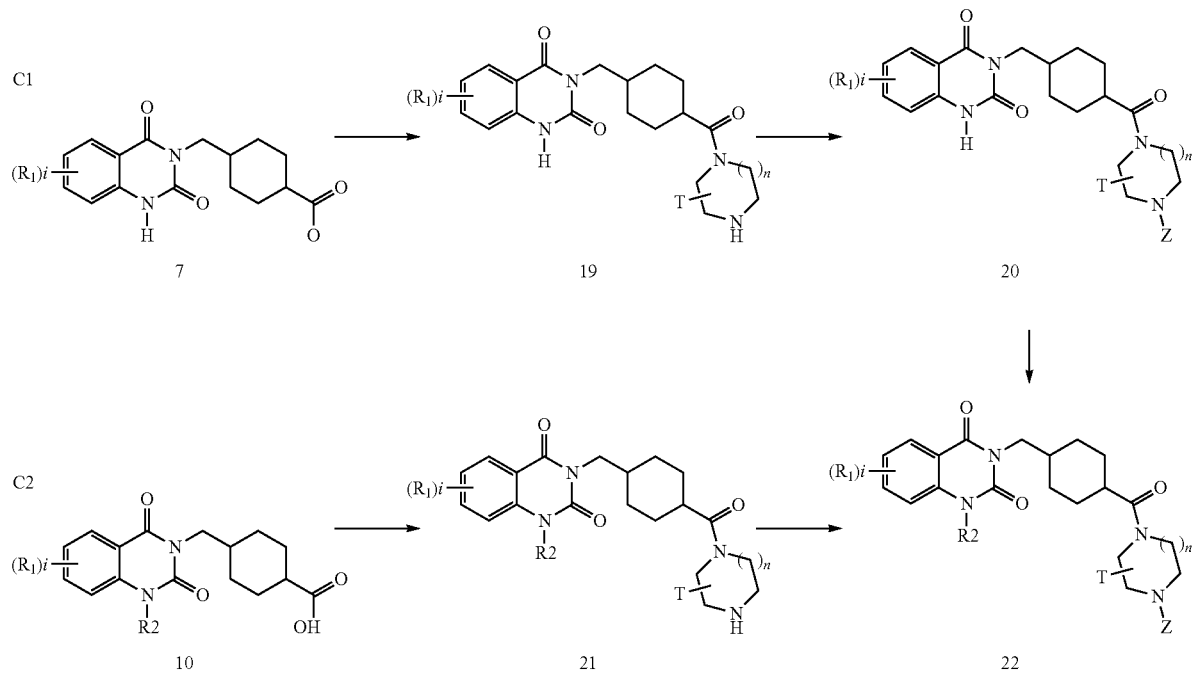

Compounds of formula Ic be prepared according to method D reported in Scheme 4.

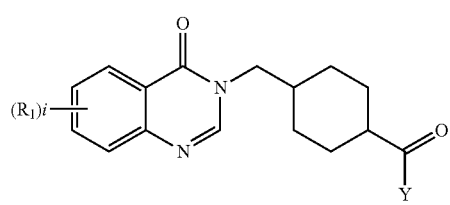
(Ic)

Reaction of compounds of the general formula 5 with formic acid at high temperature gives compounds of the formula 23. Ester hydrolysis gives compounds 24 which can react with an amine in presence of an appropriate coupling agent to give compounds of the general formula 25.

Scheme 4: Method D

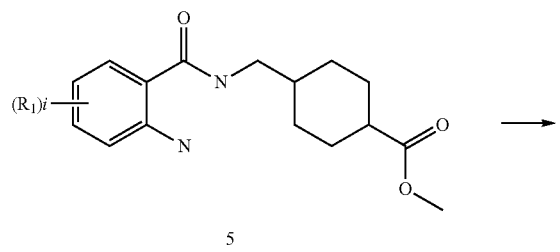
5

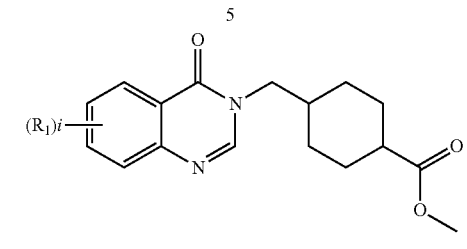
23

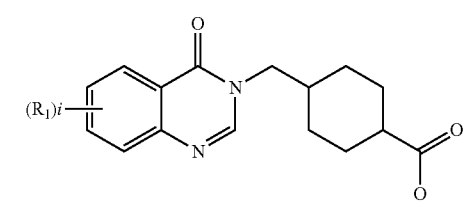
24

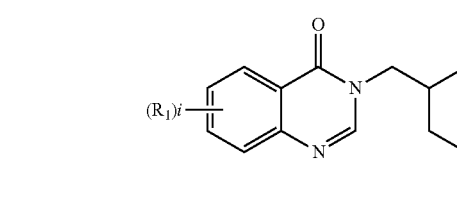
25

Compounds of formula Id can be prepared according to method E reported in Scheme 5.

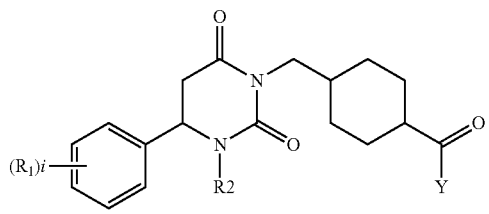
(Id)

Reaction of an appropriately substituted N-protected β-amino acid and compounds of the general formula 15 where Y is defined in formula I using standard coupling agents gives compounds of the formula 26, which can then be deprotected and reacted with CDI to give compounds of the formula 28. Compounds of the formula can be then be alkylated using standard methods to give compounds 29 where R2=Alkyl Scheme 5: Method E

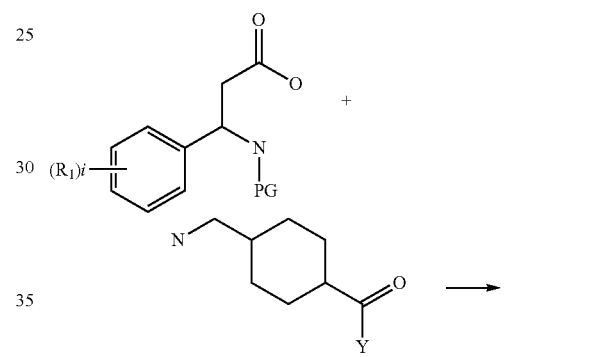
15

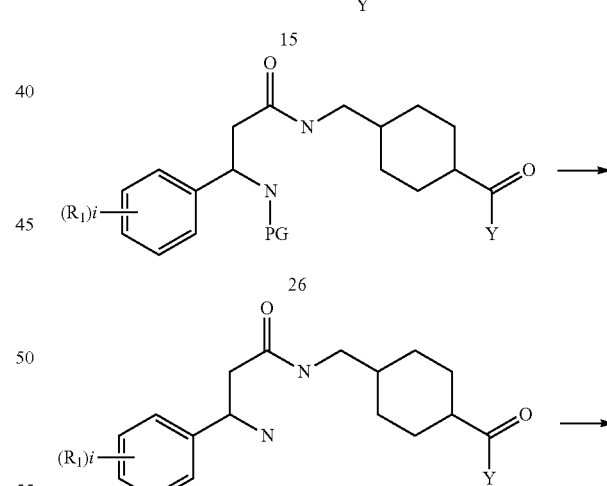
26

27

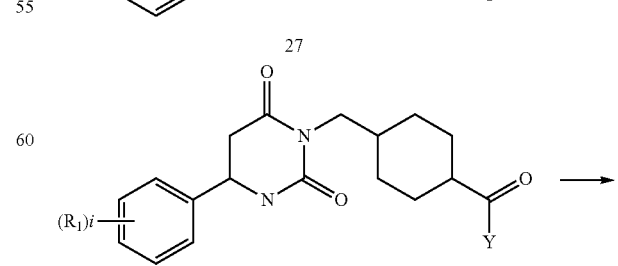
28

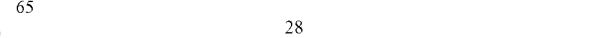

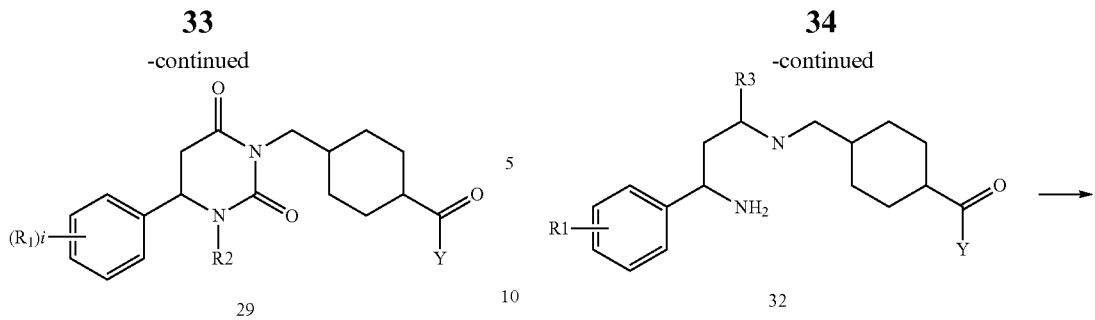

Compounds of formula Ie can be prepared according to method F reported in Scheme 6.

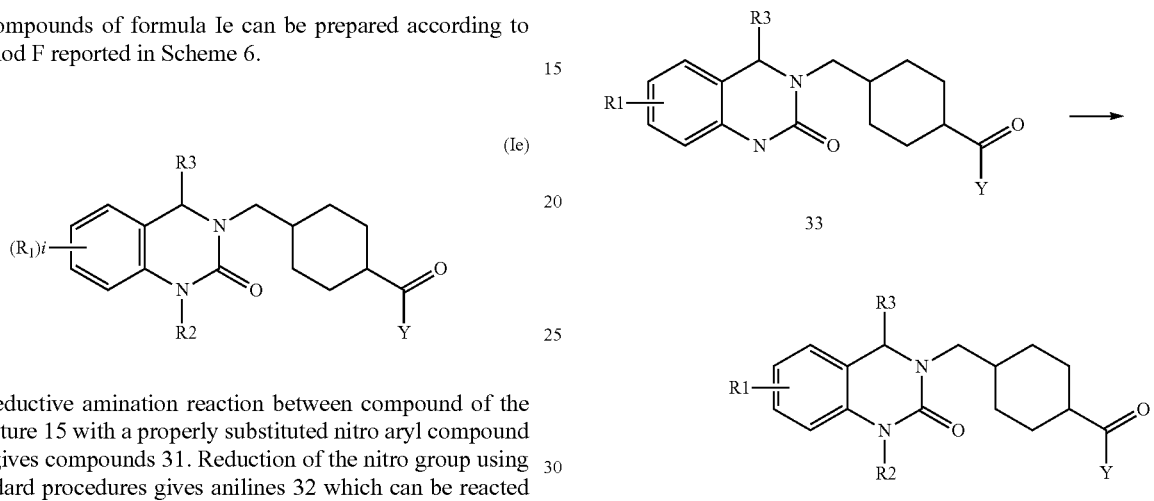

Reductive amination reaction between compound of the structure 15 with a properly substituted nitro aryl compound 30, gives compounds 31. Reduction of the nitro group using standard procedures gives anilines 32 which can be reacted with CDI to afford compounds of the general structure 33. Compounds 33 can be eventually alkylated to yield compounds of the structure 34.

Scheme 6: Method F

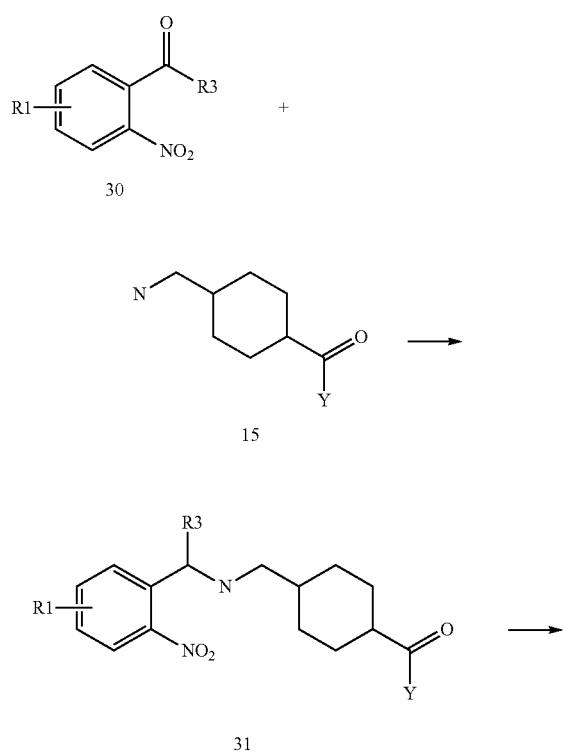

Compounds of formula If can be prepared according to method G reported in Scheme 7.

Reaction of 4-aminomethyl-cyclohexanecarboxylic methyl ester with the appropriate nitro-fluoro-benzene or substituted chloro nitro pyridines gives compounds of the general formula 35 which can then be reduced to the dianilines 36 using standard reduction procedures. Substituted fluoro-nitrobenzenes or chloro-nitro-pyridines are commercially available or have been described in the literature or can be synthesised using standard procedures. Cyclization of 36 with CDI or triphosgene affords compounds of general formula 37. Compounds of this type 37 can then be hydrolysed to corresponding acid 38 and coupled with an amine to give compounds of the general formula 39. Compounds 40 can then be obtained by alkylation of the analogous compound of the formula 39.

Alternatively compounds of the formula 40 can be obtained starting from compounds 37 which can be alkylated to give intermediates 41. Hydrolysis of the acid and then coupling with an amine gives compound 40.

In addition compounds of the structure 40 can be obtained starting from the amines 15. The nitro compounds 43 can be reduced to the corresponding dianiline and then reacted with CDI or triphogene to give the imidazoles 44. Compounds where R2=alkyl such as 40 can then be obtained by alkylation using a suitable alkylating agent and a strong base.

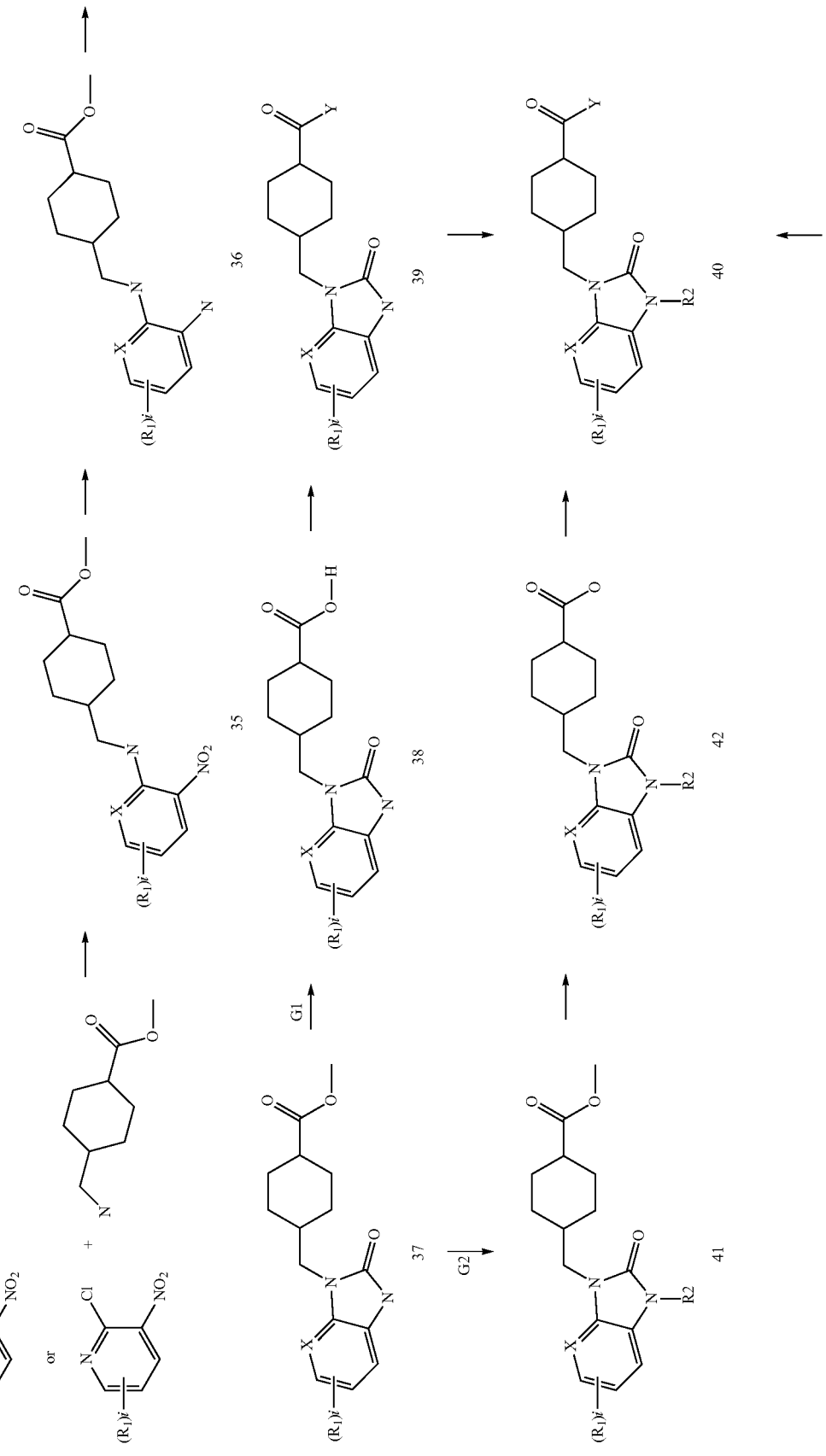
Scheme 7: Method G

-continued
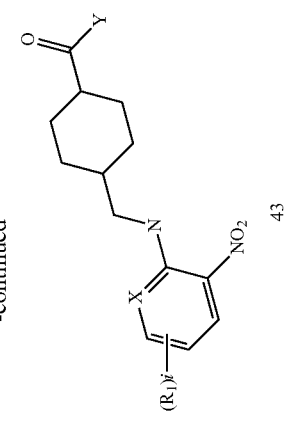
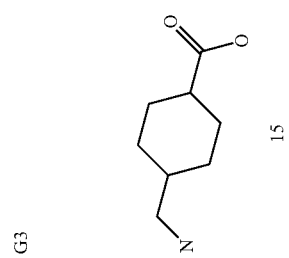
G3
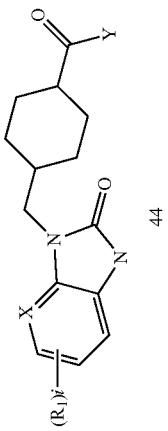
15
+
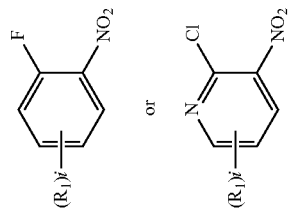
X = C, N

Compounds of formula Ig can be prepared according to method H reported in Scheme 8.

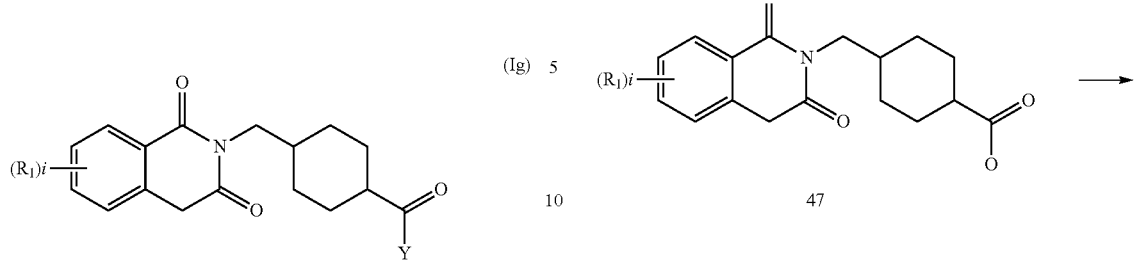

Reaction of homophthalic anhydrides 45 with 4-aminomethyl-cyclohexanecarboxylic methyl ester in acetic acid at reflux temperature gives compounds 46. Ester hydrolysis and amide coupling gives compounds of the general structure 48.

Scheme 8: Method H

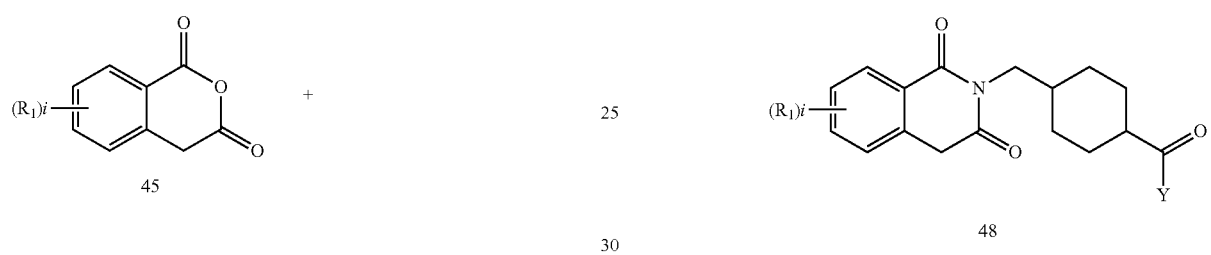

Compounds of formula Ih can be prepared according to method I reported in Scheme 9.

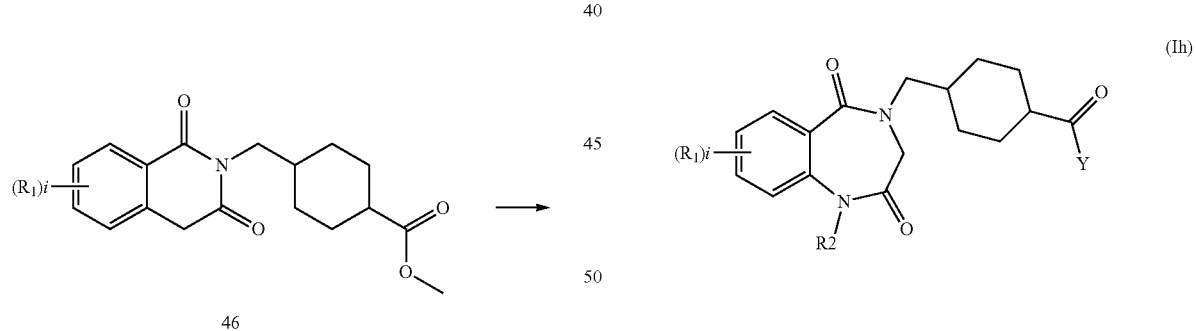

Scheme 9: Method I

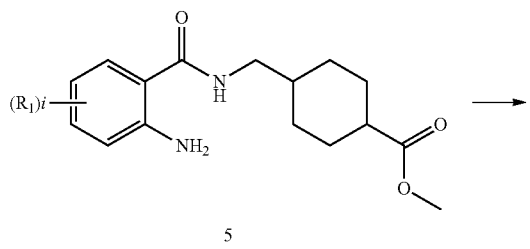

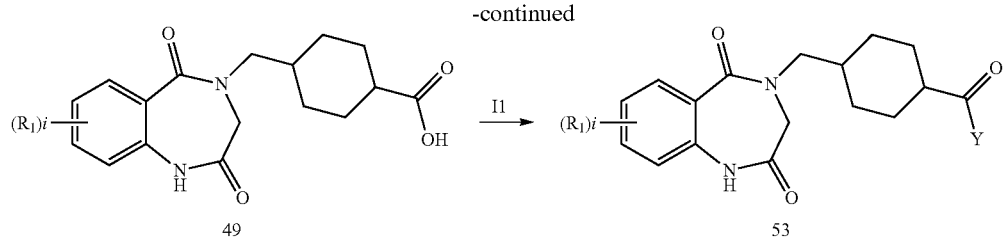

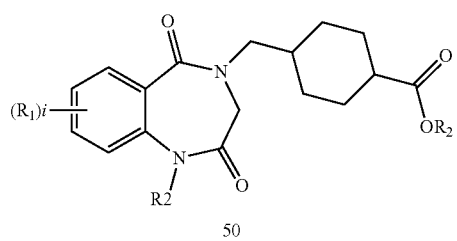

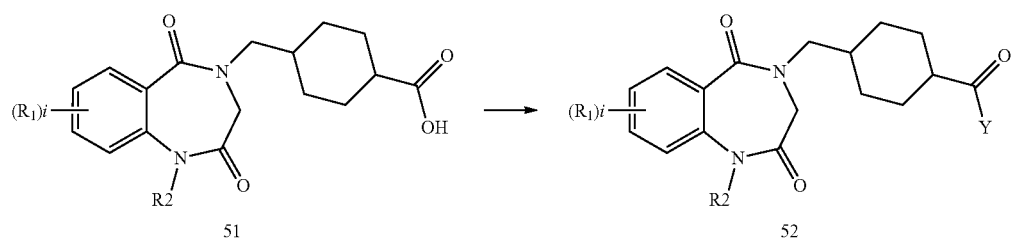

Reaction of compound 5 with bromoacetyl chloride and further cyclization in presence of a base gives intermediates of the formula 49, which can be alkylated and esterified in one pot to give intermediates such as 50. Direct coupling of acids 49 with an amine gives the compounds 53 where R2 = H. Alternatively hydrolysis of the ester 50 and coupling with an amine affords compounds 52 where R2 = alkyl Compounds of formula Ii can be prepared according to method L reported in Scheme 10.

Scheme 10: Method L

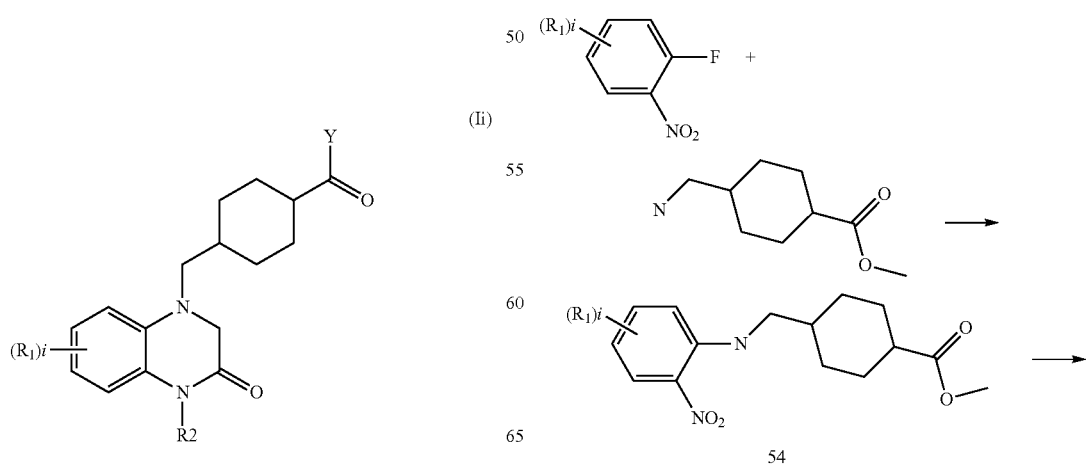

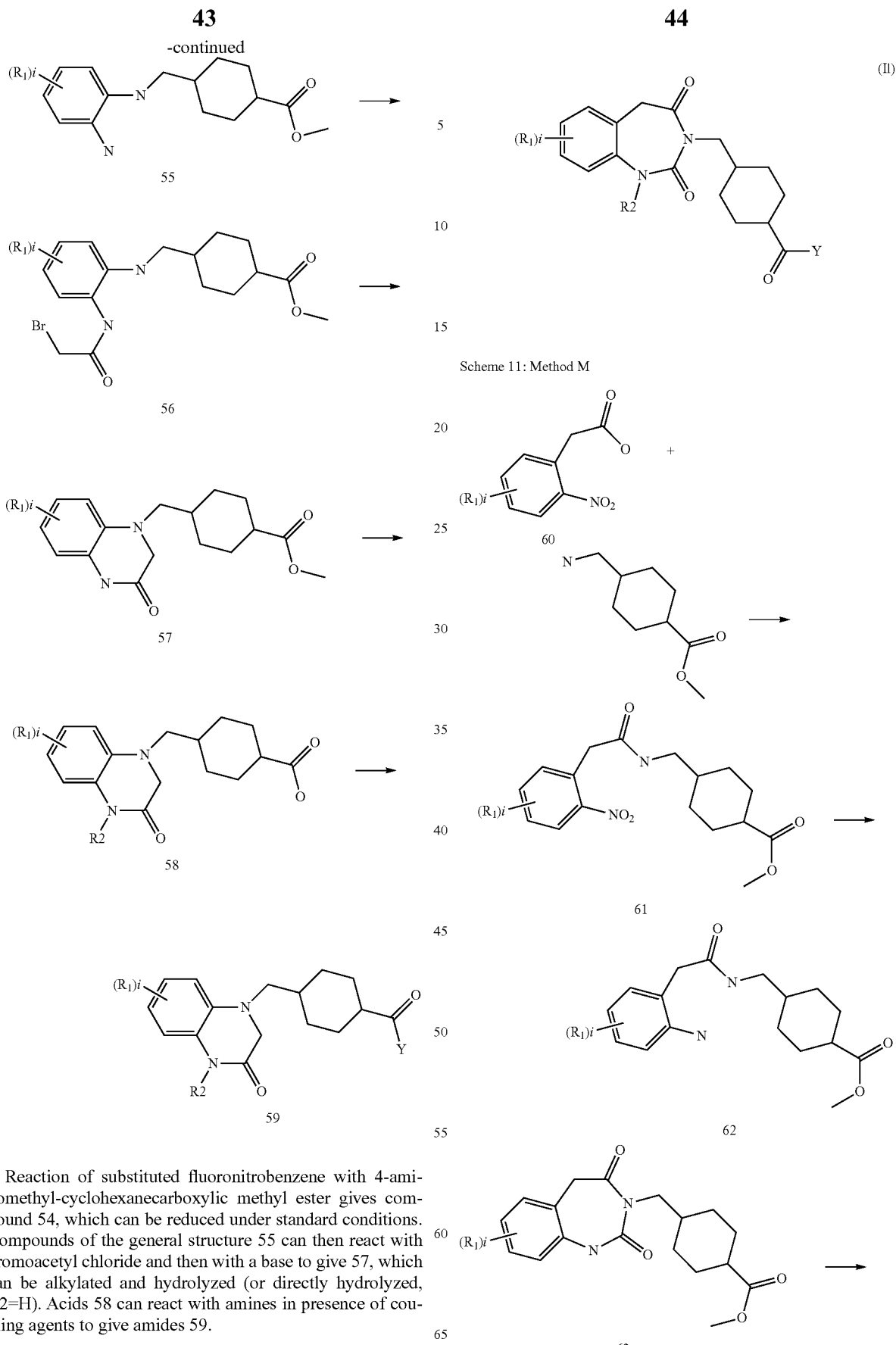

Scheme 11: Method M

Reaction of substituted fluoronitrobenzene with 4-aminomethyl-cyclohexanecarboxylic methyl ester gives compound 54, which can be reduced under standard conditions. Compounds of the general structure 55 can then react with bromoacetyl chloride and then with a base to give 57, which can be alkylated and hydrolyzed (or directly hydrolyzed, R2=H). Acids 58 can react with amines in presence of coupling agents to give amides 59.

Compounds of formula II can be prepared according to method M reported in Scheme 11.

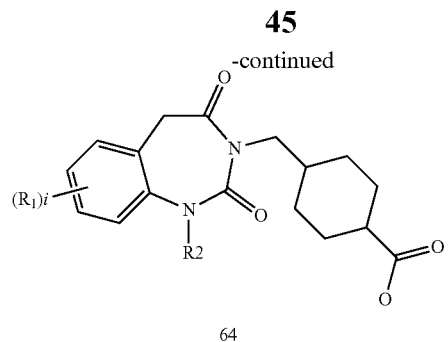

64

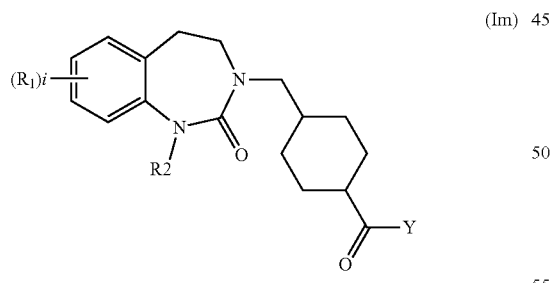

65

Reaction of and acid of the general formula 60 with 4-aminomethyl-cyclohexanecarboxylic methyl ester gives 61, which can be reduced under standard conditions. Anilines 62 are cyclised with CDI or triphosgene to give compounds 63. These can be alkylated and hydrolyzed (or eventually directly hydrolyzed, R2=H) to give acid 64, which can react with amines in presence of a coupling agent affording amides 65.

Compounds of formula Im can be prepared according to method N reported in Scheme 12.

(Im)

Reacting an acid of the generic formula 66 with morpholine gives an intermediate 67 that can be converted to the aldehydes 68 (see for example Stamos, I. K. et al. Tetrahedron Lett., 23, 4, 459, 1982). Reductive amination of the resultant aldehydes with 4-aminomethyl-cyclohexanecarboxylic methyl ester gives nitro amines 69, which can be reduced under standard conditions. Diamine 70 can then be cyclised in presence of CDI affording compound 71, which can be alkylated and then hydrolised (or eventually directly hydrolised, R2=H). Acids 72 reacts with amines in presence of a coupling agent to give amides 73.

Scheme 12: Method N

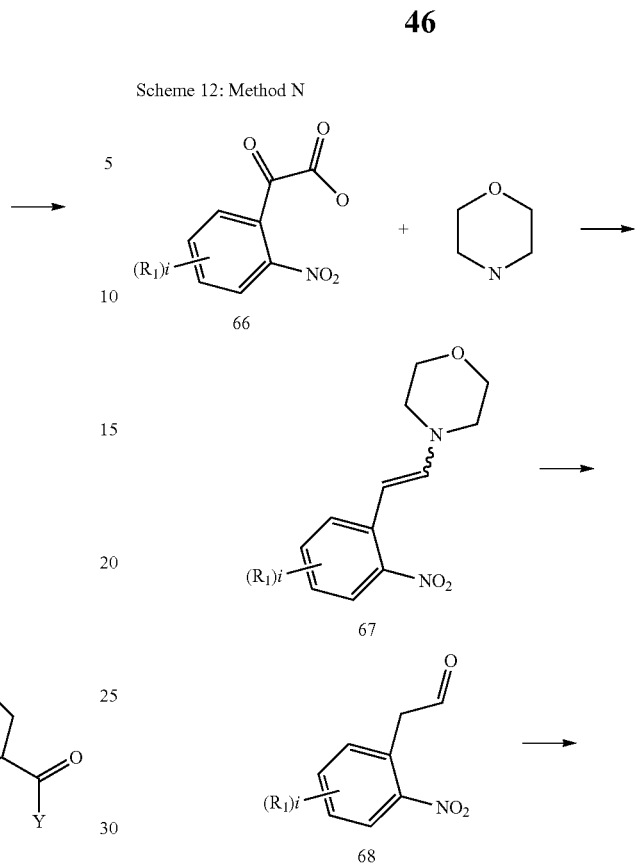

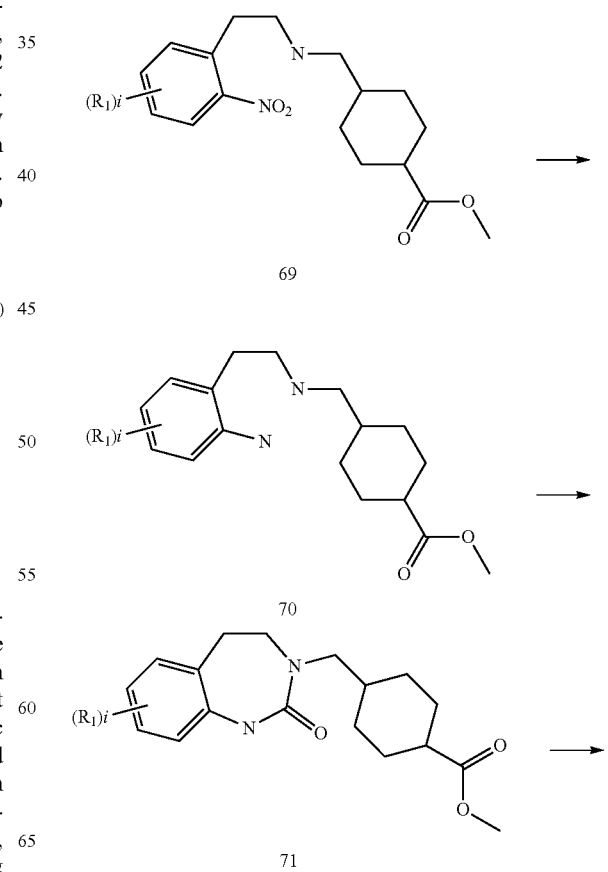

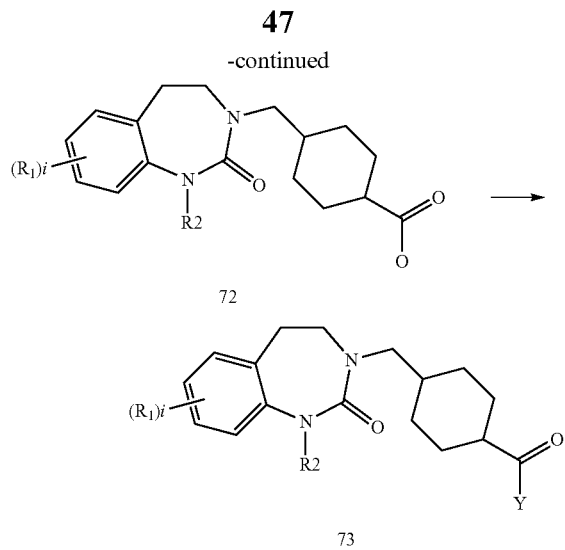

72

73

Compounds of formula In can be prepared according to method T reported in Scheme 13.

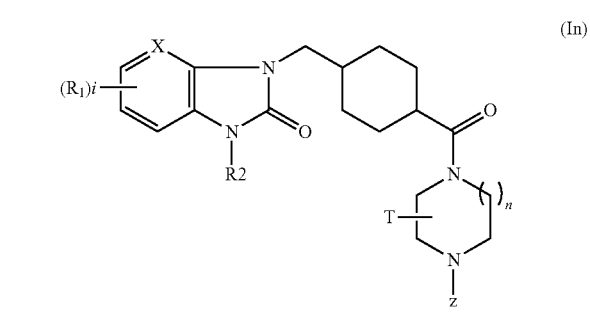

(In)

X = C, N

Scheme 13: Method T

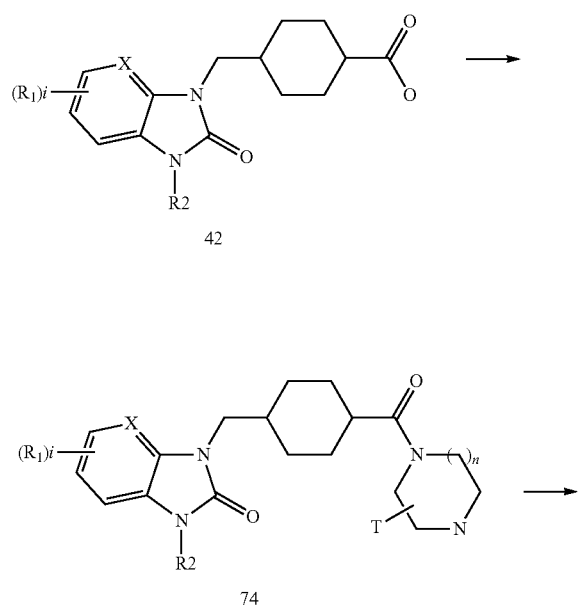

42

74

75

X = C, N

Reaction of intermediate acid 42 (described in Method G) with a mono protected diamine and subsequent removal of the protecting group gives intermediate 74. Compounds 75 can then be obtained by reaction of 74 with acyl chlorides or acids in presence of standard coupling agents, known to those skilled in the art. Alternatively the amine intermediate 74 may be functionalized by other methods know to those skilled in the art such as reductive amination, alkylation, Buchwald coupling, aromatic nucleophilic substitution or direct reaction with isocyanate Assays Used to Identify Small Molecule Inhibitors of the Wnt Signaling Pathway.

The pharmacological activity of the exemplary compounds of the invention was first demonstrated in vitro in a Wnt reporter assay.

A Wnt-responsive Luciferase (TCF-Luciferase (Firefly) and a Wnt-independent (Renilla Luciferase (TA-Renilla) reporter plasmid (alone and in combination) were stably transfected in DBTRG-05MG glioblastoma cell line (ATCC) which according to the Wellcome Trust Sanger Institute Database showed no mutations involving APC, Axin and/or β-catenin genes and then considered to have an intact Wnt pathway cascade.

TCF-Luciferase: Three copies of a 4×TCF responsive elements were cloned into the pcDNA3.1/Zeo(+) vector (Invitrogen) after deletion of the constitutive CMV promoter and the insertion of the Firefly Luciferase from Promega (phFL-TK) to measure the activity of the Wnt/β-catenin pathway. The resulting plasmid was sequenced for quality control.

TA-*Renilla*: Both vectors (pcDNA3.1/Hygro(−) from Invitrogen) and phRL-TK were digested with restriction enzymes MluI and BamH1 and ligated by T4-Ligase to form the final construct, containing the full length cDNA for hRL (human codons optimized *Renilla* Luciferase) with in 5' the TA-minimal promoter and the backbone of the mammalian expression vector pcDNA3.1/Hygro(−) in which the constitutive CMV promoter was ablated. The construct was fully sequenced for quality control and used as internal control for cell number and toxicity.

Cells were grown in 20 µg/ml Zeocin and 20 µg/ml Zeocin plus 30 µg/ml Hygromicin respectively. The cells were plated at a density of 6500 cells/well in poly-D-lysine pre-treated 96 well-plates.

IC50 determination: 36 hours after plating cells were incubated with 8-points (60 µM-40 µM-20 µM-10 µM-5 µM-1.66 µM-0.55 µM-0.185 µM) dilutions compound (0.6% DMSO (v/v)). Each compound was tested in triplicate in single plate. Luciferase detection was done with Dual-Luciferase Reporter Assay System (Promega). 24 hours after compound addition, media was removed and 30 µl of 1× lysis buffer was added to each well for 30 minutes. To each well 45 µl of Dual-Glo Luciferase reagent (Promega) were added and after 1 second delay Luciferase was detected for 1 second using Mithras LB940 instrument. After Firefly luciferase quantification 45 μl of Dual Stop & Glo reagent (Promega) were added to each well and Firefly *Renilla* was detected using the same parameters described before.

Data were expressed as % of control for Firefly and *Renilla* luciferase independently; values were calculated using XLFit version 4.2, with a four parameters sigmoid function (XLFit model 205).

A secondary screen using a luciferase biochemical assay enabled the identification of compounds acting directly on the enzyme (luciferase modulators and/or quenchers) rather than true inhibitors of the Wnt pathway.

Luciferase assay: Quantilum recombinant Luciferase (Promega) was diluted $10^6$-fold in 1× Cell Culture Lysis Reagent (Promega) containing 1 mg/ml acetylated BSA. Five microliters of compound dilution (10 μM final) was then mixed with 35 μl of diluted Quantilum recombinant Luciferase in a 96-well white plate. To each well 20 μl of LAR1 (Luciferase assay reagent from Promega) were added and luciferase was detected for 1 second with Mithras LB940 instrument. Each compound was tested in single data point on two different copy cell plates. Data were expressed as % of negative control (DMSO).

Other Assays

The pharmacological activity of the compounds of the invention may be tested in vitro for growth inhibition against tumour cell lines. Such cell lines may, for example be representative of glioblastoma (such as DBTRG-05MG), or colorectal (for example DLD-1, HCT116) cancer. The different genetic background of the cancer cell will facilitate to understand to which level of the pathway the compounds work. If the cells harbour a truncated APC allele, the destruction complex activity is affected; if cells carry a gain of function mutation in the β-catenin gene, which prevents β-catenin protein degradation, this leads to constitutive activation of downstream genes. There are many assays available for testing the growth inhibition. Such assays include the so called soft agar assay (Freedman et al., *Cell* 3 (1974), 355-359 and Macpherson et al., *Virology* 23 (1964), pp. 291-294) whereby the growth inhibition does not depend from adhesion of the cells to the plastic material of the well where the assay takes place.

Soft Agar Anchorage Independent Assay

DBTRG cells were seeded into a 24-well format in the presence of carrier alone or compound (0.6% DMSO (v/v)). Each well is composed of two agar layers: the bottom layer consists of 0.6% Agar while the top has 0.35% Agar plus cells and compound. Cells (2500 per well) were incubated with 7 points dilution compound the day of the plating and the colonies were scored 3 weeks later after o/n staining with MTT solution. Imaging and counting of the colonies was done with the GelCount™ instrument (Oxford Optronix, UK). For IC50 determination the data were expressed as % of control, values were calculated using XLFit version 4.2, with a four parameters sigmoid function (XLFit model 205).

The pharmacological activity of the compounds of the invention may further be tested in vivo in animal models mimicking the disease. These animal models may include those where the cancerous cells are implanted subcutaneously or orthotopically.

Formulation and Administration

Compounds under formula I are formulated preferably in admixture with a pharmaceutically acceptable carrier, excipient or the like. In general, it is preferable to administer the pharmaceutical composition in orally-administrable form, but certain formulations may be administered via a parenteral, intravenous, intramuscular, transdermal, buccal, subcutaneous, suppository, nasal or other route.

One of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including ester and ether derivatives, as well as various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favourable pharmacokinetic parameters of the pro-drug forms, where applicable, in delivering the present compounds to a targeted site within the host organism or patient to maximize the intended effect of the compound.

Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated.

While human dosage levels have yet to be optimized for the compounds of the invention, generally, a daily dose is from about 0.05 mg/kg to about 100 mg/kg of body weight. The amount of active compound administered will, of course, be dependent on the subject and disease state being treated, the severity of the affliction, the manner and schedule of administration and the judgment of the prescribing physician.

For purposes of the present invention, a prophylactically or preventive effective amount of the compositions according to the present invention (i.e., an amount which substantially reduces the risk that a patient will either succumb to a disease state or condition or that the disease state or condition will worsen) falls within the same concentration range as set forth above for therapeutically effective amounts and is usually the same as a therapeutically effective amount.

In some embodiments of the present invention, one or more compounds of formula (I) are administered in combination with one or more other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition.

Rather, so long as both (or more) agents remain in the subject's body, they are considered to be administered "in combination".

EXAMPLES

All reagents and solvents were obtained commercially. Air and moisture sensitive liquid solutions were transferred via syringe. The course of reactions was followed by thin-layer chromatography (TLC) and/or liquid chromatography-mass spectrometry (HPLC-MS or HPLC-Ms). TLC analyses were performed on silica (Merck 60 F254) and spots revealed by UV visualisation at 254 nm and $KMnO_4$ or ninhydrin stain. Purifications by column chromatography were performed using silica cartridges isolute flash Si or silica (Merck 60) or with flash purification instruments from Biotage. Compounds purities were above 90%.

All nuclear magnetic resonance spectra were recorded using a Varian Mercury Plus 400 MHz spectrometer equipped with a PFG ATB Broadband probe or a Bruker Avance AV 600 System 600 MHz equipped with a BBO probe or Bruker Avance AV 400 System (400.13 MHz for $^1H$) equipped with BBI a probe Analytical Methods Method a Anaytical HPLC-MS were run using a Waters 2795 separation module equipped with a Waters Micromass ZQ (ES ionisation) and Waters PDA 2996, using a Gemini NH C18 3.0 μm 2.00×50 mm column. Temperature: 40° C. UV Detection at 215 nm and 254. ESI+ detection in the 80-1000 m/z range. Gradient: 0.1% formic acid/water and 0.1% formic acid/acetonitrile with gradient 95/5 to 5/95 flow 1.0 ml/min over 10 minutes.

Method b

Anaytical HPLC-MS were run using a Waters 2795 separation module equipped with a Waters Micromass ZQ (ES ionisation) and Waters PDA 2996, using a Gemini NH C18 3.0 μm 2.00×50 mm column. Temperature: 40° C. UV Detection at 215 nm and 254. ESI+ detection in the 80-1000 m/z range. Gradient: 0.1% formic acid/water and 0.1% formic acid/acetonitrile with gradient 95/5 to 5/95 flow 1.0 ml/min over 5 minutes.

Method c

Anaytical HPLC-MS were run using a Waters 2795 separation module equipped with a Waters Micromass ZQ (ES ionisation) and Waters PDA 2996, using a X-Bridge C18 3.5 μm 2.10×50 mm column. Temperature: 40° C.UV Detection at 215 nm and 254. ESI+ detection in the 80-1000 m/z range Gradient: 0.1% ammonia/water and acetonitrile with gradient 85715 to 95/5 flow 0.8 ml/min over 10 minutes.

Method d

Anaytical HPLC-MS were run using a Waters 2795 separation module equipped with a Waters Micromass ZQ (ES ionisation) and Waters PDA 2996, using a X-Bridge C18 3.5 μm 2.10×50 mm column. Temperature: 40° C.UV Detection at 215 nm and 254. ESI+ detection in the 80-1000 m/z range Gradient: 0.1% ammonia/water and acetonitrile with gradient 85715 to 95/5 flow 0.8 ml/min over 5 minutes.

Method e

Analytical HPLC-MS were run using a Acquity Waters HPLC with equipped with a Waters SQD (ES ionization) and Waters Acquity PDA detector, using a column BEH C18 1.7 μm, 2.1×5.00. Temperature: 40° C.UV Detection at 215 nm and 254. ESI+ detection in the 80-1000 m/z range Gradient 0.1% ammonia/water and acetonitrile with a gradient 85/15 to 5/95 flow: 0.8 ml/min over 3 min.

Method f

Analytical HPLC-MS were run using a Acquity Waters HPLC with equipped with a Waters SQD (ES ionization) and Waters Acquity PDA detector, using a column BEH C18 1.7 μm, 2.1×5.00. Temperature: 40° C. UV Detection at 215 nm and 254. ESI+ detection in the 80-1000 m/z range. Gradient 0.1% formic acid/water and 0.1% formic acid/$CH_3CN$ with a gradient 95/5 to 5/95 flow: 0.6 ml/min.

Method g

Analytical HPLC-MS: were run using an Agilent 1100 equipped with a Bruker ion-trap Esquire 3000+ with ESI with a Supelco Discovery Column: 150×4.6, 5 μm. Partitioned after UV detector (50% to MS ESI). Temperature: 40° C. UV Detection at 215 nm with reference at 500 nm (40 nm bandwith). ESI+ detection in the 50-1000 m/z range with alternating MS/MS Gradient: Phase A: Milli-Q water containing 0.05% (v/v) TFA. Phase B: Acetonitrile (LC-MS grade) containing 0.05% TFA. Flow: 1 mL/min Gradient: from 20% B to 90% B in 15 min, washing at 100% B for 1 min, equilibration at 20% B in the next 4 min.

Method h

Analytical HPLC-MS: were run using an Agilent 1100 equipped with a Bruker ion-trap Esquire 3000+ with ESI with a Supelco Discovery Column: 150×4.6, 5 μm. Partitioned after UV detector (50% to MS ESI). Temperature: 40° C. UV Detection at 215 nm with reference at 500 nm (40 nm bandwith). ESI+ detection in the 50-1000 m/z range with alternating MS/MS. Gradient: Phase A: Milli-Q water containing 0.05% (v/v) TFA. Phase B: Acetonitrile (LC-MS grade) containing 0.05% TFA. Flow: 1 mL/min, partitioned after UV detector (50% to MS ESI). Gradient: from 5% B to 50% B in 15 min, washing at 100% B for 1 min, equilibration at 5% B in the next 4 min.

Preparative HPLC Method

Method a

Preparative HPLC was run using a Waters 2767 system with a binary gradient Module Waters 2525 pump and coupled to a Waters Micromass ZQ25 (ES) or Waters 2487 DAD, using a Gemini NX C18 5 μm, 100×21.2. Gradient 0.1% formic acid/water and 0.1% formic acid/methanol flow: 40 ml/min.

Method b

Preparative HPLC was run using a Waters 2767 system with a binary gradient Module Waters 2525 pump and coupled to a Waters Micromass ZQ 25 (ES) or Waters 2487 DAD, using a X-Bridge C18 5 μm 19×150. Gradient 0.1% ammonia/water and methanol flow: 17 ml/min.

Method c

Preparative HPLC was run using a Waters 2767 system with a binary gradient Module Waters 2525 pump and coupled to a Waters MS3100 SQ or Waters 2487 DAD, using a X-Bridge C18 5 μm 19×150. Gradient 0.1% formic acid/water and 0.1% formic acid/methanol flow: 17 ml/min.

Method d

Preparative HPLC was run using a Waters 2767 system and coupled to a Waters Micromass ZQ 25 (ES), using a X-Terra C18 5 μm 19×100. Gradient 0.1% ammonia/water and acetonitrile flow: 20 ml/min.

Method e

Preparative HPLC was run using a Waters 2767 system and coupled to a Waters Micromass ZQ 25 (ES), using a X-Terra C18 5 μm 19×100 0.1% trifluoroacetic acid/water and 0.1% trifluoroacetic acid/acetonitrile flow: 20 ml/min.

Example 1 (Method A1)

trans-3-[4-(4-Pyrimidin-2-yl-piperazine-1-carbonyl)-cyclohexylmethyl]-1H-quinazoline-2,4-dione trans-4-[(2-Amino-benzoylamino)-methyl]-cyclohexanecarboxylic acid methyl ester

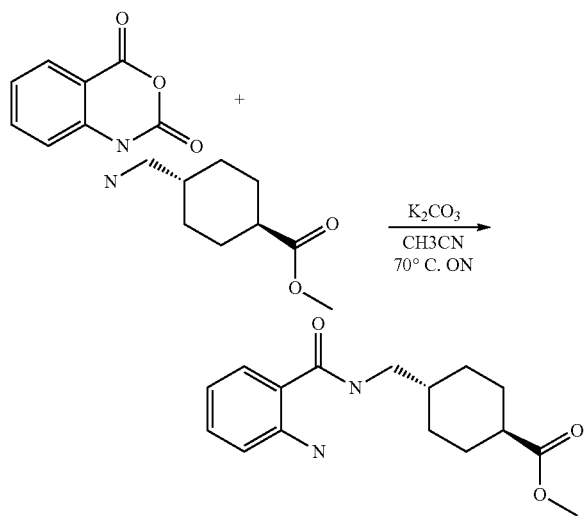

To a solution of trans-4-Aminomethyl-cyclohexanecarboxylic acid methyl ester (21.7 g, 127 mmol) in CH₃CN (500 mL), K₂CO₃ (35 g, 254 mmol) and isatoic anhydride (20.7 g, 127 mmol) were added. The reaction was stirred at 70° C. overnight. The mixture was concentrated under reduced pressure and the residue was washed with 200 mL of H₂O and the solid obtained was filtered. The titled compound (31.1 g, quantitative yield) was obtained as a white solid.

C16H22N2O3 Mass (calculated) [290.37]. found [M+H⁺] =291.4.

Lc RT=1.83 (method b)

trans-4-[(2-Nitro-benzoylamino)-methyl]-cyclohexanecarboxylic acid methyl ester

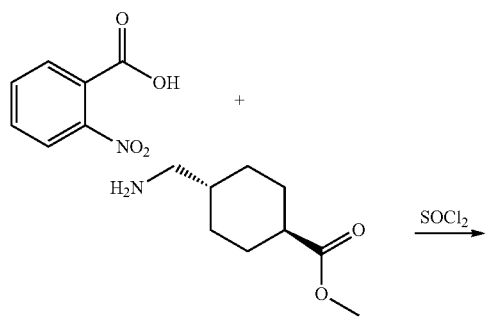

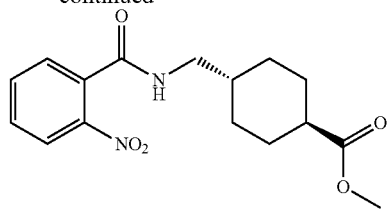

A solution of 2-nitrobenzoic acid (1.8 g, 10.7 mmol) in SOCl₂ (25 mL) was heated under reflux for 1 h. After reaction completion, the solvent was removed under reduced pressure and the crude product was diluted with toluene and concentrated again to dryness. The crude product was diluted in Et₂O (8 mL) and added at 0° C. to a mixture of trans-4-aminomethyl-cyclohexanecarboxylic acid methyl ester hydrogen chloride salt with H₂O (5 mL), acetone (25 mL), Et₂O (25 mL) and TEA (5 mL). The mixture was stirred for 30 minutes and finally the solvent was removed under reduced pressure. The crude was diluted in DCM (50 mL) and washed with a saturated solution of NaHCO₃ (2×50 mL) and then with NaOH 1M (1×50 mL). The organic layer was dried over Na₂SO₄, and then the solvent removed under reduced pressure. Finally, the crude product was purified by flash chromatography on silica (1:1 ethyl acetate-petrolium ether) to obtain the titled compound (1.8 g, yield 52%).

$C_{16}H_{20}N_2O_5$ Mass (calculated) [320.14]. found [M+H]⁺ =321.

Lc RT=1.88 (method b)

¹H-NMR (CDCl₃): 1.04 (2H, q); 1.44 (2H, q); 1.66 (1H, m); 1.98 (2H, d); 2.08 (2H, d); 2.29 (1H, t); 3.37 (2H, t); 5.89 (1H, broad m); 7.52 (1H, d); 7.57 (1H, t); 7.70 (1H, t); 8.08 (1H, d).

trans-4-[(2-Amino-benzoylamino)-methyl]-cyclohexanecarboxylic acid methyl ester

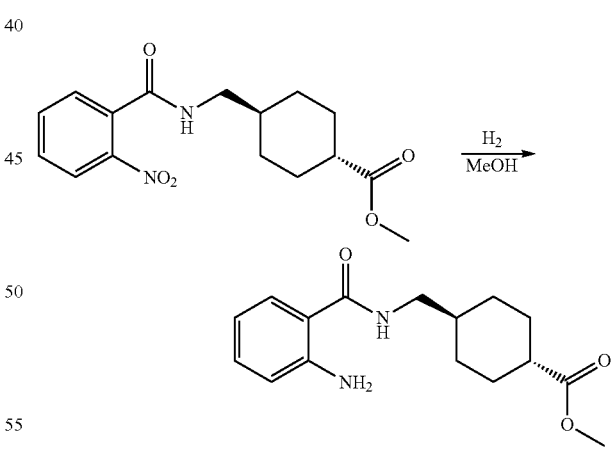

A solution 0.01 M of trans-4-[(2-Nitro-benzoylamino)-methyl]-cyclohexanecarboxylic acid methyl ester (1.8 g) in MeOH (550 mL) with ~1% of glacial AcOH (5.5 mL) was submitted to continuous flow rate hydrogenation by H-Cube (ThalesNano®) using a 10% Pd/C cartridge (small cartridge, full hydrogen mode, flowrate of 1 mL/min). Finally, the solvent was removed under reduced pressure to obtain the titled compound as acetate salt (1.9 g, quantitative yield).

$C_{16}H_{22}N_2O_3$ Mass (calculated) [290.16]. found [M+H]⁺ =291.

Lc RT=1.07 (method b)

$^1$H-NMR (CDCl$_3$): 1.10 (2H, q); 1.47 (2H, q); 1.51 (1H, m); 1.89 (2H, d); 2.03 (2H, d); 2.27 (1H, t); 3.28 (2H, t); 3.32 (3H, S); 6.21 (1H, broad m); 6.75 (1H, t); 6.78 (1H, d); 7.23 (1H, t); 7.26 (1H, d).

trans-4-(2,4-Dioxo-1,4-dihydro-2H-quinazolin-3-ylmethyl)cyclohexane carboxylic acid methyl ester

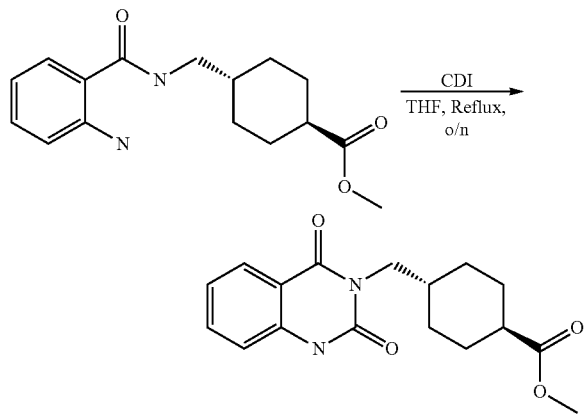

To a solution of 1,1-carbonyldiimidazole (17 g, 103.5 mmol) in THF (200 mL), trans-4-[(2-Amino-benzoylamino)-methyl]-cyclohexanecarboxylic acid methyl ester (15 g, 51.72 mmol) was added and the reaction was heated to reflux temperature for 16 hours. The mixture was allowed to cool down to room temperature and the solvent was removed under reduced pressure. The residue was washed with 100 mL of H$_2$O and the precipitate was filtered. The tiled compound (15.9 g, yield 97%) was obtained as a white solid.

C17H20N2O4 Mass (calculated) [316.36]. found [M+H$^+$]=317.

Lc RT=1.97 (method b)

trans-4-(2,4-Dioxo-1,4-dihydro-2H-quinazolin-3-ylmethyl)cyclohexane carboxylic acid

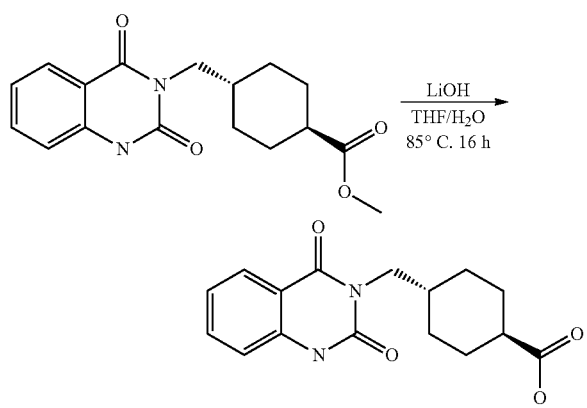

To a solution of trans-4-(2,4-Dioxo-1,4-dihydro-2H-quinazolin-3-ylmethyl)-cyclohexanecarboxylic acid methyl ester (15 g, 51.7 mmol) in a mixture of THF (240 mL) and H$_2$O (60 mL), LiOH was added and the reaction was heated at 85° C. for 16 hours. The mixture was allowed to cool down to room temperature and the solvent removed under reduced pressure. The residue was dissolved in 100 mL of H$_2$O and the solution acidified to pH 3. The precipitate formed was filtered and washed with 100 mL of CH$_3$CN. The titled compound (11.9 g, 79%) was obtained as a white solid.

C16H18N2O4 Mass (calculated) [302.33]. found [M+H$^+$]=303.

Lc RT=1.65 (method b)

$^1$H-NMR (d$^6$-DMSO): 0.98 (2H, m); 1.95 (2H, m); 1.66 (5H, m); 1.85 (2H, m); 2.08 (1H, m); 3.74 (2H, d, J=7.0 Hz); 7.17 (2H, m); 7.63 (1H, m); 7.90 (1H, m).

trans-3-[4-(4-Pyrimidin-2-yl-piperazine-1-carbonyl)-cyclohexylmethyl]-1H-quinazoline-2,4-dione

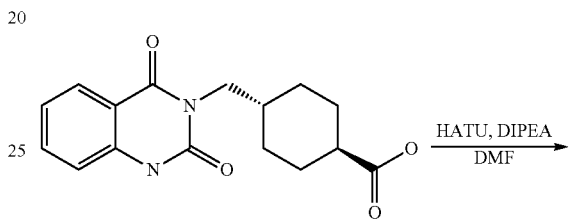

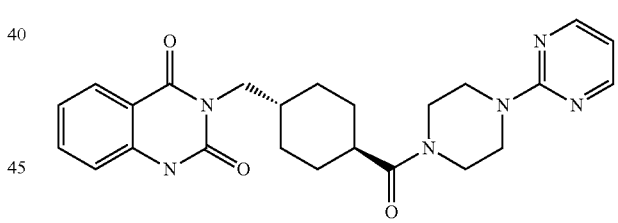

To a solution of trans-4-(2,4-Dioxo-1,4-dihydro-2H-quinazolin-3-ylmethyl)-cyclohexanecarboxylic acid (100 mg, 0.33 mmol) in DMF(2 mL), diisopropylethylamine (58 µL, 0.33 mmol) and HATU (126 mg, 0.33 mmol) were added. The mixture was left 6 hours stirring at room temperature and then 1-(2-pyrimidyl)piperazine was added. After 16 hours at room temperature the solvent was removed under reduced pressure; the residue was dissolved in 2 mL of DCM and washed with 2 mL of 0.4N Na$_2$CO$_3$ solution. The organic layer was separated, dried over Na2SO4 and the solvent removed under reduced pressure. The titled compound (58 mg, yield 39%) was purified by precipitation from methanol.

C24H28N6O3 Mass (calculated) [448.5]. found [M+H$^+$]=449.4.

Lc RT=2.85 (method a)

$^1$H-NMR (d$^6$-DMSO): 1.1 (2H, m); 1.27 (2H, m); 1.65 (4H, m); 1.72 (1H, m); 2.58 (1H, m); 3.51 (4H, m); 3.68 (4H, m); 3.77 (2H, d, J=7.1 Hz); 6.63 (1H, t, J=4.7 Hz); 7.17 (2H, m); 7.63 (1H, m); 7.90 (1H, m); 8.36 (2H, d, J=4.7 Hz); 11.41 (1H, s).

Example 2 (Method A2)

trans-1-Methyl-3-[4-(4-phenyl-piperazine-1-carbonyl)-cyclohexylmethyl]-1H-quinazoline-2,4-dione trans-4-(1-Methyl-2,4-dioxo-1,4-dihydro-2H-quinazolin-3-ylmethyl)-cyclohexane carboxylic acid

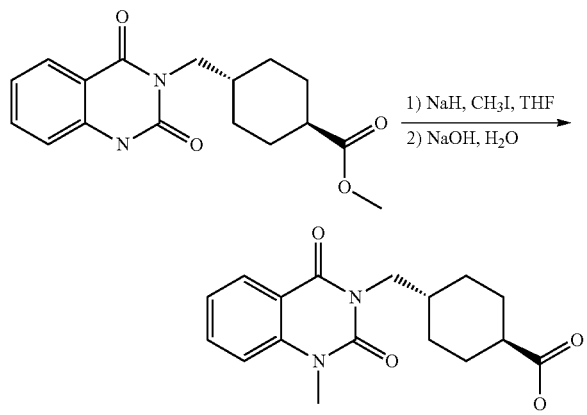

trans-4-(2,4-Dioxo-1,4-dihydro-2H-quinazolin-3-ylmethyl)-cyclohexane carboxylic acid methyl ester (1.5 g, 4.7 mmol) was dissolved in dry THF (20 ml) under nitrogen atmosphere. NaH (0.125 g, 5.2 mmol 60% in mineral oil) was added at 0° C. The reaction mixture was allowed to reach ambient temperature and then CH$_3$I (324 µL, 5.2 mmol) was added. The reaction mixture was left stirring at room temperature for 24 hours, few drops of water were added and the solvent was removed under reduced pressure. The residue was suspended in water and 112 mg of NaOH were added. The mixture was heated at 100° C. for 30 minutes. The solution was allowed to reach room temperature and acidified to pH 3 with HCl 6N with the formation of a white precipitate which was isolated by filtration. (1.0 g, yield 66%)

C17H20N2O4 Mass (calculated) [316.3]. found [M+H$^+$]=317.3.

Lc RT=3.47 (method b)

trans-1-Methyl-3-[4-(4-phenyl-piperazine-1-carbonyl)-cyclohexylmethyl]-1H-quinazoline-2,4-dione

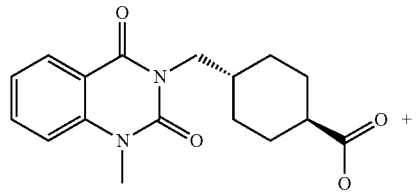

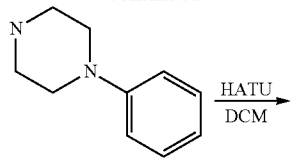

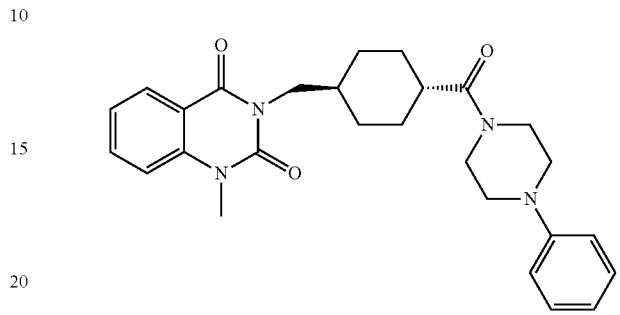

trans-4-(1-trans-4-(1-methyl-2,4-dioxo-1,4-dihydro-2H-quinazolin-3-ylmethyl)-cyclohexanecarboxylic acid (65 mg, 0.2 mmol) was dissolved in 5 ml of DCM. HATU (80 mg, 0.2 mmol) was added and the mixture was stirred for half hour. Phenyl piperazine (35 mg, 0.2 mmol) was added and the mixture was stirred for the week-end. 2 ml of a 0.4 M solution of Na$_2$CO$_3$ were added and the mixture was shaken for 10 minutes. The organic solution was separated, the solvent was removed under reduced pressure and the crude purified by preparative HPLC (method a). The isolated compound was further purified by triturating with Et$_2$O in order to remove some aliphatic impurities. 12 mg (yield 13%) of the titled compound were isolated.

C27H32N4O3 Mass (calculated) [460.6]. found [M+H$^+$]=461.6.

Lc RT=3.83 (method a)

$^1$H-NMR (d$^6$-DMSO): 1.07-1.16 (2H, s); 1.22-1.31 (4H, m); 1.62-1.67 (4H, m), 1.72-1.73 (1H, m), 2.55-2.61 (1H, m), 3.04-3.10 (4H, m), 3.50 (3H, s), 3.54-3.61 (4H, m), 3.81 (2H, d, J=8.2 Hz), 6.78 (1H, t, J=8 Hz), 6.92 (2H, d, J=8.2 Hz), 7.18-7.22 (2H, m) 7.28 (1H, t, J=8 Hz), 7.43 (1H, d, J=8 Hz), 7.74-7.78 (1H, m), 8.03 (1H, dd, J=8 Hz, 2 Hz).

Example 3 (Method B)

3-[trans-4-(4-Isobutyryl-piperazine-1-carbonyl)-cyclohexylmethyl]-6-methoxy-1H-quinazoline-2,4-dione trans-4-(tert-Butoxycarbonylamino-methyl)-cyclohexanecarboxylic acid

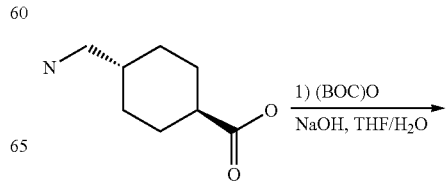

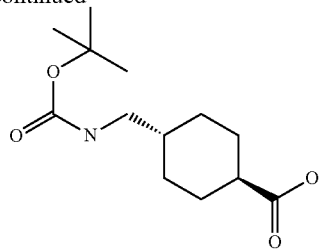

To a solution of trans-4-aminomethyl-cyclohexanecarboxylic (5.0 g, 31.8 mmol) in H₂O (30 mL) and dioxane (30 mL) NaOH was added (2.5 g, 63.7 mmol). The mixture was cooled down to 0° C. and di-tert-butyl dicarbonate (10.4 g, 48 mmol) was added. The reaction was allowed to warm up to room temperature. After 4 hours the reaction was completed and the solvent was removed under reduced pressure. The residue was diluted with 50 mL of H₂O and acidified with 6N HCl to pH3. The precipitate formed was filtered and washed with cyclohexane. The titled compound (8.1 g, quantitative yield) was obtained as a white solid.

¹H-NMR (d⁶-DMSO): 0.84 (2H, m); 1.22 (2H, m); 1.35 (9H, s); 1.67 (2H, m); 1.85 (2H, m); 2.07 (1H, m), 2.73 (2H, t, J=6.4 Hz); 6.78 (1H, m).

2-Methyl-1-piperazin-1-yl-propan-1-one

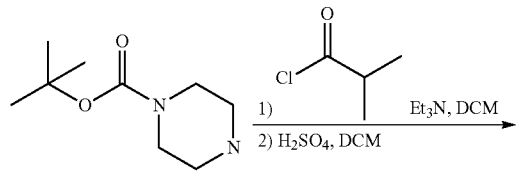

To a solution of tert-butyl-1-piperazinecarboxylate (5.0 g, 26.8 mmol) in DCM (100 mL) triethylamine (5.6 mL, 40.3 mmol) was added, the mixture was cooled down to 0° C. and isobutyryl chloride (4.2 mL, 40.3 mmol) was added. The reaction was allowed to warm up to room temperature and after 3 hours the reaction was complete. The mixture was washed with 50 mL of 0.4M Na₂CO₃ solution and then with 50 mL of saturated NH₄Cl solution. The organic phase was dried over Na₂SO₄, filtered and the solvent removed under reduced pressure, affording 7.0 g of 4-isobutyryl-piperazine-1-carboxylic acid tert-butyl ester. The product was dissolved in 100 mL of DCM. H₂SO₄ (2.91 mL, 54.7 mmol) was added and the reaction left stirring for 16 hours. The precipitate formed was filtered affording 6.7 g of the titled compound (96%, yield)

¹H-NMR (d⁶-DMSO): 0.97 (6H, d, J=6.72); 2.86 (1H, m); 3.08 (4H, m); 3.65 (4H, m); 8.78 (2H, bs).

1-[trans-4-(4-Aminomethyl-cyclohexanecarbonyl)-piperazin-1-yl]-2-methyl-propan-1-one

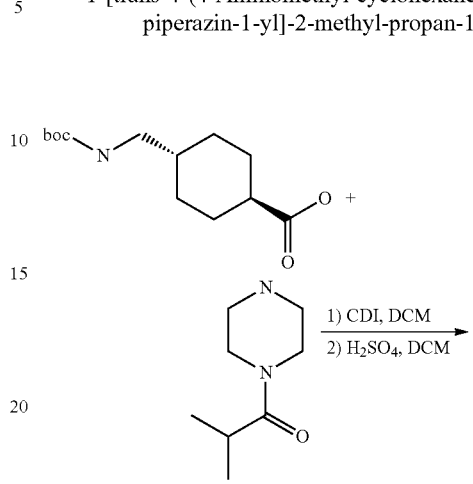

To a solution of trans-4-(tert-Butoxycarbonylamino-methyl)-cyclohexanecarboxylic acid (8.5 g, 32.8 mmol) in DCM (100 mL) 1,1-carbonyldiimidazole (4.87 g, 30.1 mmol) was added and the reaction was left stirring for 2 hours. Then isobutyryl-piperazine (6.95 g, 27.3 mmol) was also added and the reaction was left stirring for 16 h at room temperature. The mixture was diluted with 50 mL of H₂O, the organic phase collected and the solvent removed under reduced pressure. The residue was washed with 1N NaOH solution and the precipitate was filtered, affording 8.7 g (21.9 mmol) of [4-(4-Isobutyryl-piperazine-1-carbonyl)-cyclohexylmethyl]-carbamic acid tert-butyl ester. The product obtained was dissolved in 100 mL of DCM and H₂SO₄ (2.92 mL, 54.9 mmol) was added. The reaction was stirred for 18 hours and the mixture was washed with 50 mL of 15% NaOH solution, the organic phase was collected and concentrated under reduced pressure. 3.85 g of the titled product were obtained (yield=48%).

C16H29N3O2 Mass (calculated) [295.4]. found [M+H⁺] =296.9.

Lc RT=1.10 (method b)

6-Methoxy-1H-benzo[d][1,3]oxazine-2,4-dione

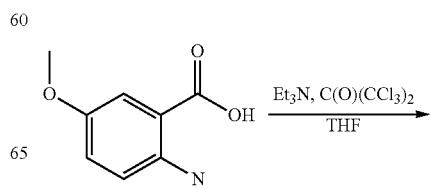

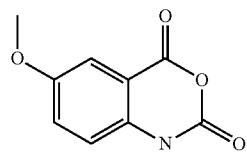

To a solution of 2-amino-5-methoxy-benzoic acid (1.2 g, 7 mmol) in anhydrous THF (50 mL) triethylamine (1.0 mL, 7 mmol) was added and the mixture was cooled down to 0° C. Then triphosgene (2.0 g, 7 mmol) was added portion wise and the reaction allowed to reach room temperature and left stirring for 18 hours. 1 mL of H$_2$O was carefully added to the mixture and the solvent was removed under reduced pressure. The residue was precipitated from H$_2$O, affording 1.3 g of the titled compound (96% yield).

$^1$H-NMR (d$^6$-DMSO): 3.78 (3H, s); 7.09 (1H, d, J=8.9 Hz); 7.31 (1H, d, J=2.9 Hz); 7.35 (1H, dd, J$_1$=2.9 Hz, J$_2$=8.8 Hz); 11.59 (1H, s).

2-Amino-N-[trans-4-(4-isobutyryl-piperazine-1-carbonyl)cyclohexyl methyl]-5-methoxy-benzamide

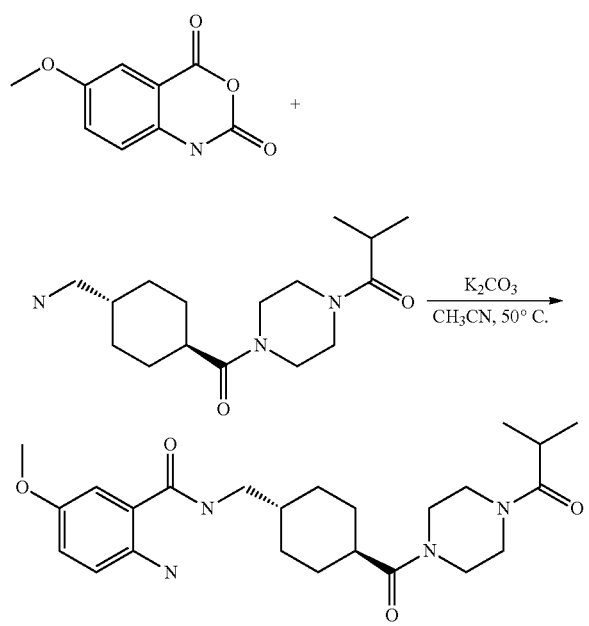

To a solution of 6-Methoxy-1H-benzo[d][1,3]oxazine-2,4-dione (96 mg, 0.5 mmol) in CH$_3$CN (5 mL) K$_2$CO$_3$ (140 mg, 1 mmol) and 1-[trans-4-(4-Aminomethyl-cyclohexanecarbonyl)-piperazin-1-yl]-2-methyl-propan-1-one (148 mg, 0.5 mmol) were added and the reaction was heated at 50° C. for 16 h. The solvent was removed under reduced pressure, 5 mL of 0.4M Na$_2$CO$_3$ solution were added and the mixture was stirred for 1 h. Then 5 mL of DCM were added, the organic phase collected, dried over Na$_2$SO$_4$ and the solvent removed under reduced pressure. 156 mg of the titled product were obtained (yield=68%).

C24H36N4O4 Mass (calculated) [444.6]. found [M+H$^+$]=445.3.

Lc RT=3.55 (method a)

3-[trans-4-(4-Isobutyryl-piperazine-1-carbonyl)-cyclohexylmethyl]-6-methoxy-1H-quinazoline-2,4-dione A solution of 2-amino-N-[trans-4-(4-isobutyryl-piperazine-1-carbonyl)-cyclohexylmethyl]-5-methoxy-benzamide (156 mg, 0.35 mmol) and 1,1-carbonyldiimidazole (130 mg, 0.8 mmol) in THF (4 mL) was irradiated with microwave at 150° C. (250 W) for 20 minutes. The desired product precipitated from the reaction mixture and was filtered. 85 mg of the titled compound were obtained (yield 52%).

C25H34N4O5 Mass (calculated) [470.6]. found [M+H$^+$]=471.2.

Lc RT=5.37 (method a)

$^1$H-NMR (d$^6$-DMSO): 0.97 (6H, d, J=6.6 Hz), 1.09 (2H, m), 1.24 (2H, m), 1.62 (4H, m), 1.72 (1H, m), 2.53 (1H, m), 2.83 (1H, sett, J=6.6 Hz), 3.43 (8H, m), 3.76 (2H, d, J=6.72 Hz), 3.77 (31-1, s), 7.11 (1H, d, J=8.84 Hz), 7.28 (1H, dd, J1=8.84 Hz), 7.33 (1H, d, J=2.96), 11.28 (1H, s).

Example 4 (Method C1)

3-{4-[4-(Tetrahydro-furan-2-carbonyl)-piperazine-1-carbonyl]-cyclohexyl methyl}-1H-quinazoline-2,4-dione 4-[trans-4-(2,4-Dioxo-1,4-dihydro-2H-quinazolin-3-ylmethyl)cyclohexanecarbonyl]-piperazine-1-carboxylic acid tert-butyl ester

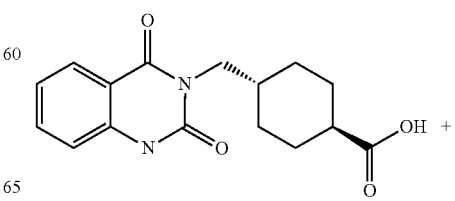

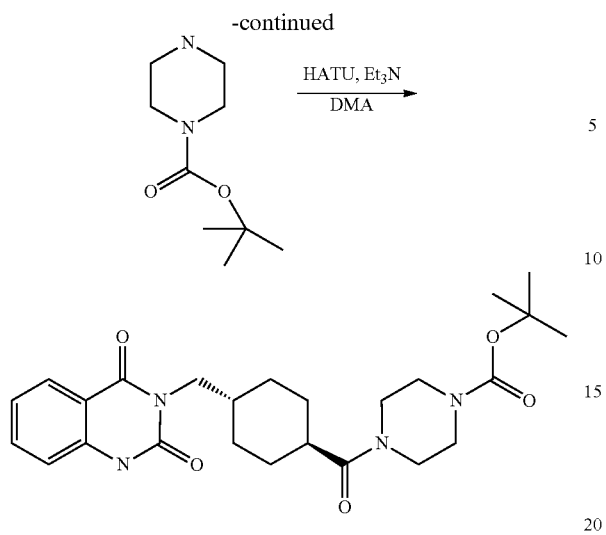

To a solution of trans-4-(2,4-Dioxo-1,4-dihydro-2H-quinazolin-3-ylmethyl)-cyclohexanecarboxylic acid (1.5 g, 4.96 mmol) in dimethylacetamide (10 mL), HATU (1.88 g, 4.96 mmol) and triethylamine (0.76 mL, 5.45 mmol) were added and the mixture left stirring at room temperature for 1 hour. Then tert-butyl-1-piperazinecarboxylate (0.92 g, 4.96 mmol) was added and the reaction left stirring for 18 h at room temperature. The solvent was removed under reduced pressure and the residue was washed with a 0.4M Na$_2$CO$_3$ solution. The titled compound was obtained as a white solid (2.3 g, quantitative yield).

C25H34N4O5 Mass (calculated) [470.6]. found [M+H$^+$]= 471.3.

Lc RT=3.52 (method b)

3-[trans-4-(piperazine-1-carbonyl)-cyclohexylmethyl]-1H-quinazoline-2,4-dione

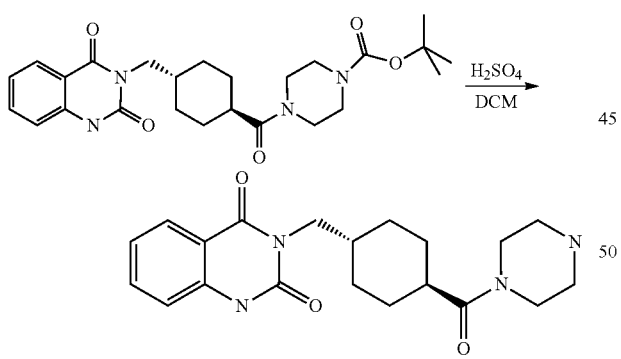

To a solution of 4-[trans-4-(2,4-Dioxo-1,4-dihydro-2H-quinazolin-3-ylmethyl)cyclohexanecarbonyl]-piperazine-1-carboxylic acid tert-butyl ester (1.16 g, 2.5 mmol) in DCM (10 mL) H$_2$SO$_4$ (0.26 mL, 5 mmol) was added and the reaction was stirred at room temperature for 18 hours. The reaction mixture was washed with 10 mL of 0.4 M solution Na$_2$CO$_3$ and the organic phase was collected and concentrated under reduced pressure. 0.57 g of the titled compound were obtained (yield 63%).

C20H26N4O3 Mass (calculated) [370.5]. found [M+H$^+$]= 371.2.

Lc RT=1.63 (method b)

3-{4-[4-(Tetrahydro-furan-2-carbonyl)-piperazine-1-carbonyl]-cyclohexyl methyl}-1H-quinazoline-2,4-dione

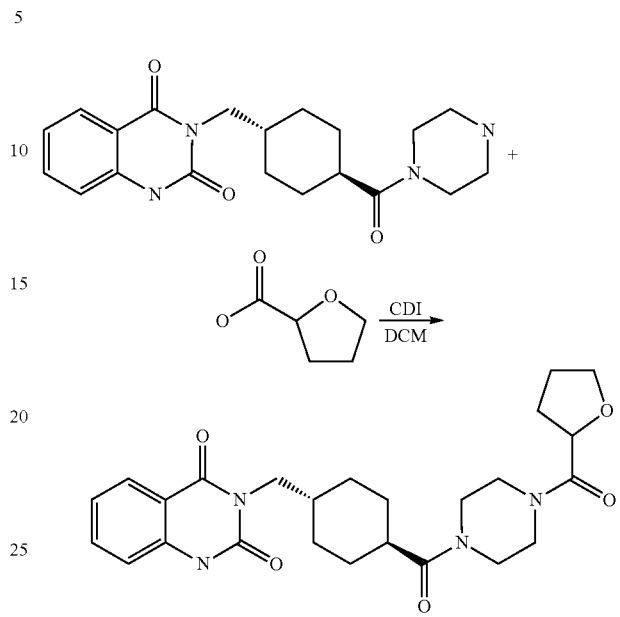

To a suspension of tetrahydro-2-furoic acid (38 mg, 0.32 mmol) in DCM (3 mL) 1,1-carbonyldiimidazole (52 mg, 0.32 mmol) was added and the mixture was stirred for 6 hours at room temperature. Then 3-[trans-4-(piperazine-1-carbonyl)-cyclohexylmethyl]-1H-quinazoline-2,4-dione (100 mg, 0.27 mmol) was added and the reaction left stirring for 18 hours. The mixture was washed with 0.4 M Na$_2$CO$_3$ solution and the organic phase collected and concentrated under reduced pressure. The crude was purified by silica column eluting with DCM:MeOH (98:2). 70 mg of the titled compound were obtained (yield 55%).

C25H32N4O5 Mass (calculated) [468.6]. found [M+H$^+$]= 469.3.

Lc RT=4.65 (method a)

$^1$H-NMR (d$^6$-DMSO): 1.09 (2H, m), 1.24 (2H, m), 1.64 (7H, m), 1.97 (2H, m), 2.53 (1H, m), 3.43 (8H, m), 3.76 (2H, d, J=6.7 Hz), 3.74 (4H, m), 4.63 (1H, m), 7.16 (2H, m), 7.62 (1H, m), 7.90 (1H, m), 11.38 (1H, s).

Example 5 (Method C2)

3-[trans-4-(4-Butyryl-piperazine-1-carbonyl)-cyclohexylmethyl]-1-methyl-1H-quinazoline-2,4-dione 1-Methyl-3-[trans-4-(piperazine-1-carbonyl)-cyclohexylmethyl]-1H-quinazoline-2,4-dione

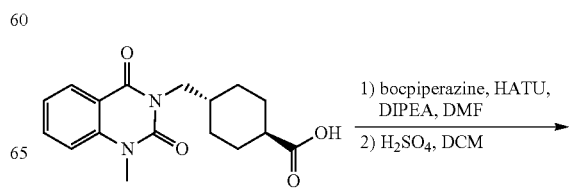

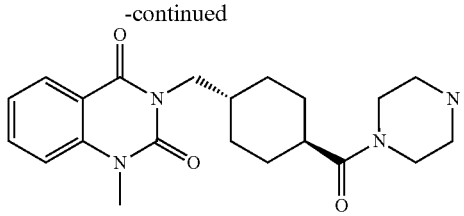

trans-4-(1-Methyl-2,4-dioxo-1,4-dihydro-2H-quinazolin-3-ylmethyl)-cyclohexanecarboxylic acid (1.0 g, 3.2 mmol), DIPEA (560 µL, 3.2 mmol), HATU (1.2 g, 0.32 mmol) were dissolved in 20 ml of DMF. The mixture was stirred at room temperature for 2 hours and then 14 ml of the solution were transferred in a different flask. To this solution Boc-piperazine (411 mg, 2.2 mmol) was added and the mixture was stirred at room temperature for 18 hours. The solvent was removed under reduced pressure and the residue dissolved in DCM and washed with 0.4 M solution of $Na_2CO_3$. The organic phase was separated and the solvent removed under reduced pressure to give 900 mg of crude boc protected intermediate. The compound was dissolved in 10 ml of DCM, 255 µL of $H_2SO_4$ were added and the mixture was left stirring at room temperature for 18 hours. The solution was washed with a solution of NaOH (10% W/W), the organic phase was separated and concentrated under reduced pressure to give 570 mg (yield 80%) of the titled compound.

C21H28N4O3 Mass (calculated) [384.5]. found [M+H$^+$]= 385.3.

Lc RT=1.82 (method b)

3-[trans-4-(4-Butyryl-piperazine-1-carbonyl)-cyclohexylmethyl]-1-methyl-1H-quinazoline-2,4-dione

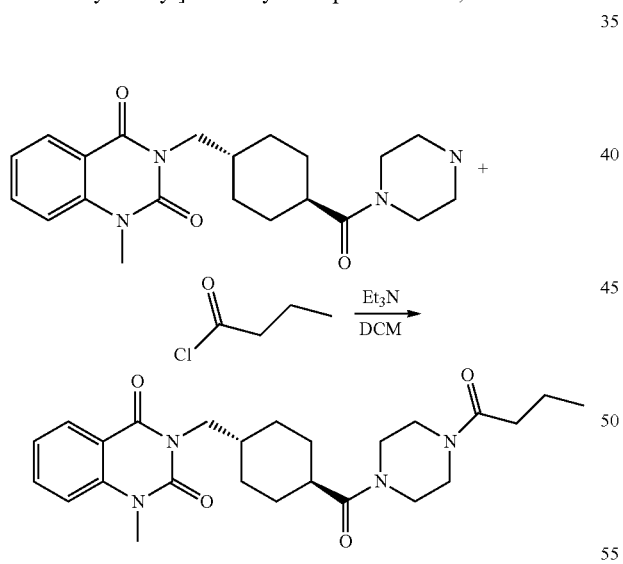

100 mg (0.26 mmol) of 1-Methyl-3-[trans-4-(piperazine-1-carbonyl)-cyclohexylmethyl]-1H-quinazoline-2,4-dione was dissolved in DCM (3 ml). 75 µL (0.52 mmol) of $Et_3N$ and then 41 µL (0.39 mmol) of butyryl chloride were added and the mixture was stirred at room temperature overnight. The solution was washed with a 0.4 M solution of $Na_2CO_3$, the organic phase was separated and dried over $Na_2SO_4$. The solvent was removed under reduced pressure and the crude material purified by column chromatography using acetone as eluent. In total 28 mg (yield 24%) of the titled compound were isolated.

C25H34N4O4 Mass (calculated) [454.6]. found [M+H$^+$]= 455.2.

Lc RT=5.5 (method a)

$^1$H-NMR (d6-DMSO): 0.86 (3H, t, J=7 Hz), 1.05-1.14 (2H, m), 1.20-1.29 (2h, m), 1.46-1.51 (2H, m), 1.62-1.64 (4H, m), 1.72 (1H, m), 2.26 (1H, m), 2.54 (1H, m), 3.31-3.48 (8H, m), 3.81 (2H, d, 7 Hz), 7.28 (1H, t, J=7 Hz), 7.42 (1H, d, J=8 Hz), 7.75 (1H, m), 8.02 (1H, m).

Example 6 (Method E)

3-[trans-4-(4-Isobutyryl-piperazine-1-carbonyl)-cyclohexylmethyl]-6-phenyl-dihydro-pyrimidine-2,4-dione 3-tert-Butoxycarbonylamino-3-phenyl-propionic acid

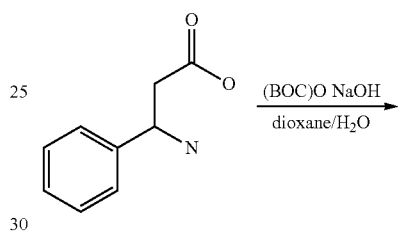

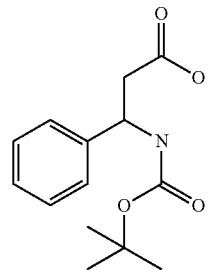

To a solution of 3-Amino-3-phenyl-propionic acid (1.0 g, 6.06 mmol) in dioxane (10 mL) and $H_2O$ (10 mL), NaOH (0.48 g, 12.12 mmol) and di-tert-butyl dicarbonate (1.98 g, 9.09 mmol) were added and the reaction was vigorously stirred for 18 at room temperature. The solvents were removed under reduced pressure, the residue was dissolved in 20 mL of $H_2O$ and the product precipitated adding 6N HCl solution up to pH 3. The solid was filtered and washed with cyclohexane. The titled compound was obtained as a white solid (1.54 g, 95%)

C14H19NO4 Mass (calculated) [265.3]. found [M+H$^+$]= 266.0.

Lc RT=3.07 (method b)

67

(2-{[trans-4-(4-Isobutyryl-piperazine-1-carbonyl)-cyclohexylmethyl]-carbamoyl}-1-phenyl-ethyl)-carbamic acid tert-butyl ester

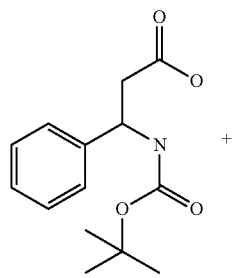

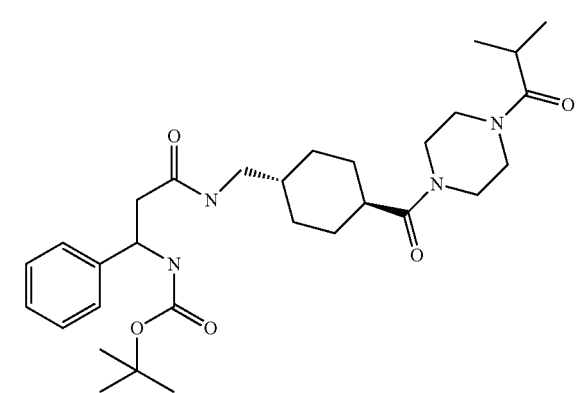

To a solution of 3-tert-Butoxycarbonylamino-3-phenyl-propionic acid (0.43 g, 1.63 mmol) in DCM (20 mL), 1,1-carbonyldiimidazole (0.24 g, 1.48 mmol) was added and the reaction was stirred for 2 hours at room temperature. Then 1-[trans-4-(4-Aminomethyl-cyclohexanecarbonyl)-piperazin-1-yl]-2-methyl-propan-1-one (0.40 g, 1.36 mmol) was added and the mixture was left for 18 hours at room temperature. The mixture was diluted with 10 mL of 0.4 M $Na_2CO_3$, the organic phase was collected and the solvent removed under reduced pressure. The residue was washed with 20 mL solution of $NH_4Cl$ and the precipitate filtered. The titled compound was isolated as a white solid (0.65 g, 88% yield).

C30H46N4O5 Mass (calculated) [542.7]. found [M+H$^+$]= 543.4.

Lc RT=3.37 (method b)

68

3-Amino-N-[trans-4-(4-isobutyryl-piperazine-1-carbonyl)-cyclohexyl methyl]-3-phenyl-propionamide

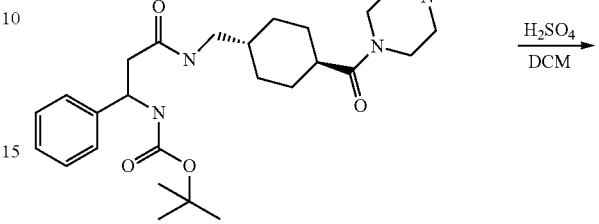

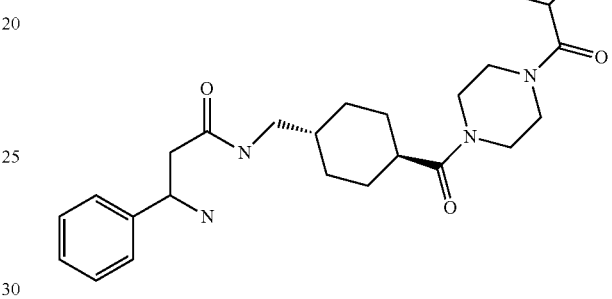

To a solution of (2-{[trans-4-(4-Isobutyryl-piperazine-1-carbonyl)-cyclohexylmethyl]-carbamoyl}-1-phenyl-ethyl)-carbamic acid tert-butyl ester (0.65 g, 1.21 mmol) in DCM (20 mL), $H_2SO_4$ (0.16 mL, 3.02 mmol) was added and the reaction was left stirring at room temperature for 18 hours. The mixture was diluted with 20 mL of NaOH 2N solution and the aqueous phase was concentrated under reduced pressure to give a white solid. The titled compound was extracted with EtOH. The solvent was removed under reduced pressure affording 0.13 g of the titled compound (24% yield).

C25H38N4O3 Mass (calculated) [442.6]. found [M+H$^+$]= 443.3.

Lc RT=1.87 (method b)

3-[trans-4-(4-Isobutyryl-piperazine-1-carbonyl)-cyclohexylmethyl]-6-phenyl-dihydro-pyrimidine-2,4-dione

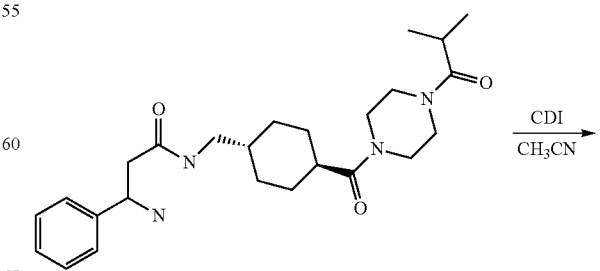

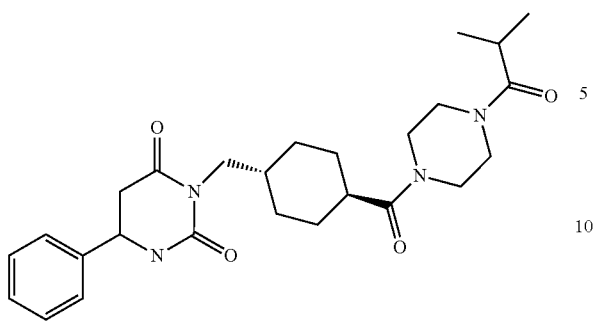

A solution of 3-amino-N-[trans-4-(4-isobutyryl-piperazine-1-carbonyl)-cyclohexylmethyl]-3-phenyl-propionamide (0.13 g, 0.29 mmol) and 1,1-carbonyldiimidazole (0.10 g, 0.58 mmol) in $CH_3CN$ was irradiated with microwave at 100° C. (250 watt) for 10 minutes. The solvent was removed under reduced pressure and the residue was washed with $H_2O$ and then with diethylether, affording 31 mg of the titled compound (22% yield).

C26H36N4O4 Mass (calculated) [468.6]. found [M+H$^+$]=469.3.

Lc RT=4.93 (method a)

$^1$H-NMR (d$^6$-DMSO): 1.00 (2H, m), 1.07 (6H, d, J=6.8 Hz), 1.46 (2H, m), 1.68 (4H, m), 2.34 (1H, m), 2.68-2.94 (3H, m), 3.41 (4H, m), 3.55 (4H, m), 3.63 (2H, m), 4.62 (1H, m), 5.37 (1H, s), 7.24-7.37 (5H, m).

Example 7 (Method F)

3-[trans-4-(4-Cyclopropanecarbonyl-piperazine-1-carbonyl)cyclohexylmethyl]-3,4-dihydro-1H-quinazolin-2-one (4-Cyclopropanecarbonyl-piperazin-1-yl)-{trans-4-[(2-nitrobenzylamino)-methyl]-cyclohexyl}-methanone

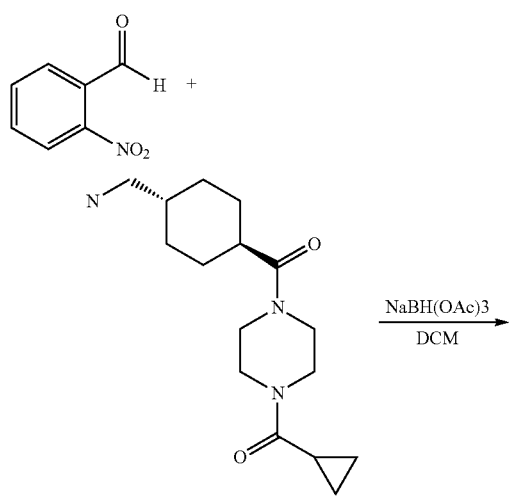

A solution of 2-nitrobenzaldehyde (214 mg, 1.42 mmol) and (4-aminomethyl-cyclohexyl)-(trans-4-cyclopropanecarbonyl-piperazin-1-yl)-methanone (500 mg, 1.71 mmol) in DCM (10 mL) was stirred at room temperature for 6 hours. NaBH(OAc)$_3$ (900 mg, 4.27 mmol) was added and the reaction was stirred for 18 hours. The mixture was washed with 10 mL of $H_2O$ and the organic phase recovered and concentrated under reduced pressure to give 272 mg of the titled compound (yield 45%).

C23H32N4O4 Mass (calculated) [428.5]. found [M+H$^+$]=429.3.

Lc RT=1.68 (method b)

{trans-4-[(2-Amino-benzylamino)-methyl]-cyclohexyl}-(4-cyclopropane carbonyl-piperazin-1-yl)-methanone

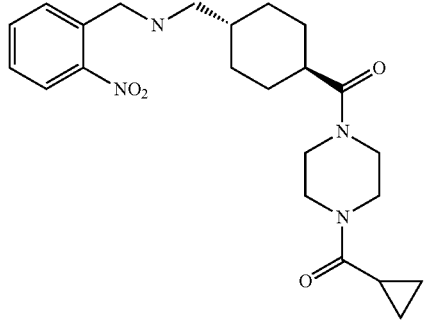

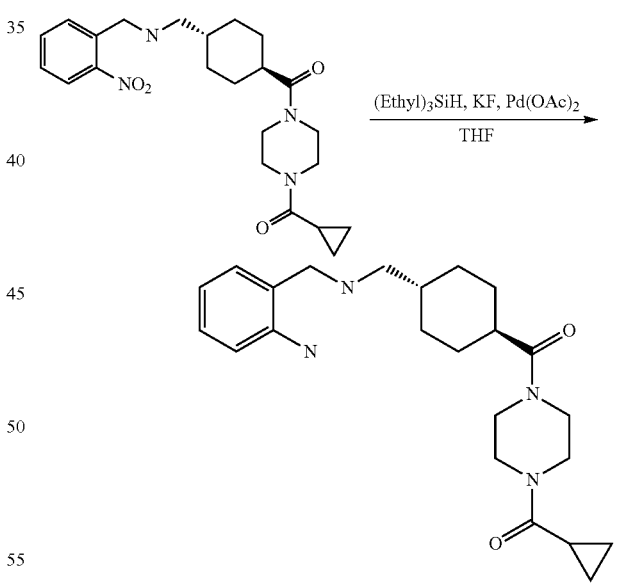

(4-Cyclopropanecarbonyl-piperazin-1-yl)-{trans-4-[(2-nitrobenzylamino)-methyl]-cyclohexyl}methanone (272 mg, 0.63 mmol) and Pd(OAc)$_2$ (7 mg, 0.03 mmol) were weighed into a flask and flushed with nitrogen for 5 minutes. THF (10 mL) was added, followed by a solution of KF (73 mg, 1.26 mmol in 1.2 ml of $H_2O$). Then triethylsilane (0.40 mL, 2.52 mmol) was added drop wise and the reaction was left stirring for 3 h at room temperature. The mixture was filtered on a celite bed to remove palladium and the solution was concentrated under reduced pressure. The residue was suspended in DCM (4 mL) and washed with H$_2$O (4 mL). The organic phase was collected and concentrated, the crude product was purified by SiO$_2$ column, eluting with AcOEt: MeOH 80:20, affording 146 mg of the titled compound (57% yield).

C23H34N4O2 Mass (calculated) [398.5]. found [M+H$^+$]=399.2.

Lc RT=1.70 (method b)

3-[trans-4-(4-Cyclopropanecarbonyl-piperazine-1-carbonyl)cyclohexyl methyl]-3,4-dihydro-1H-quinazolin-2-one

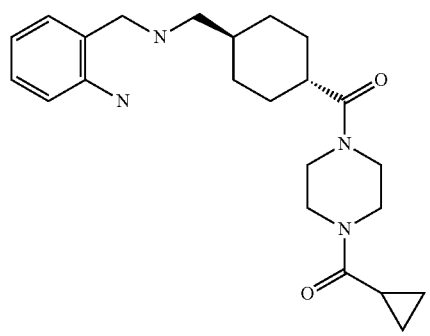

A solution of {4-[(2-Amino-benzylamino)-methyl]-cyclohexyl}-(trans-4-cyclopropanecarbonyl-piperazin-1-yl)-methanone (146 mg, 0.37 mmol) and 1,1-carbonyldiimidazole (120 mg, 0.74 mmol) in CH$_3$CN (5 mL) was irradiated with microwave for 10 minutes at 100° C. (200 watt). When the reaction was allowed to cool down to room temperature the product precipitated from the mixture. The solid was filtered and washed with 2 mL of H$_2$O, obtaining 51 mg of the titled compound (33% yield).

C24H32N4O3 Mass (calculated) [424.6]. found [M+H$^+$]=425.3.

Lc RT=4.98 (10 min method)

$^1$H-NMR (d$^6$-DMSO): 0.70 (4H, m), 1.02 (2H, m), 1.31 (2H, m) 1.66 (5H, m), 1.94 (1H, m), 2.54 (1H, m), 3.15 (2H, d, J=7.64 Hz), 3.34-3.73 (8H, m), 4.37 (2H, s), 6.74 (1H, m), 6.83 (1H, m), 7.08 (2H, m), 9.08 (1H, s).

Example 8 (Method G1)

6-Methoxy-1-[trans-4-(morpholine-4-carbonyl)-cyclohexylmethyl]-1,3-dihydro-benzoimidazol-2-one And Example 9 (Method G1)

5-Methoxy-1-methyl-3-[trans-4-(morpholine-4-carbonyl)-cyclohexylmethyl]-1,3-dihydro-benzoimidazol-2-one trans-4-[(5-Methoxy-2-nitro-phenylamino)-methyl]-cyclohexanecarboxylic acid methyl ester

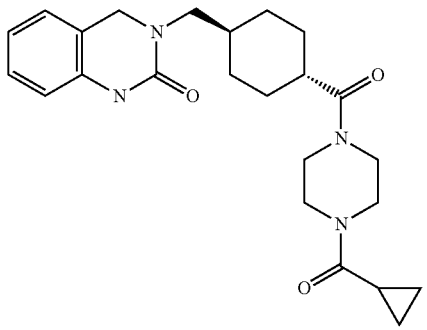

K$_2$CO$_3$ (9.04 g, 65.5 mmol) was added to a solution of 2-Fluoro-4-methoxy-1-nitro-benzene (5.6 g, 32.7 mmol) in DMF (20 ml). The mixture was stirred at room temperature for 30 minutes and then trans-4-Aminomethyl-cyclohexanecarboxylic acid methyl ester (5.60 g, 32.7 mmol) was added. The reaction mixture was heated for 2 hours at 50° C. and then at room temperature overnight. The solvent was removed under reduced pressure and the crude product dissolved in DCM (150 ml) and washed with water (2×150 ml) and then with a solution of citric acid (2×150 ml). The organic solution was dried over Na$_2$SO$_4$, filtered and the solvent removed by evaporation to give 9.6 g of the titled compound.

C16H22N2O5 Mass (calculated) [322.4]. found [M+H$^+$]=322.3.

Lc RT=1.72 (method e)

trans-4-[(2-Amino-5-methoxy-phenylamino)-methyl]-cyclohexane carboxylic acid methyl ester

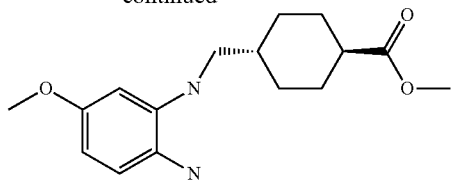

trans-4-[(5-Methoxy-2-nitro-phenylamino)-methyl]cyclohexane carboxylic acid methyl ester (800 mg, 2.48 mmol) was dissolved in 10 ml of EtAc mixed with 80 mg of Pd/C (10%, wet) and transferred in a Eyela reactor. The mixture was left overnight under 5 bar of hydrogen, then the solution was filtered through cellulose and the solvent removed under reduced pressure to give the titled compound as a brown solid. (700 mg, yield=96%)

C16H24N2O3 Mass (calculated) [292.4]. found [M+H$^+$]=293.4.

Lc RT=1.08 (method e)

trans-4-(6-Methoxy-2-oxo-2,3-dihydro-benzoimidazol-1-ylmethyl)cyclohexanecarboxylic acid methyl ester

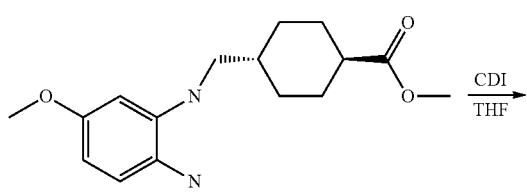

trans-4-[(2-Amino-5-methoxy-phenylamino)-methyl]-cyclohexane carboxylic acid methyl ester (5.4 g, 18.5 mmol) was dissolved in 40 ml of anhydrous THF. 1,1-carbonyldiimidazole (8.9 g, 55.5 mmol) was added and the mixture was stirred for 22 hours. Few drops of water were added and the solvent was removed under reduced pressure and the crude was dissolved in DCM (100 ml) and washed with H$_2$O, a citric acid solution (2×70 ml) and H$_2$O. The organic phase was separated, dried over Na$_2$SO$_4$, filtered and the solvent was removed under reduced pressure. The crude material was filtered through a silica pad using EtAc/cyclohexane and then EtAc as eluent. The solvent was evaporated and the crude was purified by silica column using EtAc/hexane as eluent. In total 3.2 g of the titled compound were obtained (yield=54%)

C17H22N2O4 Mass (calculated) [318.4]. found [M+H$^+$]=319.3.

Lc RT=1.24 (method e)

trans-4-(6-Methoxy-2-oxo-2,3-dihydro-benzoimidazol-1-ylmethyl)-cyclo hexanecarboxylic acid

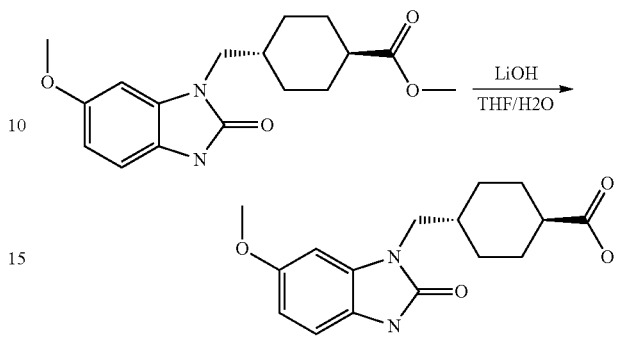

A solution of LiOH (24 mg, 2.4 mmol) in water (1 ml) was added to a solution of trans-4-(6-methoxy-2-oxo-2,3-dihydro-benzoimidazol-1-ylmethyl)-cyclohexanecarboxylic acid methyl ester (260 mg, 0.8 mmol) in THF (2 ml). The mixture was stirred at room temperature for six hours and then 5 ml of H$_2$O were added. The THF was evaporated under reduced pressure. The pH was adjusted to 4 using HCl 6M with the formation of a precipitate which was then isolated by filtration and washed with DCM. In total 230 mg (yield 92%) of the title compound were isolated C16H20N2O4 Mass (calculated) [304.3]. found [M–H$^+$]=303.3.

Lc RT=0.16 (method e)

$^1$HNMR (CD$_3$OD): 1.14 (2H, m), 1.36 (2H, m), 1.76 (2H, m), 1.85 (1H, m), 1.99 (2H, m), 2.24 (1H, m), 3.70 (2H, d, J=7.3), 3.80 (3H, s), 6.65 (1H, dd, J=8.5, j=2.4), 6.73 (1H, d, J=2.3), 6.95 (1H, d, J=8.5).

6-Methoxy-1-[trans-4-(morpholine-4-carbonyl)-cyclohexylmethyl]-1,3-dihydro-benzoimidazol-2-one

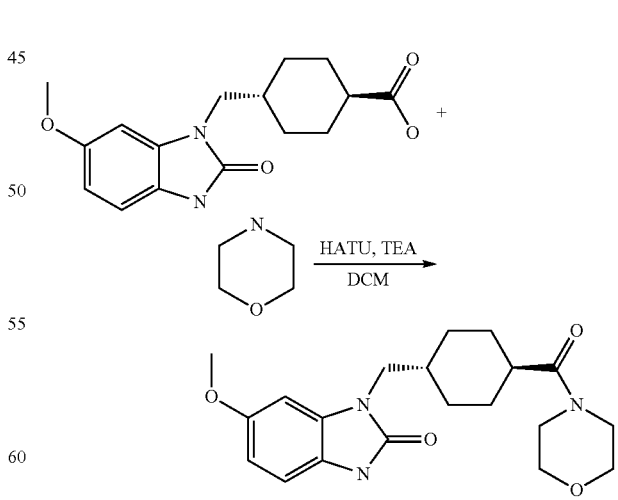

A mixture of 6-Methoxy-1-[trans-4-(morpholine-4-carbonyl)-cyclohexylmethyl]-1,3-dihydro-benzoimidazol-2-one (100 mg, 0.33 mmol), triethyl amine (55 µL, 0.39 mmol), HATU (150 mg, 0.39 mmol) and morpholine (34 µL, 0.39 mmol) in DCM 2 ml was stirred for 4 hours. The solution was washed with saturated Na₂CO₃ solution (2 ml) and then with H₂O (2 ml). The organic layer was separated and the solvent removed under reduced pressure. The crude material was purified by column chromatography using EtAc/MeOH (95: 5) as eluent. Further purification by trituration with MeOH gave the title compound. (101 mg, yield 82%).

C20H27N3O4 Mass (calculated) [373.5]. found [M+H⁺] =374.3.

Lc RT=0.88 (method e)

¹HNMR (CDCl₃): 1.15 (2H, m), 1.55 (2H, m), 1.75-1.87 (4H, m), 1.93 (1H, m), 2.41 (1H, m), 3.48 (2H, m), 3.60 (2H, m), 3.64-3.67 (4H, m), 3.70 (2H, d, J=7.2), 3.82 (3H, s), 6.56 (1H, d, J=2.4), 6.63 (1H, dd, J=8.5, j=2.4), 6.96 (1H, d, J=8.5), 8.76 (1H, bs).

5-Methoxy-1-methyl-3-[trans-4-(morpholine-4-carbonyl)-cyclohexyl methyl]-1,3-dihydro-benzoimidazol-2-one

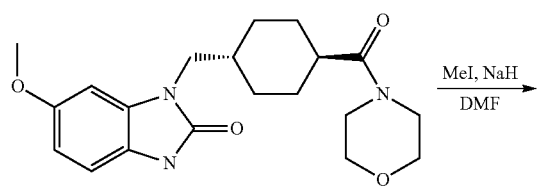

NaH (60% in mineral oil, 12 mg, 0.3 mmol) was added to a solution of 6-Methoxy-1-[trans-4-(morpholine-4-carbonyl)-cyclohexylmethyl]-1,3-dihydro-benzoimidazol-2-one (56 mg, 0.15 mmol) in DMF (1.5 ml). MeI (19 μL, 0.3 mmol) was added and the mixture was stirred at room temperature for six hours. The solvent was evaporated, the crude was dissolved in 2 ml of DCM and the solution was washed with H₂O. The organic layer was separated and the solvent was removed under reduced pressure. The crude material was purified by column chromatography with EtAc/MeOH (9/1) as eluent. 45 mg (yield 78%) of the title compound were isolated.

C21H29N3O4 Mass (calculated) [387.5]. found [M+H⁺] =388.5.

Lc RT=1.13 (method e)

¹HNMR (CDCl₃): 1.05 (2H, m), 1.44 (2H, m), 1.62-1.76 (4H, m), 1.82 (1H, m), 2.31 (1H, m), 3.30 (3H, s), 3.39 (2H, m), 3.51 (2H, m), 3.55-3.57 (4H, m), 3.61 (2H, d, J=7.1), 3.74 (3H, s), 6.48 (1H, d, J=2.3), 6.56 (1H, dd, J=8.5, J=2.3 Hz), 6.77 (1H, d, J=8.5 Hz).

Example 10 (Method G2)

1-Methyl-3-[trans-4-(morpholine-4-carbonyl)-cyclohexylmethyl]-5-trifluoromethyl-1,3-dihydro-benzoimidazol-2-one trans-4-[(2-Nitro-5-trifluoromethyl-phenylamino)-methyl]-cyclohexane carboxylic acid methyl ester

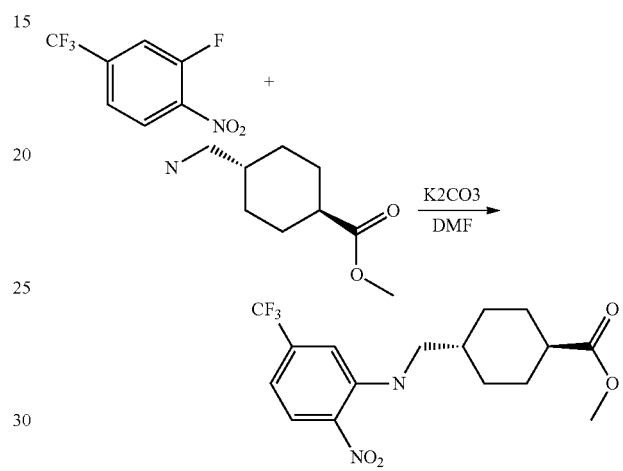

K₂CO₃ (1.6 g, 11.7 mmol), 2-Fluoro-1-nitro-4-trifluoromethyl-benzene (1.22 g, 5.8 mmol) and trans-4-Aminomethyl-cyclohexanecarboxylic acid methyl ester (1.00 g, 5.84 mmol) were dissolved in DMF (10 ml). The mixture was stirred at 50° C. overnight. The solvent was removed under reduced pressure and the crude product dissolved in DCM (15 ml) and washed with water (20 ml) and then with a solution of citric acid (1M, 5 ml). The organic solution was dried over Na₂SO₄, filtered and the solvent removed by evaporation to give solid material. This was washed with cyclohexane and then with isopropyl ether and purified by silica column using DCM/cyclo hexane (1:1) as eluent. 1.8 g (yield 86%) of the title compound were isolated.

C16H19F3N2O4 Mass (calculated) [360.34]. found [M+H⁺]=361.4.

Lc RT=1.13 (method e)

¹HNMR (CDCl₃): 1.12 (2H, m), 1.50 (2H, m), 1.71 (1H, m), 1.98 (2H, m), 2.08 (2H, m), 2.29 (1H, m), 3.20 (2H, dd, J=6.6 Hz, J=5.4 Hz), 3.68 (3H, s), 6.84 (1H, d, J=8.9 Hz), 7.07 (1H, s), 8.16 (1H, bs), 8.27 (1H, d, J=8.9 Hz).

trans-4-(2-Oxo-6-trifluoromethyl-2,3-dihydro-benzoimidazol-1-ylmethyl)-cyclohexanecarboxylic acid methyl ester

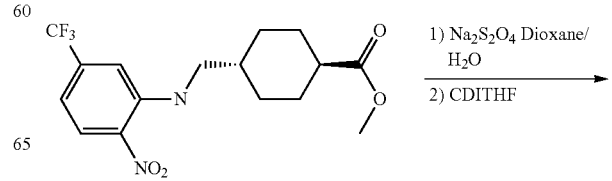

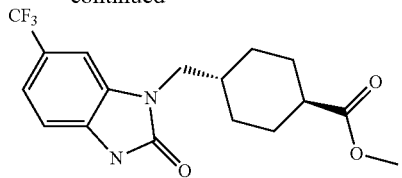

trans 4-[(2-Nitro-5-trifluoromethyl-phenylamino)-methyl]-cyclohexane carboxylic acid methyl ester (1.8 g, 5.0 mmol) was dissolved in 35 ml of a mixture 4:1 of dioxane and 25% ammonium hydroxide. $Na_2S_2O_4$ (2.6 g, 15.0 mmol) was added and the mixture was stirred at 50° C. for 4 hours. The solvent was evaporated and the crude dissolved in 20 ml MeOH. 4 ml of concentrated (37%) HCl and 10 ml of water were added and the mixture was stirred at 50° C. for three hours and then at room temperature overnight. The MeOH was evaporated under reduced pressure and 20 ml of DCM and 5 ml of a saturated solution of $Na_2CO_3$ were added. The organic phase was separated and the solvent removed. The crude material was dissolved in THF (40 ml) and 1,1-carbonyldiimidazole (1.62 g, 10 mmol) was added. The mixture was stirred at room temperature overnight. The solvent was evaporated and the crude dissolved in DCM (20 ml). The organic solution was washed with 10 ml of 1M HCl and the solvent removed under reduced pressure. The titled compound was purified by silica column using ethyl acetate cyclohexane 1:1 as eluent. 0.87 g (yield 49%) of the titled compound were isolated.

C17H19F3N2O3 Mass (calculated) [356.35]. found [M+H+]=357.2.

Lc RT=1.48 (method e)

$^1$HNMR (CDCl$_3$): 1.08 (2H, m), 1.35 (2H, m), 1.77 (2H, m), 1.83 (1H, m), 1.96 (2H, m), 2.21 (1H, m), 3.59 (3H, s), 3.70 (2H, d, J=7.3), 7.10-7.12 (2H, m), 7.31 (1H, d, J=7.4), 9.67 (1H, bs).

trans-4-(3-Methyl-2-oxo-6-trifluoromethyl-2,3-dihydro-benzoimidazol-1-ylmethyl)-cyclohexanecarboxylic acid methyl ester trans-4-(2-Oxo-6-trifluoromethyl-2,3-dihydro-benzoimidazol-1-ylmethyl)-cyclohexanecarboxylic acid methyl ester (0.87 mg, 2.44 mmol) was dissolved in anhydrous DMF. NaH (1.95 g, 4.9 mmol, 60% in mineral oil) and MeI (0.30 ml, 4.9 mmol) were added and the mixture was stirred at room temperature for two days. H$_2$O was added and the solvents were evaporated. The crude was dissolved in DCM (15 ml) and washed with H$_2$O (10 ml). The organic layer was dried over Na$_2$SO$_4$, filtered and the solvent removed to give 0.93 g (yield quantitative) of the titled compound.

C18H21F3N2O3 Mass (calculated) [370.37]. found [M−H+]=369.3.

Lc RT=1.58 (method e)

$^1$HNMR (CDCl$_3$): 1.12 (2H, m), 1.39 (2H, m), 1.80 (2H, m), 1.86 (1H, m), 2.00 (2H, m), 2.26 (1H, m), 3.44 (3H, s), 3.64 (3H, s), 3.73 (2H, d, J=7.3 Hz), 7.02 (1H, d, J=8.2 Hz), 7.16 (1H, s), 7.38 (1H, d, J=8.2 Hz).

trans-4-(3-Methyl-2-oxo-6-trifluoromethyl-2,3-dihydro-benzoimidazol-1-ylmethyl)-cyclohexanecarboxylic acid

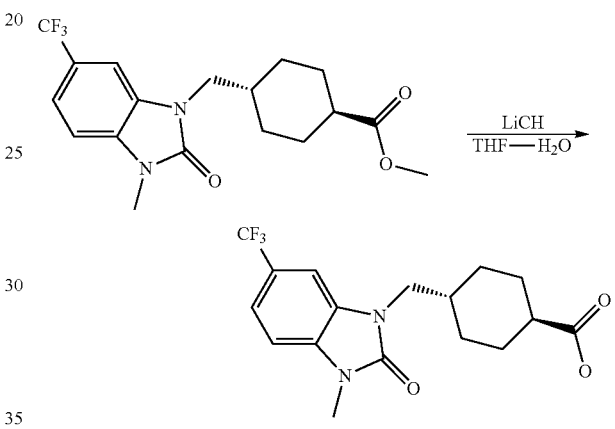

trans-4-(3-Methyl-2-oxo-6-trifluoromethyl-2,3-dihydro-benzoimidazol-1-ylmethyl)cyclohexanecarboxylic acid methyl ester (0.93 g, 2.44 mmol) were dissolved in THF/H$_2$O (9 ml, 2/1). LiOH (129 mg, 5.4 mmol) was added and the mixture stirred at room temperature over night. The THF was evaporated with the formation of a white solid which was collected by filtration. 0.82 g (yield 94%) of the titled compound were isolated.

C17H19F3N2O3 Mass (calculated) [356.35]. found [M−H+]=355.2.

1-Methyl-3-[trans-4-(morpholine-4-carbonyl)-cyclohexylmethyl]-5-trifluoromethyl-1,3-dihydro-benzoimidazol-2-one

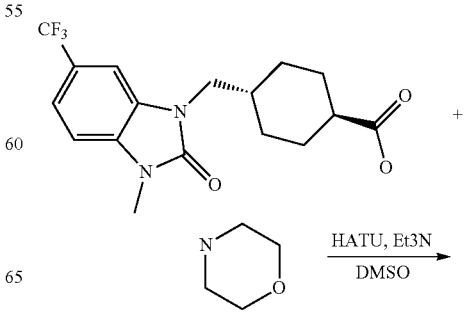

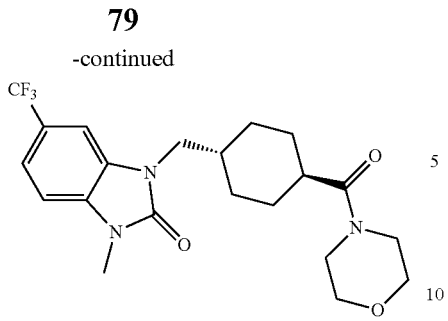

trans-4-(3-Methyl-2-oxo-6-trifluoromethyl-2,3-dihydro-benzoimidazol-1-ylmethyl)cyclohexanecarboxylic acid (78 mg, 0.22 mmol), HATU (100 mg, 0.26 mmol), morpholine (23 mg, 0.26 mmol) and triethyl amine (0.04 ml, 0.26 mmol) were dissolved in DMSO and the mixture were shaken overnight. 3 ml of a saturated solution of ammonium chloride and 2 ml of DCM were added and the organic layer was separated and washed with water. The organic solvent was evaporated and the crude was purified by silica column using ethyl acetate as eluent. 25 mg (yield 27%) of the titled compound were isolated.

C21H26F3N3O3 Mass (calculated) [425.45]. found [M+H$^+$]=426.4.

Lc RT=1.36 (method f)

$^1$HNMR (CDCl$_3$): 1.14 (2H, m), 1.56 (2H, m), 1.76-1.84 (4H, m), 1.92 (1H, m), 2.42 (1H, m), 3.45 (3H, s), 3.48 (2H, m), 3.59 (2H, m), 3.64-3.66 (4H, m), 3.76 (2H, d, J=7.2 Hz), 7.03 (1H, d, J=8.2 Hz), 7.17 (1H, s), 7.39 (1H, d, J=8.2 Hz)

Example 11 (Method G3)

6-Chloro-1-[trans-4-(4-cyclopropane carbonyl-piperazine-1-carbonyl)cyclohexylmethyl]-1,3-dihydro-benzoimidazol-2-one {trans-4-[(5-Chloro-2-nitro-phenylamino)-methyl]-cyclohexyl}-(4-cyclopropanecarbonyl-piperazin-1-yl)-methanone

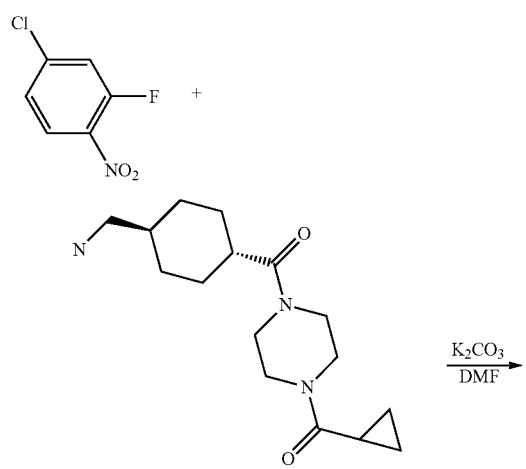

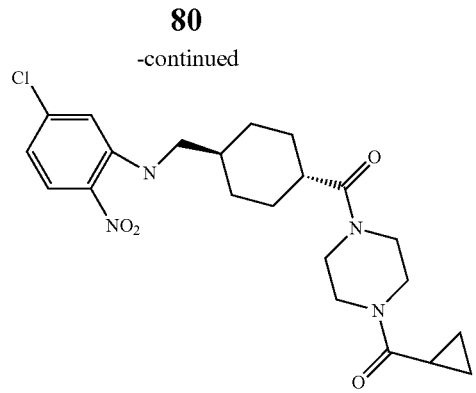

To a solution of (trans-4-aminomethyl-cyclohexyl)-(4-cyclopropanecarbonyl-piperazin-1-yl)-methanone (600 mg, 2.1 mmol) in DMF (5 mL) K$_2$CO$_3$ (565 mg, 4.1 mmol) and 4-chloro-2-fluoronitrobenzene (360 mg, 2.1 mmol) were added and the mixture was heated at 90° C. for 4 hours. Then the solvent was removed under reduced pressure and the residue was washed with 7 mL of H$_2$O and the precipitate was filtered affording 788 mg of the titled compound (78% yield).

C22H29ClN4O4 Mass (calculated) [448]. found [M+H$^+$]=449.

Lc RT=3.75 (method b)

{trans-4-[(2-Amino-5-chloro-phenylamino)-methyl]-cyclohexyl}-(4-cyclopropane carbonyl-piperazin-1-yl)-methanone

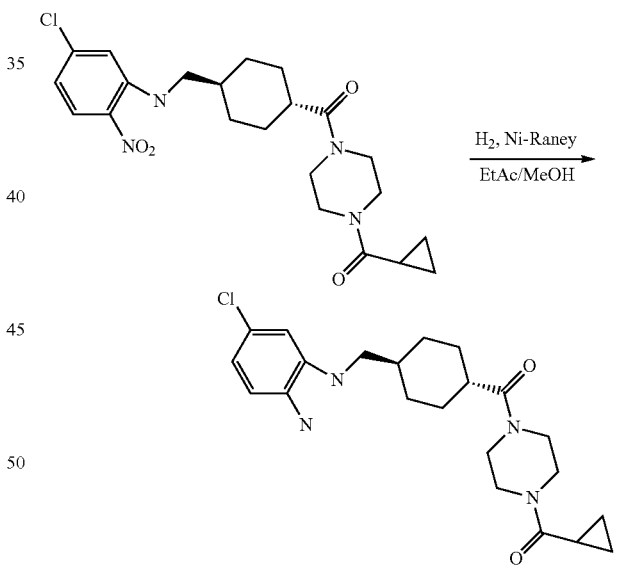

{-4-[trans-(5-Chloro-2-nitro-phenylamino)-methyl]-cyclohexyl}-(4-cyclopropane carbonyl-piperazin-1-yl)-methanone (500 mg, 1.11 mmol) was dissolved in a mixture of ethyl acetate (45 mL) and methanol (5 mL) and reduced in continuous flow with H-Cube using a Ni-Raney cartridge (Flow: 1 mL/minute; Temperature: 40° C.; H$_2$ pressure: full H$_2$). After one cycle the reduction was complete and solvent removal from the reaction mixture to give 448 mg of the titled compound (96% yield).

C22H31ClN4O2 Mass (calculated) [418]. found [M+H$^+$]=419.

Lc RT=3.03 (5 min method).

6-Chloro-1-[trans-4-(4-cyclopropanecarbonyl-piperazine-1-carbonyl)cyclohexylmethyl]-1,3-dihydro-benzoimidazol-2-one

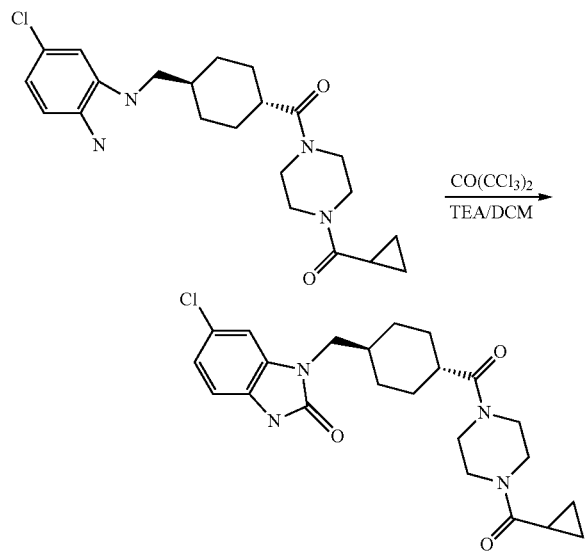

A solution of {trans-4-[(2-Amino-5-chloro-phenylamino)-methyl]-cyclohexyl}-(4-cyclopropane carbonyl-piperazin-1-yl)-methanone (448 mg, 1.07 mmol), triethylamine (0.45 mL, 3.22 mmol) in DCM (10 mL) was cooled at 0° C. Triphosgene (104 mg, 0.35 mmol) was added and the reaction was allowed to warm up to room temperature and left stirring for 18 hours. The reaction was diluted with 0.4 M Na$_2$CO$_3$ solution, the organic phase collected and the solvent removed under reduced pressure. The crude product was purified by SiO$_2$ column eluting with ethylacectate-methanol (9:1), affording 230 mg of the pure product (49% yield).

C23H29ClN4O3 Mass (calculated) [444.97]. found [M+H$^+$]=445.2.

Lc RT=5.53 (10 min method)

$^1$H-NMR (CDCl$_3$): 0.74 (2H, m), 0.94 (2H, m), 1.09 (2H, m), 1.52 (2H, m) 1.65 (1H, m), 1.73 (4H, m) 1.86 (1H, m) 1.94 (1H, m), 2.39 (1H, m), 3.43 (2H, m), 3.59 (6H, m), 3.62 (2H, d, J=7.16 Hz), 6.89 (1H, d, J=1.92 Hz), 6.89 (1H, d, J=8.28 Hz), 6.97 (1H, dd, J1=1.92 Hz, J2=8.28 Hz), 8.21 (1H, s).

Example 12 (Method H)

2-[trans-4-(4-Acetyl-piperazine-1-carbonyl)-cyclohexylmethyl]-4H-isoquinoline-1,3-dione trans-4-(1,3-Dioxo-3,4-dihydro-1H-isoquinolin-2-ylmethyl)cyclohexane carboxylic acid methyl ester

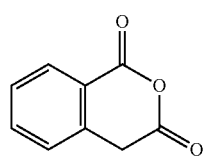 +

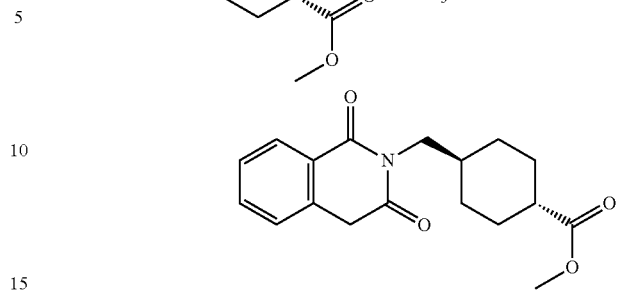

To solution of trans-4-Aminomethyl-cyclohexanecarboxylic acid methyl ester (3.0 g, 17.5 mmol) in 50 mL of CH$_3$COOH homophthalic anhydride (2.8 g, 17.5 mmol) was added and the mixture was stirred at 100° C. for 18 hours. The reaction was allowed to cool down to room temperature and 100 mL of H$_2$O were added. The precipitate formed was filtered, washed with H$_2$O and dried under reduced pressure, affording 2.2 g of the titled compound (40% yield)

C18H21NO4 Mass (calculated) [315.4]. found [M+H$^+$]=316.3.

Lc RT=3.48 (method b)

trans-4-(1,3-Dioxo-3,4-dihydro-1H-isoquinolin-2-ylmethyl)cyclohexane carboxylic acid

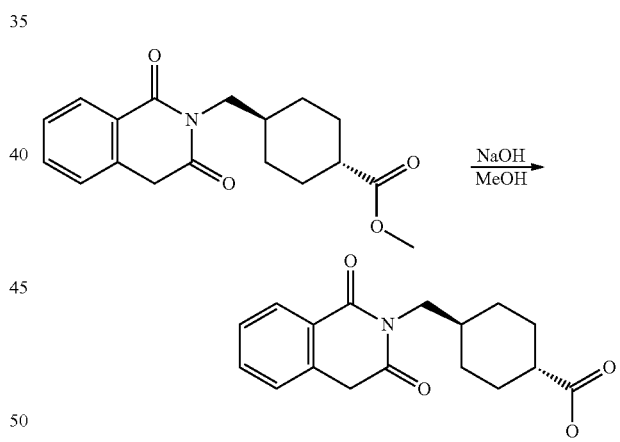

trans-4-(1,3-Dioxo-3,4-dihydro-1H-isoquinolin-2-ylmethyl)-cyclo hexanecarboxylic acid methyl ester (2.2 g, 6.98 mmol) was dissolved in 20 mL of methanol, 5 mL of 15% NaOH solution were added and the mixture heated at 40° C. for 4 hours. The reaction was allowed to cool down to room temperature and the mixture neutralized with 2N HCl solution and extracted with DCM. The organic phase was dried over Na$_2$SO$_4$ and the solvent removed under reduced pressure. The residue was crystallized from a mixture of acetone-H$_2$O (1:1), affording 700 mg of the desired product (33% yield).

C17H19NO4 Mass (calculated) [301.4]. found [M−H$^+$]=300.5.

Lc RT=3.17 (method b)

2-[trans-4-(4-Acetyl-piperazine-1-carbonyl)-cyclohexylmethyl]-4H-isoquinoline-1,3-dione

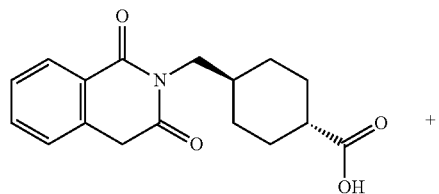
+
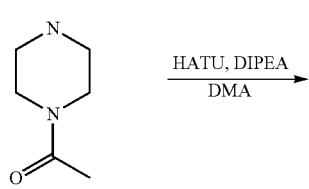
→ HATU, DIPEA / DMA →
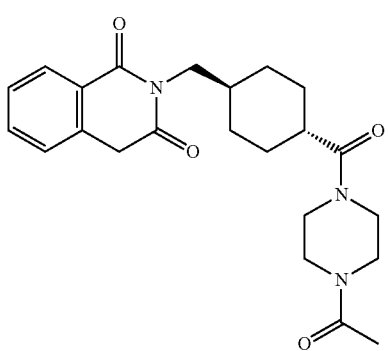

trans-4-(1,3-Dioxo-3,4-dihydro-1H-isoquinolin-2-ylmethyl)-cyclo hexanecarboxylic acid (100 mg, 0.33 mmol) was dissolved in N,N-dimethyl acetamide (3 mL), HATU (125 mg, 0.33 mmol) and diisopropyl ethylamine (0.06 mL, 0.33 mmol) were added and the mixture was left stirring for 1 h. Then 1-acetylpiperazine (128 mg, 0.3 mmol) was added and the reaction stirred for 18 hours. The solvent was removed under reduced pressure and the residue was dissolved in 2 mL of DCM and washed with 2 mL of 0.4M Na2CO3 solution. The organic phase was collected and the solvent removed under reduced pressure. The crude was purified by SiO2 column, eluting with DCM-MeOH (97:3) and the fractions containing the desired product collected and further purified by prep HPLC. 42 mg of the title product were obtained (31% yield).

C23H29N3O4 Mass (calculated) [411.5]. found [M+H$^+$]= 412.4.

Lc RT=4.78 (method a)

$^1$H-NMR (CDCl$_3$): 1.06 (2H, m), 1.23 (2H, m), 1.63 (5H, m), 2.88 (3H, s) 2.53 (1H, m), 3.29 (8H, m), 3.73 (2H, d, J=6.72 Hz), 4.15 (2H, s), 7.37 (1H, m), 7.45 (1H, m), 7.64 (1H, m), 8.03 (1H, m).

Example 13 (Method I1)

4-[trans-4-(4-pyridin-2-yl-piperazine-1-carbonyl)-cyclohexylmethyl]-3,4-dihydro-1H-benzo[e][1,4]diazepine-2,5-dione trans-4-(2,5-Dioxo-1,2,3,5-tetrahydro-benzo[e][1,4]diazepin-4-ylmethyl)-cyclohexanecarboxylic acid

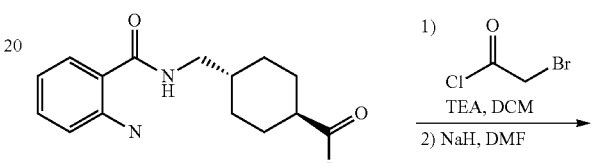
1) chloroacetyl chloride, TEA, DCM
2) NaH, DMF →
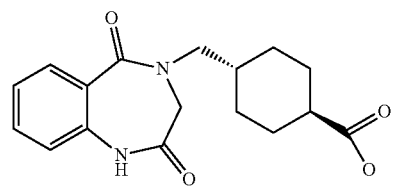

A solution of chloroacetyl chloride (470 µL) in dry DCM (6 mL) was added dropwise to a stirred solution of trans-4-[(2-Amino-benzoylamino)-methyl]-cyclohexanecarboxylic acid methyl ester acetate (3 mmol, 0.850 g) and TEA (9 mmol, 1.2 mL) in dry DCM (44 mL) under argon at 0° C. The mixture was allowed to reach room temperature within 30 minutes. After reaction completion, the reaction mixture was poured into 2N HCl solution (10 mL) and extracted with DCM (3×40 mL). The organic layer was washed with a saturated solution of NaHCO$_3$ (1×30 mL) and brine (2×30 mL). Finally, the solvent was removed under reduced pressure. NaH (60% on mineral oil 13.5 mmol, 0.54 g) was added to a solution of the crude product in dry DMF (11 mL) and the mixture was heated at 80° C. for 4 h, then the reaction mixture was allowed to reach room temperature. A saturated ammonium chloride solution (10 mL) was added to the mixture and the final mixture was washed with DCM (2×20 mL) and then the mixture was acidified with (2 N) HCl and extracted with DCM (3×10 mL). The organic layer was washed with brine (2×10 mL) dried over Na$_2$SO$_4$ anhydrous, concentrated under reduced pressure and filtrate on silica pad. The silica pad was washed 3 times with a DCM-MeOH 95-5 all the washings were collected together and the solvent was removed under reduced pressure to afford the titled compound (0.49 g, yield 57%).

C$_{17}$H$_{20}$N$_2$O$_4$ Mass (calculated) [316.14]. found [M+H]$^+$= 317.3.

LC RT=1.28 (method i)

¹H-NMR (CDCl₃): 1.09 (2H, q); 1.46 (2H, q); 1.80 (2H, d); 2.30 (1H, t); 3.57 (2H, d); 3.91 (2H, s); 7.00 (1H, d); 7.32 (1H, t); 7.48 (1H, t); 7.97 (1H, d); 8.64 (1H, s).

4-[trans-4-(4-pyridin-2-yl-piperazine-1-carbonyl)-cyclohexylmethyl]-3,4-dihydro-1H-benzo[e][1,4]diazepine-2,5-dione

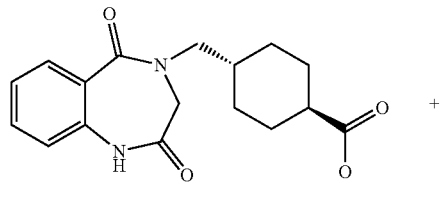

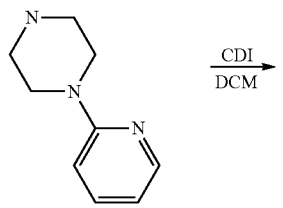

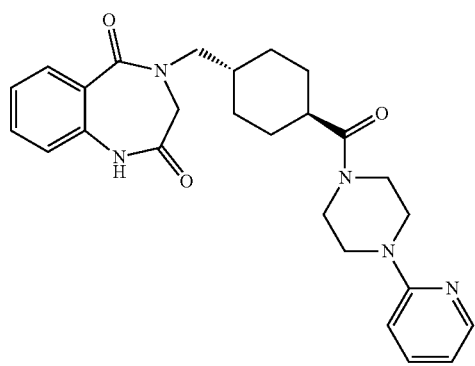

CDI (0.18 mmol, 0.03 g) was added to a solution of trans-4-(2,5-Dioxo-1,2,3,5 tetrahydrobenzo[e][1,4]diazepin-4-ylmethyl)-cyclohexanecarboxylic acid (0.16 mmol, 0.05 g) in dry DCM (1 mL) under argon. After 1 h at room temperature, 1-Pyridin-2-yl-piperazine (0.24 mmol, 35 μL) was added and the reaction mixture was left stirring at room temperature under argon overnight. The DCM solution was washed with water, the solvent was removed under reduced pressure and the crude purified by column chromatography on silica gel using DCM/MeOH 95/5 as eluent to give 45 mg (yield 59%) of the titled compound.

C26H31N5O3; Mass calculated [461.24]. found [M+H]+= 462 m/z.

LC-RT=8.9 (method g)

Example 14 (Method I2)

1-Methyl-4-[trans-4-(4-pyridin-2-yl-piperazine-1-carbonyl)-cyclohexylmethyl]-3,4-dihydro-1H-benzo[e][1,4]diazepine-2,5-dione trans-4-(1-Methyl-2,5-dioxo-1,2,3,5-tetrahydro-benzo[e][1,4]diazepin-4-ylmethyl)-cyclohexanecarboxylic acid methyl ester

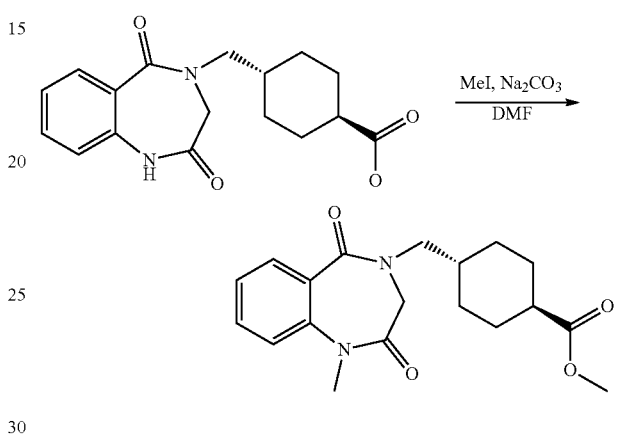

A stirred solution of trans-4-(2,5-Dioxo-1,2,3,5-tetrahydro-benzo[e][1,4]diazepin-4-ylmethyl)-cyclohexanecarboxylic acid (0.54 mmol, 0.17 g) in DMF dry (4 ml) under argon was sequentially added MeI (5.4 mmol, 0.34 mL) and Na₂CO₃ (3.2 mmol, 0.34 g). The mixture was irradiated in the microwave at 100° C. for 1.5 h. After reaction completion the mixtures was diluted with DCM (5 mL) and washed with water (2×10 mL). The organic phase was dried over Na₂SO₄ anhydrous and the solved was removed under reduced pressure. Finally, the crude product was purified by flash chromatography on silica (AcOEt-ETP gradient from 20:80 to 50:50) to obtain titled compound (0.09 g, yield 50%).

C₁₉H₂₄N₂O₄ Mass (calculated) [344.17]. found [M+H]⁺= 345.4.

LC RT=1.79 (method i)

¹H-NMR (CDCl₃): 1.11 (2H, q); 1.47 (2H, q); 1.81 (1H, d); 2.01 (2H, t); 2.28 (1H, t); 3.41 (3H, s); 3.57 (2H, d); 3.74 (3H, s); 4.01 (1H, d); 7.23 (1H, d); 7.33 (1H, t); 7.54 (1H, t); 7.89 (1H, d).

trans-4-(1-Methyl-2,5-dioxo-1,2,3,5-tetrahydro-benzo[e][1,4]diazepin-4-ylmethyl)-cyclohexanecarboxylic acid

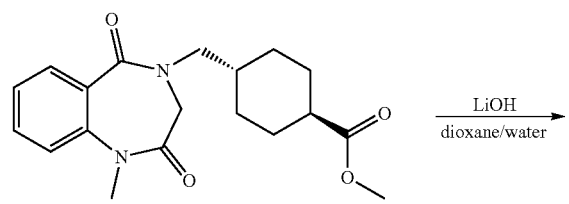

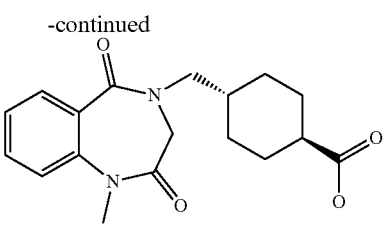

LiOH (0.77 mmol, 0.02 g) was added to a solution of trans-4-(1-Methyl-2,5-dioxo-1,2,3,5-tetrahydro-benzo[e][1,4]diazepin-4-ylmethyl)-cyclohexane carboxylic acid methyl ester (0.64 mmol, 0.22 g) in 1:1 dioxane/water (16 mL) at 0° C. After 1 h at 0° C. the ice bath was removed and the mixture was allowed to reach room temperature. The reaction mixture was washed with DCM (1×20 mL). To the aqueous layer HCl 2N was added until acid pH, then extract with DCM (3×15 mL). The organic layer was washed with brine dried over $Na_2SO_4$ anhydrous and the solvent was removed under reduced pressure to obtain the titled compound (0.18 g, yield 85%).

$C_{18}H_{22}N_2O_4$ Mass (calculated) [330.16]. found $[M+H]^+=$ 331.3.

LC RT=1.41 (method i)

$^1$H-NMR (CDCl$_3$): 1.42 (2H, q); 1.52 (2H, q); 1.77 (2H, t); 2.08 (2H, t); 2.32 (1H, t); 3.41 (3H, s); 3.57 (2H, d); 4.08 (1H, d); 4.01 (1H, d); 7.21 (1H, d); 7.30 (1H, t); 7.54 (1H, t); 7.91 (1H, d).

1-Methyl-4-[trans-4-(4-pyridin-2-yl-piperazine-1-carbonyl)-cyclohexyl methyl]-3,4-dihydro-1H-benzo[e][1,4]diazepine-2,5-dione

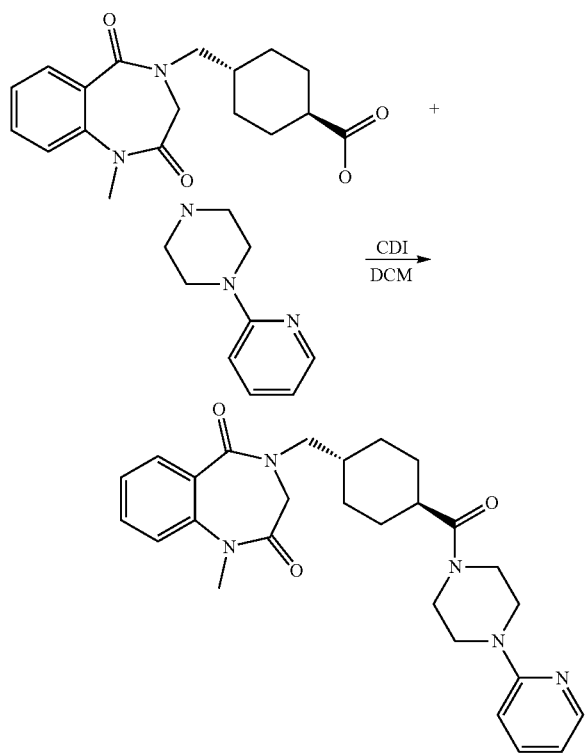

Solid CDI (0.18 mmol, 0.03 g) was added to a solution of trans-4-(1-Methyl-2,5-dioxo-1,2,3,5-tetrahydro-benzo[e][1,4]diazepin-4-ylmethyl)-cyclo hexanecarboxylic acid (0.16 mmol, 0.05 g) in dry DCM (1 mL) under argon. After 1 h at room temperature, 1-Pyridin-2-yl-piperazine (0.22 mmol, 32 μL) was added and the reaction mixture was left stirring at room temperature under argon overnight. The solvent was removed under reduced pressure and the crude purified by column chromatography on silica gel using DCM/MeOH 95/5 as eluent to give 42 mg (yield 59%) of the titled compound $C_{27}H_{33}N_5O_3$; Mass calculated [475.26]. found $[M+H]^+=$ 476.2.

LC-RT=9.8 (method h)

Example 15 (Method M)

1-Methyl-3-[trans-4-(4-pyridin-2-yl-piperazine-1-carbonyl)-cyclohexylmethyl]-1,5-dihydro-benzo[d][1,3]diazepine-2,4-dione trans-4-{[2-(2-Nitro-phenyl)-acetylamino]-methyl}-cyclohexanecarboxylic acid methyl ester

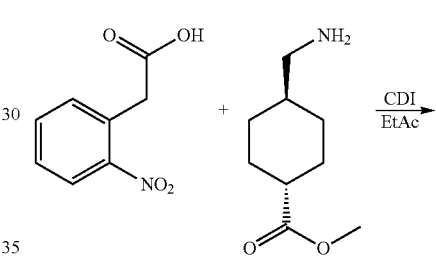

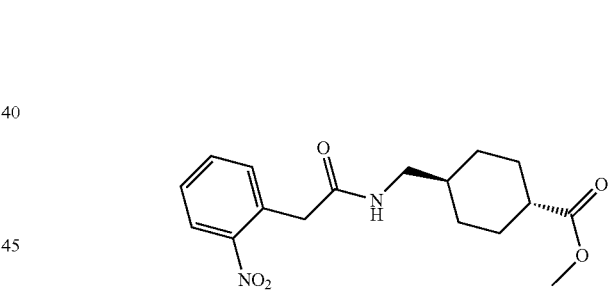

CDI (27.6 mmol, 4.47 g) was added portion wise to a stirring solution of o-nitrophenyl acetic acid (27.6 mmol, 5.00 g) in ethyl acetate (20 mL) at room temperature. The mixture was left stirring for 1 h and then was sequentially added of a solution of 4-Aminomethyl-cyclohexanecarboxylic acid methyl ester hydrogen chloride salt in ethyl acetate (20 mL), triethyl amine (72.5 mmol, 10 mL), DCM (5 mL) and acetone (5 mL). The final mixture was stirred at room temperature overnight. The reaction mixture was filtered through a paper filter, the filtered solution was washed with a (1N) NaOH (2×15 mL) and then with brine, the organic phase was dried over anhydrous $Na_2SO_4$, the solvent was removed under reduced pressure to obtain the titled compound. (8.2 g, 90%).

$C_{17}H_{22}N_2O_5$ Mass (calculated) [334.17]. found $[M+H]^+=$ 335.4.

LC RT=1.96 (method i)

$^1$H-NMR (CDCl$_3$): 0.98 (2H, q); 1.47 (2H, q); 1.49 (2H, t); 1.78 (2H, d); 2.01 (2H, d); 2.19 (1H, t); 3.13 (2H, t); 3.65 (3H, s); 3.83 (2H, s); 5.96 (1H, d); 7.30 (1H, broad); 7.49 (1H, t); 7.51 (1H, d); 7.64 (1H, t); 803 (1H, d).

trans-4-{[2-(2-amino-phenyl)-acetylamino]-methyl}-cyclohexane carboxylic acid methyl ester

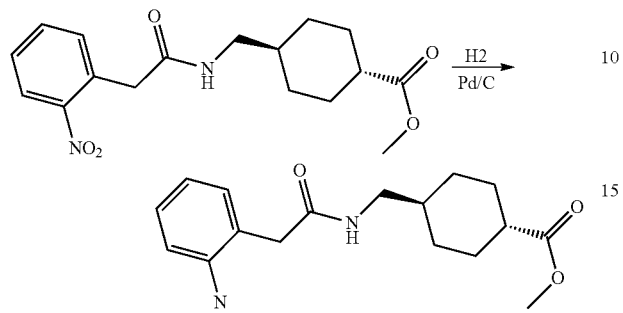

A solution of trans-4-{[2-(2-Nitro-phenyl)-acetylamino]-methyl}-cyclohexanecarboxylic acid methyl ester (4 g) in MeOH (600 mL) was submitted to continuous flow rate hydrogenation by H-Cube (ThalesNano®) using a 10% Pd/C cartridge (small cartridge, full hydrogen mode, flux 0.6 ml/min, P=1 atm). Finally, the solvent was removed under reduced pressure to obtain the titled compound (3.64 g, quantitative yield).

$C_{17}H_{24}N_2O_3$ Mass (calculated) [304.18]. found $[M+H]^+$= 305.4.

LC RT=1.34 (method i)

$^1$H-NMR (CDCl$_3$): 0.91 (2H, q); 1.41 (2H, q); 1.71 (2H, d); 1.97 (2H, d); 2.19 (1H, t); 3.06 (2H, t); 3.49 (2H, s); 3.67 (3H, s); 5.75 (1H, broad); 6.74 (1H, d); 6.76 (1H, d); 7.04 (1H, d); 7.13 (1H, t).

trans-4-(2,4-Dioxo-1,2,4,5-tetrahydro-benzo[d][1,3]diazepin-3-ylmethyl)-cyclohexanecarboxylic acid methyl ester

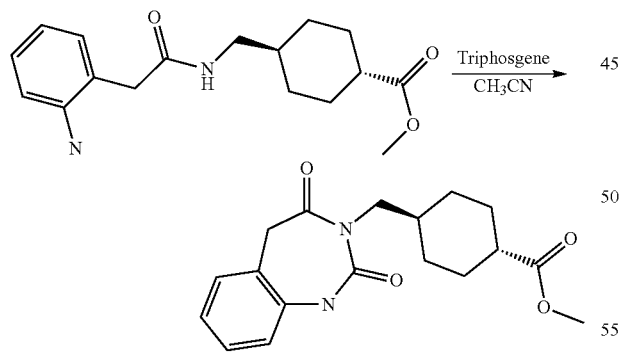

Triphosgene (1.3 mmol, 0.39 g) was added portion wise to a solution of trans-4-{[2-(2-amino-phenyl)-acetylamino]-methyl}-cyclohexanecarboxylic acid methyl ester (2.6 mmol, 0.75 g) in dry CH$_3$CN (20 mL) under argon at 0° C. Then the mixture was heated at 80° C. for 1 h with microwave irradiation. The excess of reagent was quenched by careful addition of H$_2$O (2 mL), the solvent was removed under reduced pressure and the crude was purify by flash chromatography on silica (EtOAc-ETP 10:90 to 50:50) to obtain the titled compound (0.24 g, yield 30%).

$C_{18}H_{22}N_2O_4$ Mass (calculated) [330.16]. found $[M+H]^+$= 331.5.

LC RT=1.95 (method i)

$^1$H-NMR (CDCl$_3$): 0.98 (2H, q); 1.29 (2H, q); 1.54 (1H, d); 1.57 (1H, d); 1.89 (2H, d); 2.16 (1H, t); 3.64 (3H, s); 3.73 (2H, d); 3.78 (2H, s); 7.06 (1H, d); 7.25 (1H, t); 7.32 (2H, d); 7.78 (1H, s).

trans-4-(1-Methyl-2,4-dioxo-1,2,4,5-tetrahydro-benzo[d][1,3]diazepin-3-ylmethyl)-cyclohexanecarboxylic acid methyl ester

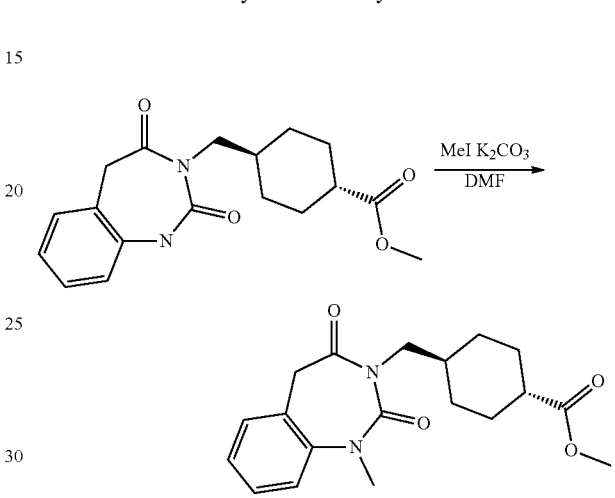

To a stirred solution of trans-4-(2,4-Dioxo-1,2,4,5-tetrahydro-benzo[d][1,3]diazepin-3-ylmethyl)-cyclohexanecarboxylic acid methyl ester (1 mmol, 0.35 g) in DMF dry (6 mL) under argon was sequentially added K$_2$CO$_3$ (1.6 mmol, 0.22 g) and MeI (2.2 mmol, 140 µL). The mixture was stirred at room temperature overnight. Then H$_2$O (10 mL) was added and the solution was loaded on a C18 cartridge, wash with water (3×5 mL) and then the desired product was eluted with MeOH. The solvent was removed under reduced pressure to give the pure titled compound (0.29 g, yield 80%).

$C_{19}H_{24}N_2O_4$ Mass (calculated) [344.17]. found $[M+H]^+$= 345.4.

LC RT=2.15 (method i)

$^1$H-NMR (CDCl$_3$): 0.82 (2H, q); 1.27 (2H, q); 1.41 (1H, d); 1.49 (2H, t); 1.87 (2H, d); 3.53 (3H, s); 3.61 (3H, s); 3.82 (2H, t); 7.27 (2H, m); 7.32 (1H, d); 7.43 (1H, t).

trans-4-({2-[2-(Carboxy-methyl-amino)-phenyl]-acetylamino}-methyl)-cyclohexanecarboxylic acid

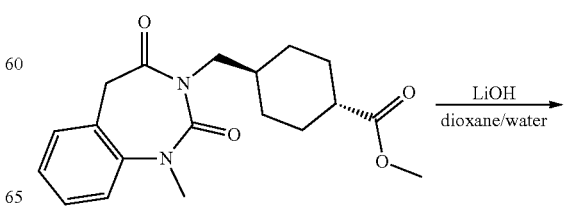

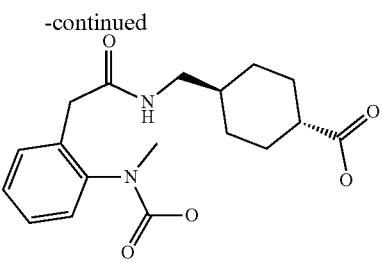

LiOH (1.3 mmol, 0.03 g) was added to a solution of trans-4-(1-Methyl-2,4-dioxo-1,2,4,5-tetrahydro-benzo[d][1,3]diazepin-3-ylmethyl)-cyclohexane carboxylic acid methyl ester (0.84 mmol, 0.29 g) in dioxane (3 mL) and water (3 mL) at 0° C. The mixture was stirred at 0° C. for 2 h. The reaction mixture was washed with DCM, then HCl (1N) was added until reached pH 1, then extract with DCM (3×10 mL) and AcOEt (3×10 mL). The organic layers were washed with brine (2×10 mL) dried over $Na_2SO_4$ collected together and concentrated under reduced pressure to give the title compound in quantitative yield (0.29 g).

$C_{18}H_{24}N_2O_5$ Mass (calculated) [348.17]. found $[M+H]^+$= 349.4.

LC RT=1.36 (method i)

$^1$H-NMR (DMSO): 0.82 (2H, q); 1.15 (2H, q); 1.56 (2H, d); 1.85 (2H, d); 2.09 (1H, t); 2.82 (2H, t); 3.00 (3H, s); 3.17 (2H, d); 5.37 (1H, broad); 7.20-7.40 (4H, m).

1-Methyl-3-[trans-4-(4-pyridin-2-yl-piperazine-1-carbonyl)-cyclohexyl methyl]-1,5-dihydro-benzo[d][1,3]diazepine-2,4-dione

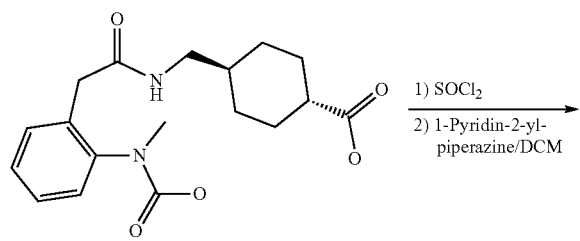

A solution of trans-4-({2-[2-(Carboxy-methyl-amino)-phenyl]-acetylamino}-methyl)-cyclohexanecarboxylic acid (0.14 mmol, 0.05 g) in $SOCl_2$ (0.8 mL) was heated under reflux for 1.5 hours. The solvent was removed under reduced pressure and the residue was put under vacuum overnight. Then crude product was diluted with 5 ml of dry DCM. 1 ml of this stock solution was transferred in a glass vial. 39 μL (0.27 mmol) of 1-Pyridin-2-yl-piperazine were added and the reaction mixture was left stirring at room temperature under argon over night. The solvent was removed under vacuum and the crude purified by preparative HPLC (Method d) to give 26 mg of the titled compound (yield 39%).

C27H33N5O3; Mass calculated [475.26]. found $[M+H]^+$= 476 m/z.

LC-RT=11.5 (method h),

Example 16 (Method N)

3-[trans-4-(4-pyridin-2-yl-piperazine-1-carbonyl)-cyclohexylmethyl]-1,3,4,5-tetrahydro-benzo[d][1,3]diazepin-2-one (2-Nitro-phenyl)-acetaldehyde

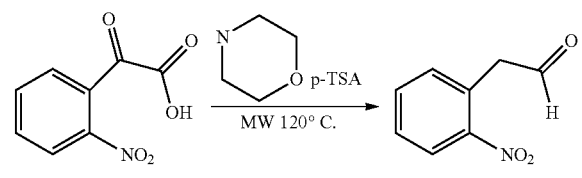

To a solution of 2-Nitrophenylpyruvic acid (1.3 g, 6.22 mmol) in dry dioxane 12 mL was added morpholine (1.5 ml, 17.23 mmol) and a catalytical quantity of p-TSA. Then the resulting mixture was firstly sonicated and then heated in microwave conditions at 120° C. for 30 min. Dioxane was evaporated at reduced pressure and the crude vigourously stirred in 1/1 EtOAc/$H_2O$ (10 mL) overnight. The organic layer was separated and the aqueous phase washed with EtOAc (×2). The combined organic layer was dried over $Na_2SO_4$ anhydrous and solvent was removed at reduced pressure. Finally, the crude product was purified by flash chromatography on silica (ETP to 1:1 ETP/EtOAc) to obtain the titled compound (3.34 g, yield 64%).

LC RT=1.63 (method i)

$^1$H-NMR (CDCl$_3$): 4.12 (2H, s); 7.35 (1H, d); 7.50 (1H, m); 7.64 (1H, m); 8.14 (1H, d); 9.84 (1H, s).

trans-4-{[2-(2-Nitro-phenyl)-ethylamino]-methyl}-cyclohexanecarboxylic acid methyl ester

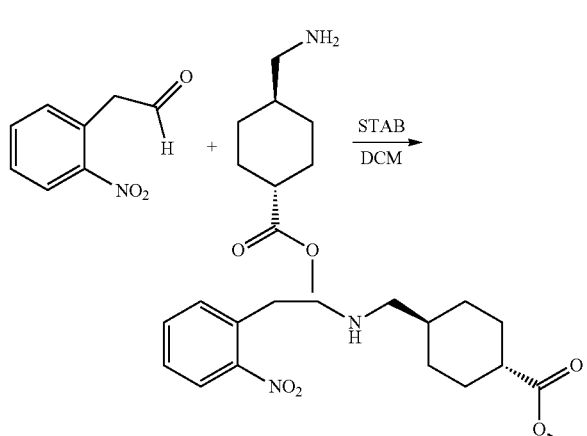

A solution of (2-Nitro-phenyl)-acetaldehyde (1 g, 5.98 mmol), trans-4-Aminomethyl cyclohexanecarboxylic acid methyl ester hydrogen chloride salt (1.37 g, 6.58 mmol) and TEA (0.92 mL, 6.58 mmol) in dry DCM was stirred at room temperature for 2.5 h. Sodium triacetoxy borohydride (2.53 g, 11.96 mmol) was added and the mixture stirred at room temperature for 25 min. Then (2N) HCl was added until acidic pH and the aqueous layer extracted with DCM. The organic layer was washed with a saturated solution of NaHCO$_3$ and dried over Na$_2$SO$_4$ anhydrous and then evaporated to afford crude product. Finally, the crude product was purified by flash chromatography on silica (ETP/EtOAc 9/1→0/1) to obtain the titled compound (0.51 g, yield: 27%).

C$_{17}$H$_{24}$N$_2$O$_4$ Mass calculated [320.17]. found [M+H+]=321.

LC RT=1.56 (method i)

$^1$H-NMR (CDCl$_3$): 0.95 (2H, m); 1.45 (3H, m); 1.85 (2H, d); 1.95 (2H, d); 2.25 (1H, m); 2.50 (2H, dd). 2.90 (2H, m); 3.07 (2H, m); 3.64 (3H, s); 7.35 (2H, m); 7.50 (1H, m); 7.90 (1H, d).

trans-4-{[2-(2-Amino-phenyl)-ethylamino]-methyl}-cyclohexanecarboxylic acid methyl ester

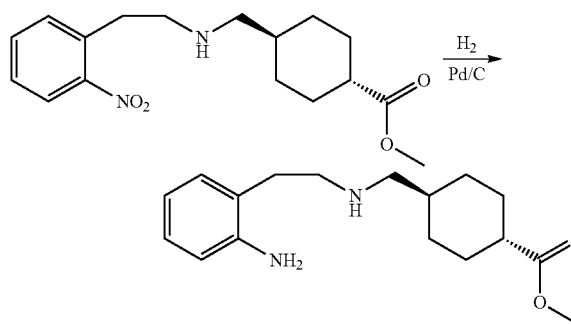

A solution 0.01 M of trans-4-{[2-(2-Nitro-phenyl)-ethylamino]-methyl}-cyclohexanecarboxylic acid methyl ester (2 g, 6.25 mmol) in MeOH (625 mL) with ~1% of glacial AcOH (6.25 mL) was submitted to continuous flow rate hydrogenation by H-Cube (ThalesNano®) using a 10% Pd/C cartridge (small type cartridge, full hydrogen mode, flowrate of 1 mL/min). Finally, the solvent was removed under reduced pressure to obtain the titles compound (3.07 g, quantitative yield).

C$_{17}$H$_{26}$N$_2$O$_4$ Mass calculated [290.20]. found [M+H+]=291.

LC RT=1.12 (method i)

trans-4-(2-Oxo-1,2,4,5-tetrahydro-benzo[d][1,3]diazepin-3-ylmethyl)-cyclohexanecarboxylic acid methyl ester

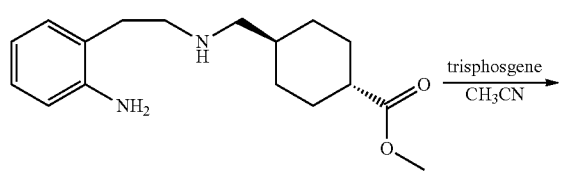

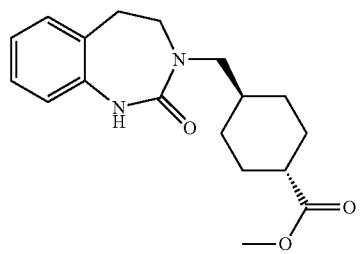

To a solution of trans-4-{[2-(2-Amino-phenyl)-ethylamino]-methyl}-cyclohexanecarboxylic acid methyl ester (2.99 g, 7.97 mmol) in CH$_3$CN (100 mL) at 0° C. under argon was added portion wise triphosgene (1.53 g, 5.15 mmol) over 30 min. The reaction mixture was stirred at 0° C. for 30 min, warmed to room temperature and stirred additionally for 7 h. Then an excess of TEA was added and a precipitate was formed. Solvent was removed under reduced pressure and the crude product purified by flash chromatography on silica to afford the titled compound (4.3 g, yield 59%).

C$_{18}$H$_{24}$N$_2$O$_3$ Mass calculated [316.18]. found [M+H+]=317.

LC RT=2.16 (method i)

trans-4-(2-oxo-1,2,4,5-tetrahydro-benzo[d][1,3]diazepin-3-ylmethyl)-cyclohexanecarboxylic acid

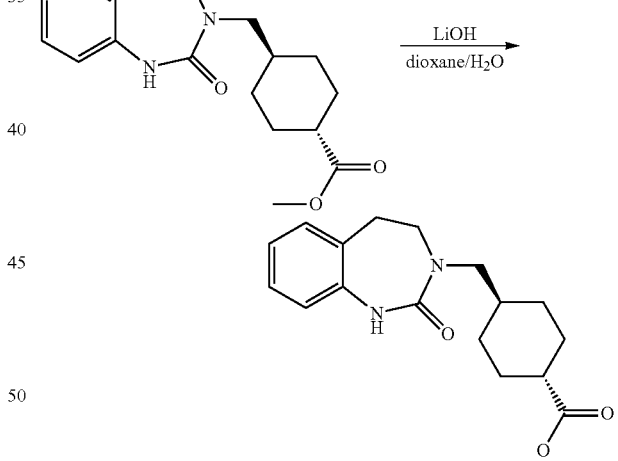

To a solution of trans-4-(2-oxo-1,2,4,5-tetrahydro-benzo[d][1,3]diazepin-3-ylmethyl)-cyclohexanecarboxylic acid methyl ester (0.3 g, 0.95 mmol) in dioxane (7 mL) at 0° C. was added a 2N solution of LiOH. The reaction mixture was stirred at 0° C. for 20 min, allowed to reach ambient temperature and stirred additionally for 2 h. Then a 1N solution of HCl was added until acid pH, and the mixture was extracted with EtOAc, The organic layer was dried over Na$_2$SO$_4$ and solvent removed under reduced pressure to afford the titled compound (0.3 g, 96%).

C17H22N2O3 calculated [302.4]. found [M+H+]=303.4.

LC RT=1.75 (method i)

¹H-NMR (d6-DMSO): 0.90 (2H, m); 1.20 (2H, m); 1.55 (1H, m); 1.61 (2H, d); 1.83 (2H, d); 2.07 (1H, m). 2.90 (2H, m); 3.12 (2H, d); 3.40 (2H, m); 6.77 (1H, m); 7.00 (3H, m); 8.40 (1H, s).

3-[trans-4-(4-pyridin-2-yl-piperazine-1-carbonyl)-cyclohexylmethyl]-1,3,4,5-tetrahydro-benzo[d][1,3]diazepin-2-one

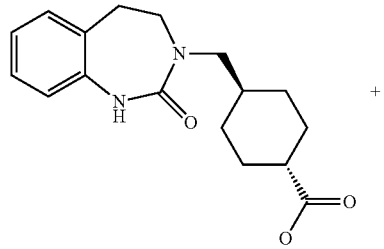

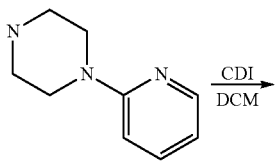

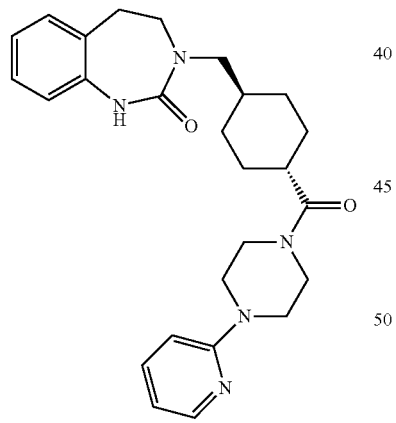

To a suspension of trans-4-(2-oxo-1,2,4,5-tetrahydro-benzo[d][1,3]diazepin-3-ylmethyl)-cyclohexanecarboxylic acid (52 mg, 0.17 mmol) in dry DCM (2 mL) was added CDI (50 mg, 0.31 mmol). The resulting mixture was stirred at room temperature for 2 h, then 1-Pyridin-2-yl-piperazine (44 µL, 0.56 mmol) was added. The reaction mixture was stirred at room temperature for 1.5 h. Then solvent was removed under reduced pressure and crude was purified by crystallization from acetonitrile.

C26H33N5O2; Mass calculated [447.26]. found [M+H]⁺= 448 m/z.

LC-RT=6.1 min (method g)

Example 17 (Method T)

3-[trans-4-(4-Acetyl-piperazine-1-carbonyl)-cyclohexylmethyl]-5-methoxy-1-methyl-1,3-dihydro-benzoimidazol-2-one trans-4-[4-(6-Methoxy-3-methyl-2-oxo-2,3-dihydro-benzoimidazol-1-ylmethyl)-cyclohexanecarbonyl]-piperazine-1-carboxylic acid tert-butyl ester

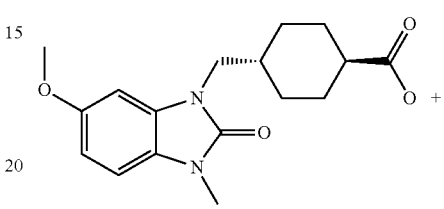

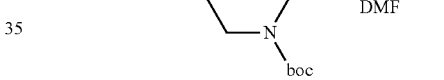

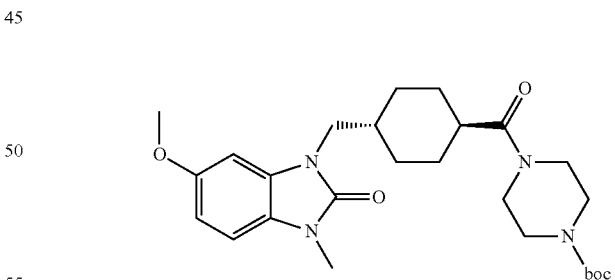

Triethyl amine (0.39 ml, 2.77 mmol) was added to solution of HATU (1.05 g, 2.77 mmol) and trans-4-(6-Methoxy-3-methyl-2-oxo-2,3-dihydro-benzoimidazol-1-ylmethyl)-cyclohexanecarboxylic acid (0.8 g, 2.5 mmol) in DMF (15 ml). The mixture was stirred at room temperature for 20 minutes and then tert-butyl-1-piperazinecarboxylate (0.47 g, 2.52 mmol) was added. The mixture was stirred at room temperature overnight, the solvent was removed under reduced pressure and the crude product was dissolved in DCM (50 ml). The organic solution was washed with HCl 1M (2×40 ml) and then with a saturated solution of NaHCO₃. The organic solution was dried over Na$_2$SO$_4$, filtered and the solvent removed. Purification by silica column using cyclohexane/EtOAc (8/1) as eluent gave the titled compound (960 mg, 78%).

C26H38N4O5; Mass calculated [486.62]. found [M+H]$^+$= 487.4 m/z.

LC-RT=1.46 min (method f)

5-Methoxy-1-methyl-3-[trans-4-(piperazine-1-carbonyl)cyclohexyl methyl]-1,3-dihydro-benzoimidazol-2-one

Trifluoro acetic acid (8 ml) was added to a solution of trans-4-[4-(6-Methoxy-3-methyl-2-oxo-2,3-dihydro-benzoimidazol-1-ylmethyl)-cyclohexanecarbonyl]-piperazine-1-carboxylic acid tert-butyl ester in DCM (19 ml). The solution was stirred at room temperature overnight and then 10 ml of water were added. The mixture was concentrated under reduced pressure and DCM (20 ml) were added. The organic solution was washed with a saturated solution of NaHCO$_3$ (2×20 ml), dried over Na$_2$SO$_4$, filtered and the solvent evaporated to give the titled compound C21H30N4O3; Mass calculated [386.50]. found [M+H]$^+$= 387.2 m/z.

LC-RT=0.88 min (method f)

3-[trans-4-(4-Acetyl-piperazine-1-carbonyl)-cyclohexylmethyl]-5-methoxy-1-methyl-1,3-dihydro-benzoimidazol-2-one

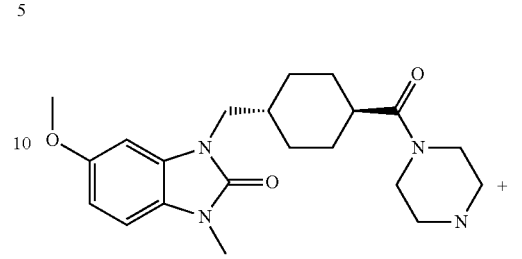

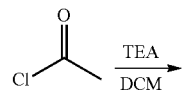

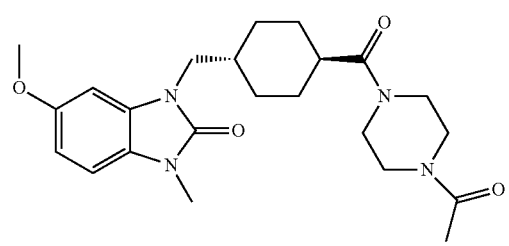

5-Methoxy-1-methyl-3-[trans-4-(piperazine-1-carbonyl)-cyclohexylmethyl]-1,3-dihydro-benzoimidazol-2-one (85 mg, 0.22 mmol) was dissolved in anhydrous DCM (4 ml). Triethyl amine (0.12 ml, 0.66 mmol) and acetyl chloride (0.02 ml, 0.26 mmol) were added and the mixture was stirred at room temperature overnight. The solution was washed with saturated NaHCO$_3$ the organic phase was concentrated and the crude product purified on silica column using EtOAc as eluent to give the titled compound (60 mg, 64%).

C23H32N4O4; Mass calculated [428.54]. found [M+H]$^+$= 429.4 m/z.

LC-RT=1.07 min (method f)

$^1$H-NMR (CDCl$_3$): 1.08-1.20 (2H, m), 1.49-1.58 (2H, m), 1.64-1.90 (5H, m), 2.1 (3h, s), 2.36-2.49 (1H, m), 3.38 (3H, s), 3.44-3.50 (4H, m), 3.53-3.64 (4H, m), 3.70 (2h, d, J=8 Hz), 3.85 (3H, s), 6.57 (1H, d, J=2 Hz), 6.64 (1H, dd, J=8 Hz, J=2 Hz), 6.85 (1H, d, J=8 Hz)

Examples 18-211 listed in table 1 (where *=commercial and **=Not applicable) were made or purchased according to the method of column 3 and characterised by NMR (data not shown), and HPLC-MS (columns 4, 6, 7 and 8).

| Example | Structure | Synthesis method | Retention time | Expected MW | Found MW (M + 1) | Purity | Analytical Method |
|---|---|---|---|---|---|---|---|
| 18 | 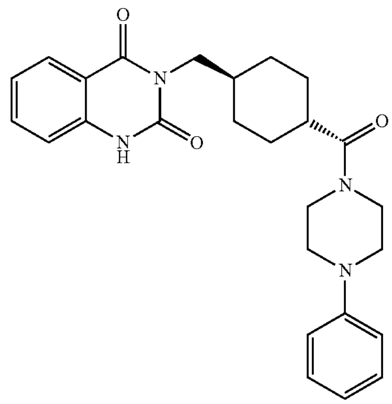 | c* |  | 446.6 |  |  |  |
| 19 | 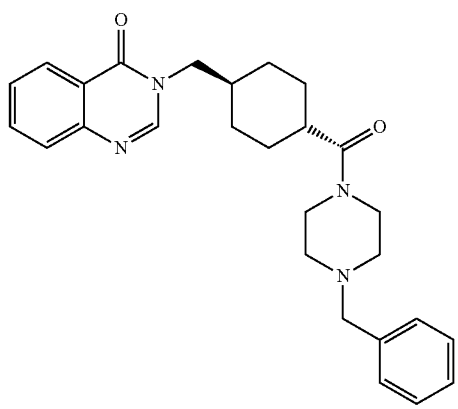 | c* |  | 446.6 |  |  |  |
| 20 | 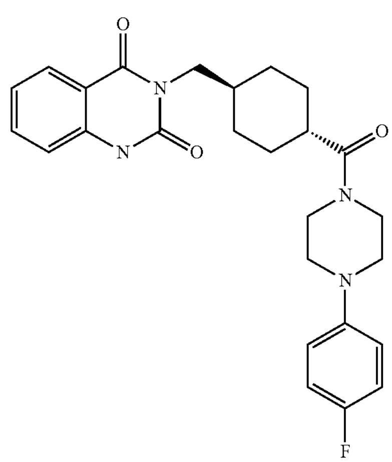 [SMILES: O=c1[nH]c2ccccc2c(=O)n1C[C@H]1CC[C@H](C(=O)N2CCN(c3ccc(F)cc3)CC2)CC1] | c* |  | 464.5 |  |  |  |

-continued

| Example | Structure | Synthesis method | Retention time | Expected MW | Found MW (M + 1) | Purity | Analytical Method |
|---|---|---|---|---|---|---|---|
| 21 | 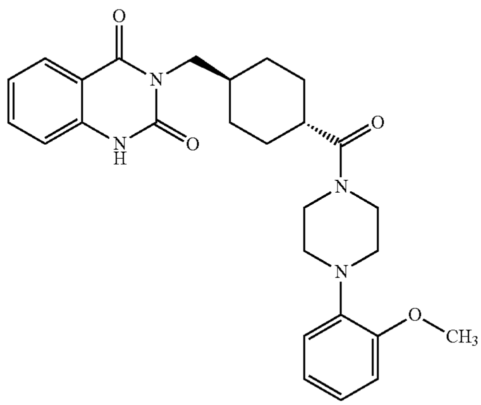 [SMILES: COc1ccccc1N1CCN(C(=O)[C@H]2CC[C@H](Cn3c(=O)[nH]c4ccccc4c3=O)CC2)CC1] | A1 | 3.2 | 476.6 | 477.6 | 93 | a |
| 22 | 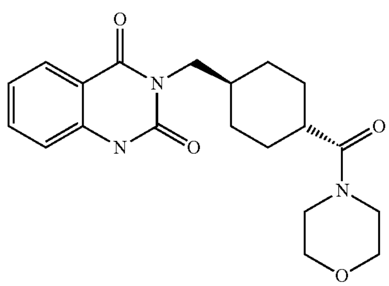 | c* |  | 371.4 |  |  |  |
| 23 | 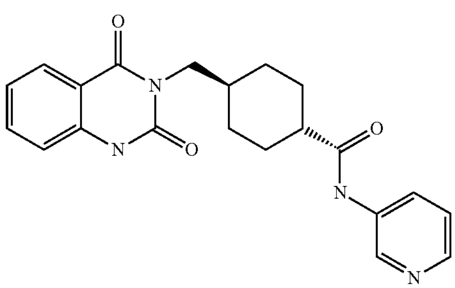 | c* |  | 378.4 |  |  |  |
| 24 | 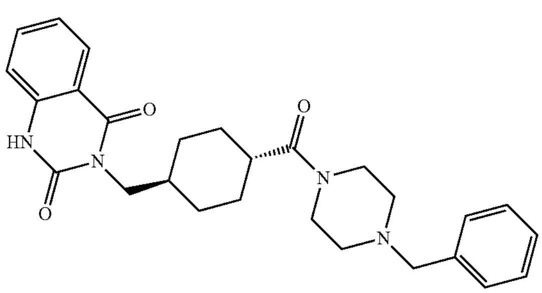 [SMILES: O=c1[nH]c2ccccc2c(=O)n1C[C@H]1CC[C@H](C(=O)N2CCN(Cc3ccccc3)CC2)CC1] | A1 | 1.9 | 460.6 | 461.6 | 100 | a |
| 25 | 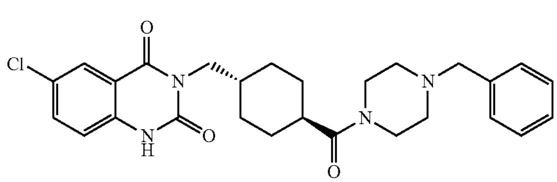 [SMILES: O=c1[nH]c2ccc(Cl)cc2c(=O)n1C[C@H]1CC[C@H](C(=O)N2CCN(Cc3ccccc3)CC2)CC1] | A1 | 2.2 | 495.0 | 496.0 | 100 | a |

-continued

| Example | Structure | Synthesis method | Retention time | Expected MW | Found MW (M + 1) | Purity | Analytical Method |
|---|---|---|---|---|---|---|---|
| 26 | 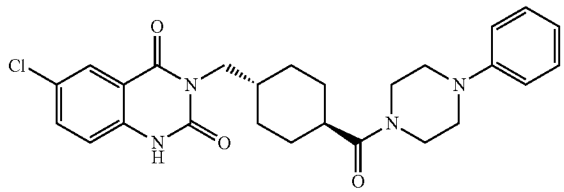 [SMILES: O=c1[nH]c2ccc(Cl)cc2c(=O)n1C[C@H]1CC[C@H](C(=O)N2CCN(c3ccccc3)CC2)CC1] | A1 | 3.9 | 481.0 | 482.0 | 95 | a |
| 27 | 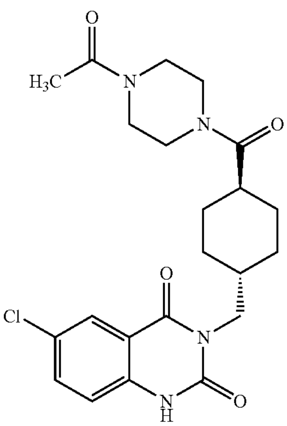 [SMILES: CC(=O)N1CCN(C(=O)[C@H]2CC[C@H](Cn3c(=O)[nH]c4ccc(Cl)cc4c3=O)CC2)CC1] | A1 | 2.8 | 446.9 | 447.9 | 97 | a |
| 28 | 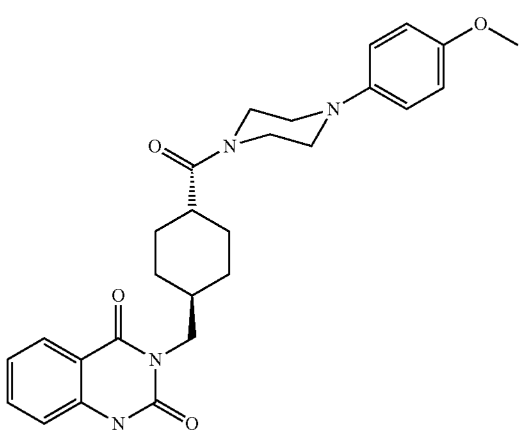 | c* |  | 476.6 |  |  |  |
| 29 | 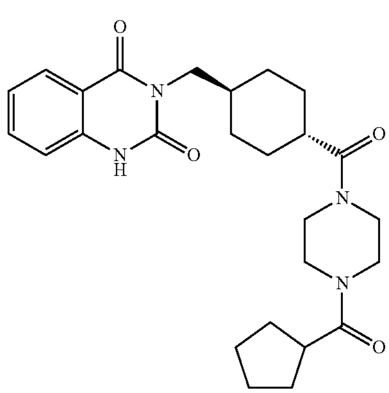 [SMILES: O=C(C1CCCC1)N1CCN(C(=O)[C@H]2CC[C@H](Cn3c(=O)[nH]c4ccccc4c3=O)CC2)CC1] | C1 | 3.1 | 466.6 | 467.6 | 91 | a |

-continued

| Example | Structure | Synthesis method | Retention time | Expected MW | Found MW (M + 1) | Purity | Analytical Method |
|---|---|---|---|---|---|---|---|
| 30 | 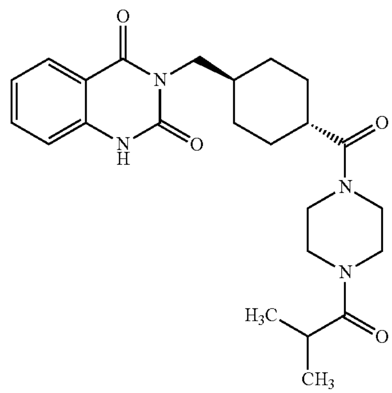 [SMILES: CC(C)C(=O)N1CCN(C(=O)[C@H]2CC[C@H](Cn3c(=O)[nH]c4ccccc4c3=O)CC2)CC1] | C1 | 2.7 | 440.5 | 441.5 | 95 | a |
| 31 | 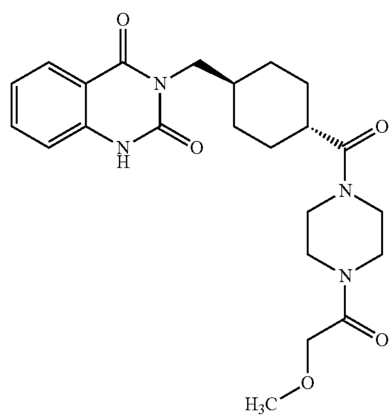 [SMILES: COCC(=O)N1CCN(C(=O)[C@H]2CC[C@H](Cn3c(=O)[nH]c4ccccc4c3=O)CC2)CC1] | C1 | 2.3 | 442.5 | 443.5 | 95 | a |
| 32 | 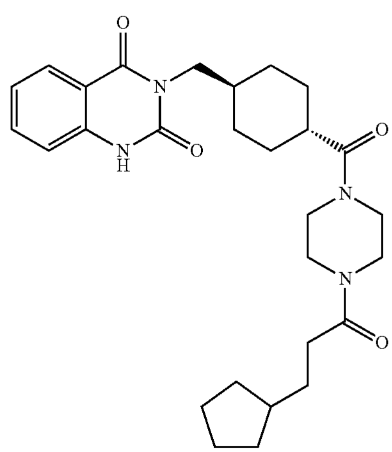 [SMILES: O=C(CCC1CCCC1)N1CCN(C(=O)[C@H]2CC[C@H](Cn3c(=O)[nH]c4ccccc4c3=O)CC2)CC1] | C1 | 3.6 | 494.6 | 495.6 | 95 | a |

-continued

| Example | Structure | Synthesis method | Retention time | Expected MW | Found MW (M + 1) | Purity | Analytical Method |
|---|---|---|---|---|---|---|---|
| 33 | 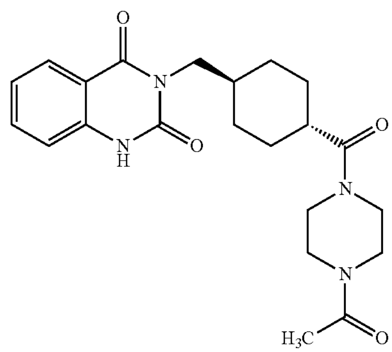 [SMILES: CC(=O)N1CCN(C(=O)[C@H]2CC[C@H](Cn3c(=O)[nH]c4ccccc4c3=O)CC2)CC1] | C1 | 2.3 | 412.5 | 413.5 | 91 | a |
| 34 | 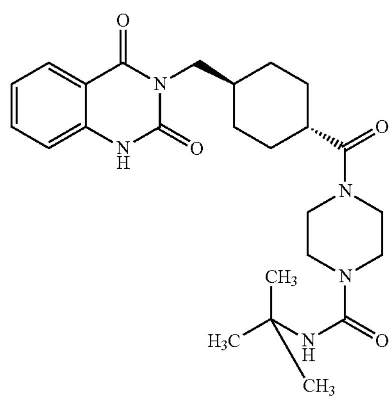 [SMILES: CC(C)(C)NC(=O)N1CCN(C(=O)[C@H]2CC[C@H](Cn3c(=O)[nH]c4ccccc4c3=O)CC2)CC1] | C1 | 2.9 | 469.6 | 470.6 | 95 | a |
| 35 | 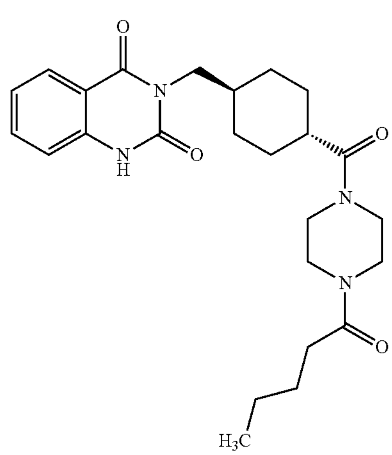 [SMILES: CCCCC(=O)N1CCN(C(=O)[C@H]2CC[C@H](Cn3c(=O)[nH]c4ccccc4c3=O)CC2)CC1] | C1 | 3.0 | 454.6 | 455.6 | 95 | a |

-continued

| Example | Structure | Synthesis method | Retention time | Expected MW | Found MW (M + 1) | Purity | Analytical Method |
|---|---|---|---|---|---|---|---|
| 36 | 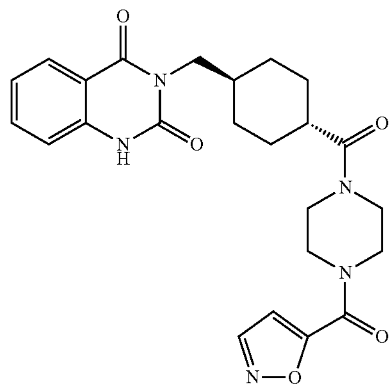 [SMILES: O=C(c1ccno1)N1CCN(C(=O)[C@H]2CC[C@H](Cn3c(=O)[nH]c4ccccc4c3=O)CC2)CC1] | C1 | 2.6 | 465.5 | 466.5 | 97 | a |
| 37 | 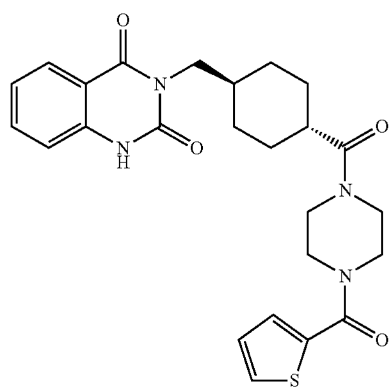 [SMILES: O=C(c1cccs1)N1CCN(C(=O)[C@H]2CC[C@H](Cn3c(=O)[nH]c4ccccc4c3=O)CC2)CC1] | C1 | 2.9 | 480.6 | 481.6 | 98 | a |
| 38 | 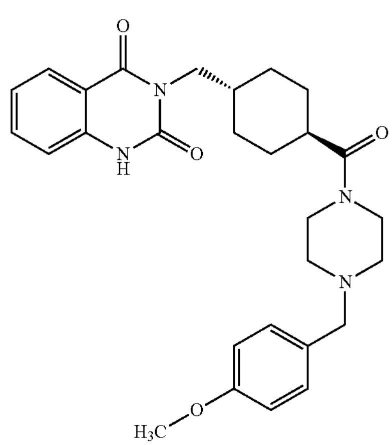 [SMILES: COc1ccc(CN2CCN(C(=O)[C@H]3CC[C@H](Cn4c(=O)[nH]c5ccccc5c4=O)CC3)CC2)cc1] | C1 | 1.9 | 490.6 | 491.6 | 98 | a |

-continued

| Example | Structure | Synthesis method | Retention time | Expected MW | Found MW (M + 1) | Purity | Analytical Method |
|---|---|---|---|---|---|---|---|
| 39 | 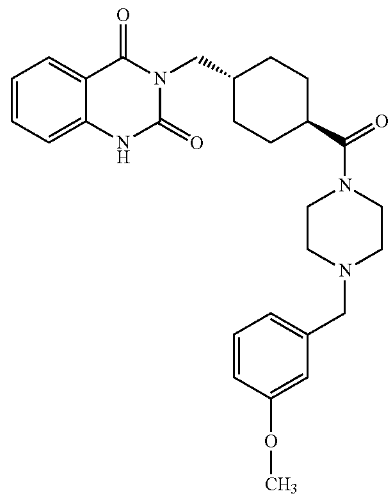 [SMILES: COc1cccc(CN2CCN(C(=O)[C@H]3CC[C@H](Cn4c(=O)[nH]c5ccccc5c4=O)CC3)CC2)c1] | C1 | 2.0 | 490.6 | 491.6 | 98 | a |
| 40 | 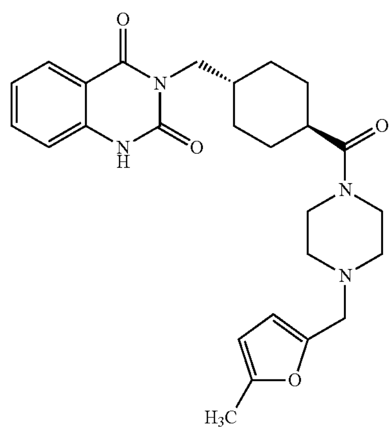 [SMILES: Cc1ccc(CN2CCN(C(=O)[C@H]3CC[C@H](Cn4c(=O)[nH]c5ccccc5c4=O)CC3)CC2)o1] | C1 | 1.9 | 464.6 | 465.6 | 94 | a |
| 41 | 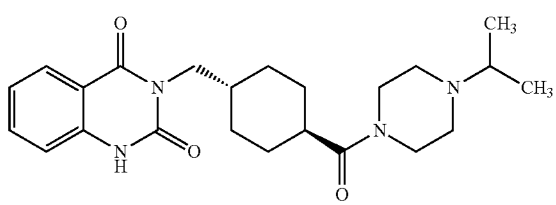 [SMILES: CC(C)N1CCN(C(=O)[C@H]2CC[C@H](Cn3c(=O)[nH]c4ccccc4c3=O)CC2)CC1] | A1 | 1.5 | 412.5 | 413.5 | 98 | a |
| 42 | 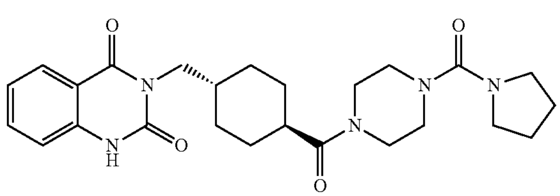 [SMILES: O=C(N1CCCC1)N1CCN(C(=O)[C@H]2CC[C@H](Cn3c(=O)[nH]c4ccccc4c3=O)CC2)CC1] | A1 | 2.8 | 467.6 | 468.6 | 96 | a |
| 43 | 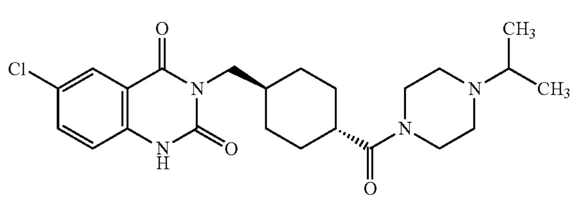 [SMILES: CC(C)N1CCN(C(=O)[C@H]2CC[C@H](Cn3c(=O)[nH]c4ccc(Cl)cc4c3=O)CC2)CC1] | A1 | 3.2 | 447.0 | 448.0 | 93 | a |

-continued

| Example | Structure | Synthesis method | Retention time | Expected MW | Found MW (M + 1) | Purity | Analytical Method |
|---|---|---|---|---|---|---|---|
| 44 | 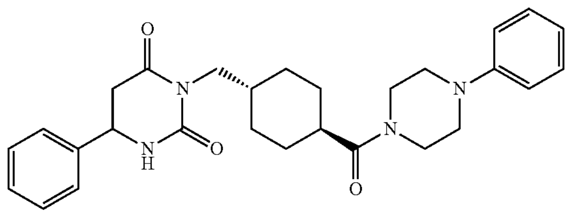 [SMILES: O=C1CC(c2ccccc2)NC(=O)N1C[C@H]1CC[C@H](C(=O)N2CCN(c3ccccc3)CC2)CC1] | E | 6.0 | 474.6 | 475.6 | 96 | a |
| 45 | 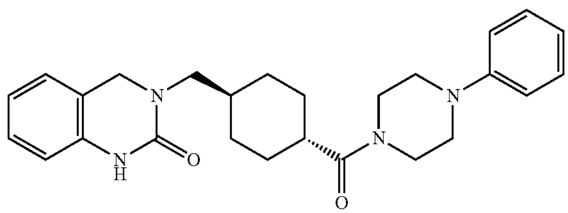 [SMILES: O=C1Nc2ccccc2CN1C[C@H]1CC[C@H](C(=O)N2CCN(c3ccccc3)CC2)CC1] | F | 6.3 | 432.6 | 433.6 | 95 | a |
| 46 | 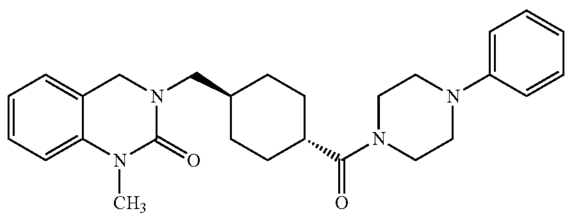 [SMILES: CN1C(=O)N(C[C@H]2CC[C@H](C(=O)N3CCN(c4ccccc4)CC3)CC2)Cc2ccccc21] | F | 6.6 | 446.6 | 447.6 | 95 | a |
| 47 | 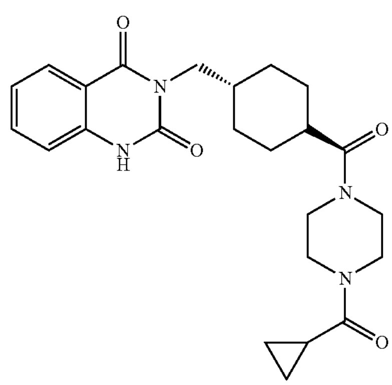 | C1 | 5.3 | 438.5 | 439.5 | 97 | a |
| 48 | 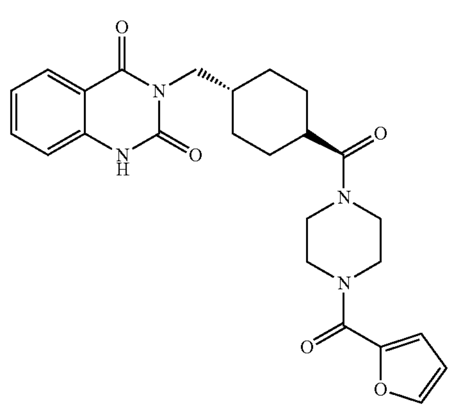 | C1 | 5.2 | 464.5 | 465.5 | 99 | a |

-continued

| Example | Structure | Synthesis method | Retention time | Expected MW | Found MW (M + 1) | Purity | Analytical Method |
|---|---|---|---|---|---|---|---|
| 49 | 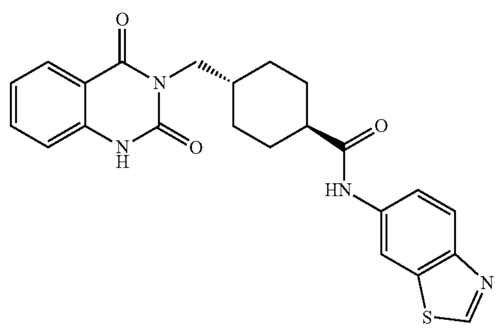 [SMILES: O=c1[nH]c2ccccc2c(=O)n1C[C@H]1CC[C@H](C(=O)Nc2ccc3ncsc3c2)CC1] | A1 | 5.8 | 434.5 | 435.5 | 96 | a |
| 50 | 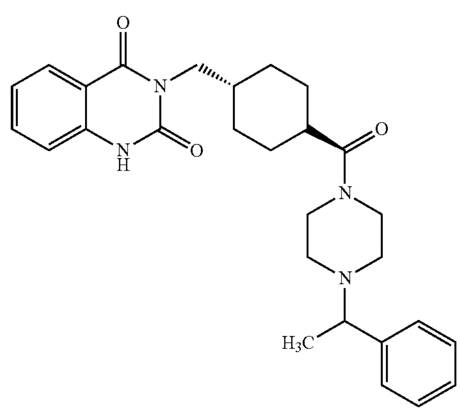 | A1 | 3.5 | 474.6 | 475.6 | 97 | a |
| 51 | 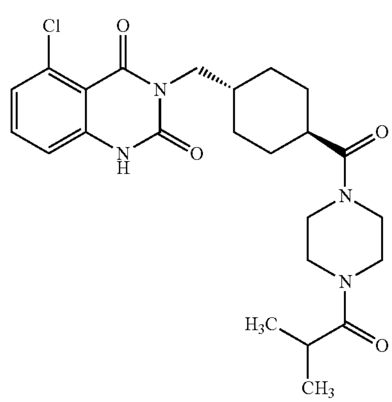 [SMILES: CC(C)C(=O)N1CCN(C(=O)[C@H]2CC[C@H](Cn3c(=O)[nH]c4cccc(Cl)c4c3=O)CC2)CC1] | B | 5.5 | 475.0 | 476.0 | 90 | a |
| 52 | 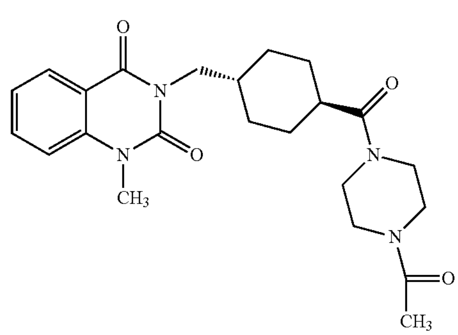 [SMILES: CC(=O)N1CCN(C(=O)[C@H]2CC[C@H](Cn3c(=O)c4ccccc4n(C)c3=O)CC2)CC1] | C2 | 4.8 | 426.5 | 427.5 | 94 | a |

| Example | Structure | Synthesis method | Retention time | Expected MW | Found MW (M + 1) | Purity | Analytical Method |
|---|---|---|---|---|---|---|---|
| 53 | 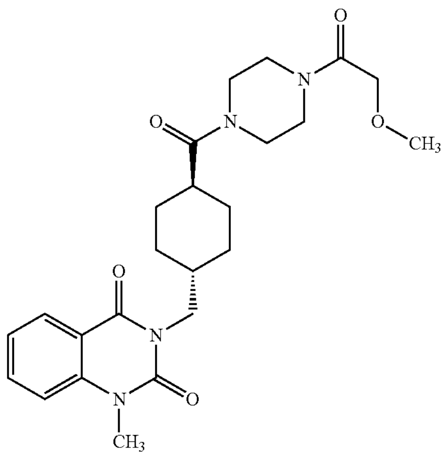 [SMILES: COCC(=O)N1CCN(C(=O)[C@H]2CC[C@H](Cn3c(=O)c4ccccc4n(C)c3=O)CC2)CC1] | C2 | 4.8 | 456.5 | 457.5 | 97 | a |
| 54 | 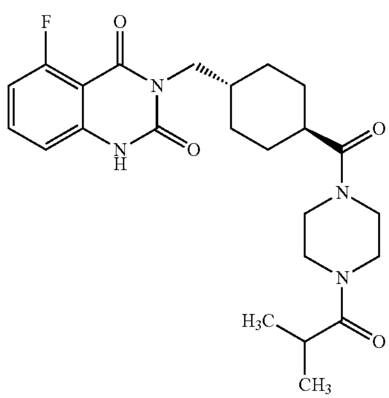 | B | 5.0 | 458.5 | 459.5 | 92 | a |
| 55 | 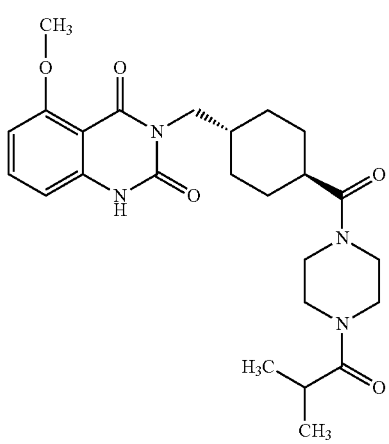 [SMILES: COc1cccc2[nH]c(=O)n(C[C@H]3CC[C@H](C(=O)N4CCN(C(=O)C(C)C)CC4)CC3)c(=O)c12] | B | 4.8 | 470.6 | 471.6 | 94 | a |

-continued
| Example | Structure | Synthesis method | Retention time | Expected MW | Found MW (M + 1) | Purity | Analytical Method |
|---|---|---|---|---|---|---|---|
| 56 | 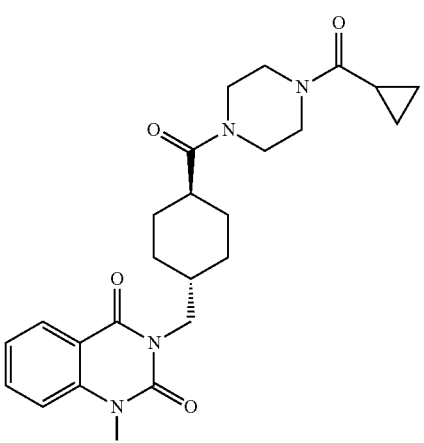 | C2 | 5.3 | 452.6 | 453.6 | 90 | a |
| 57 | 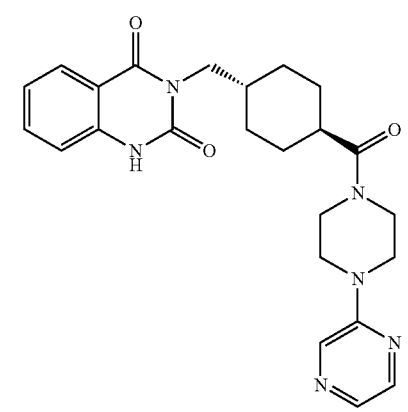 [SMILES: O=c1[nH]c2ccccc2c(=O)n1C[C@H]1CC[C@H](C(=O)N2CCN(c3cnccn3)CC2)CC1] | A1 | 5.4 | 448.5 | 449.5 | 98 | a |
| 58 | 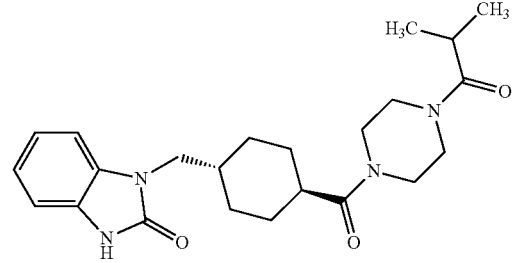 [SMILES: CC(C)C(=O)N1CCN(C(=O)[C@H]2CC[C@H](Cn3c(=O)[nH]c4ccccc43)CC2)CC1] | G3 | 5.1 | 412.5 | 413.5 | 98 | a |
| 59 | 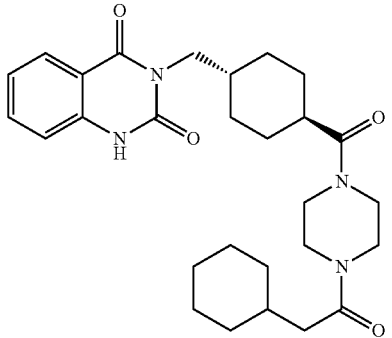 [SMILES: O=C(CC1CCCCC1)N1CCN(C(=O)[C@H]2CC[C@H](Cn3c(=O)[nH]c4ccccc4c3=O)CC2)CC1] | C1 | 6.4 | 494.6 | 495.6 | 95 | a |

| Example | Structure | Synthesis method | Retention time | Expected MW | Found MW (M + 1) | Purity | Analytical Method |
|---------|-----------|------------------|----------------|-------------|------------------|--------|-------------------|
| 60 | 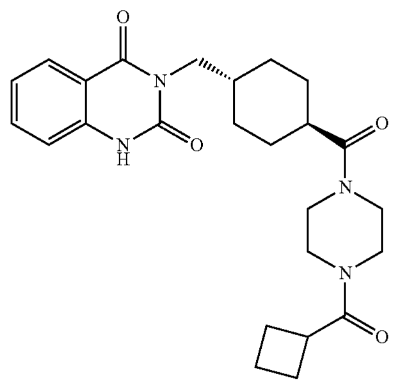 [SMILES: O=C(C1CCC1)N1CCN(C(=O)[C@H]2CC[C@H](Cn3c(=O)[nH]c4ccccc4c3=O)CC2)CC1] | C1 | 5.4 | 452.6 | 453.6 | 90 | a |
| 61 | 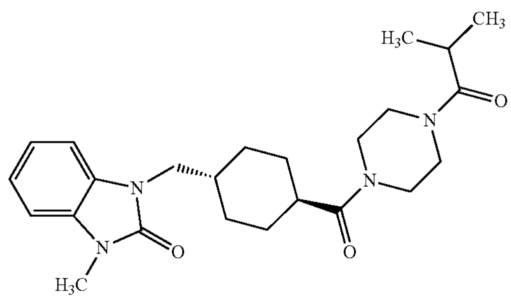 [SMILES: CC(C)C(=O)N1CCN(C(=O)[C@H]2CC[C@H](Cn3c(=O)n(C)c4ccccc43)CC2)CC1] | G3 | 5.4 | 426.6 | 427.6 | 97 | a |
| 62 | 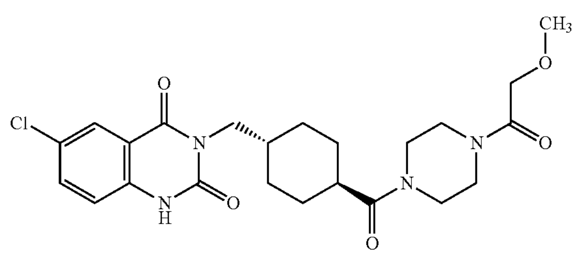 [SMILES: COCC(=O)N1CCN(C(=O)[C@H]2CC[C@H](Cn3c(=O)[nH]c4ccc(Cl)cc4c3=O)CC2)CC1] | C1 | 5.4 | 477.0 | 478.0 | 90 | a |
| 63 | 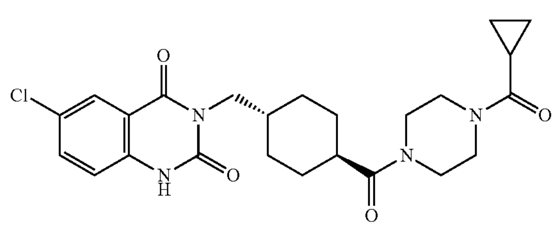 [SMILES: O=C(C1CC1)N1CCN(C(=O)[C@H]2CC[C@H](Cn3c(=O)[nH]c4ccc(Cl)cc4c3=O)CC2)CC1] | C1 | 5.9 | 473.0 | 474.0 | 94 | a |
| 64 | 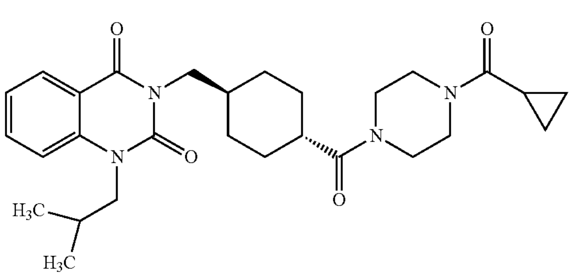 [SMILES: CC(C)Cn1c(=O)n(C[C@H]2CC[C@H](C(=O)N3CCN(C(=O)C4CC4)CC3)CC2)c(=O)c2ccccc21] | C2 | 6.3 | 494.6 | 495.6 | 95 | a |

-continued

| Example | Structure | Synthesis method | Retention time | Expected MW | Found MW (M + 1) | Purity | Analytical Method |
|---|---|---|---|---|---|---|---|
| 65 | 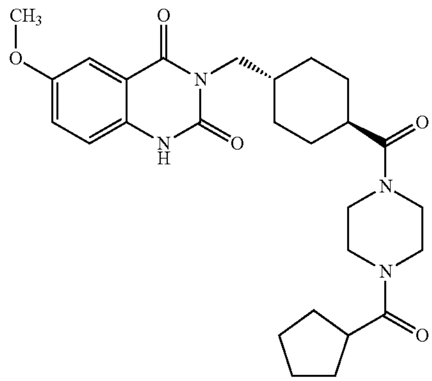 [SMILES: COc1ccc2[nH]c(=O)n(C[C@H]3CC[C@H](C(=O)N4CCN(C(=O)C5CCCC5)CC4)CC3)c(=O)c2c1] | C1 | 5.9 | 496.6 | 497.6 | 93 | a |
| 66 | 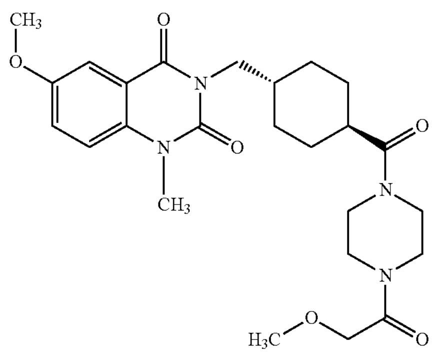 [SMILES: COCC(=O)N1CCN(C(=O)[C@H]2CC[C@H](Cn3c(=O)c4cc(OC)ccc4n(C)c3=O)CC2)CC1] | C1 | 5.1 | 486.6 | 487.6 | 97 | a |
| 67 | 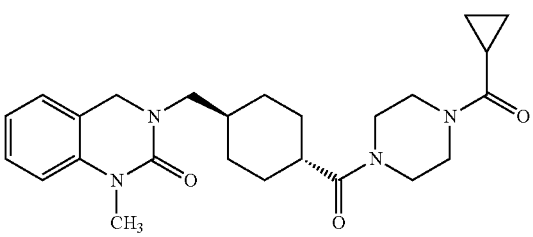 [SMILES: CN1C(=O)N(C[C@H]2CC[C@H](C(=O)N3CCN(C(=O)C4CC4)CC3)CC2)Cc2ccccc21] | F | 5.5 | 438.6 | 439.6 | 90 | a |
| 68 | 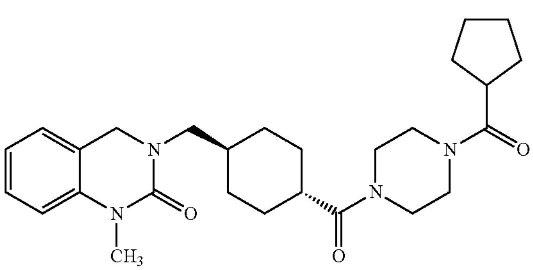 [SMILES: CN1C(=O)N(C[C@H]2CC[C@H](C(=O)N3CCN(C(=O)C4CCCC4)CC3)CC2)Cc2ccccc21] | F | 6.2 | 466.6 | 467.6 | 97 | a |
| 69 | 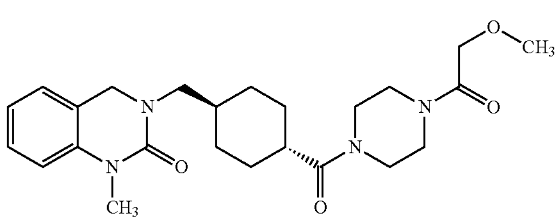 [SMILES: COCC(=O)N1CCN(C(=O)[C@H]2CC[C@H](CN3Cc4ccccc4N(C)C3=O)CC2)CC1] | F | 5.1 | 442.6 | 443.6 | 92 | a |

-continued

| Example | Structure | Synthesis method | Retention time | Expected MW | Found MW (M + 1) | Purity | Analytical Method |
|---|---|---|---|---|---|---|---|
| 70 | 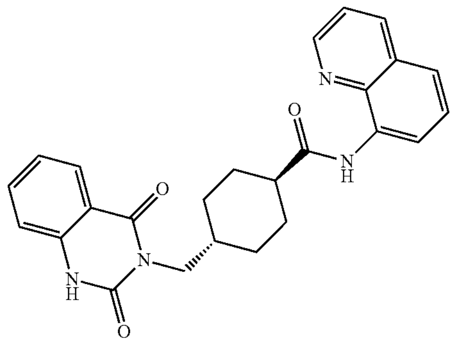 [SMILES: O=c1[nH]c2ccccc2c(=O)n1C[C@H]1CC[C@H](C(=O)Nc2cccc3cccnc23)CC1] | A1 | 6.5 | 428.5 | 429.5 | 95 | a |
| 71 | 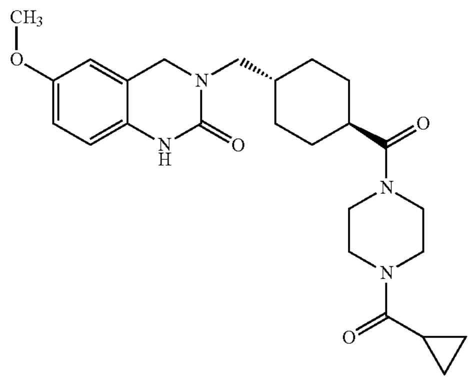 [SMILES: COc1ccc2c(c1)CN(C[C@H]1CC[C@H](C(=O)N3CCN(C(=O)C4CC4)CC3)CC1)C(=O)N2] | F | 4.9 | 454.6 | 455.6 | 99 | a |
| 72 | 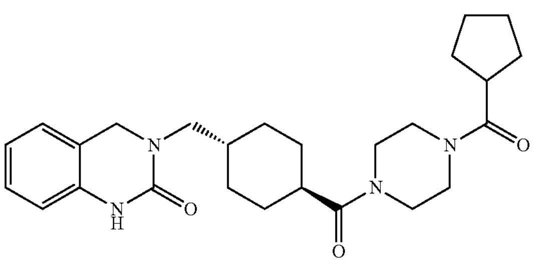 [SMILES: O=C(C1CCCC1)N1CCN(C(=O)[C@H]2CC[C@H](CN3Cc4ccccc4NC3=O)CC2)CC1] | F | 5.7 | 452.6 | 453.6 | 98 | a |
| 73 | 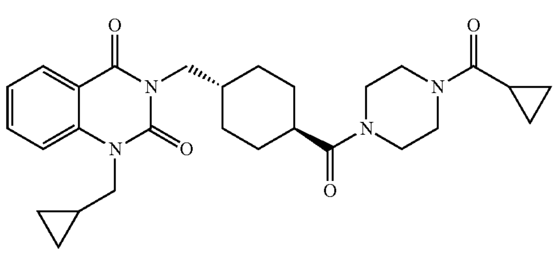 [SMILES: O=C(C1CC1)N1CCN(C(=O)[C@H]2CC[C@H](Cn3c(=O)c4ccccc4n(CC4CC4)c3=O)CC2)CC1] | B | 6.0 | 492.6 | 493.6 | 93 | a |
| 74 | 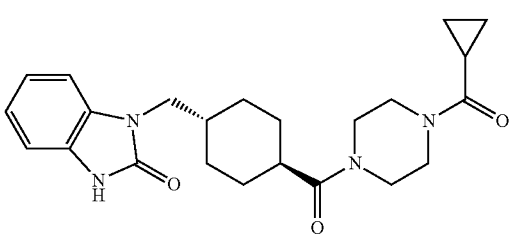 [SMILES: O=C(C1CC1)N1CCN(C(=O)[C@H]2CC[C@H](Cn3c(=O)[nH]c4ccccc43)CC2)CC1] | G3 | 4.8 | 410.5 | 411.5 | 98 | a |

-continued

| Example | Structure | Synthesis method | Retention time | Expected MW | Found MW (M + 1) | Purity | Analytical Method |
|---------|-----------|------------------|----------------|-------------|------------------|--------|-------------------|
| 75 | 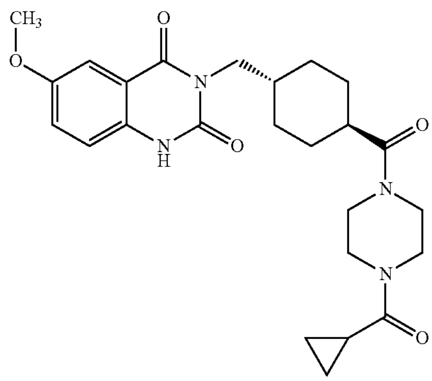 [SMILES: COc1ccc2[nH]c(=O)n(C[C@H]3CC[C@H](C(=O)N4CCN(C(=O)C5CC5)CC4)CC3)c(=O)c2c1] | C1 | 5.3 | 468.6 | 469.6 | 91 | a |
| 76 | 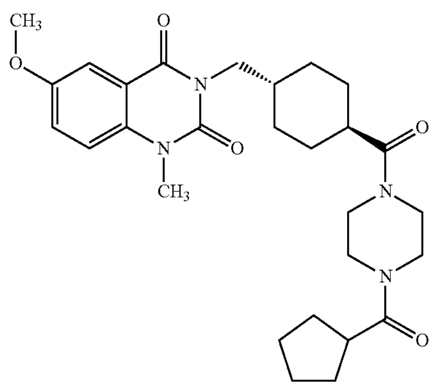 [SMILES: COc1ccc2c(c1)c(=O)n(C[C@H]1CC[C@H](C(=O)N3CCN(C(=O)C4CCCC4)CC3)CC1)c(=O)n2C] | C2 | 6.2 | 510.6 | 511.6 | 96 | a |
| 77 | 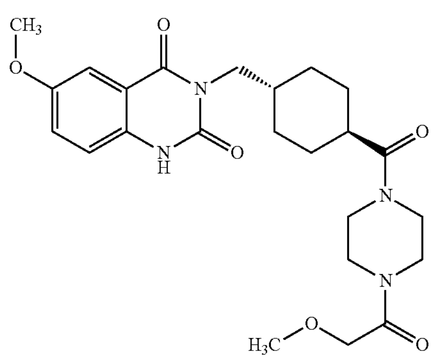 [SMILES: COCC(=O)N1CCN(C(=O)[C@H]2CC[C@H](Cn3c(=O)[nH]c4ccc(OC)cc4c3=O)CC2)CC1] | C1 | 4.8 | 472.5 | 473.5 | 97 | a |
| 78 | 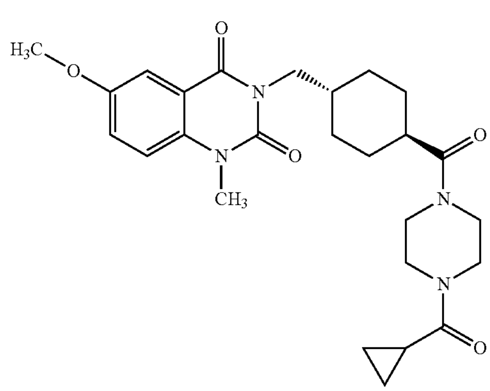 [SMILES: COc1ccc2c(c1)c(=O)n(C[C@H]1CC[C@H](C(=O)N3CCN(C(=O)C4CC4)CC3)CC1)c(=O)n2C] | C1 | 5.4 | 482.6 | 483.6 | 94 | a |

| Example | Structure | Synthesis method | Retention time | Expected MW | Found MW (M + 1) | Purity | Analytical Method |
|---|---|---|---|---|---|---|---|
| 79 | 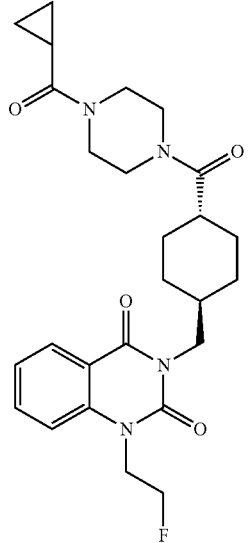 [SMILES: O=C(C1CC1)N1CCN(C(=O)[C@H]2CC[C@H](Cn3c(=O)c4ccccc4n(CCF)c3=O)CC2)CC1] | B | 5.2 | 484.6 | 485.6 | 95 | a |
| 80 | 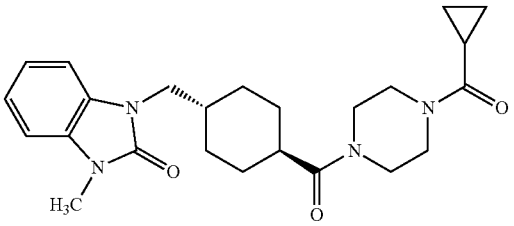 [SMILES: Cn1c(=O)n(C[C@H]2CC[C@H](C(=O)N3CCN(C(=O)C4CC4)CC3)CC2)c2ccccc21] | G3 | 5.2 | 424.5 | 425.5 | 98 | a |
| 81 | 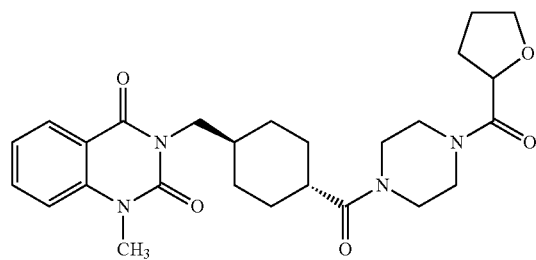 [SMILES: Cn1c(=O)n(C[C@H]2CC[C@H](C(=O)N3CCN(C(=O)C4CCCO4)CC3)CC2)c(=O)c2ccccc21] | C1 | 5.0 | 482.6 | 483.6 | 90 | a |
| 82 | 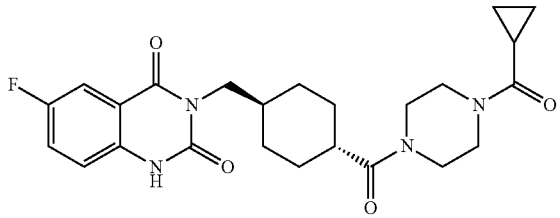 [SMILES: O=C(C1CC1)N1CCN(C(=O)[C@H]2CC[C@H](Cn3c(=O)[nH]c4ccc(F)cc4c3=O)CC2)CC1] | B | 5.3 | 456.5 | 457.5 | 97 | a |

-continued

| Example | Structure | Synthesis method | Retention time | Expected MW | Found MW (M + 1) | Purity | Analytical Method |
|---|---|---|---|---|---|---|---|
| 83 | 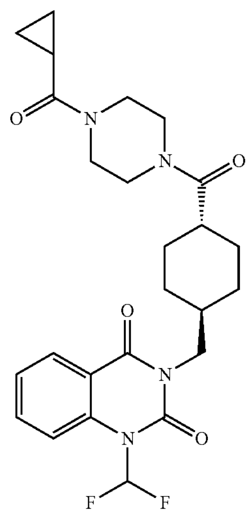 [SMILES: O=C(C1CC1)N1CCN(C(=O)[C@H]2CC[C@H](Cn3c(=O)c4ccccc4n(C(F)F)c3=O)CC2)CC1] | B | 5.9 | 488.5 | 489.5 | 98 | a |
| 84 | 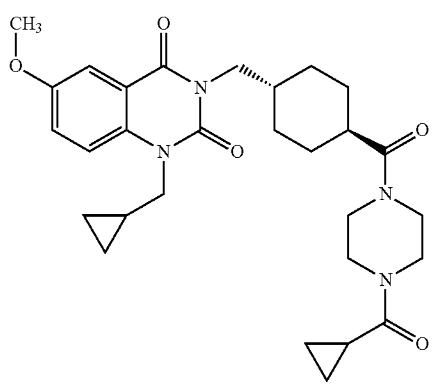 [SMILES: COc1ccc2c(c1)c(=O)n(C[C@H]1CC[C@H](C(=O)N3CCN(C(=O)C4CC4)CC3)CC1)c(=O)n2CC1CC1] | B | 6.2 | 522.7 | 523.7 | 96 | a |
| 85 | 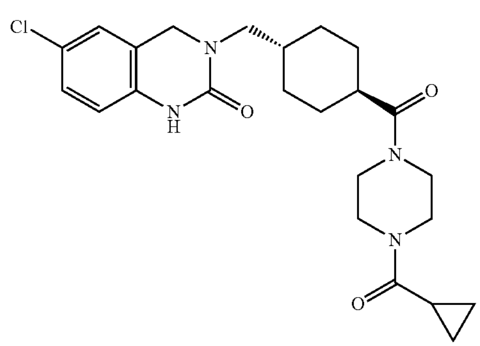 [SMILES: O=C(C1CC1)N1CCN(C(=O)[C@H]2CC[C@H](CN3Cc4cc(Cl)ccc4NC3=O)CC2)CC1] | F | 5.6 | 459.0 | 460.0 | 99 | a |
| 86 | 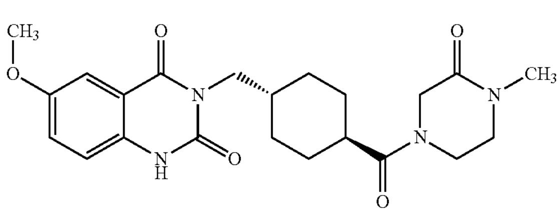 [SMILES: COc1ccc2[nH]c(=O)n(C[C@H]3CC[C@H](C(=O)N4CCN(C)C(=O)C4)CC3)c(=O)c2c1] | B | 4.8 | 428.5 | 429.5 | 91 | a |

-continued

| Example | Structure | Synthesis method | Retention time | Expected MW | Found MW (M + 1) | Purity | Analytical Method |
|---------|-----------|------------------|----------------|-------------|------------------|--------|-------------------|
| 87 | 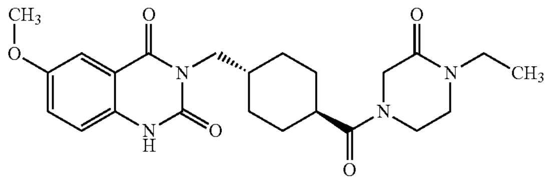 [SMILES: CCN1CCN(C(=O)[C@H]2CC[C@H](Cn3c(=O)[nH]c4ccc(OC)cc4c3=O)CC2)CC1=O] | B | 5.0 | 442.5 | 443.5 | 91 | a |
| 88 | 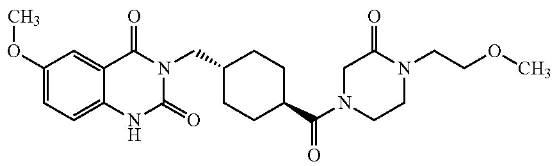 [SMILES: COCCN1CCN(C(=O)[C@H]2CC[C@H](Cn3c(=O)[nH]c4ccc(OC)cc4c3=O)CC2)CC1=O] | B | 4.99 | 472.5 | 473 | 91 | a |
| 89 | 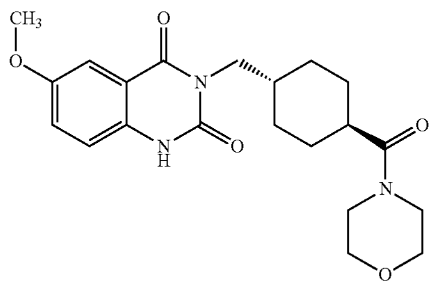 [SMILES: COc1ccc2[nH]c(=O)n(C[C@H]3CC[C@H](C(=O)N4CCOCC4)CC3)c(=O)c2c1] | A1 | 5.05 | 401.5 | 402 | 94 | a |
| 90 | 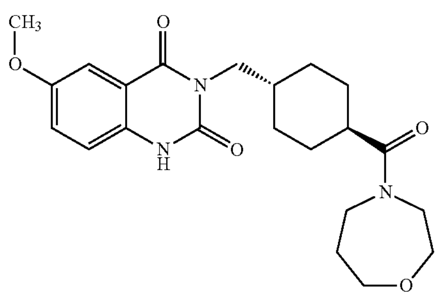 [SMILES: COc1ccc2[nH]c(=O)n(C[C@H]3CC[C@H](C(=O)N4CCCOCC4)CC3)c(=O)c2c1] | A1 | 5.2 | 415.5 | 416 | 95 | a |
| 91 | 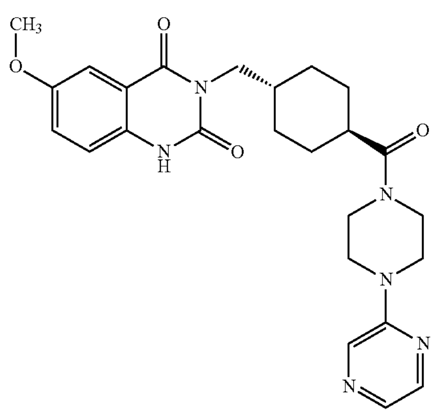 [SMILES: COc1ccc2[nH]c(=O)n(C[C@H]3CC[C@H](C(=O)N4CCN(c5cnccn5)CC4)CC3)c(=O)c2c1] | A1 | 5.94 | 478.5 | 479 | 95 | a |
| 92 | 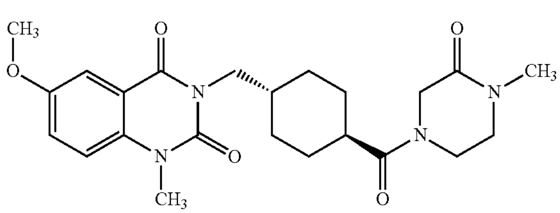 [SMILES: COc1ccc2c(c1)c(=O)n(C[C@H]1CC[C@H](C(=O)N3CCN(C)C(=O)C3)CC1)c(=O)n2C] | B | 5.17 | 442.5 | 443 | 94 | a |

-continued

| Example | Structure | Synthesis method | Retention time | Expected MW | Found MW (M + 1) | Purity | Analytical Method |
|---|---|---|---|---|---|---|---|
| 93 | 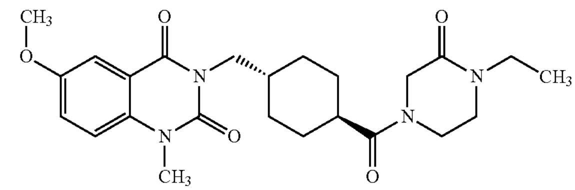 [SMILES: CCN1CCN(C(=O)[C@H]2CC[C@H](Cn3c(=O)c4cc(OC)ccc4n(C)c3=O)CC2)CC1=O] | B | 1.09 | 456.5 | 457 | 100 | a |
| 94 | 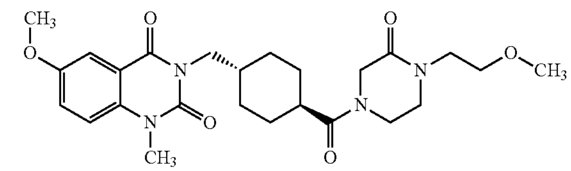 [SMILES: COCCN1CCN(C(=O)[C@H]2CC[C@H](Cn3c(=O)c4cc(OC)ccc4n(C)c3=O)CC2)CC1=O] | B | 5.4 | 486.6 | 487 | 95 | a |
| 95 | 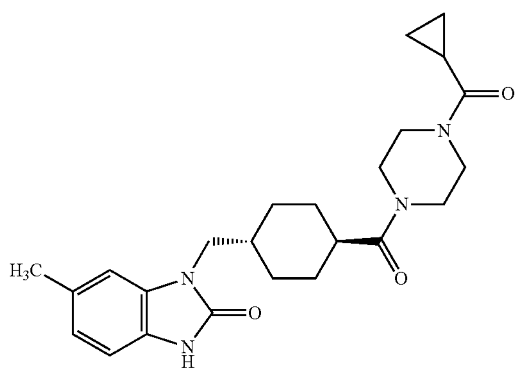 [SMILES: Cc1ccc2[nH]c(=O)n(C[C@H]3CC[C@H](C(=O)N4CCN(C(=O)C5CC5)CC4)CC3)c2c1] | G3 | 1.08 | 424.5 | 423 | 98 | e |
| 96 | 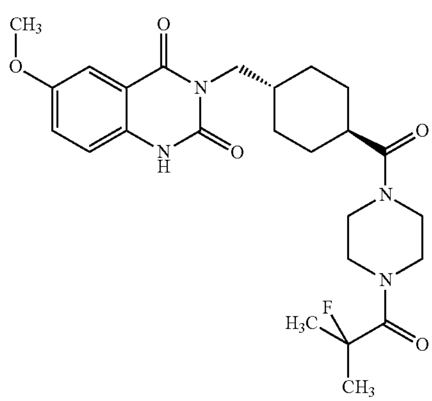 [SMILES: COc1ccc2[nH]c(=O)n(C[C@H]3CC[C@H](C(=O)N4CCN(C(=O)C(C)(C)F)CC4)CC3)c(=O)c2c1] | A1 | 5.95 | 488.6 | 489 | 94 | e |
| 97 | 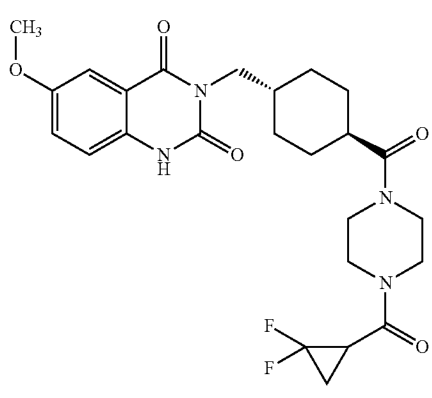 [SMILES: COc1ccc2[nH]c(=O)n(C[C@H]3CC[C@H](C(=O)N4CCN(C(=O)C5CC5(F)F)CC4)CC3)c(=O)c2c1] | A1 | 5.69 | 504.5 | 505 | 93 | e |

-continued

| Example | Structure | Synthesis method | Retention time | Expected MW | Found MW (M + 1) | Purity | Analytical Method |
|---|---|---|---|---|---|---|---|
| 98 | 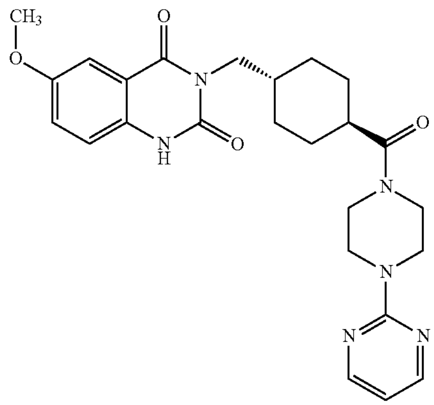 [SMILES: COc1ccc2[nH]c(=O)n(C[C@H]3CC[C@H](C(=O)N4CCN(c5ncccn5)CC4)CC3)c(=O)c2c1] | A1 | 6.09 | 478.5 | 479 | 99 | e |
| 99 | 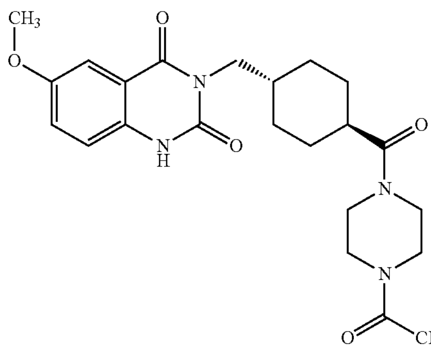 | A1 | 5.04 | 442.5 | 443 | 94 | e |
| 100 | 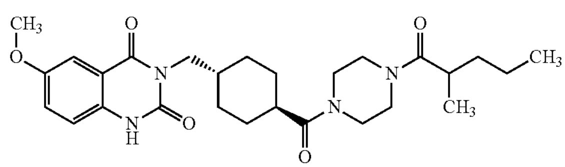 [SMILES: CCCC(C)C(=O)N1CCN(C(=O)[C@H]2CC[C@H](Cn3c(=O)[nH]c4ccc(OC)cc4c3=O)CC2)CC1] | C1 | 1.3 | 498.6 | 499 | 100 | e |
| 101 | 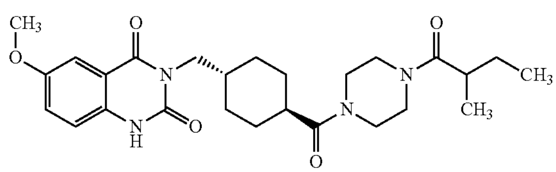 [SMILES: CCC(C)C(=O)N1CCN(C(=O)[C@H]2CC[C@H](Cn3c(=O)[nH]c4ccc(OC)cc4c3=O)CC2)CC1] | C1 | 1.14 | 484.6 | 483 | 97 | e |
| 102 | 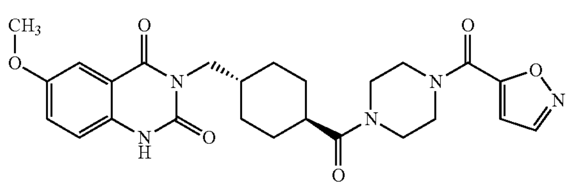 [SMILES: COc1ccc2[nH]c(=O)n(C[C@H]3CC[C@H](C(=O)N4CCN(C(=O)c5ccno5)CC4)CC3)c(=O)c2c1] | C1 | 0.97 | 495.5 | 494 | 95 | e |
| 103 | 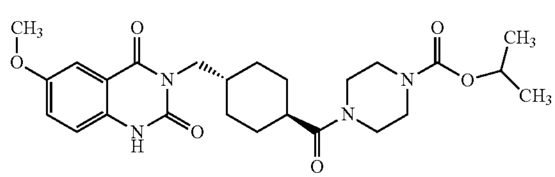 [SMILES: COc1ccc2[nH]c(=O)n(C[C@H]3CC[C@H](C(=O)N4CCN(C(=O)OC(C)C)CC4)CC3)c(=O)c2c1] | C1 | 1.29 | 486.6 | 487 | 98 | e |

-continued

| Example | Structure | Synthesis method | Retention time | Expected MW | Found MW (M + 1) | Purity | Analytical Method |
|---|---|---|---|---|---|---|---|
| 104 | 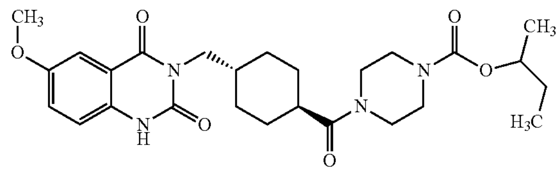 [SMILES: CCC(C)OC(=O)N1CCN(C(=O)[C@H]2CC[C@H](Cn3c(=O)[nH]c4ccc(OC)cc4c3=O)CC2)CC1] | C1 | 1.45 | 500.6 | 501 | 96 | e |
| 105 | 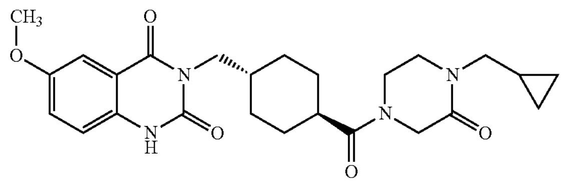 [SMILES: COc1ccc2[nH]c(=O)n(C[C@H]3CC[C@H](C(=O)N4CCN(CC5CC5)C(=O)C4)CC3)c(=O)c2c1] | B | 1.05 | 468.5 | 467 | 98 | e |
| 106 | 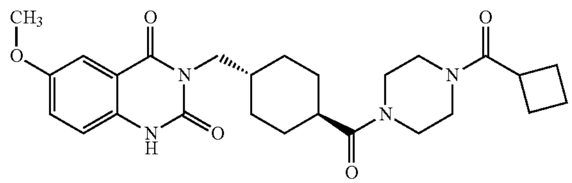 [SMILES: COc1ccc2[nH]c(=O)n(C[C@H]3CC[C@H](C(=O)N4CCN(C(=O)C5CCC5)CC4)CC3)c(=O)c2c1] | B | 1.11 | 482.6 | 481 | 96 | e |
| 107 | 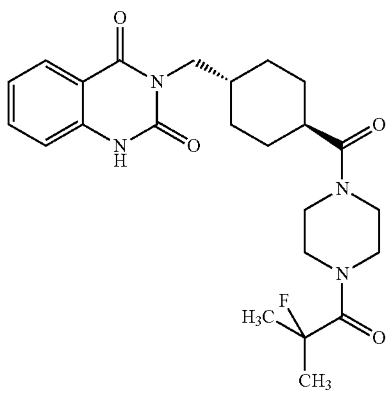 [SMILES: CC(C)(F)C(=O)N1CCN(C(=O)[C@H]2CC[C@H](Cn3c(=O)[nH]c4ccccc4c3=O)CC2)CC1] | A1 | 1.37 | 458.5 | 457 | 93 | e |
| 108 | 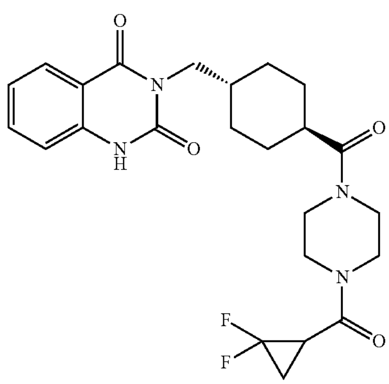 [SMILES: O=C(C1CC1(F)F)N1CCN(C(=O)[C@H]2CC[C@H](Cn3c(=O)[nH]c4ccccc4c3=O)CC2)CC1] | A1 | 1.27 | 474.5 | 473 | 98 | e |
| 109 | 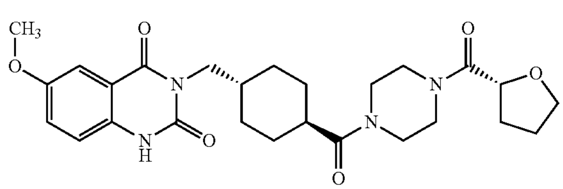 [SMILES: COc1ccc2[nH]c(=O)n(C[C@H]3CC[C@H](C(=O)N4CCN(C(=O)[C@H]5CCCO5)CC4)CC3)c(=O)c2c1] | C1 | 0.9 | 498.6 | 499 | 98 | e |

-continued

| Example | Structure | Synthesis method | Retention time | Expected MW | Found MW (M + 1) | Purity | Analytical Method |
|---|---|---|---|---|---|---|---|
| 110 | 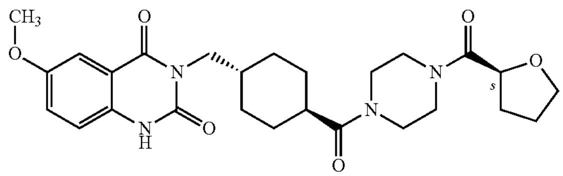 [SMILES: COc1ccc2[nH]c(=O)n(C[C@H]3CC[C@H](C(=O)N4CCN(C(=O)[C@@H]5CCCO5)CC4)CC3)c(=O)c2c1] | C1 | 0.9 | 498.6 | 499 | 98 | e |
| 111 | 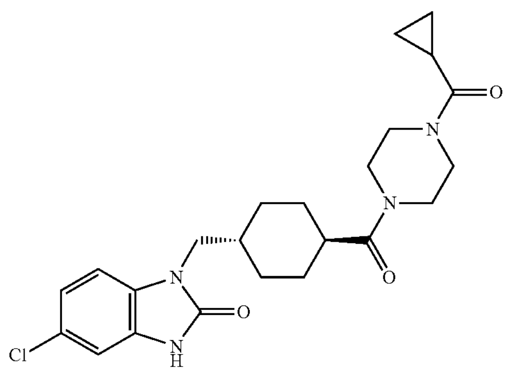 [SMILES: O=C(C1CC1)N1CCN(C(=O)[C@H]2CC[C@H](Cn3c(=O)[nH]c4cc(Cl)ccc43)CC2)CC1] | G3 | 5.42 | 445.0 | 445 | 96 | e |
| 112 | 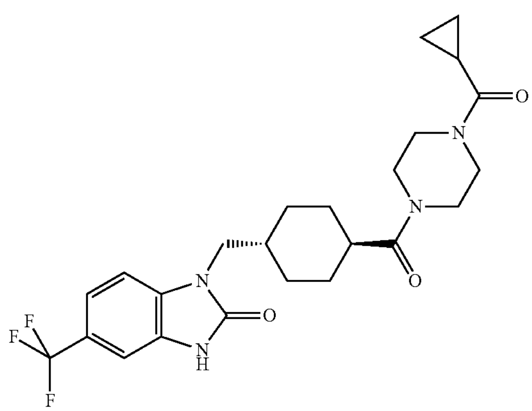 [SMILES: O=C(C1CC1)N1CCN(C(=O)[C@H]2CC[C@H](Cn3c(=O)[nH]c4cc(C(F)(F)F)ccc43)CC2)CC1] | G3 | 1.26 | 478.5 | 477 | 100 | e |
| 113 | 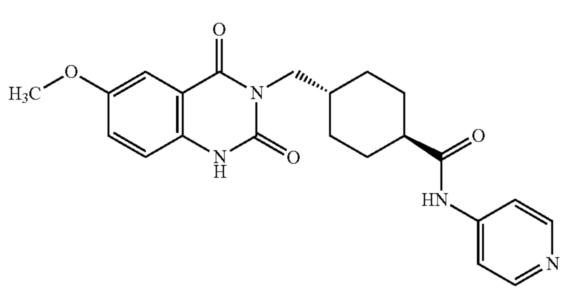 [SMILES: COc1ccc2[nH]c(=O)n(C[C@H]3CC[C@H](C(=O)Nc4ccncc4)CC3)c(=O)c2c1] | A1 | 1.01 | 408.5 | 409 | 100 | e |

| Example | Structure | Synthesis method | Retention time | Expected MW | Found MW (M + 1) | Purity | Analytical Method |
|---|---|---|---|---|---|---|---|
| 114 | 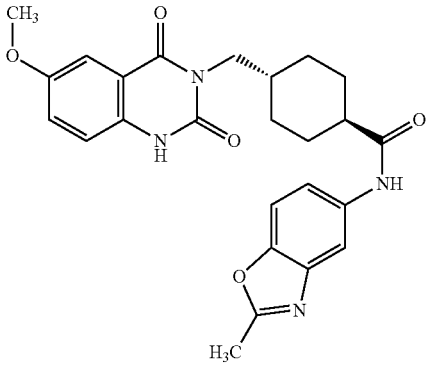 [SMILES: COc1ccc2[nH]c(=O)n(C[C@H]3CC[C@H](C(=O)Nc4ccc5oc(C)nc5c4)CC3)c(=O)c2c1] | A1 | 1.21 | 462.5 | 463 | 100 | e |
| 115 | 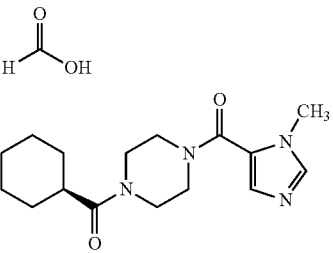 | C1 | 0.85 | 508.6 | 509 | 95 | e |
| 116 | 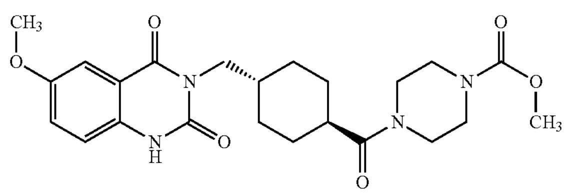 [SMILES: COC(=O)N1CCN(C(=O)[C@H]2CC[C@H](Cn3c(=O)[nH]c4ccc(OC)cc4c3=O)CC2)CC1] | C1 | 1 | 458.5 | 457 | 100 | e |
| 117 | 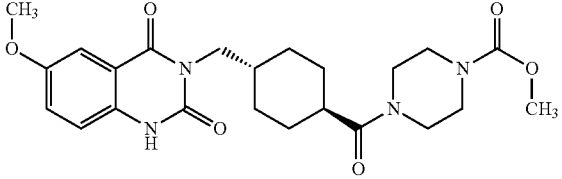 | C1 | 0.87 | 506.6 | 507 | 96 | e |
| 118 | 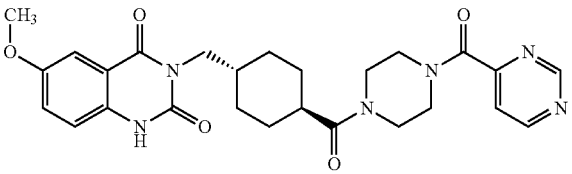 [SMILES: COc1ccc2[nH]c(=O)n(C[C@H]3CC[C@H](C(=O)N4CCN(C(=O)c5ccncn5)CC4)CC3)c(=O)c2c1] | N | 11 | 407.5 | 408 | 96 | g |

-continued

| Example | Structure | Synthesis method | Retention time | Expected MW | Found MW (M + 1) | Purity | Analytical Method |
|---|---|---|---|---|---|---|---|
| 119 | 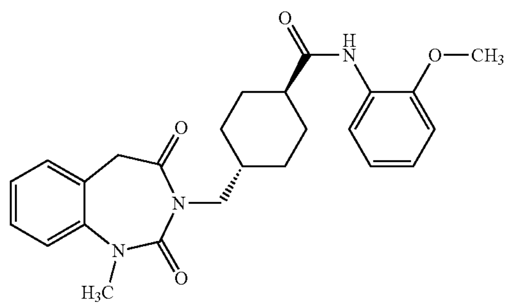 [SMILES: COc1ccccc1NC(=O)[C@H]1CC[C@H](CN2C(=O)Cc3ccccc3N(C)C2=O)CC1] | M | 10.9 | 435.5 | 436 | 91 | g |
| 120 | 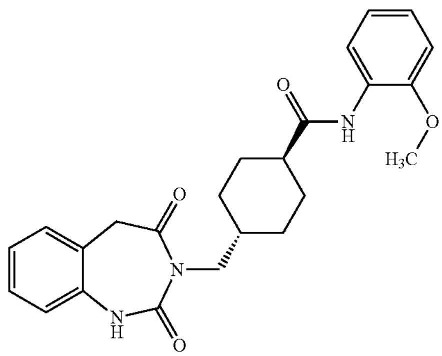 [SMILES: COc1ccccc1NC(=O)[C@H]1CC[C@H](CN2C(=O)Cc3ccccc3NC2=O)CC1] | M | 10 | 421.5 | 422 | 96 | g |
| 121 | 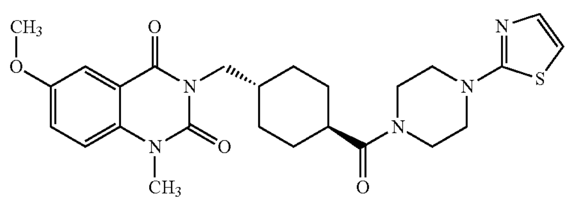 [SMILES: COc1ccc2c(c1)c(=O)n(C[C@H]1CC[C@H](C(=O)N3CCN(c4nccs4)CC3)CC1)c(=O)n2C] | A2 | 1.42 | 497.6 | 498 | 95 | e |
| 122 | 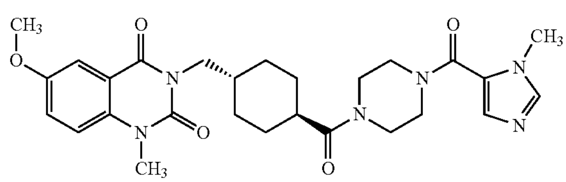 [SMILES: COc1ccc2c(c1)c(=O)n(C[C@H]1CC[C@H](C(=O)N3CCN(C(=O)c4cncn4C)CC3)CC1)c(=O)n2C] | C2 | 1.03 | 522.6 | 523 | 100 | e |
| 123 | 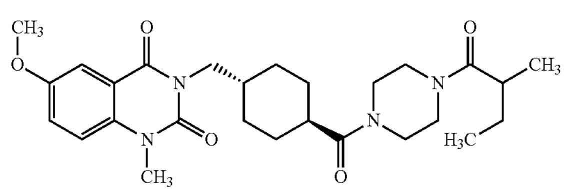 [SMILES: CCC(C)C(=O)N1CCN(C(=O)[C@H]2CC[C@H](Cn3c(=O)c4cc(OC)ccc4n(C)c3=O)CC2)CC1] | B | 1.37 | 498.6 | 499 | 100 | e |
| 124 | 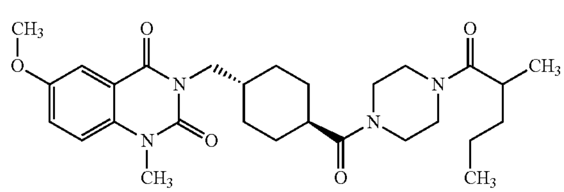 [SMILES: CCCC(C)C(=O)N1CCN(C(=O)[C@H]2CC[C@H](Cn3c(=O)c4cc(OC)ccc4n(C)c3=O)CC2)CC1] | B | 1.52 | 512.6 | 513 | 100 | e |

-continued

| Example | Structure | Synthesis method | Retention time | Expected MW | Found MW (M + 1) | Purity | Analytical Method |
|---|---|---|---|---|---|---|---|
| 125 | 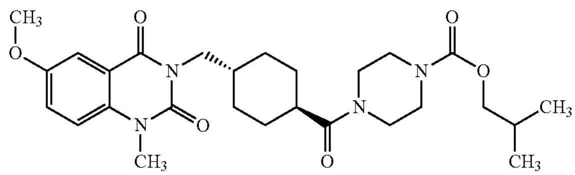 [SMILES: COc1ccc2c(c1)c(=O)n(C[C@H]1CC[C@H](C(=O)N3CCN(C(=O)OCC(C)C)CC3)CC1)c(=O)n2C] | B | 1.68 | 514.6 | 515 | 100 | e |
| 126 | 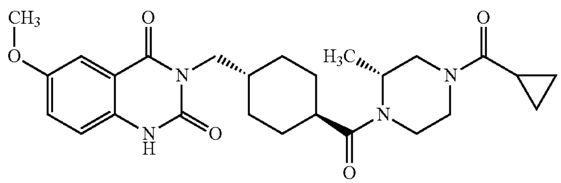 [SMILES: COc1ccc2[nH]c(=O)n(C[C@H]3CC[C@H](C(=O)N4CCN(C(=O)C5CC5)C[C@H]4C)CC3)c(=O)c2c1] | C1 | 1.03 | 482.6 | 481 | 100 | e |
| 127 | 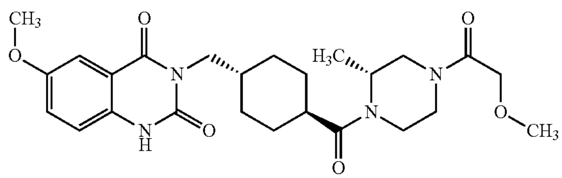 [SMILES: COCC(=O)N1CCN(C(=O)[C@H]2CC[C@H](Cn3c(=O)[nH]c4ccc(OC)cc4c3=O)CC2)[C@H](C)C1] | C1 | 0.87 | 486.6 | 485 | 97 | e |
| 128 | 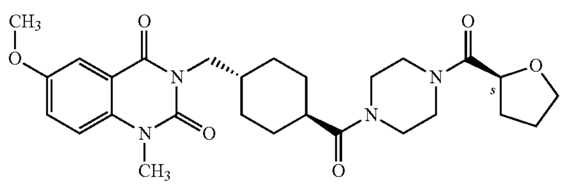 [SMILES: COc1ccc2c(c1)c(=O)n(C[C@H]1CC[C@H](C(=O)N3CCN(C(=O)[C@@H]4CCCO4)CC3)CC1)c(=O)n2C] | C2 | 1.12 | 512.6 | 513 | 100 | e |
| 129 | 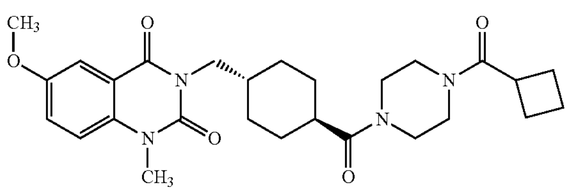 [SMILES: COc1ccc2c(c1)c(=O)n(C[C@H]1CC[C@H](C(=O)N3CCN(C(=O)C4CCC4)CC3)CC1)c(=O)n2C] | C2 | 1.33 | 496.6 | 497 | 92 | e |
| 130 | 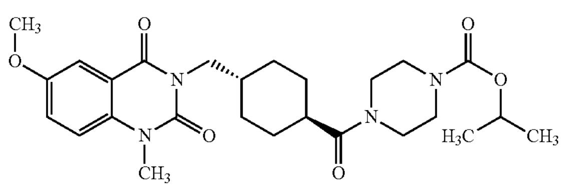 [SMILES: COc1ccc2c(c1)c(=O)n(C[C@H]1CC[C@H](C(=O)N3CCN(C(=O)OC(C)C)CC3)CC1)c(=O)n2C] | C2 | 1.52 | 500.6 | 501 | 97 | e |
| 131 | 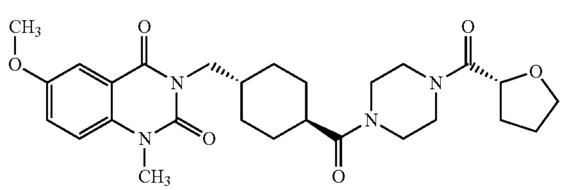 [SMILES: COc1ccc2c(c1)c(=O)n(C[C@H]1CC[C@H](C(=O)N3CCN(C(=O)[C@H]4CCCO4)CC3)CC1)c(=O)n2C] | C2 | 1.12 | 512.6 | 513 | 92 | e |
| 132 | 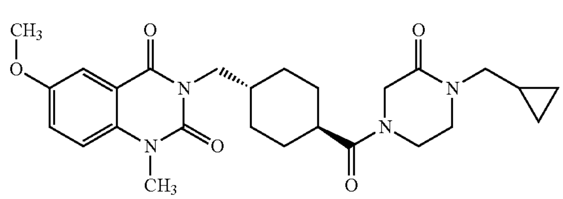 [SMILES: COc1ccc2c(c1)c(=O)n(C[C@H]1CC[C@H](C(=O)N3CCN(CC4CC4)C(=O)C3)CC1)c(=O)n2C] | B | 1.28 | 482.6 | 483 | 95 | e |

-continued

| Example | Structure | Synthesis method | Retention time | Expected MW | Found MW (M + 1) | Purity | Analytical Method |
|---|---|---|---|---|---|---|---|
| 133 | 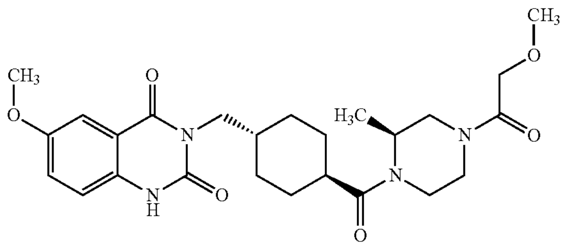 [SMILES: COCC(=O)N1CCN(C(=O)[C@H]2CC[C@H](Cn3c(=O)[nH]c4ccc(OC)cc4c3=O)CC2)[C@@H](C)C1] | B | 0.89 | 486.6 | 487 | 100 | e |
| 134 | 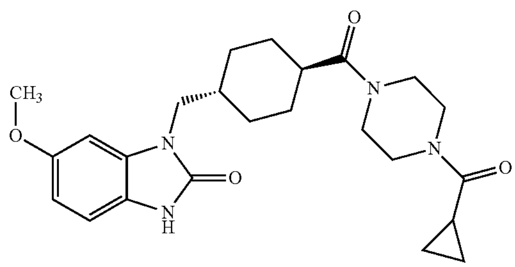 [SMILES: COc1ccc2[nH]c(=O)n(C[C@H]3CC[C@H](C(=O)N4CCN(C(=O)C5CC5)CC4)CC3)c2c1] | G1 | 1.14 | 440.5 | 439 | 98 | e |
| 135 | 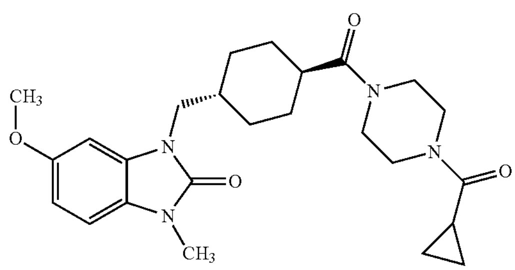 [SMILES: COc1ccc2c(c1)n(C[C@H]1CC[C@H](C(=O)N3CCN(C(=O)C4CC4)CC3)CC1)c(=O)n2C] | G1 | 1.34 | 454.6 | 455 | 92 | e |
| 136 | 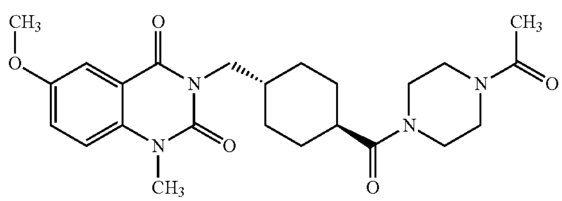 [SMILES: COc1ccc2c(c1)c(=O)n(C[C@H]1CC[C@H](C(=O)N3CCN(C(C)=O)CC3)CC1)c(=O)n2C] | C2 | 1.03 | 456.5 | 457 | 100 | e |
| 137 | 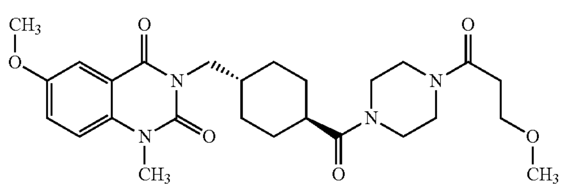 [SMILES: COCCC(=O)N1CCN(C(=O)[C@H]2CC[C@H](Cn3c(=O)c4cc(OC)ccc4n(C)c3=O)CC2)CC1] | C2 | 1.09 | 500.6 | 501 | 100 | e |
| 138 | 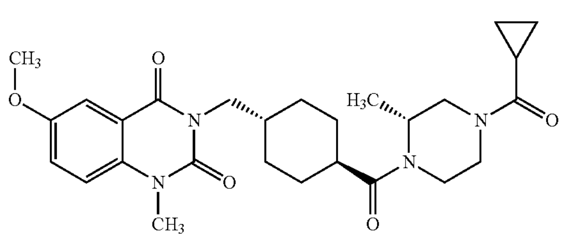 [SMILES: COc1ccc2c(c1)c(=O)n(C[C@H]1CC[C@H](C(=O)N3CCN(C(=O)C4CC4)C[C@H]3C)CC1)c(=O)n2C] | B | 1.27 | 496.6 | 497 | 100 | e |

-continued

| Example | Structure | Synthesis method | Retention time | Expected MW | Found MW (M + 1) | Purity | Analytical Method |
|---|---|---|---|---|---|---|---|
| 139 | 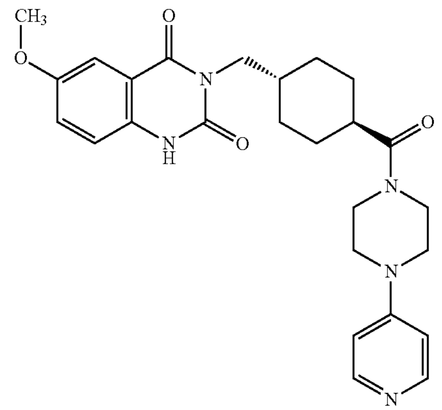 [SMILES: COc1ccc2[nH]c(=O)n(C[C@H]3CC[C@H](C(=O)N4CCN(c5ccncc5)CC4)CC3)c(=O)c2c1] | A1 | 1.02 | 477.6 | 478 | 100 | e |
| 140 | 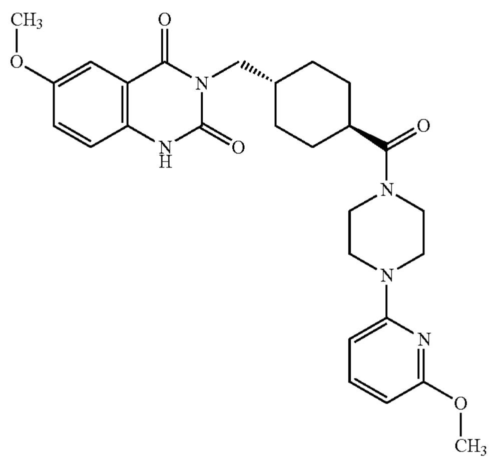 [SMILES: COc1ccc2[nH]c(=O)n(C[C@H]3CC[C@H](C(=O)N4CCN(c5cccc(OC)n5)CC4)CC3)c(=O)c2c1] | A1 | 1.56 | 507.6 | 508 | 100 | e |
| 141 | 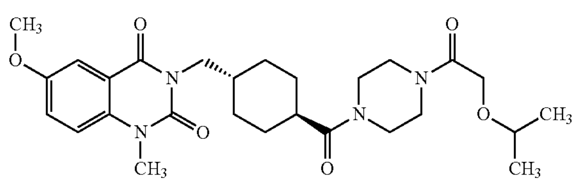 [SMILES: COc1ccc2c(c1)c(=O)n(C[C@H]1CC[C@H](C(=O)N3CCN(C(=O)COC(C)C)CC3)CC1)c(=O)n2C] | A2 | 1.25 | 514.6 | 515 | 100 | e |
| 142 | 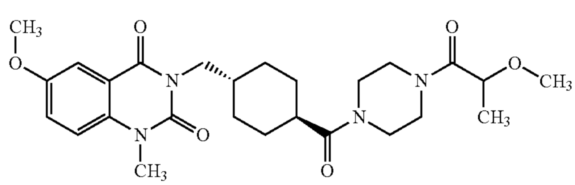 [SMILES: COc1ccc2c(c1)c(=O)n(C[C@H]1CC[C@H](C(=O)N3CCN(C(=O)C(C)OC)CC3)CC1)c(=O)n2C] | A2 | 1.11 | 500.6 | 501 | 97 | e |

-continued

| Example | Structure | Synthesis method | Retention time | Expected MW | Found MW (M + 1) | Purity | Analytical Method |
|---|---|---|---|---|---|---|---|
| 143 | 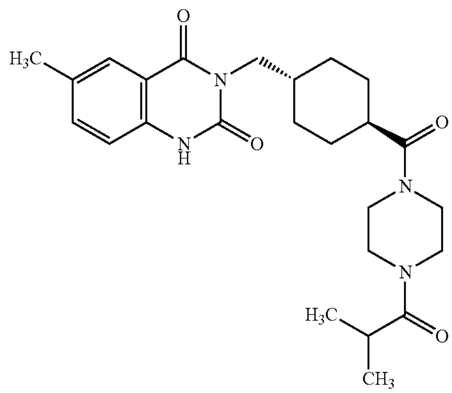 [SMILES: Cc1ccc2[nH]c(=O)n(C[C@H]3CC[C@H](C(=O)N4CCN(C(=O)C(C)C)CC4)CC3)c(=O)c2c1] | A1 | 1.14 | 454.6 | 455 | 97 | e |
| 144 | 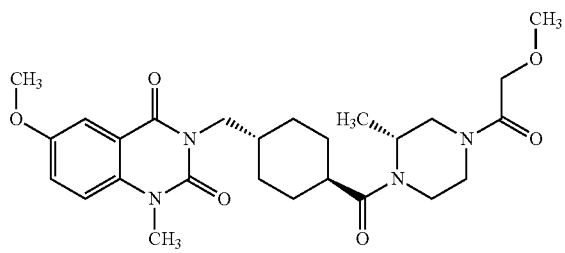 [SMILES: COCC(=O)N1CCN(C(=O)[C@H]2CC[C@H](Cn3c(=O)c4cc(OC)ccc4n(C)c3=O)CC2)[C@H](C)C1] | B | 1.11 | 500.6 | 501 | 100 | e |
| 145 | 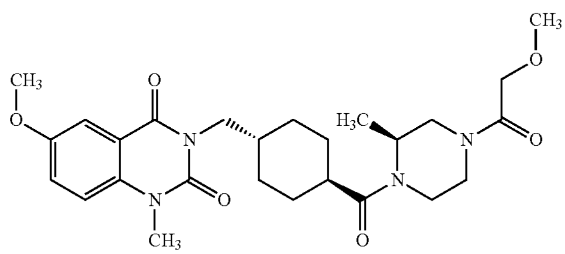 [SMILES: COCC(=O)N1CCN(C(=O)[C@H]2CC[C@H](Cn3c(=O)c4cc(OC)ccc4n(C)c3=O)CC2)[C@@H](C)C1] | B | 0.89 | 500.6 | 501 | 100 | e |
| 146 | 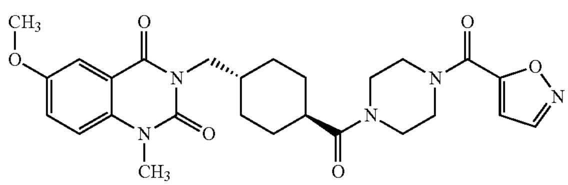 [SMILES: COc1ccc2c(c1)c(=O)n(C[C@H]1CC[C@H](C(=O)N3CCN(C(=O)c4ccno4)CC3)CC1)c(=O)n2C] | B | 1.2 | 509.6 | 510 | 100 | e |
| 147 | 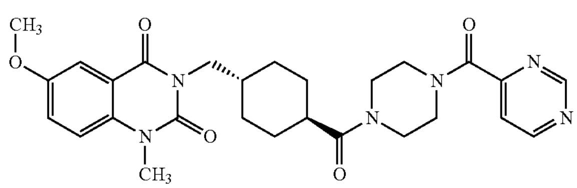 [SMILES: COc1ccc2c(c1)c(=O)n(C[C@H]1CC[C@H](C(=O)N3CCN(C(=O)c4ccncn4)CC3)CC1)c(=O)n2C] | B | 1.06 | 520.6 | 521 | 100 | e |
| 148 | 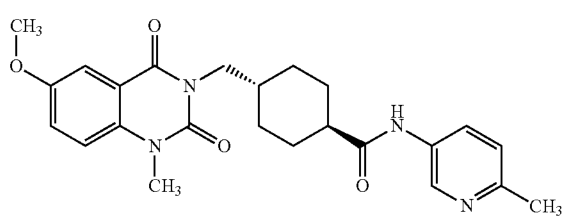 [SMILES: COc1ccc2c(c1)c(=O)n(C[C@H]1CC[C@H](C(=O)Nc3ccc(C)nc3)CC1)c(=O)n2C] | A2 | 1.55 | 436.5 | 437 | 100 | e |

-continued

| Example | Structure | Synthesis method | Retention time | Expected MW | Found MW (M + 1) | Purity | Analytical Method |
|---|---|---|---|---|---|---|---|
| 149 | 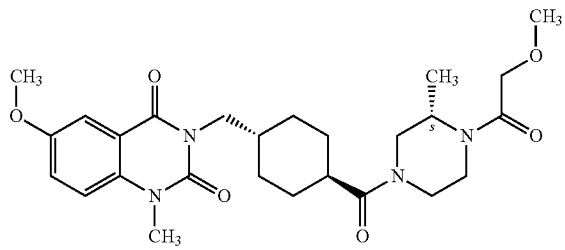 | A2 | 1.11 | 500.6 | 501 | 100 | e |
| 150 | 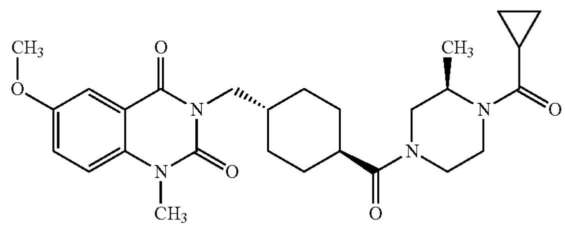 [SMILES: COc1ccc2c(c1)c(=O)n(C[C@H]1CC[C@H](C(=O)N3CCN(C(=O)C4CC4)[C@H](C)C3)CC1)c(=O)n2C] | A2 | 1.28 | 496.6 | 497 | 100 | e |
| 151 | 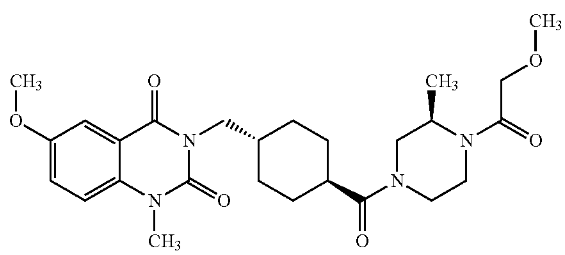 [SMILES: COCC(=O)N1CCN(C(=O)[C@H]2CC[C@H](Cn3c(=O)c4cc(OC)ccc4n(C)c3=O)CC2)C[C@H]1C] | A2 | 1.11 | 500.6 | 501 | 100 | e |
| 152 | 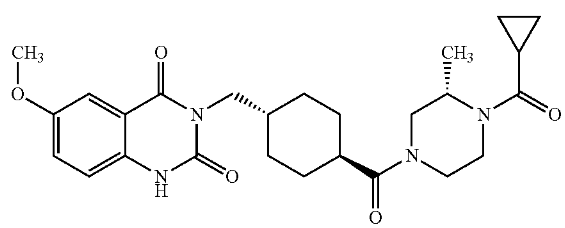 [SMILES: COc1ccc2[nH]c(=O)n(C[C@H]3CC[C@H](C(=O)N4CCN(C(=O)C5CC5)[C@@H](C)C4)CC3)c(=O)c2c1] | A1 | 1.06 | 482.6 | 483 | 100 | e |
| 153 | 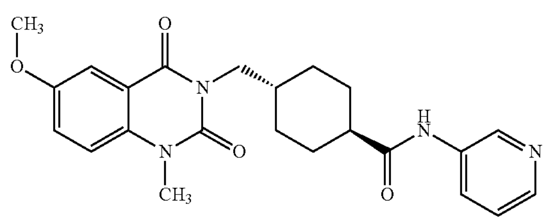 [SMILES: COc1ccc2c(c1)c(=O)n(C[C@H]1CC[C@H](C(=O)Nc3cccnc3)CC1)c(=O)n2C] | A2 | 1.22 | 422.5 | 423 | 100 | e |
| 154 | 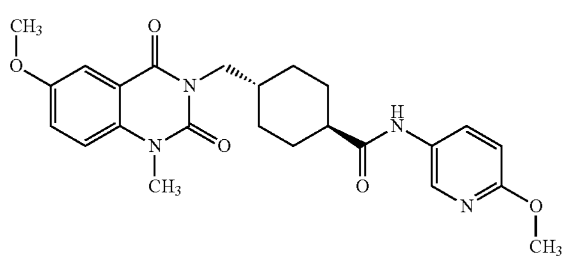 [SMILES: COc1ccc2c(c1)c(=O)n(C[C@H]1CC[C@H](C(=O)Nc3ccc(OC)nc3)CC1)c(=O)n2C] | A2 | 1.38 | 452.5 | 453 | 100 | f |

-continued

| Example | Structure | Synthesis method | Retention time | Expected MW | Found MW (M + 1) | Purity | Analytical Method |
|---|---|---|---|---|---|---|---|
| 155 | 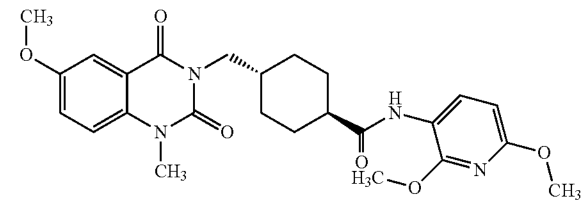 [SMILES: COc1ccc2c(c1)c(=O)n(C[C@H]1CC[C@H](C(=O)Nc3ccc(OC)nc3OC)CC1)c(=O)n2C] | A2 | 1.7 | 482.5 | 483 | 95 | f |
| 156 | 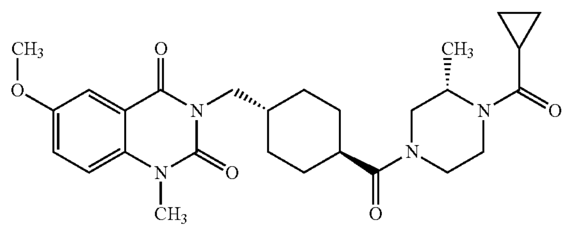 [SMILES: COc1ccc2c(c1)c(=O)n(C[C@H]1CC[C@H](C(=O)N3CCN(C(=O)C4CC4)[C@@H](C)C3)CC1)c(=O)n2C] | A2 | 1.28 | 496.6 | 497 | 100 | f |
| 157 | 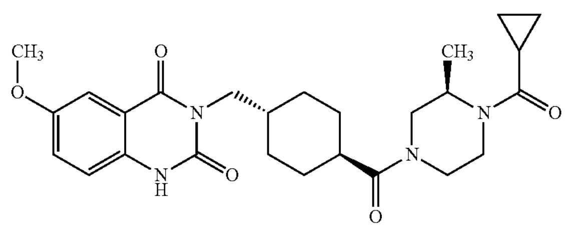 [SMILES: COc1ccc2[nH]c(=O)n(C[C@H]3CC[C@H](C(=O)N4CCN(C(=O)C5CC5)[C@H](C)C4)CC3)c(=O)c2c1] | A1 | 1.07 | 482.6 | 483 | 100 | f |
| 158 | 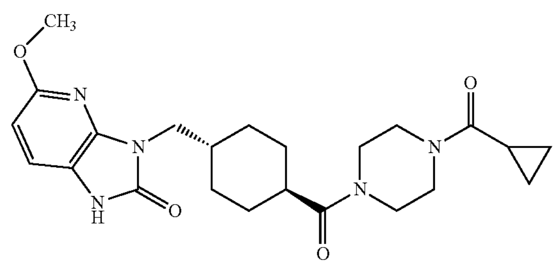 [SMILES: COc1ccc2[nH]c(=O)n(C[C@H]3CC[C@H](C(=O)N4CCN(C(=O)C5CC5)CC4)CC3)c2n1] | G3 | 0.96 | 441.5 | 442 | 95 | f |
| 159 | 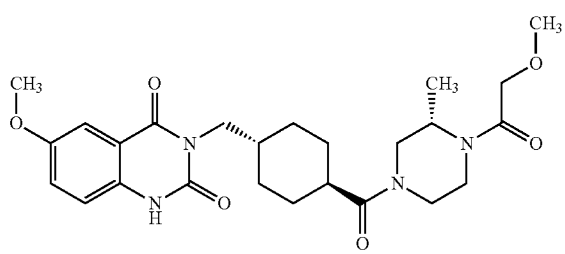 [SMILES: COCC(=O)N1CCN(C(=O)[C@H]2CC[C@H](Cn3c(=O)[nH]c4ccc(OC)cc4c3=O)CC2)C[C@@H]1C] | A1 | 0.89 | 486.6 | 487 | 100 | e |
| 160 | 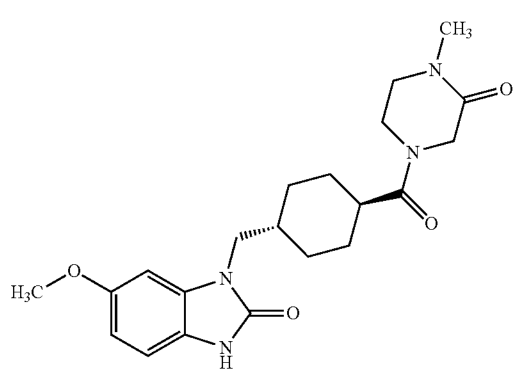 [SMILES: COc1ccc2[nH]c(=O)n(C[C@H]3CC[C@H](C(=O)N4CCN(C)C(=O)C4)CC3)c2c1] | G1 | 0.77 | 400.5 | 401 | 96 | f |

-continued

| Example | Structure | Synthesis method | Retention time | Expected MW | Found MW (M + 1) | Purity | Analytical Method |
|---|---|---|---|---|---|---|---|
| 161 | 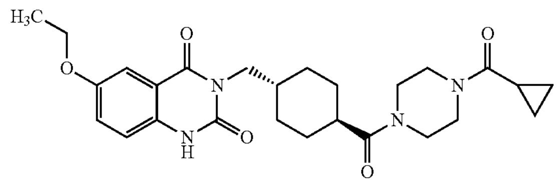 [SMILES: CCOc1ccc2[nH]c(=O)n(C[C@H]3CC[C@H](C(=O)N4CCN(C(=O)C5CC5)CC4)CC3)c(=O)c2c1] | A1 | 1.2 | 482.6 | 481 | 95 | f |
| 162 | 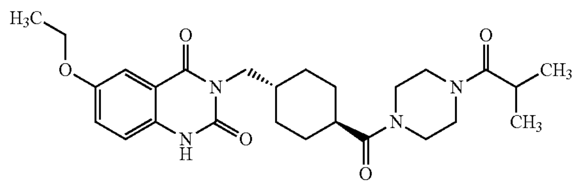 [SMILES: CCOc1ccc2[nH]c(=O)n(C[C@H]3CC[C@H](C(=O)N4CCN(C(=O)C(C)C)CC4)CC3)c(=O)c2c1] | A1 | 1.23 | 484.6 | 485 | 95 | f |
| 163 | 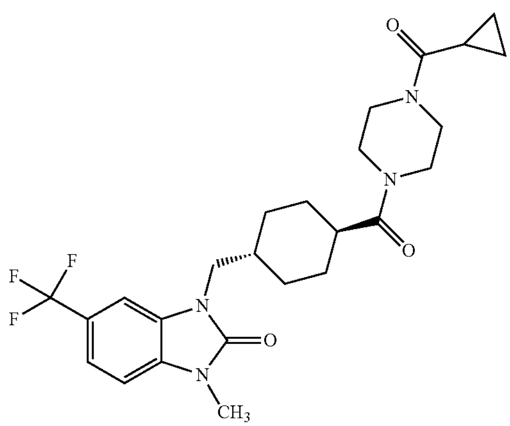 [SMILES: Cn1c(=O)n(C[C@H]2CC[C@H](C(=O)N3CCN(C(=O)C4CC4)CC3)CC2)c2cc(C(F)(F)F)ccc21] | G2 | 1.37 | 492.5 | 493 | 100 | f |
| 164 | 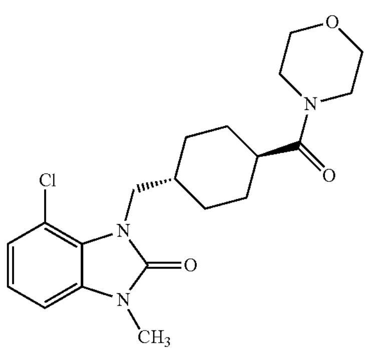 [SMILES: Cn1c(=O)n(C[C@H]2CC[C@H](C(=O)N3CCOCC3)CC2)c2c(Cl)cccc21] | G2 | 1.31 | 391.9 | 392 | 100 | f |
| 165 | 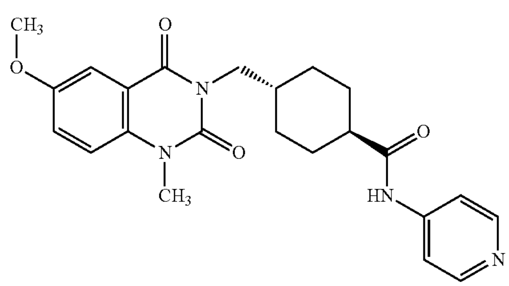 [SMILES: COc1ccc2c(c1)c(=O)n(C[C@H]1CC[C@H](C(=O)Nc3ccncc3)CC1)c(=O)n2C] | A2 | 1.25 | 422.5 | 423 | 100 | f |

-continued

| Example | Structure | Synthesis method | Retention time | Expected MW | Found MW (M + 1) | Purity | Analytical Method |
|---------|-----------|------------------|----------------|-------------|------------------|--------|-------------------|
| 166 | 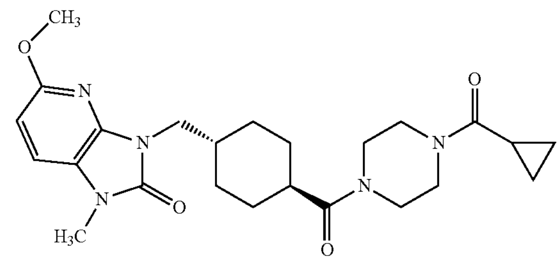 [SMILES: COc1ccc2c(n1)n(C[C@H]1CC[C@H](C(=O)N3CCN(C(=O)C4CC4)CC3)CC1)c(=O)n2C] | G2 | 1.17 | 455.6 | 456 | 95 | f |
| 167 | 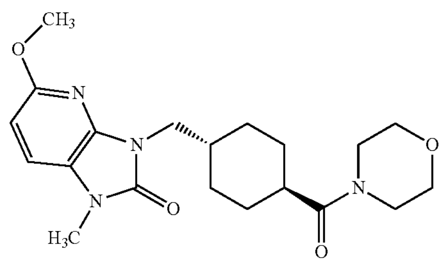 [SMILES: COc1ccc2c(n1)n(C[C@H]1CC[C@H](C(=O)N3CCOCC3)CC1)c(=O)n2C] | G2 | 1.95 | 388.5 | 389 | 95 | f |
| 168 | 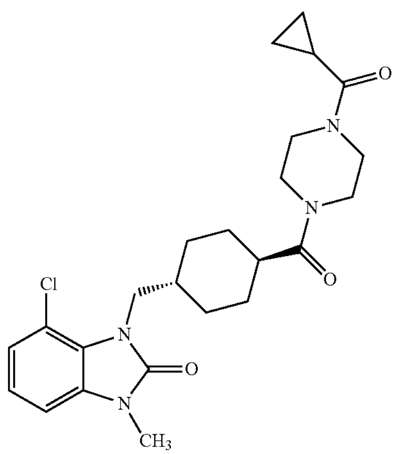 [SMILES: Cn1c(=O)n(C[C@H]2CC[C@H](C(=O)N3CCN(C(=O)C4CC4)CC3)CC2)c2c(Cl)cccc21] | G2 | 1.32 | 459.0 | 459 | 100 | f |
| 169 | 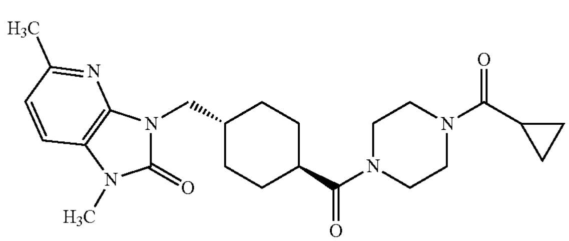 [SMILES: Cc1ccc2c(n1)n(C[C@H]1CC[C@H](C(=O)N3CCN(C(=O)C4CC4)CC3)CC1)c(=O)n2C] | G2 | 1.09 | 439.6 | 440 | 90 | f |

-continued

| Example | Structure | Synthesis method | Retention time | Expected MW | Found MW (M + 1) | Purity | Analytical Method |
|---------|-----------|------------------|----------------|-------------|------------------|--------|-------------------|
| 170 | 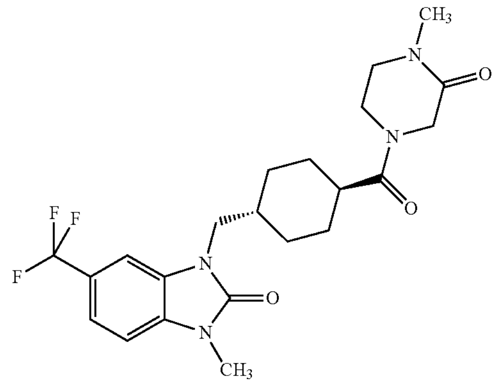 [SMILES: CN1CCN(C(=O)[C@H]2CC[C@H](Cn3c(=O)n(C)c4ccc(C(F)(F)F)cc43)CC2)CC1=O] | G2 | 1.25 | 452.5 | 453 | 100 | f |
| 171 | 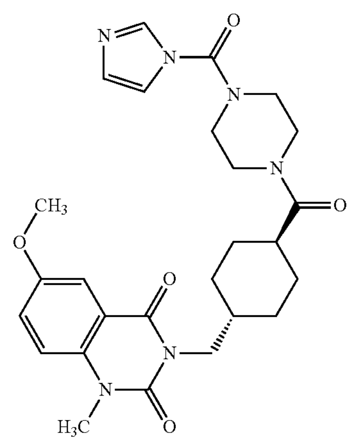 [SMILES: COc1ccc2c(c1)c(=O)n(C[C@H]1CC[C@H](C(=O)N3CCN(C(=O)n4ccnc4)CC3)CC1)c(=O)n2C] | C2 | 1.09 | 508.6 | 509 | 100 | f |
| 172 | 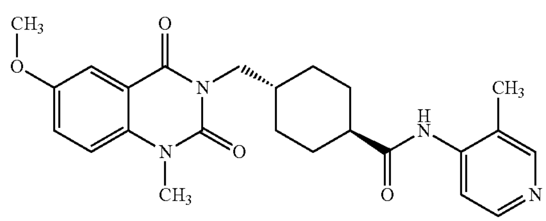 [SMILES: COc1ccc2c(c1)c(=O)n(C[C@H]1CC[C@H](C(=O)Nc3ccncc3C)CC1)c(=O)n2C] | A2 | 1.17 | 436.5 | 437 | 100 | f |
| 173 | 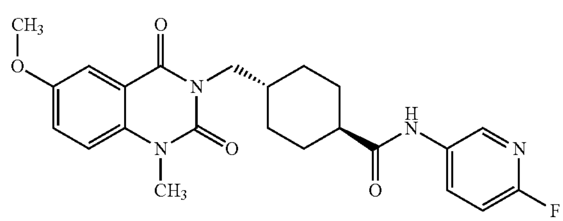 [SMILES: COc1ccc2c(c1)c(=O)n(C[C@H]1CC[C@H](C(=O)Nc3ccc(F)nc3)CC1)c(=O)n2C] | A2 | 1.36 | 440.5 | 441 | 100 | f |
| 174 | 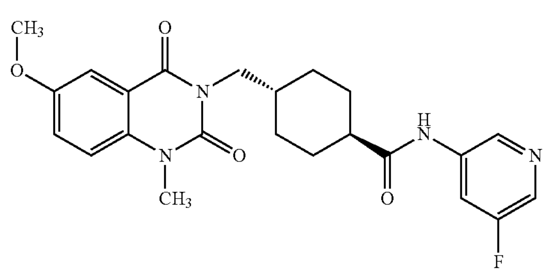 [SMILES: COc1ccc2c(c1)c(=O)n(C[C@H]1CC[C@H](C(=O)Nc3cncc(F)c3)CC1)c(=O)n2C] | A2 | 1.36 | 440.5 | 441 | 100 | f |

-continued

| Example | Structure | Synthesis method | Retention time | Expected MW | Found MW (M + 1) | Purity | Analytical Method |
|---|---|---|---|---|---|---|---|
| 175 | 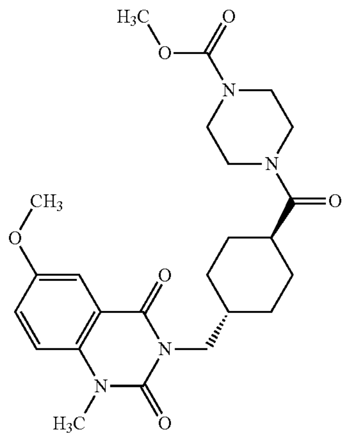 [SMILES: COC(=O)N1CCN(C(=O)[C@H]2CC[C@H](Cn3c(=O)c4cc(OC)ccc4n(C)c3=O)CC2)CC1] | C2 | 1.26 | 472.5 | 473 | 96 | f |
| 176 | 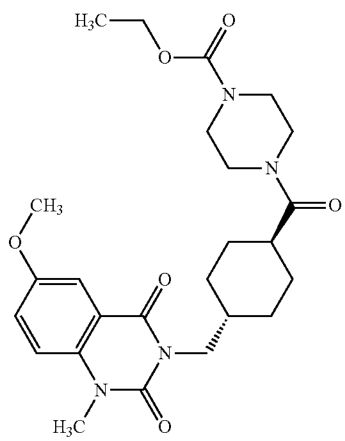 [SMILES: CCOC(=O)N1CCN(C(=O)[C@H]2CC[C@H](Cn3c(=O)c4cc(OC)ccc4n(C)c3=O)CC2)CC1] | C2 | 1.35 | 486.6 | 487 | 100 | f |
| 177 | 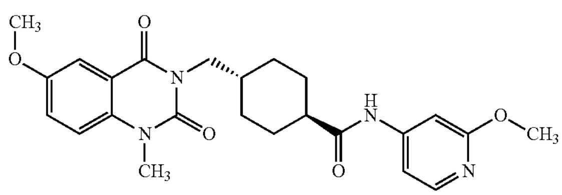 [SMILES: COc1ccc2c(c1)c(=O)n(C[C@H]1CC[C@H](C(=O)Nc3ccnc(OC)c3)CC1)c(=O)n2C] | A2 | 1.28 | 452.5 | 453 | 98 | f |
| 178 | 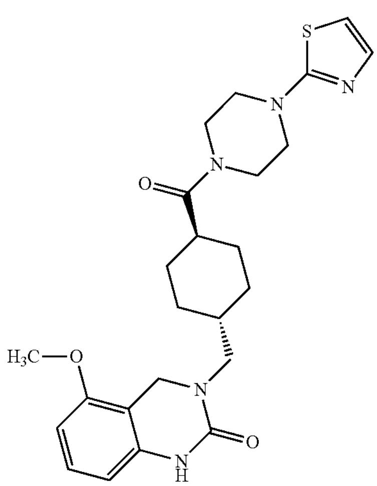 [SMILES: COc1cccc2c1CN(C[C@H]1CC[C@H](C(=O)N3CCN(c4nccs4)CC3)CC1)C(=O)N2] | F | 1.17 | 469.6 | 470 | 95 | f |

-continued

| Example | Structure | Synthesis method | Retention time | Expected MW | Found MW (M + 1) | Purity | Analytical Method |
|---|---|---|---|---|---|---|---|
| 179 | 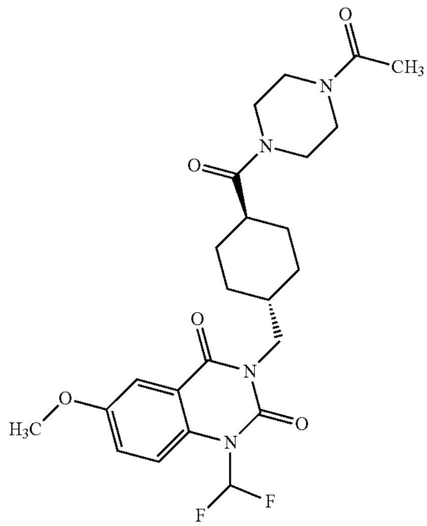 [SMILES: COc1ccc2c(c1)c(=O)n(C[C@H]1CC[C@H](C(=O)N3CCN(C(C)=O)CC3)CC1)c(=O)n2C(F)F] | A1 | 1.33 | 492.5 | 493 | 100 | f |
| 180 | 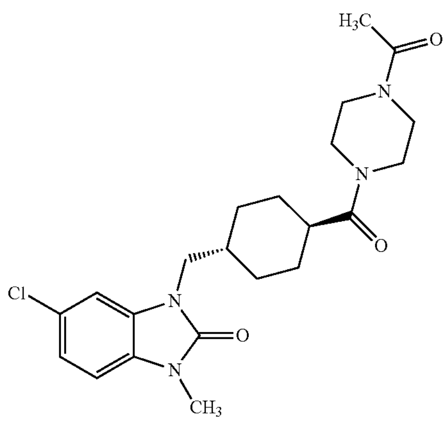 [SMILES: CC(=O)N1CCN(C(=O)[C@H]2CC[C@H](Cn3c(=O)n(C)c4ccc(Cl)cc43)CC2)CC1] | G2 | 1.19 | 432.9 | 433 | 95 | f |
| 181 | 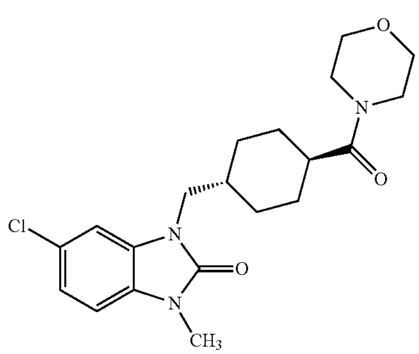 [SMILES: Cn1c(=O)n(C[C@H]2CC[C@H](C(=O)N3CCOCC3)CC2)c2cc(Cl)ccc21] | G2 | 1.29 | 391.9 | 392 | 98 | f |
| 182 | 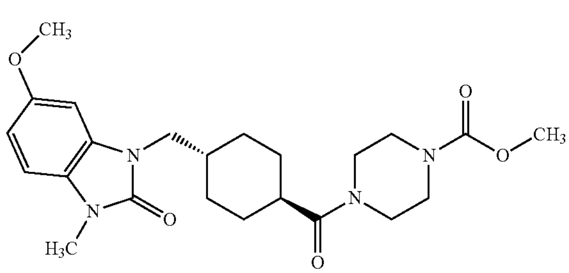 [SMILES: COC(=O)N1CCN(C(=O)[C@H]2CC[C@H](Cn3c(=O)n(C)c4ccc(OC)cc43)CC2)CC1] | G2 | 1.21 | 444.5 | 445 | 97 | f |

-continued

| Example | Structure | Synthesis method | Retention time | Expected MW | Found MW (M + 1) | Purity | Analytical Method |
|---|---|---|---|---|---|---|---|
| 183 | 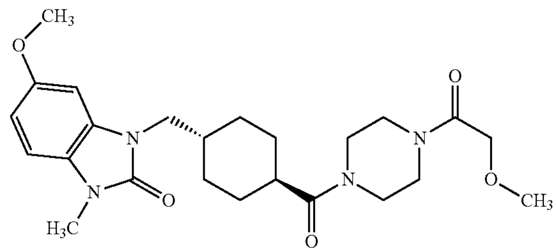 [SMILES: COCC(=O)N1CCN(C(=O)[C@H]2CC[C@H](Cn3c(=O)n(C)c4ccc(OC)cc43)CC2)CC1] | T | 1.08 | 458.6 | 459 | 100 | f |
| 184 | 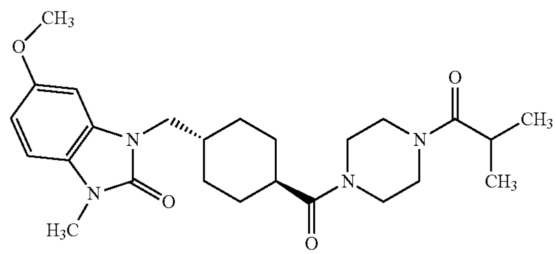 [SMILES: COc1ccc2c(c1)n(C[C@H]1CC[C@H](C(=O)N3CCN(C(=O)C(C)C)CC3)CC1)c(=O)n2C] | T | 1.21 | 456.6 | 457 | 97 | f |
| 185 | 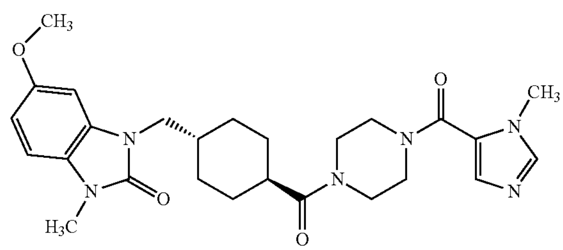 [SMILES: COc1ccc2c(c1)n(C[C@H]1CC[C@H](C(=O)N3CCN(C(=O)c4cncn4C)CC3)CC1)c(=O)n2C] | T | 2.02 | 494.6 | 495 | 100 | f |
| 186 | 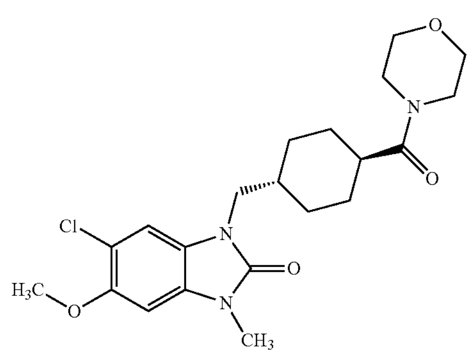 [SMILES: COc1cc2c(cc1Cl)n(C[C@H]1CC[C@H](C(=O)N3CCOCC3)CC1)c(=O)n2C] | G2 | 1.25 | 421.9 | 422 | 95 | f |
| 187 | 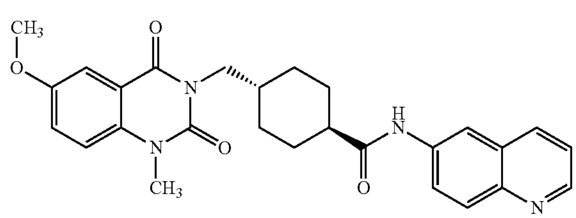 [SMILES: COc1ccc2c(c1)c(=O)n(C[C@H]1CC[C@H](C(=O)Nc3ccc4ncccc4c3)CC1)c(=O)n2C] | A2 | 2.98 | 472.5 | 473 | 100 | f |
| 188 | 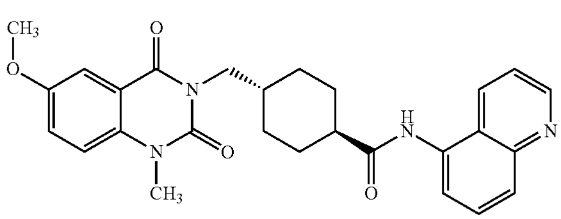 [SMILES: COc1ccc2c(c1)c(=O)n(C[C@H]1CC[C@H](C(=O)Nc3cccc4ncccc34)CC1)c(=O)n2C] | A2 | 1.14 | 472.5 | 473 | 100 | f |

-continued

| Example | Structure | Synthesis method | Retention time | Expected MW | Found MW (M + 1) | Purity | Analytical Method |
|---|---|---|---|---|---|---|---|
| 189 | 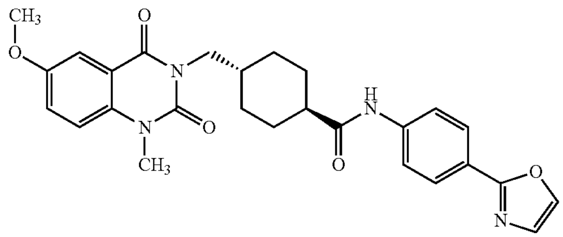 [SMILES: COc1ccc2c(c1)c(=O)n(C[C@H]1CC[C@H](C(=O)Nc3ccc(-c4ncco4)cc3)CC1)c(=O)n2C] | A2 | 1.49 | 488.5 | 489 | 100 | f |
| 190 | 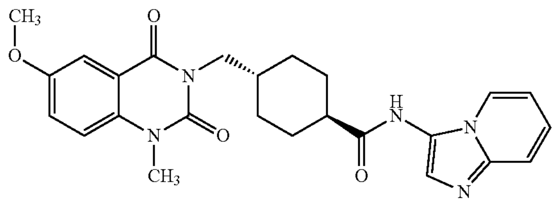 [SMILES: COc1ccc2c(c1)c(=O)n(C[C@H]1CC[C@H](C(=O)Nc3cnc4ccccn34)CC1)c(=O)n2C] | A2 | 1.02 | 461.5 | 462 | 99 | f |
| 191 | 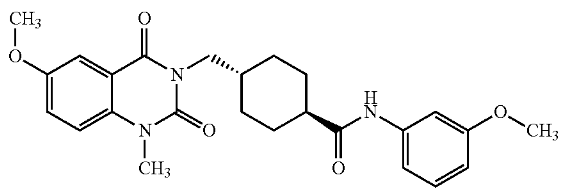 [SMILES: COc1cccc(NC(=O)[C@H]2CC[C@H](Cn3c(=O)c4cc(OC)ccc4n(C)c3=O)CC2)c1] | A2 | 1.52 | 451.5 | 452 | 100 | f |
| 192 | 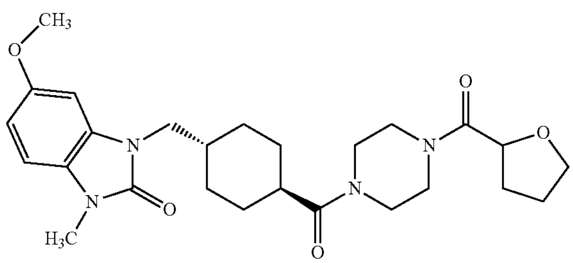 [SMILES: COc1ccc2c(c1)n(C[C@H]1CC[C@H](C(=O)N3CCN(C(=O)C4CCCO4)CC3)CC1)c(=O)n2C] | T | 1.12 | 484.6 | 485 | 96 | f |
| 193 | 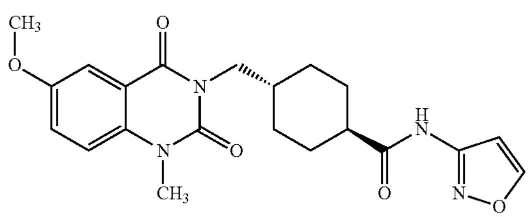 [SMILES: COc1ccc2c(c1)c(=O)n(C[C@H]1CC[C@H](C(=O)Nc3ccon3)CC1)c(=O)n2C] | A2 | 1.31 | 412.4 | 413 | 100 | f |
| 194 | 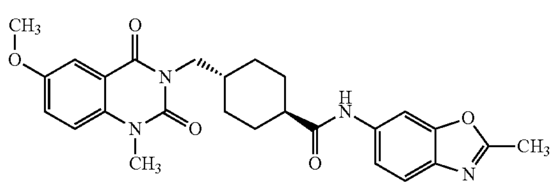 [SMILES: COc1ccc2c(c1)c(=O)n(C[C@H]1CC[C@H](C(=O)Nc3ccc4nc(C)oc4c3)CC1)c(=O)n2C] | A2 | 1.39 | 476.5 | 477 | 100 | f |
| 195 | 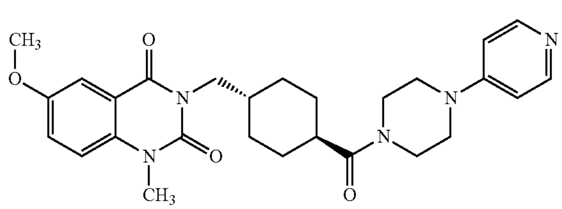 [SMILES: COc1ccc2c(c1)c(=O)n(C[C@H]1CC[C@H](C(=O)N3CCN(c4ccncc4)CC3)CC1)c(=O)n2C] | A2 | 1.02 | 491.6 | 492 | 100 | f |

-continued

| Example | Structure | Synthesis method | Retention time | Expected MW | Found MW (M + 1) | Purity | Analytical Method |
|---|---|---|---|---|---|---|---|
| 196 | 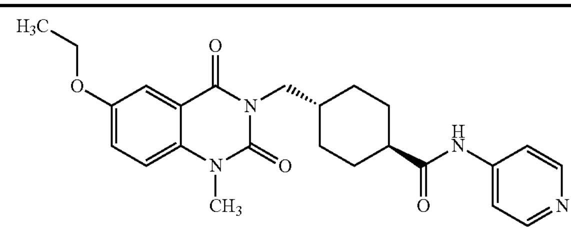 | A2 | 2.95 | 436.5 | 437 | 100 | c |
| 197 | 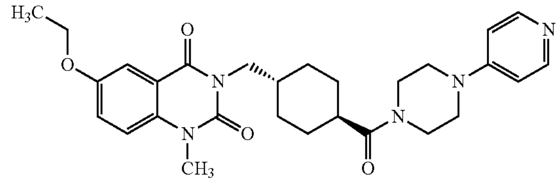 [SMILES: CCOc1ccc2c(c1)c(=O)n(C[C@H]1CC[C@H](C(=O)N3CCN(c4ccncc4)CC3)CC1)c(=O)n2C] | A2 | 1.12 | 505.6 | 506 | 100 | f |
| 198 | 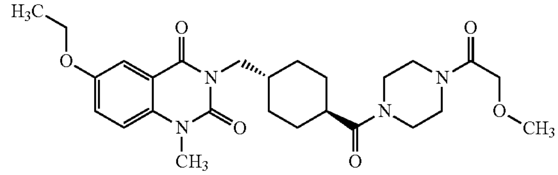 [SMILES: CCOc1ccc2c(c1)c(=O)n(C[C@H]1CC[C@H](C(=O)N3CCN(C(=O)COC)CC3)CC1)c(=O)n2C] | C2 | 1.25 | 500.6 | 501 | 97 | f |
| 199 | 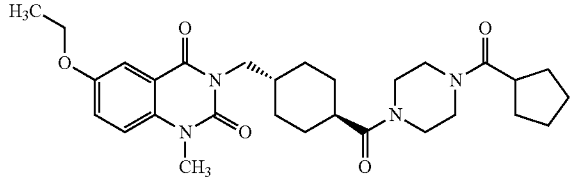 [SMILES: CCOc1ccc2c(c1)c(=O)n(C[C@H]1CC[C@H](C(=O)N3CCN(C(=O)C4CCCC4)CC3)CC1)c(=O)n2C] | C2 | 1.52 | 524.7 | 525 | 100 | f |
| 200 | 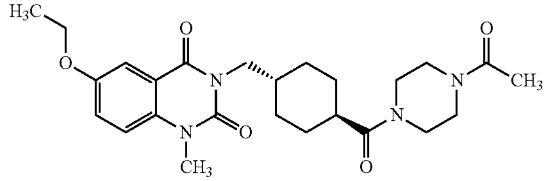 [SMILES: CCOc1ccc2c(c1)c(=O)n(C[C@H]1CC[C@H](C(=O)N3CCN(C(C)=O)CC3)CC1)c(=O)n2C] | C2 | 1.24 | 470.6 | 471 | 100 | f |
| 201 | 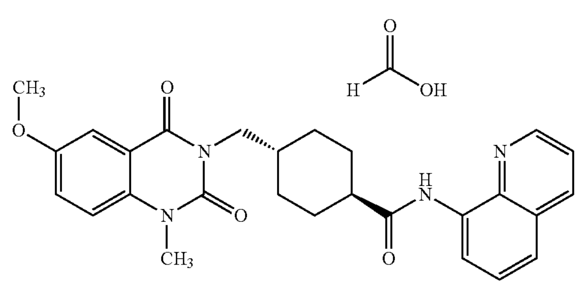 | A2 | 1.72 | 472.5 | 473 | 100 | f |
| 202 | 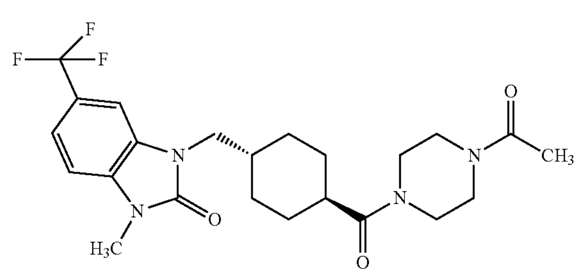 [SMILES: CC(=O)N1CCN(C(=O)[C@H]2CC[C@H](Cn3c(=O)n(C)c4ccc(C(F)(F)F)cc43)CC2)CC1] | G2 | 1.28 | 466.5 | 98 | 98 | f |

-continued

| Example | Structure | Synthesis method | Retention time | Expected MW | Found MW (M + 1) | Purity | Analytical Method |
|---|---|---|---|---|---|---|---|
| 203 | 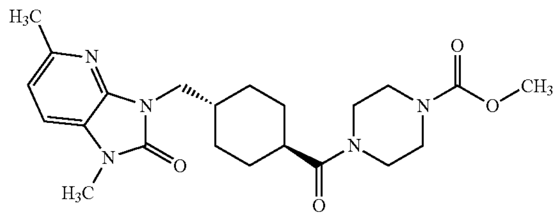 [SMILES: COC(=O)N1CCN(C(=O)[C@H]2CC[C@H](Cn3c(=O)n(C)c4ccc(C)nc43)CC2)CC1] | T | 1.13 | 429.5 | 430 | 100 | f |
| 204 | 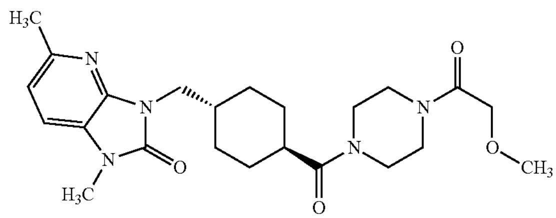 [SMILES: COCC(=O)N1CCN(C(=O)[C@H]2CC[C@H](Cn3c(=O)n(C)c4ccc(C)nc43)CC2)CC1] | T | 0.99 | 443.5 | 444 | 100 | f |
| 205 | 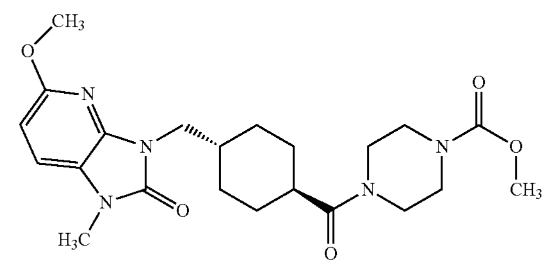 [SMILES: COC(=O)N1CCN(C(=O)[C@H]2CC[C@H](Cn3c(=O)n(C)c4ccc(OC)nc43)CC2)CC1] | T | 1.22 | 445.5 | 446 | 100 | f |
| 206 | 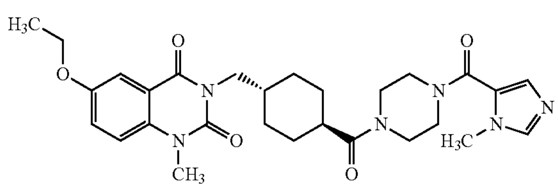 [SMILES: CCOc1ccc2c(c1)c(=O)n(C[C@H]1CC[C@H](C(=O)N3CCN(C(=O)c4cncn4C)CC3)CC1)c(=O)n2C] | C2 | 1.1 | 536.6 | 537 | 98 | f |
| 207 | 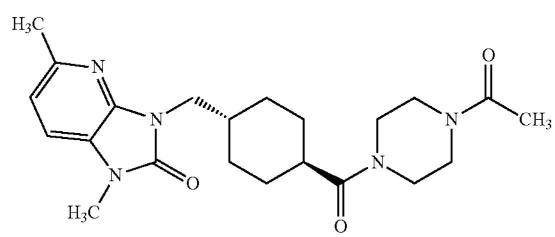 [SMILES: CC(=O)N1CCN(C(=O)[C@H]2CC[C@H](Cn3c(=O)n(C)c4ccc(C)nc43)CC2)CC1] | T | 0.98 | 413.5 | 414 | 95 | f |
| 208 | 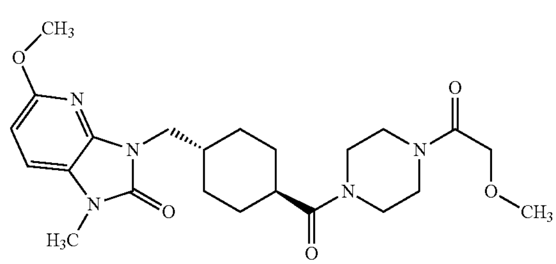 [SMILES: COCC(=O)N1CCN(C(=O)[C@H]2CC[C@H](Cn3c(=O)n(C)c4ccc(OC)nc43)CC2)CC1] | T | 1.07 | 459.5 | 460 | 95 | f |

-continued

| Example | Structure | Synthesis method | Retention time | Expected MW | Found MW (M + 1) | Purity | Analytical Method |
|---|---|---|---|---|---|---|---|
| 209 | 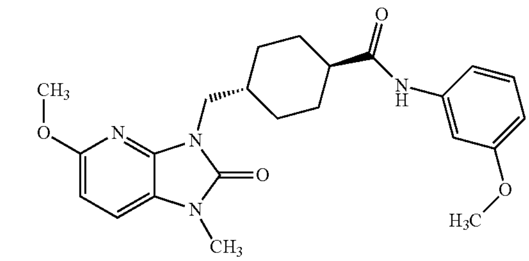 [SMILES: COc1cccc(NC(=O)[C@H]2CC[C@H](Cn3c(=O)n(C)c4ccc(OC)nc43)CC2)c1] | T | 1.47 | 424.5 | 425 | 97 | f |
| 210 | 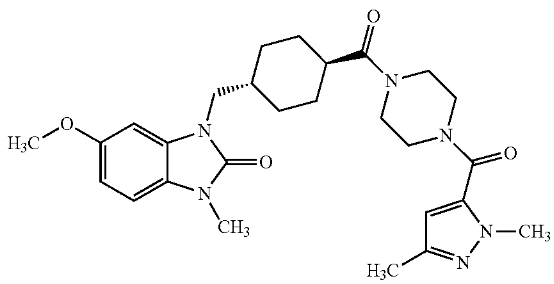 | G2 | 1.18 | 508.6 | 509 | 100 | f |
| 211 | 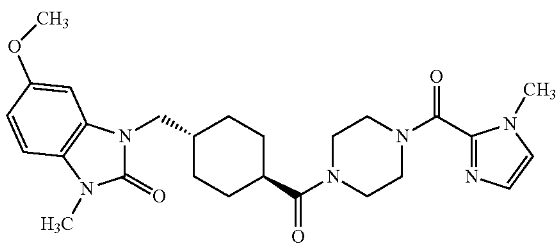 [SMILES: COc1ccc2c(c1)n(C[C@H]1CC[C@H](C(=O)N3CCN(C(=O)c4nccn4C)CC3)CC1)c(=O)n2C] | G2 | 1.04 | 494.6 | 495 | 100 | f |

Examples 1-211 display an $IC_{50}$ value in the above described reporter assay falling between 0.3 and 30 µM. In the *renilla* read out, Examples 1-211 showed a negligible effect. Moreover, selected representative compounds were assessed not to be inhibitors of the luciferase enzyme. Examples 3; 5; 10; 18; 20; 21; 26; 27; 29; 37; 47; 48; 56; 57; 58; 59; 60; 66; 71; 75; 77; 78; 79; 80; 92; 99; 109; 116; 122; 135; 136; 146; 169 and 175 display and 1050 value ranging from 0.9 uM to 30 uM in the soft agar assay.

The invention claimed is:
1. A compound of formula (I),

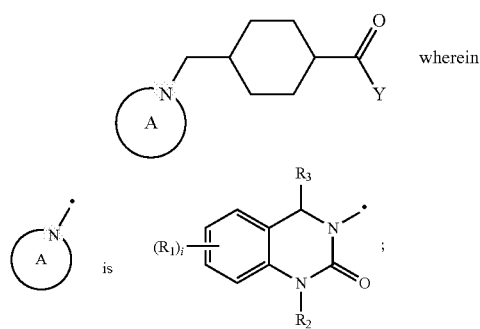

wherein

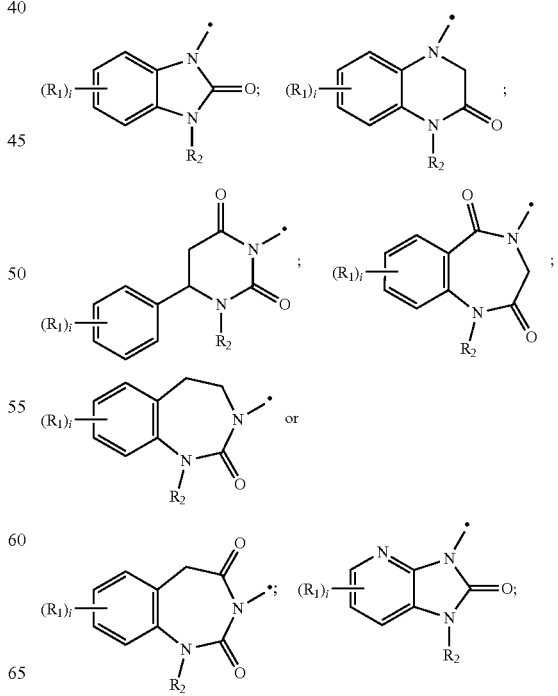

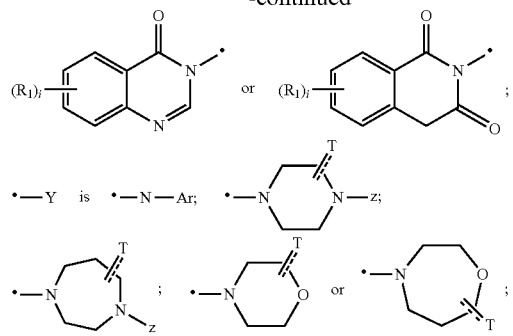

- $R_1$ is Cl, F, OH, $C_1$-$C_3$ alkyl, oxalkyl, alkyloxy, oxalkyloxy;
- i equals 0, 1 or 2;
- $R_2$ is hydrogen or $C_1$-$C_4$ linear, branched or cyclic alkyl group;
- $R_3$ may be H; a $C_1$-$C_3$ linear, branched or cyclic alkyl group; or O, with the proviso that when $R_3$ is O, ==== represents a double bond;
- Z is a linear, cyclic or branched $C_1$-$C_6$ alkyl group; a linear, cyclic or branched $C_1$-$C_8$ alkylcarbonyl, oxaalkylcarbonyl, alkyl oxycarbonyl, alkylaminocarbonyl or oxaalkylaminocarbonyl; $Ar_2$; C(O)—$Ar_2$; a benzyl or $C_2$-$C_3$ alkylphenyl optionally substituted with one or more methyl, ethyl, methoxy or chloro groups;
- $Ar_1$ is a 5 to 10 membered heteroaromatic ring containing 1 or 2 nitrogen atoms, or one nitrogen atom and one oxygen atom, said heteroaromatic ring being optionally substituted with one or more methyl, ethyl, methoxy or chloro groups;
- $Ar_2$ is 5 to 6 membered aromatic or heteroaromatic ring containing 1 or 2 nitrogen atoms, one oxygen atom, one oxygen atom and one nitrogen atom, or one sulfur atom and one nitrogen atom, said aromatic or heteroarometic ring being optionally substituted with one or more methyl, ethyl, methoxy or chloro groups;
- T may be H; a $C_1$-$C_3$ linear, branched or cyclic alkyl; or O, with the proviso that when T is O, ==== represents a double bond;
- wherein any carbon-bound hydrogen atom may optionally be substituted with a fluorine atom; or a pharmaceutically acceptable salt or stereoisomer thereof, with the exception of:

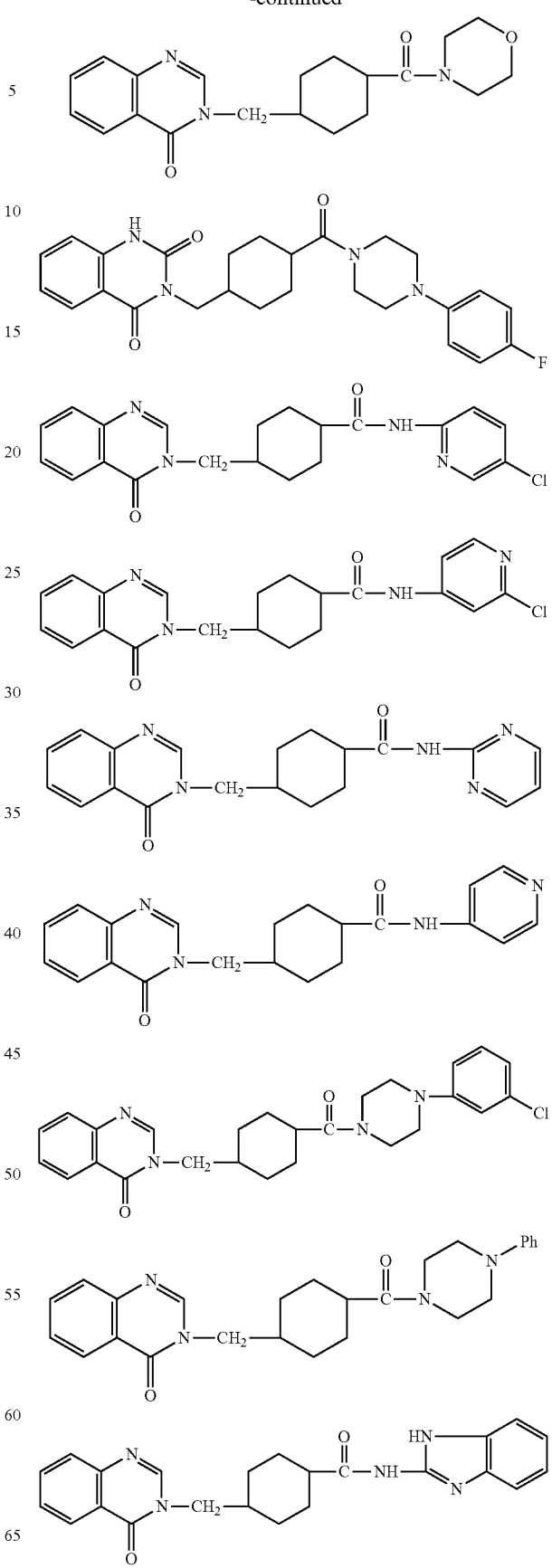

-continued
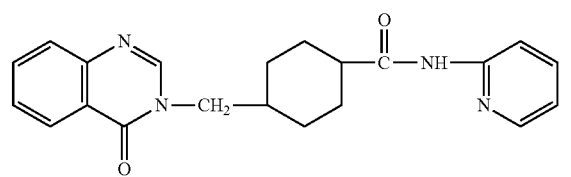
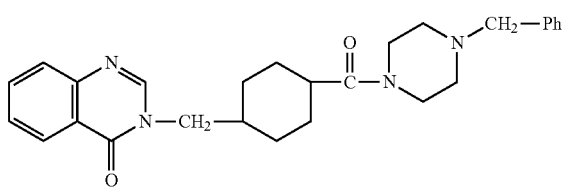
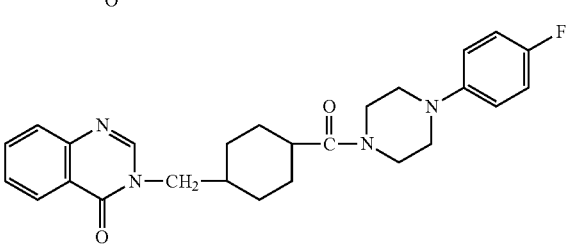
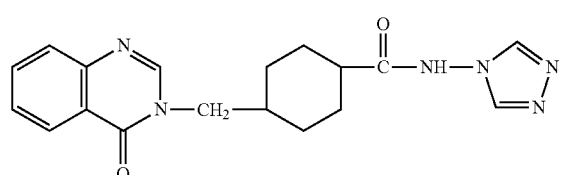
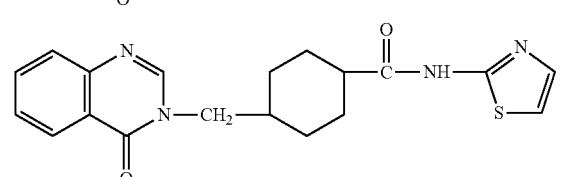
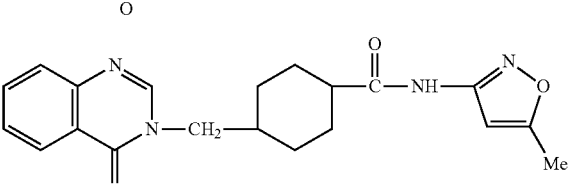
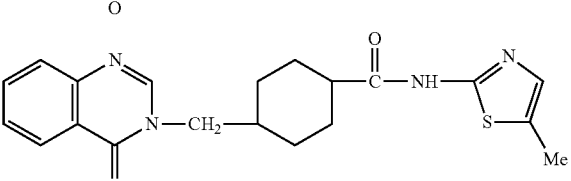
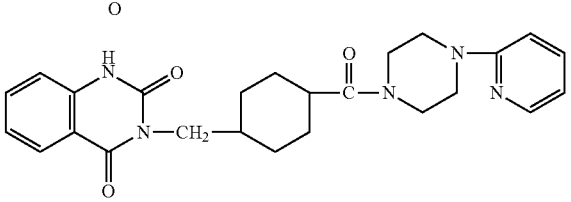
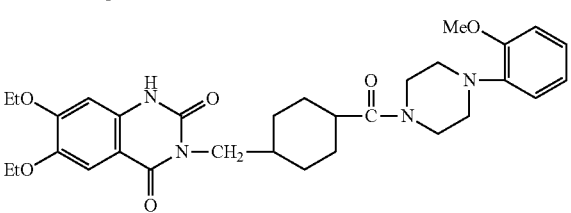
-continued
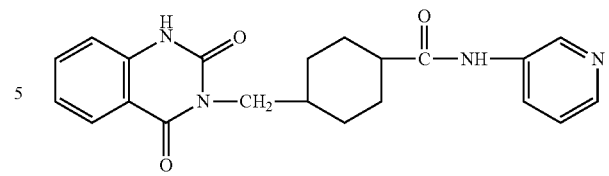
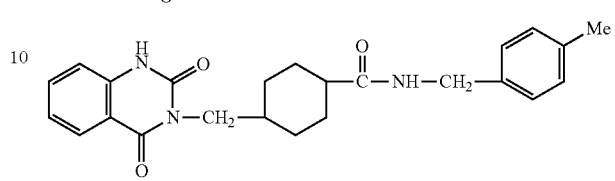
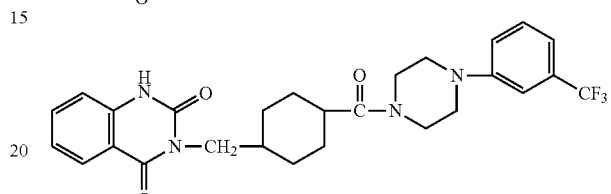
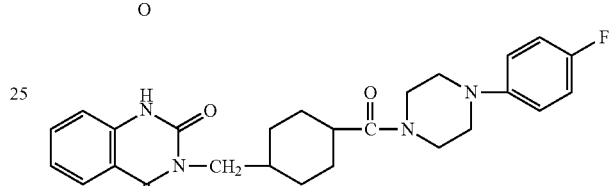
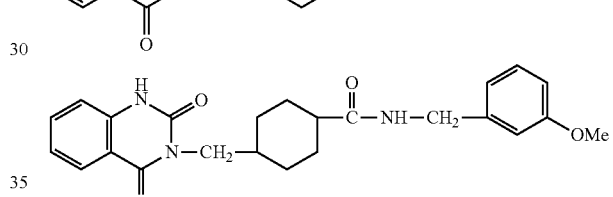
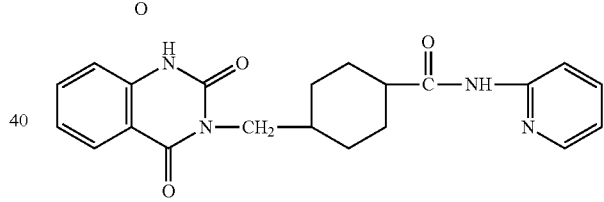
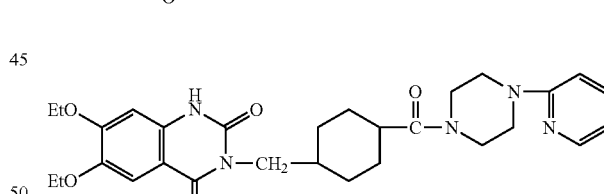
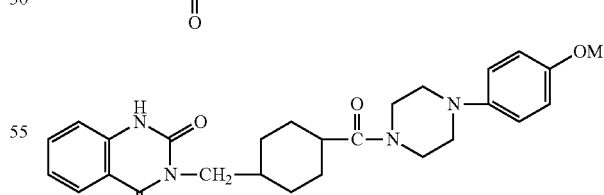
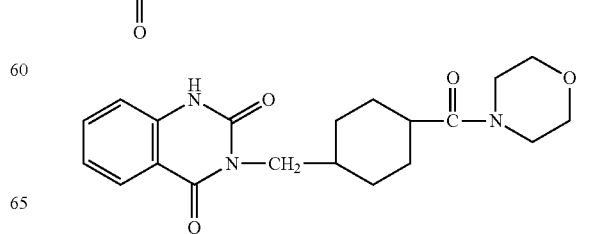

-continued
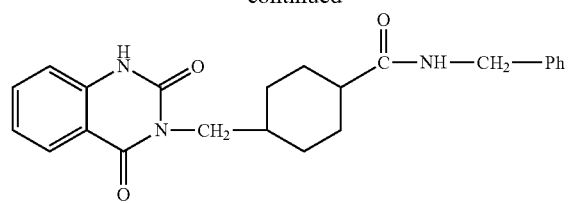
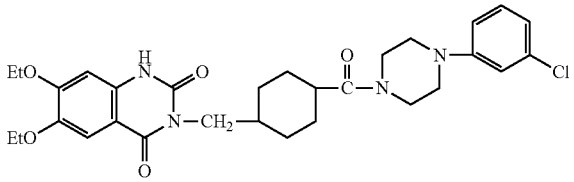
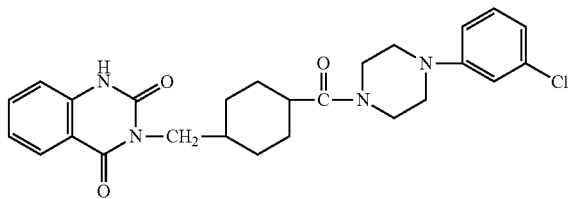
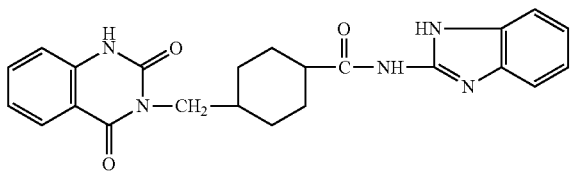
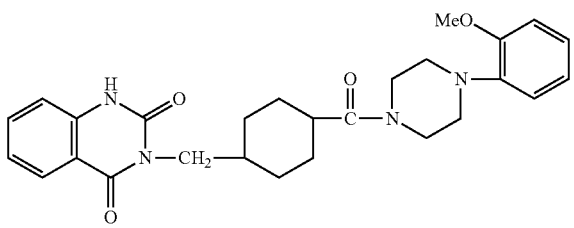
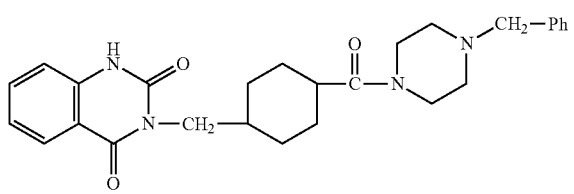
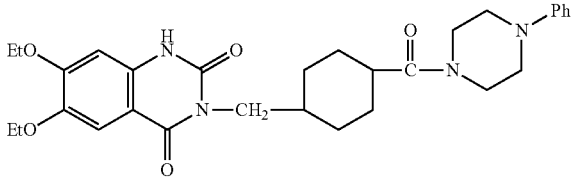
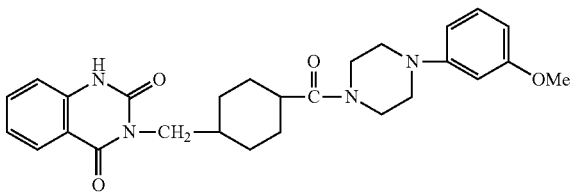
-continued
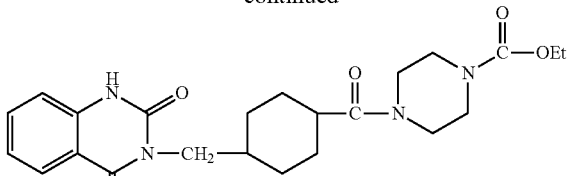
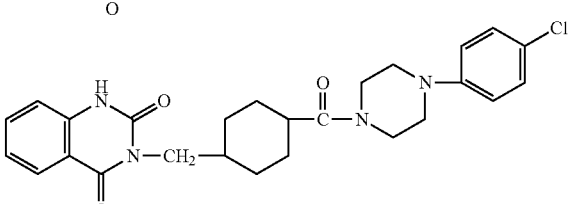
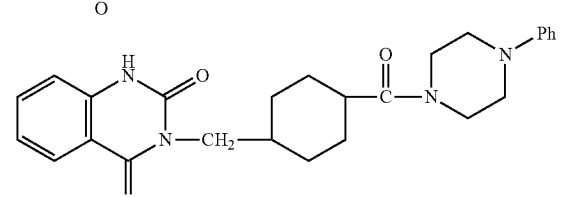
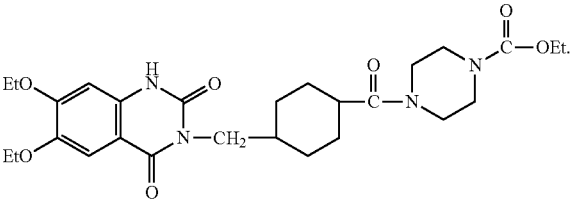
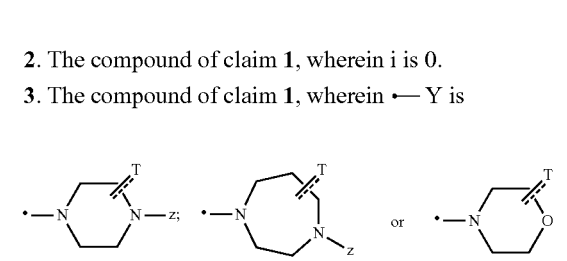
2. The compound of claim 1, wherein i is 0.
3. The compound of claim 1, wherein •—Y is
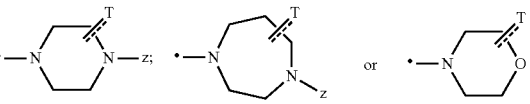
and Z is a $C_3$-$C_6$ iso- or cycloalkyl group; a linear, cyclic or branched $C_1$-$C_6$ alkylcarbonyl, oxaalkylcarbonyl, alkyloxycarbonyl, alkylaminocarbonyl or oxaalkylaminocarbonyl.
4. The compound of claim 1, where
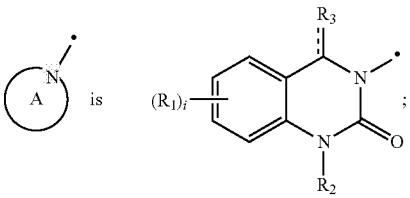
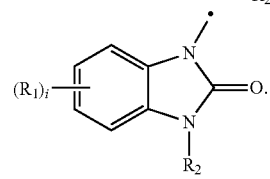

5. The compound of claim 3, where

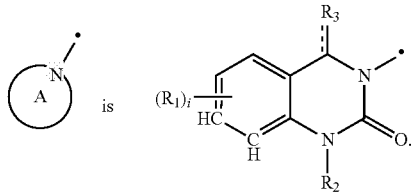 is

6. The compound of claim 5, wherein i is 1; $R_1$ is a linear or branched $C_1$-$C_3$ alkyloxy group; $R_2$ is either H or a linear, branched or cyclic $C_1$-$C_4$ alkyl group; $R_3$ is O;

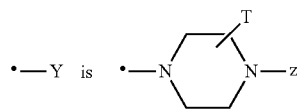

T is either H or a linear, cyclic or branched $C_1$-$C_3$ alkyl group; Z is a linear, branched or cyclic $C_1$-$C_6$ alkyl carbonyl, oxalkyl carbonyl, or alkyloxycarbonyl group; and wherein any carbon-bound hydrogen atom may optionally be substituted with a fluorine atom.

7. The compound of claim 6 selected from the group consisting of

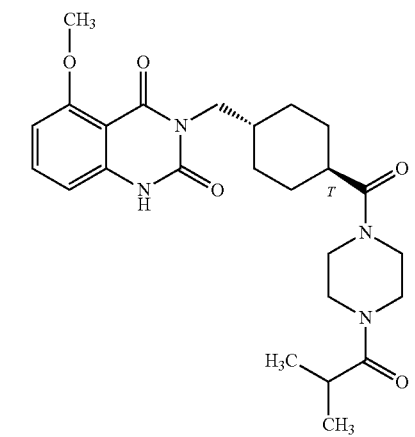

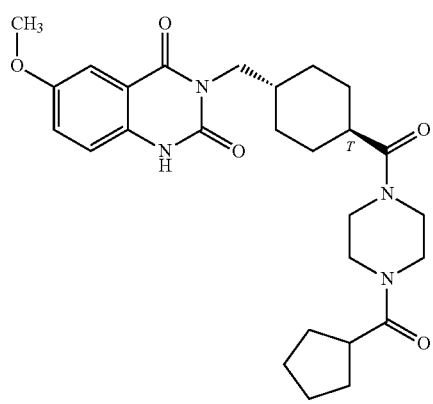

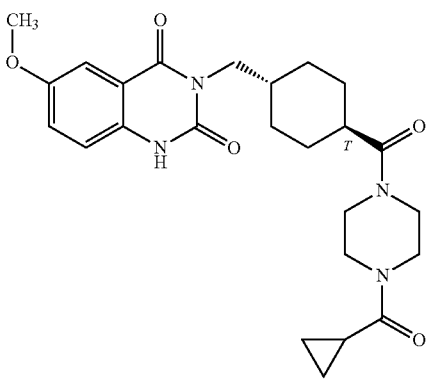

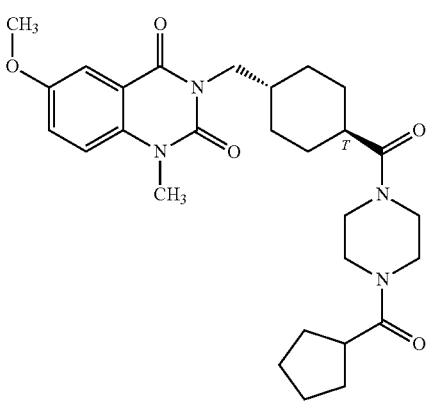

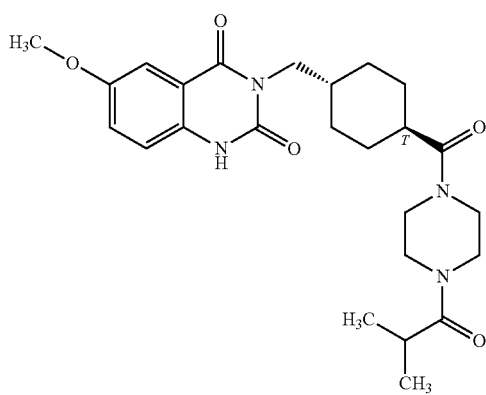

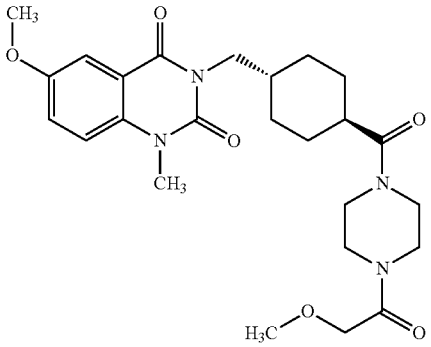

187
-continued
188
-continued
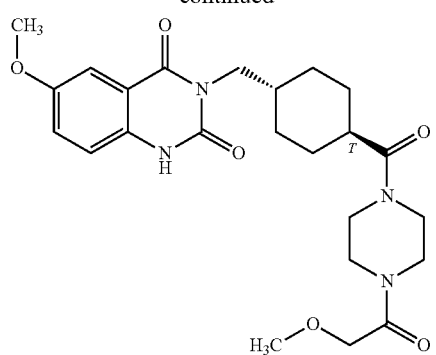
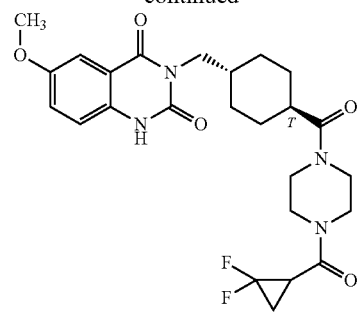
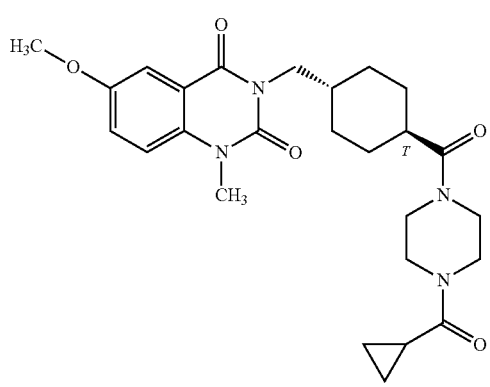
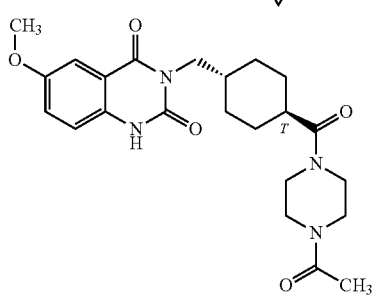
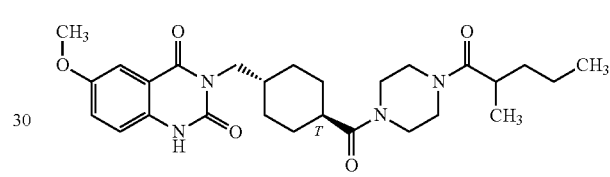
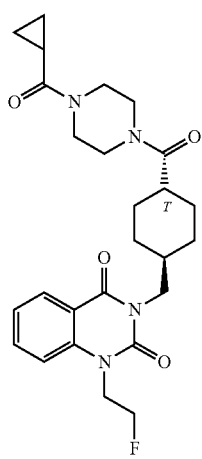
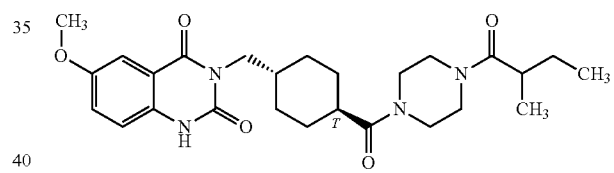
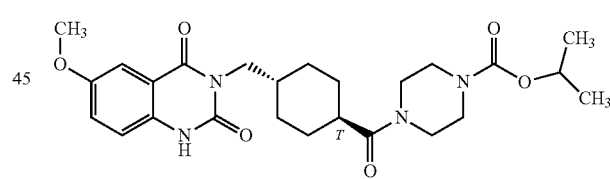
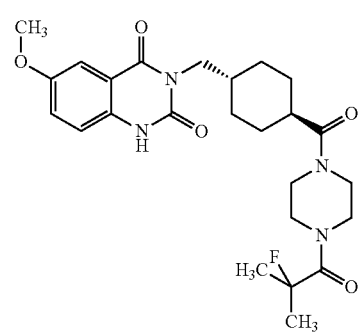
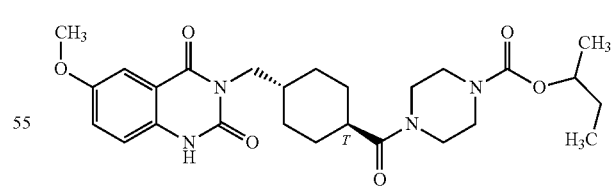
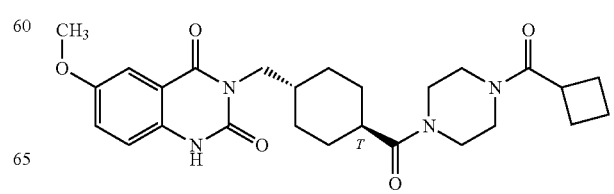

189
-continued
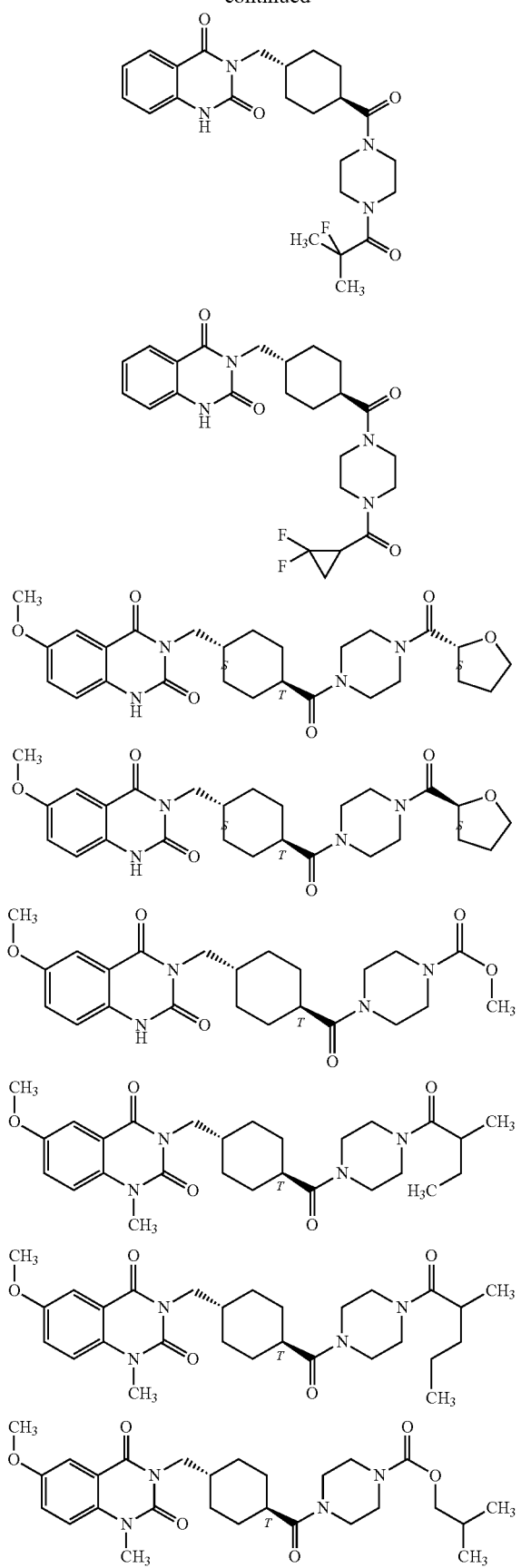
190
-continued
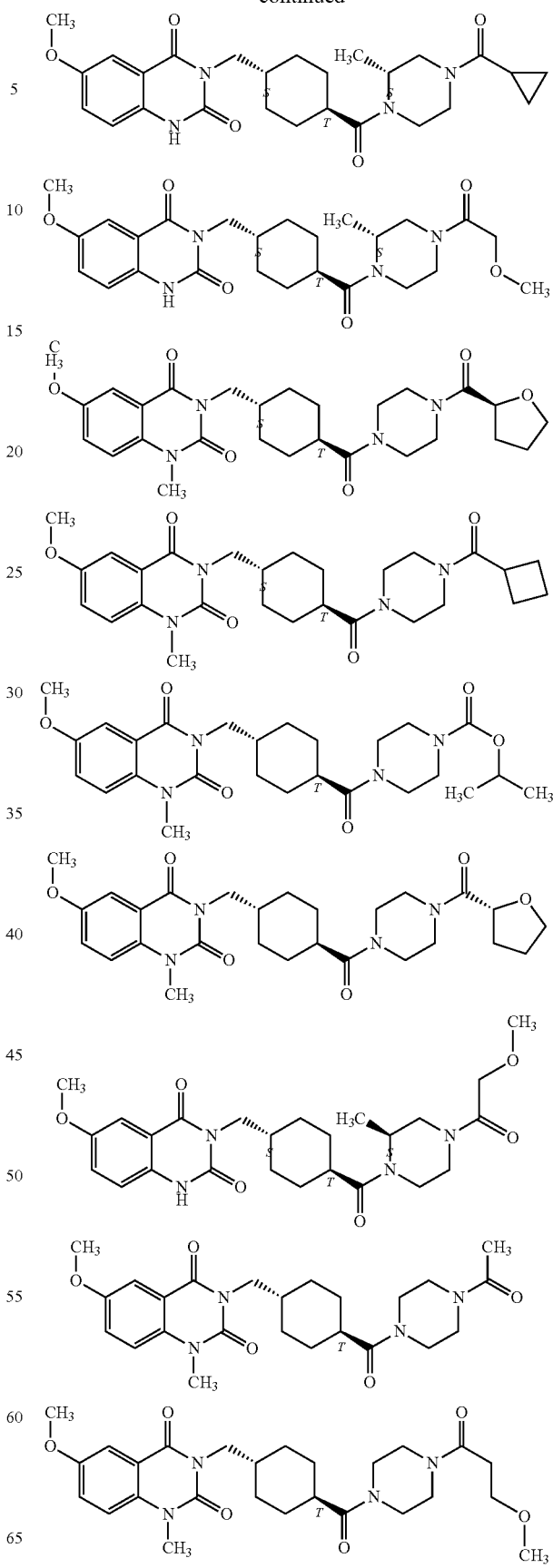

191
-continued
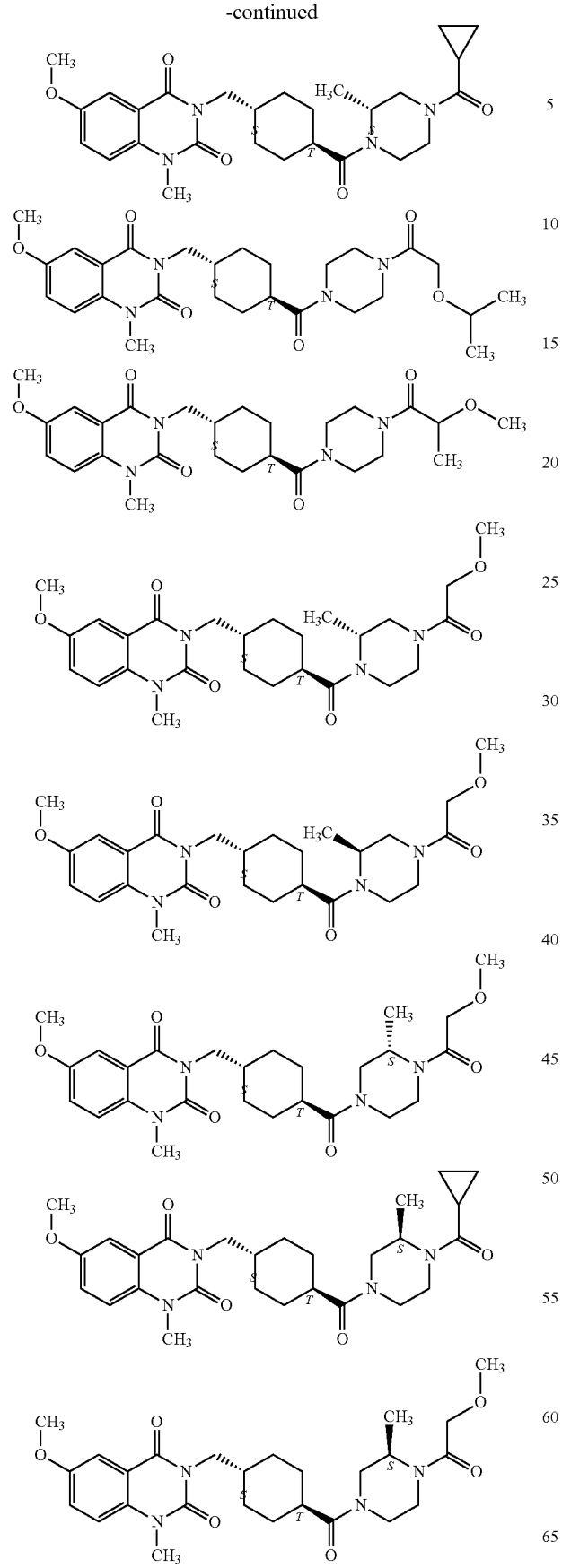
192
-continued
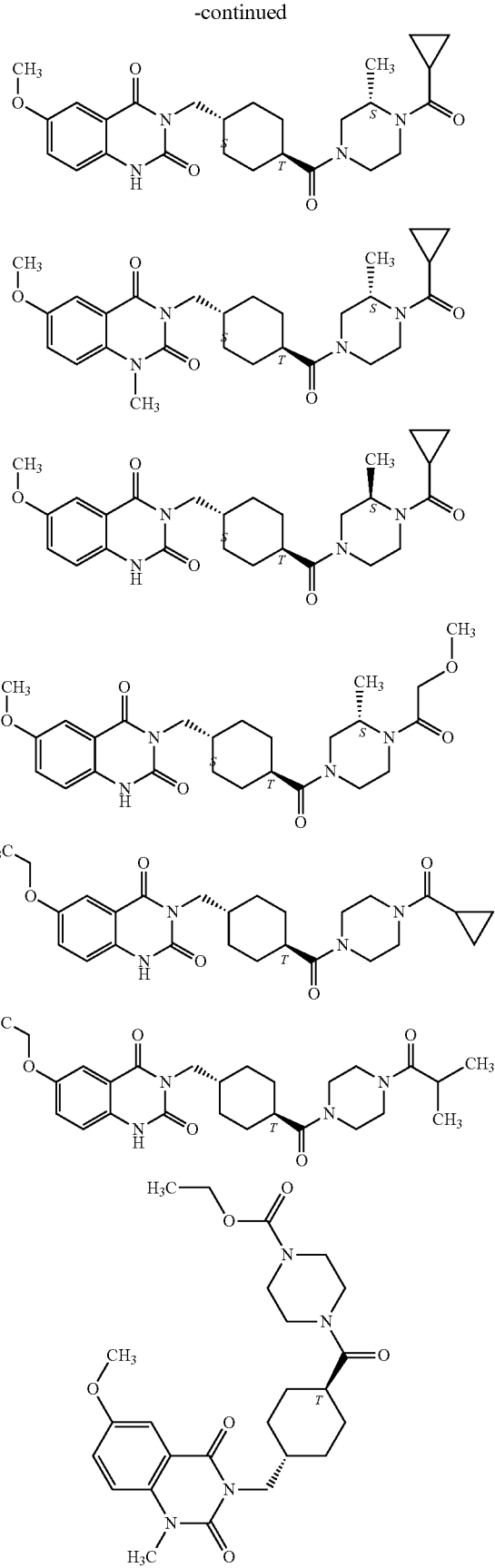

-continued

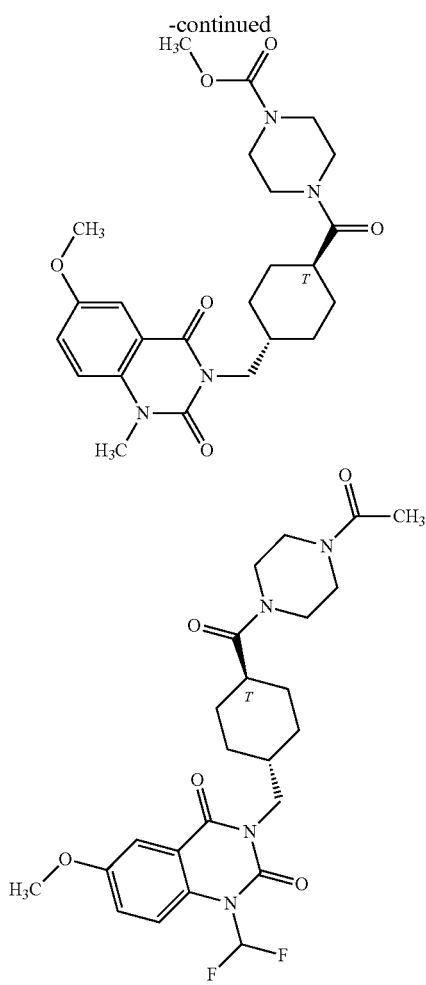

-continued

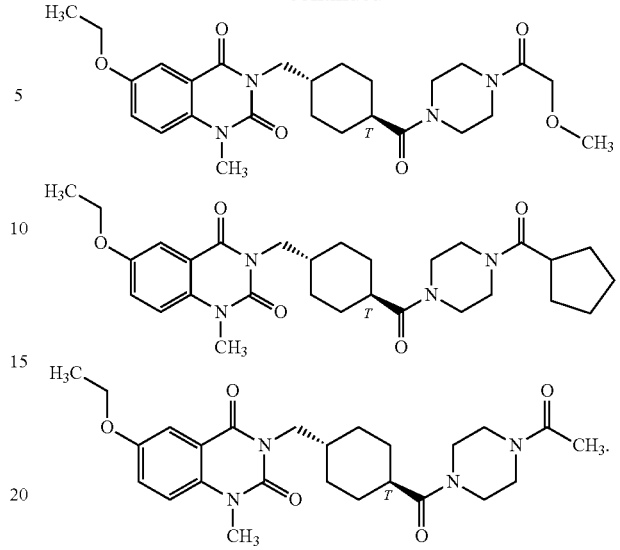

8. A pharmaceutical composition comprising a compound according to claim 1 and a pharmaceutically acceptable carrier or excipient.

9. A method for treating cancer in a subject in need thereof comprising administering to the subject an effective amount of the composition according to claim 8, wherein the cancer is selected from the group consisting of lung cancer; colon cancer; pancreatic cancer; breast cancer; melanoma; glioblastoma; medulloblastoma; gastric cancer; hepatocellular cancer; basal cell carcinoma; leukemia selected from human T-cell acute lymphoblastic leukemia, myeloid leukemia, and human chronic myelogenous leukemia; Wilm's tumour and Familial Adenomatous Polyposis.

* * * * *

UNITED STATES PATENT AND TRADEMARK OFFICE
CERTIFICATE OF CORRECTION

| | | |
|---|---|---|
| PATENT NO. | : 8,865,704 B2 | Page 1 of 1 |
| APPLICATION NO. | : 13/500582 | |
| DATED | : October 21, 2014 | |
| INVENTOR(S) | : Maurizio Varrone | |

It is certified that error appears in the above-identified patent and that said Letters Patent is hereby corrected as shown below:

TITLE PAGE: ITEM

PCT Pub. No. reads:

(87) PCT Pub. No.: WO2011/042145 should read:

(87) PCT Pub. No.: WO2011/042145 A1

Signed and Sealed this
Seventeenth Day of February, 2015

Michelle K. Lee
*Deputy Director of the United States Patent and Trademark Office*